US012662474B2

(12) United States Patent
Wu et al.

(10) Patent No.: US 12,662,474 B2
(45) Date of Patent: Jun. 23, 2026

(54) FUSED RING DERIVATIVES CONTAINING 1,4-OXAZEPANE

(71) Applicant: Shanghai Fosun Pharmaceutical Industrial Development Co., Ltd., Shanghai (CN)

(72) Inventors: Lingyun Wu, Shanghai (CN); Lele Zhao, Shanghai (CN); Deheng Chen, Shanghai (CN); Xiaoxuan Yan, Shanghai (CN); Shuhui Chen, Shanghai (CN)

(73) Assignee: Shanghai Fosun Pharmaceutical Industrial Development Co., Ltd., Shanghai (CN)

( * ) Notice: Subject to any disclaimer, the term of this patent is extended or adjusted under 35 U.S.C. 154(b) by 347 days.

(21) Appl. No.: 18/275,706

(22) PCT Filed: Jan. 26, 2022

(86) PCT No.: PCT/CN2022/074088

§ 371 (c)(1),
(2) Date: Aug. 3, 2023

(87) PCT Pub. No.: WO2022/166721

PCT Pub. Date: Aug. 11, 2022

(65) Prior Publication Data

US 2024/0150335 A1 May 9, 2024

(30) Foreign Application Priority Data

Feb. 5, 2021 (CN) ......................... 202110164857.7
Sep. 27, 2021 (CN) .......................... 202111138395.8

(51) Int. Cl.
*C07D 413/12* (2006.01)
*C07D 413/14* (2006.01)
*C07D 471/04* (2006.01)
*C07D 495/04* (2006.01)

(52) U.S. Cl.
CPC ......... *C07D 413/12* (2013.01); *C07D 413/14* (2013.01); *C07D 471/04* (2013.01); *C07D 495/04* (2013.01)

(58) Field of Classification Search
CPC .. C07D 413/12; C07D 413/14; C07D 471/04; C07D 495/04
USPC ..................................................... 514/211.15
See application file for complete search history.

(56) References Cited

U.S. PATENT DOCUMENTS

| | | | | |
|---|---|---|---|---|
| 9,815,805 | B2 | 11/2017 | Lonn et al. | |
| 11,807,635 | B2 * | 11/2023 | Li | C07D 417/12 |
| 2010/0286118 | A1 | 11/2010 | Adie | |
| 2011/0201581 | A1 | 8/2011 | Furber et al. | |
| 2014/0275025 | A1 | 9/2014 | Anderskewitz et al. | |
| 2016/0031861 | A1 | 2/2016 | Grauert et al. | |
| 2018/0028541 | A1 | 2/2018 | Lonn et al. | |
| 2019/0247400 | A1 | 8/2019 | Dipetrillo et al. | |
| 2021/0369732 | A1 | 12/2021 | Wikstroem et al. | |
| 2024/0059681 | A1 | 2/2024 | Li et al. | |

FOREIGN PATENT DOCUMENTS

| | | | | |
|---|---|---|---|---|
| CN | 101945851 | A | 1/2011 | |
| CN | 102574830 | A | 7/2012 | |
| CN | 105980367 | A | 9/2016 | |
| CN | 109789150 | A | 5/2019 | |
| CN | 111148515 | A | 5/2020 | |
| CN | 111372937 | A | 7/2020 | |
| CN | 112055593 | A | 12/2020 | |
| JP | 2011506421 | A | 3/2011 | |
| JP | 2012526093 | A | 10/2012 | |
| JP | 2016516020 | A | 6/2016 | |
| JP | 2017503832 | A | 2/2017 | |
| WO | 2010/142985 | A1 | 12/2010 | |
| WO | 2020/018547 | A1 | 1/2020 | |
| WO | 2020018551 | A1 | 1/2020 | |
| WO | WO-2022042591 | A1 * | 3/2022 | C07F 9/6527 |

OTHER PUBLICATIONS

Turk, D et al., "Structure of human dipeptidyl peptidase I (cathepsin C): exclusion domain added to an endopeptidase framework creates the machine for activation of granular serine proteases" , EMBO J. 2001, 20, 6570-6582.
Christine T.N. Pham, "Neutrophil serine proteases: specific regulators of inflammation" , Nat. Rev. Immunol. 2006, 6, 541-550.
International Search Report issued in International Patent Application No. PCT/CN2022/074088 dated Mar. 16, 2021 with English translation.
Written Opinion of the International Searching Authority issued in International Patent Application No. PCT/CN2022/074088 dated Mar. 16, 2021 with English translation.
First Office Action in Chinese Patent Application No. 202280010798.0 dated Jan. 15, 2025 with English translation.
Search Report in Chinese Patent Application No. 202280010798.0 dated Jan. 15, 2025 with English translation.
Extended European Search Report in European Patent Application No. 22749000.0 dated Jan. 2, 2025.
Kevin Doyle et al., Discovery of Second Generation Reversible Covalent DPP1 Inhibitors Leading to an Oxazepane Amidoacetonitrile Based Clinical Candidate (AZD7986), Journal of Medicinal Chemistry, vol. 59, No. 20, Oct. 11, 2016 (Oct. 11, 2016), pp. 9457-9472, CP055600426.
Japanese Search Report in Japanese Patent Application No. 2023-547665 dated Sep. 25, 2024 with English translation.
Notice of Reasons for Refusal in Japanese Patent Application No. 2023-547665 dated Oct. 8, 2024 with English translation.

(Continued)

*Primary Examiner* — Kahsay Habte
(74) *Attorney, Agent, or Firm* — Wilson Sonsini Goodrich & Rosati

(57) ABSTRACT

The present invention relates to a series of fused ring derivatives containing 1,4-oxazepane and a preparation method therefor, and in particular relates to a compound as shown in formula (II) and a pharmaceutically acceptable salt thereof.

34 Claims, 1 Drawing Sheet

(56) References Cited

OTHER PUBLICATIONS

Huang et al., 3D-QSAR, molecular docking and molecular dynamics simulations of oxazepane amidoacetonitrile derivatives as novel DPPI inhibitors, Journal of Molecular Structure, 2018, 1168, pp. 223-233.

Furber, Mark et al., Cathepsin C Inhibitors: Property Optimization and Identification of a Clinical Candidate, Journal of Medicinal Chemistry, 2014, 57 (6), pp. 2357-2367.

Canadian Office Action in Canadian Patent Application No. 3,207,466 dated Nov. 19, 2024.

Second Chinese Office Action in Chinese Patent Application No. 202280010798.0 dated Jul. 27, 2025 with English translation.

Chinese Search Report in Chinese Patent Application No. 202280010798.0 dated Jul. 27, 2025 with English translation.

First Indian Examination Report in Indian Patent Application No. 202317059196 dated Jul. 3, 2025.

* cited by examiner

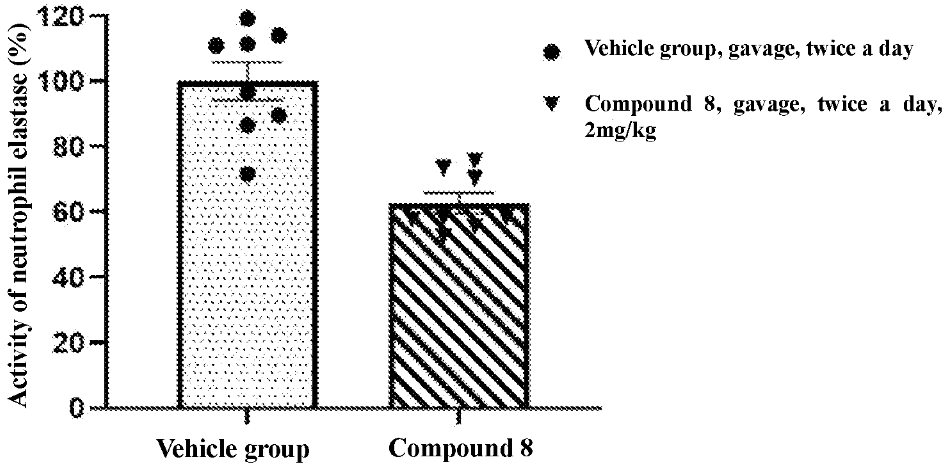
Activity of neutrophil elastase (%)
120
100
80
60
40
20
0
Vehicle group
Compound 8
Vehicle group, gavage, twice a day
Compound 8, gavage, twice a day, 2mg/kg

FUSED RING DERIVATIVES CONTAINING 1,4-OXAZEPANE

CROSS REFERENCE TO RELATED APPLICATIONS

This application is the National Stage of PCT/CN2022/074088 filed on Jan. 26, 2022, which claims priority under 35 U.S.C. § 119 of Chinese Application No. 202110164857.7, filed on Feb. 5, 2021 and Chinese Application No. 202111138395.8, filed on Sep. 27, 2021, the disclosure of which is incorporated by reference. The international application under PCT article 21 (2) was not published in English.

TECHNICAL FIELD

The present disclosure relates to a series of fused ring derivatives containing 1,4-oxazepane and a preparation method therefor, and in particular relates to a compound of formula (II) and a pharmaceutically acceptable salt thereof.

BACKGROUND

Dipeptidyl peptidase 1 (DPP1), also known as cathepsin C, is highly expressed in lung, kidney, liver, spleen, and other tissues. DPP1 is a class of lysosomal cysteine proteases, consisting of four identical subunits that form a tetramer. Each subunit consists of a heavy chain, a light chain, and an exclusive structural domain (Turk, D. et. al. EMBO J. 2001, 20, 6570-6582). The main physiological action of DPP1 is to activate pro-inflammatory neutrophil serine proteases (NSPs, including neutrophil elastase, proteinase 3, and cathepsin G) by cleaving the N-terminal dipeptide in the bone marrow. NSPs are closely related to the regulation of inflammation, which can activate a variety of cytokines, and play an important role in the elimination of pathogenic microorganisms. Studies have shown that in patients with chronic obstructive pulmonary disease (COPD) or bronchiectasis, there is often a persistent inflammatory response and excessive activation of NSPs in the airway, which degrades lung elastin and further causes lung tissue damage and bronchial wall tissue destruction (Christine T. N. Pham, Nat. Rev. Immunol. 2006, 6, 541-550). DPP1 inhibitors can fundamentally inhibit the activation of pro-inflammatory neutrophil proteases, thereby inhibiting the inflammatory response and airway injury caused by neutrophils in the airway.

Drugs regarding DPP1 inhibitors are not yet on the market. Brensocatib (INS1007, also known as AZD7986) is the drug with the fastest progress in clinical research. Its phase II clinical trial for bronchiectasis has reached its primary endpoint, and phase III clinical trials are currently underway. In addition, AZD7986 for the treatment of chronic obstructive pulmonary disease is undergoing phase II clinical research. Therefore, the development of DPP1 inhibitors has broad market prospects.

CONTENT OF THE PRESENT INVENTION

The present disclosure provides a compound of formula (II) or a pharmaceutically acceptable salt thereof, (II)

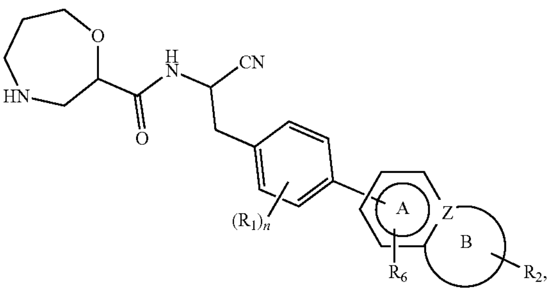

wherein

Z is selected from N and C;

the structural moiety

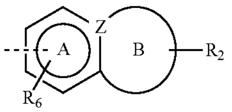

is selected from

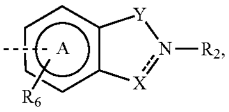

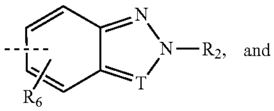 and

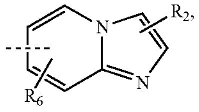

wherein the structure moiety

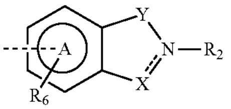

is selected from

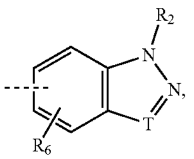

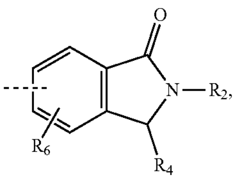

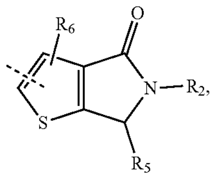

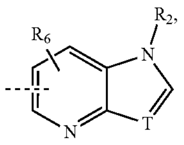 and

-continued

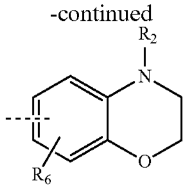

;

each ⫽ is independently selected from a single bond and a double bond, wherein when ⫽ is selected from the double bond, $R_2$ is absent;

each T is independently selected from N and $CR_3$;

each $R_1$ is independently selected from H, F, Cl, Br, I, —OH, —$NH_2$, —CN, and $C_{1-3}$ alkyl, wherein the $C_{1-3}$ alkyl is optionally substituted by 1, 2, or 3 $R_a$;

$R_2$ is selected from H, F, Cl, Br, I, =O, —OH, —$NH_2$, —CN, $C_{1-3}$ alkyl, and 5- to 6-membered heterocycloalkyl, wherein the $C_{1-3}$ alkyl and 5- to 6-membered heterocycloalkyl are each independently and optionally substituted by 1, 2, or 3 $R_b$;

$R_3$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_c$;

$R_4$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_d$;

$R_5$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_e$;

$R_6$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_f$;

each $R_a$ is independently selected from F, Cl, Br, I, =O, —OH, —$NH_2$, and —CN;

each $R_b$ is independently selected from F, Cl, Br, I, =O, —OH, —$NH_2$, —CN, and $C_{1-3}$ alkyl;

each $R_c$ is independently selected from F, Cl, Br, I, =O, —OH, —$NH_2$, and —CN;

each $R_d$ is independently selected from F, Cl, Br, I, =O, —OH, —$NH_2$, and —CN;

each $R_e$ is independently selected from F, Cl, Br, I, =O, —OH, —$NH_2$, and —CN;

each $R_f$ is independently selected from F, Cl, Br, I, =O, —OH, —$NH_2$, and —CN;

n is selected from 1, 2, 3, and 4;

the 5- to 6-membered heterocycloalkyl contains 1, 2, 3, or 4 heteroatoms or heteroatom groups independently selected from —O—, —NH—, —S—, and —N—.

The present disclosure provides a compound of formula (I) or a pharmaceutically acceptable salt thereof, (I)

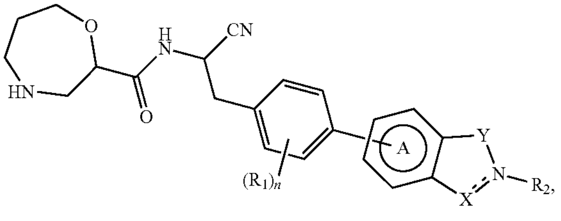

wherein

⫽ is selected from a single bond and a double bond;

the structural moiety

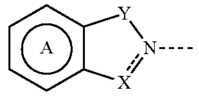

is selected from

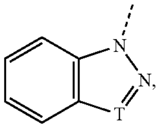

,

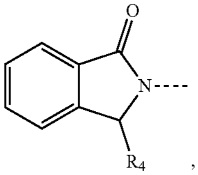

, and

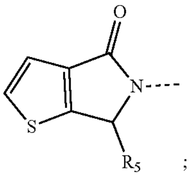

;

T is selected from N and $CR_3$;

$R_1$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_a$;

$R_2$ is selected from H and $C_{1-3}$ alkyl, wherein the $C_{1-3}$ alkyl is optionally substituted by 1, 2, or 3 $R_b$;

$R_3$ is selected from H and $C_{1-3}$ alkyl, wherein the $C_{1-3}$ alkyl is optionally substituted by 1, 2, or 3 $R_c$;

$R_4$ is selected from H and $C_{1-3}$ alkyl, wherein the $C_{1-3}$ alkyl is optionally substituted by 1, 2, or 3 $R_d$;

$R_5$ is selected from H and $C_{1-3}$ alkyl, wherein the $C_{1-3}$ alkyl is optionally substituted by 1, 2, or 3 $R_e$;

each $R_a$ is independently selected from F, Cl, Br, I, =O, —OH, —$NH_2$, and —CN;

each $R_b$ is independently selected from F, Cl, Br, I, =O, —OH, —$NH_2$, and —CN;

each $R_c$ is independently selected from F, Cl, Br, I, =O, —OH, —$NH_2$, and —CN;

each $R_d$ is independently selected from F, Cl, Br, I, =O, —OH, —$NH_2$, and —CN;

each $R_e$ is independently selected from F, Cl, Br, I, =O, —OH, —$NH_2$, and —CN;

n is selected from 1, 2, 3, and 4.

In some embodiments of the present disclosure, the compound has a structure of formula (II'):

(II')

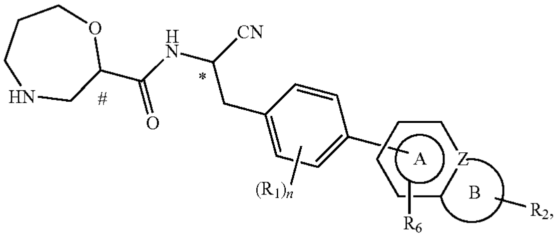

wherein the structural moiety

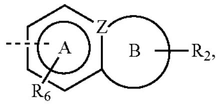

Z, $R_1$, $R_2$, $R_6$, and n are as defined in the present disclosure;

the carbon atoms with "*" and "#" are chiral carbon atoms, which exist in an (R) or (S) single enantiomer form or an (R) or (S) single enantiomer-rich form.

In some embodiments of the present disclosure, the above compound has a structure of formula (I'):

(I')

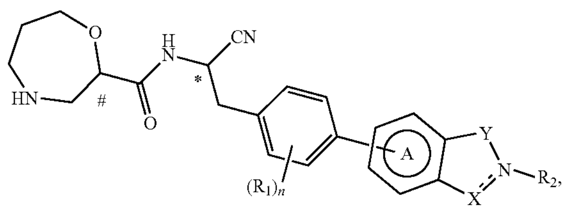

wherein the structural moiety

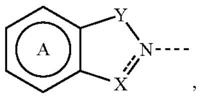

$R_1$, $R_2$, and n are as defined in the present disclosure;

the carbon atoms with "*" and "#" are chiral carbon atoms, which exist in an (R) or (S) single enantiomer form or an (R) or (S) single enantiomer-rich form.

In some embodiments of the present disclosure, the $R_a$, $R_b$, $R_d$, and $R_e$ are each independently selected from F, Cl, and Br, and other variables are as defined in the present disclosure.

In some embodiments of the present disclosure, the $R_b$ is selected from F, Cl, Br, and —$CH_3$, and other variables are as defined in the present disclosure.

In some embodiments of the present disclosure, the $R_1$ is selected from H, F, Cl, and —$CH_3$, and other variables are as defined in the present disclosure.

In some embodiments of the present disclosure, the $R_1$ is selected from H and F, and other variables are as defined in the present disclosure.

In some embodiments of the present disclosure, the $R_2$ is selected from H, —$CH_3$,

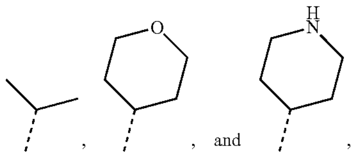

wherein the —$CH_3$,

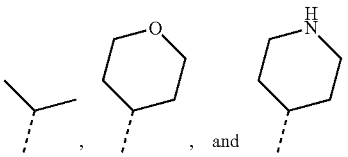

are each independently and optionally substituted by 1, 2, or 3 $R_b$, and $R_b$ and other variables are as defined in the present disclosure.

In some embodiments of the present disclosure, the $R_2$ is selected from H, —$CH_3$,

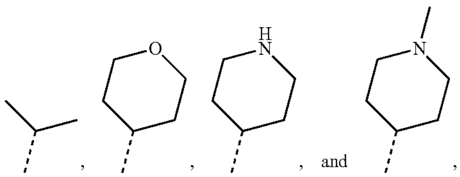

and/and other variables are as defined in the present disclosure.

In some embodiments of the present disclosure, the $R_2$ is selected from H and —$CH_3$, and other variables are as defined in the present disclosure.

In some embodiments of the present disclosure, the $R_3$ is selected from H, F, Cl, and Br, and other variables are as defined in the present disclosure. In some embodiments of the present disclosure, the $R_3$ is selected from H, and other variables are as defined in the present disclosure.

In some embodiments of the present disclosure, the $R_4$ is selected from H, and other variables are as defined in the present disclosure.

In some embodiments of the present disclosure, the $R_5$ is selected from H and —$CH_3$, and other variables are as defined in the present disclosure.

In some embodiments of the present disclosure, the $R_6$ is selected from H, F, Cl, and Br, and other variables are as defined in the present disclosure.

In some embodiments of the present disclosure, the structural moiety

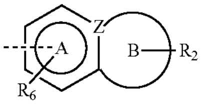

is selected from

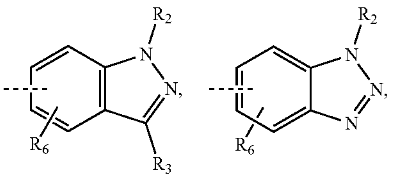

-continued

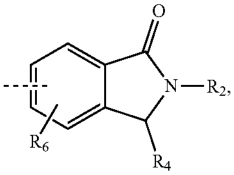
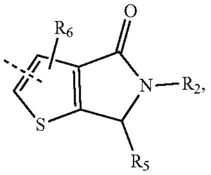
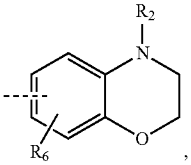
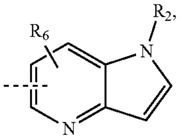
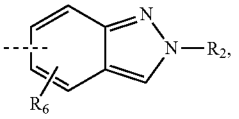
and
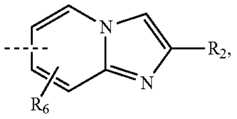

and $R_2$, $R_3$, $R_4$, $R_5$, $R_6$, and other variables are as defined in the present disclosure.

In some embodiments of the present disclosure, the structural moiety

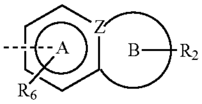

is selected from

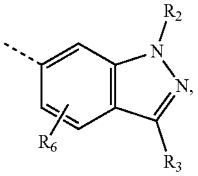
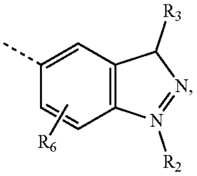
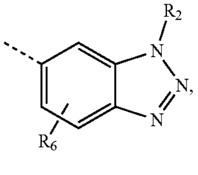
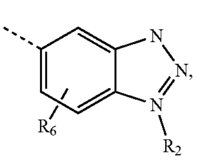
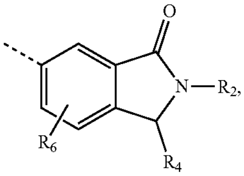
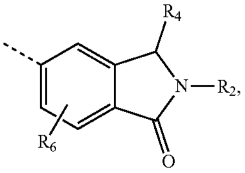
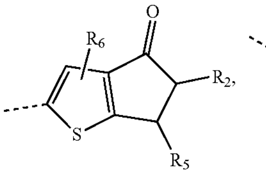
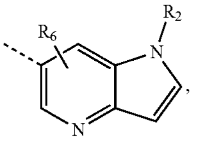

-continued

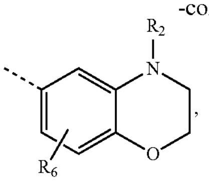
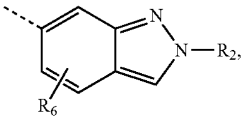
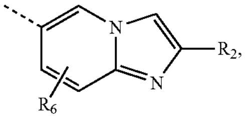
and
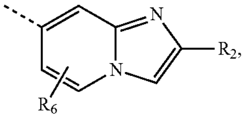

and $R_2$, $R_3$, $R_4$, $R_5$, $R_6$, and other variables are as defined in the present disclosure.

In some embodiments of the present disclosure, the structural moiety

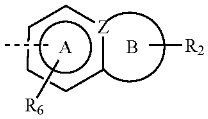

is selected from

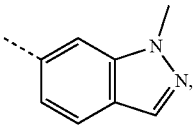
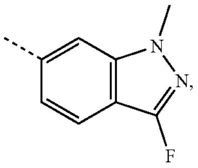
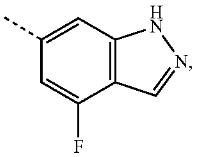
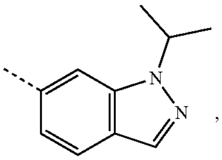
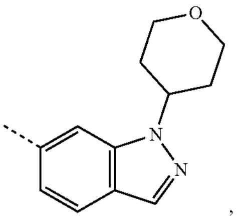
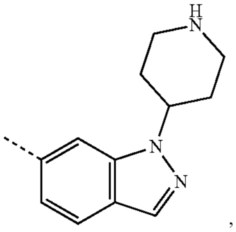
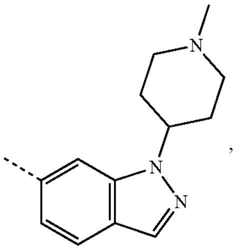
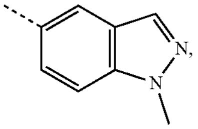
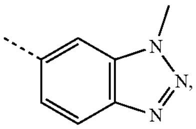
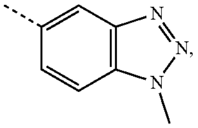

-continued

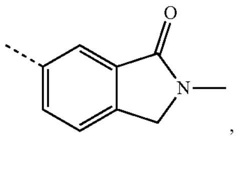 , 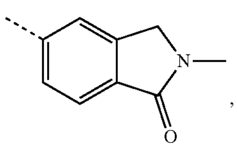 ,

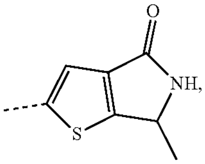 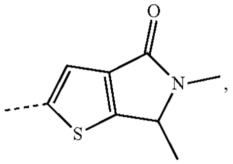

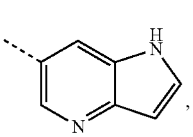 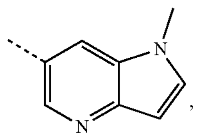

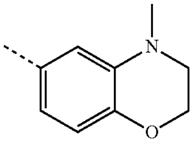 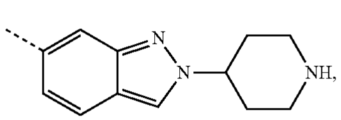

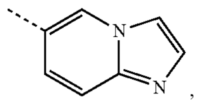 , and 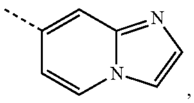 , and other variables are as defined in the present disclosure.

In some embodiments of the present disclosure, the compound has a structure of formula (II-1):

(II-1)

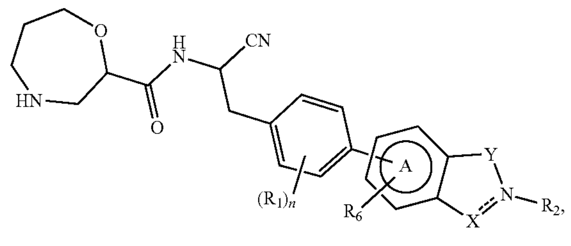

wherein the structural moiety

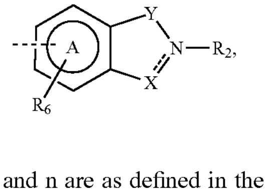

$R_1$, $R_2$, $R_6$, and n are as defined in the present disclosure.

In some embodiments of the present disclosure, the compound has a structure of formula (II'-1):

(II'-1)

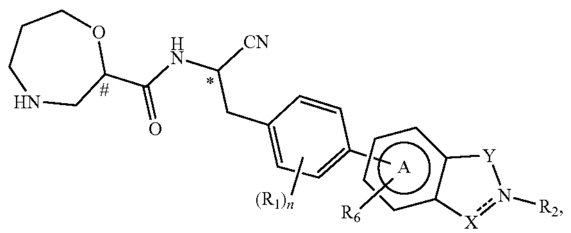

wherein the structural moiety

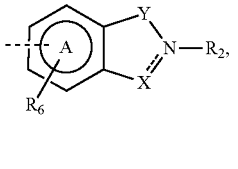

$R_1$, $R_2$, $R_6$, and n are as defined in the present disclosure;

the carbon atoms with "*" and "#" are chiral carbon atoms, which exist in an (R) or (S) single enantiomer form or an (R) or (S) single enantiomer-rich form.

In some embodiments of the present disclosure, the compound of formula (I) or the pharmaceutically acceptable salt thereof, wherein (I)

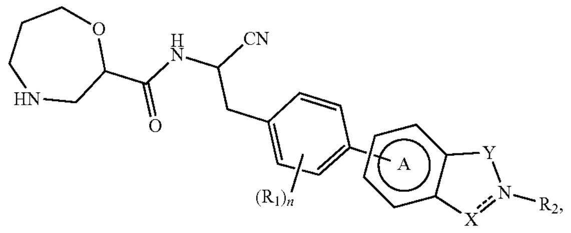

the structural moiety

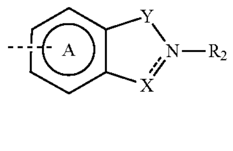

is selected from

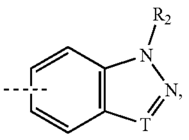 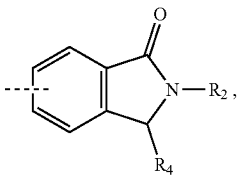

-continued

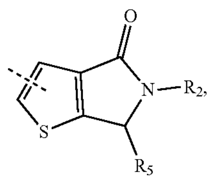

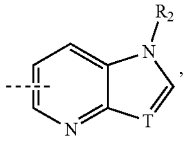

, and

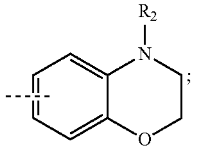

;

each  is independently selected from a single bond and a double bond, wherein when  is selected from the double bond, $R_2$ is absent;

T, $R_1$, $R_2$, $R_4$, $R_5$, and n are as defined in the present disclosure.

In some embodiments of the present disclosure, the compound has a structure of formula (I-1), (I-2), or (I-3):

(I-1)

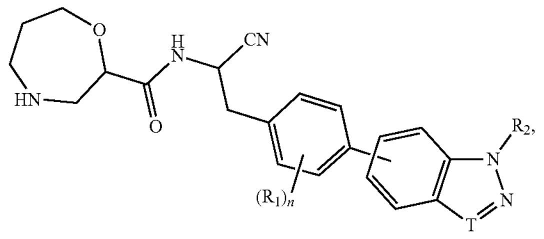

(I-2)

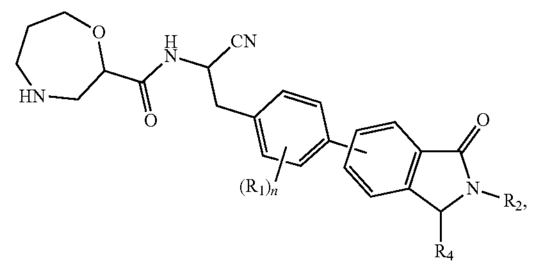

or (I-3)

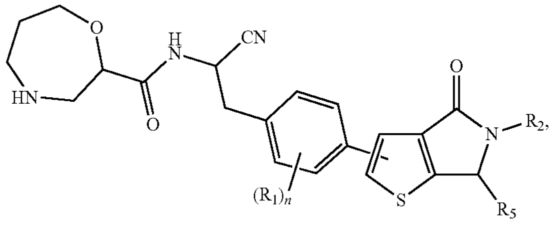

wherein T, $R_1$, $R_2$, $R_4$, $R_5$, and n are as defined in the present disclosure.

In some embodiments of the present disclosure, the compound has a structure of formula (I-1A), (I-1B), (I-2A), (I-2B), or (I-3A):

(I-1A)

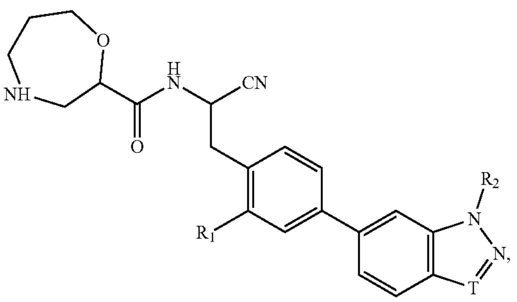

(I-1B)

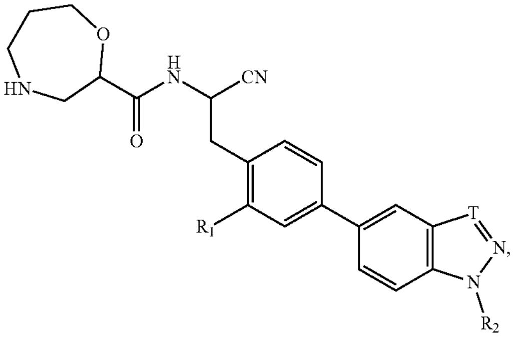

(I-2A)

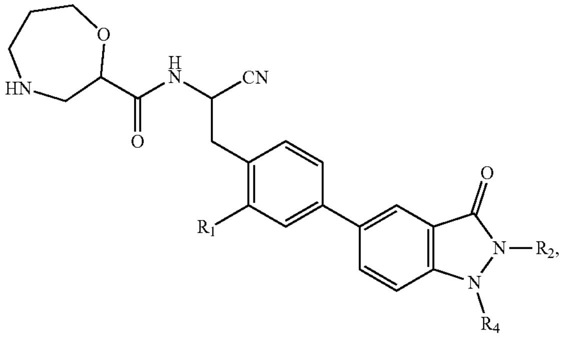

(I-2B)

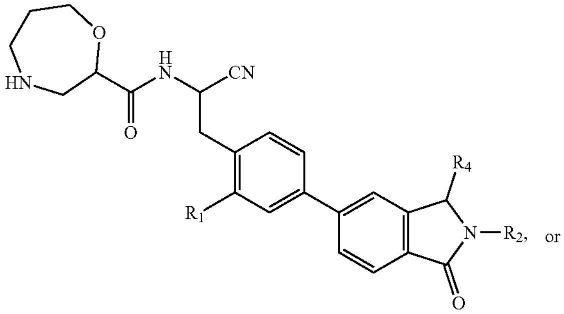

or

-continued (I-3A)

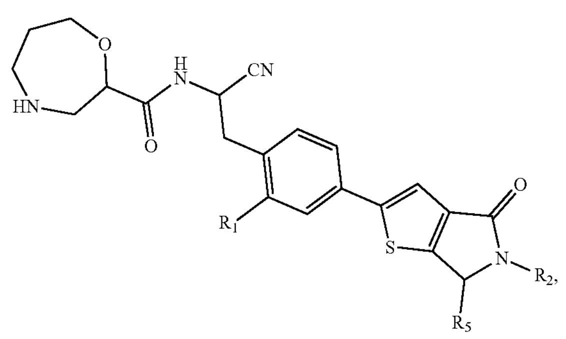

wherein T, $R_1$, $R_2$, $R_4$, and $R_5$ are as defined in the present disclosure.

In some embodiments of the present disclosure, the compound has a structure of formula (I'-1A), (I'-1B), (I'-2A), (I'-2B), or (I'-3A):

(I'-1A)

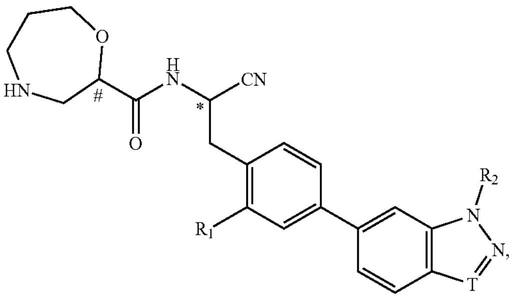

(I'-1B)

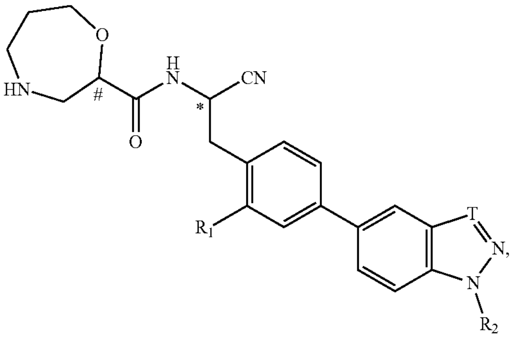

(I'-2A)

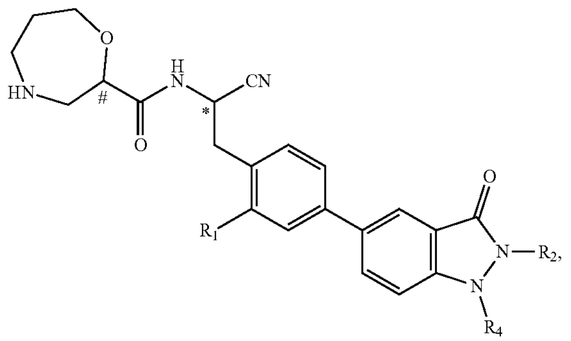

-continued (I'-2B)

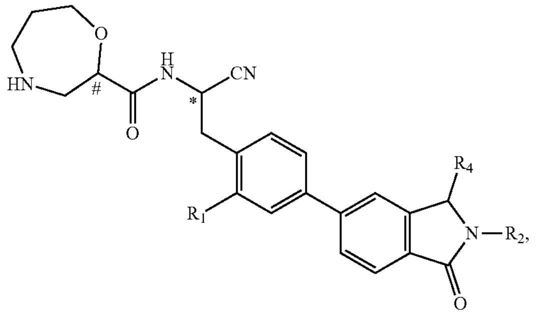

or (I'-3A)

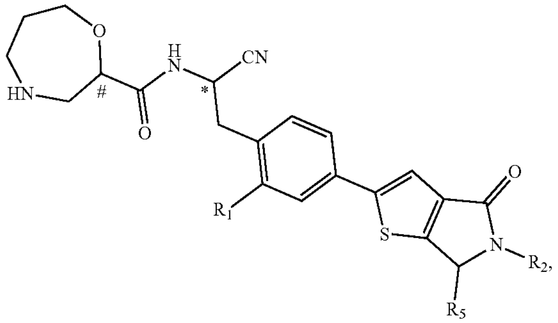

wherein T, $R_1$, $R_2$, $R_4$, and $R_5$ are as defined in the present disclosure;

the carbon atoms with "*" and "#" are chiral carbon atoms, which exist in an (R) or (S) single enantiomer form or an (R) or (S) single enantiomer-rich form.

In some embodiments of the present disclosure, the compound has a structure of formula (I'-1A-1), (I'-1B-1), (I'-2A-1), (I'-2B-1), or (I'-3A-1):

(I'-1A-1)

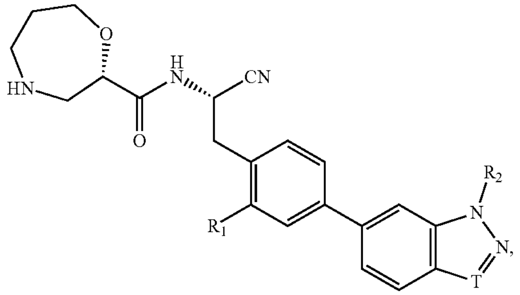

(I'-1B-1)

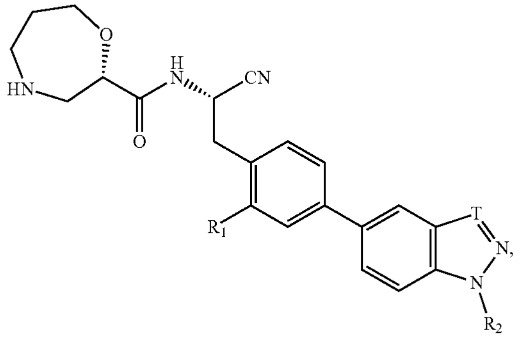

-continued
(I'-2A-1)
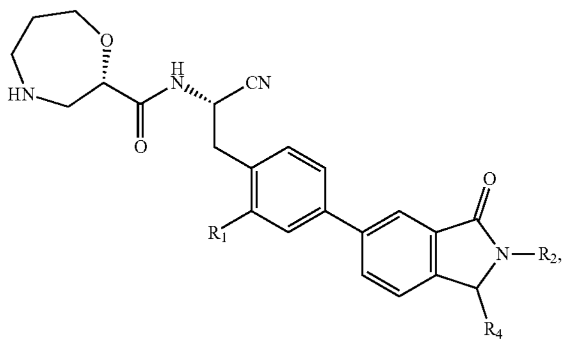
(I'-2B-1)
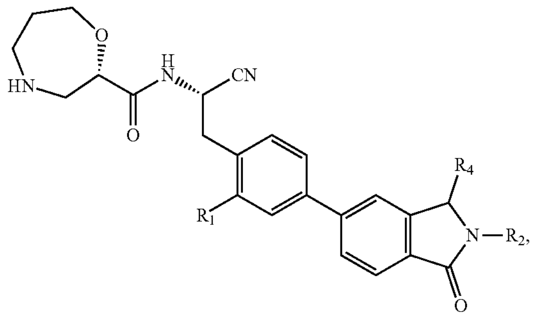
or
(I'-3A-1)
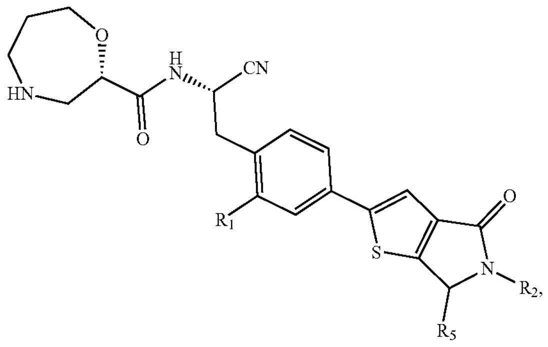
wherein T, $R_1$, $R_2$, $R_4$, and $R_5$ are as defined in the present disclosure.
There are still some embodiments of the present disclosure which are obtained by any combination of the above variables.
The present disclosure also provides a compound of the following formula or a pharmaceutically acceptable salt thereof,
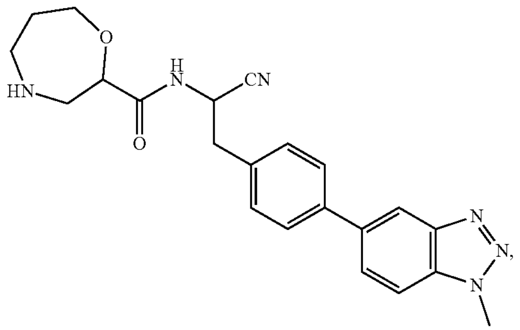
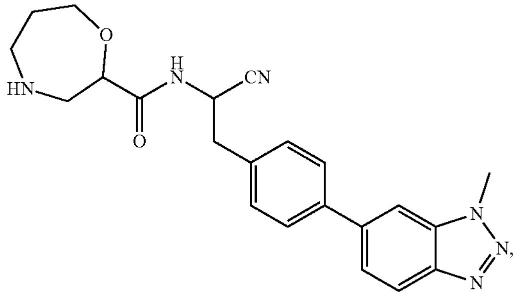
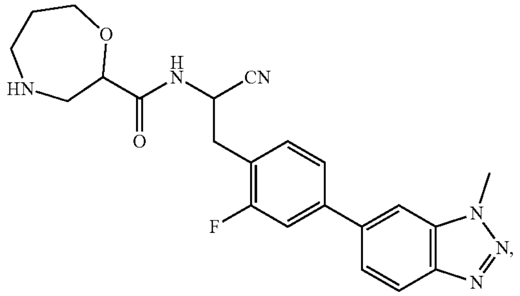
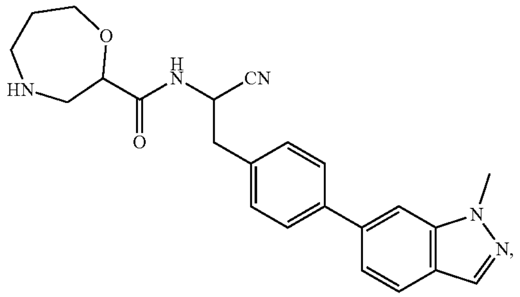
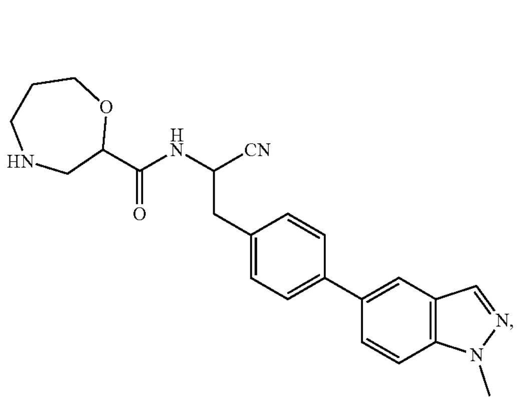

-continued
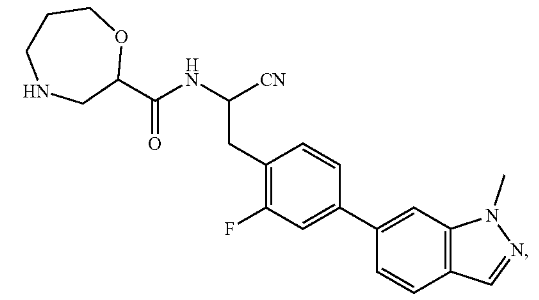
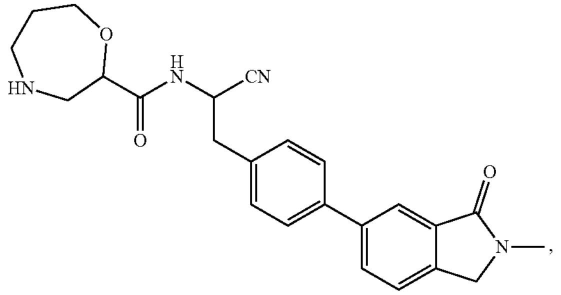
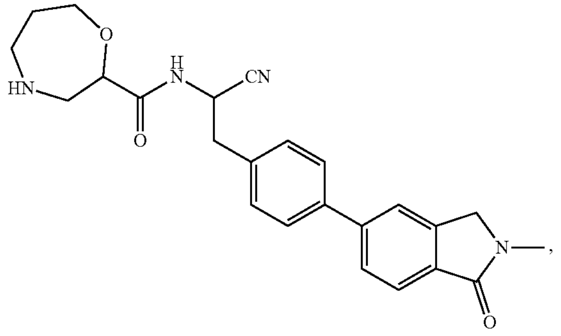
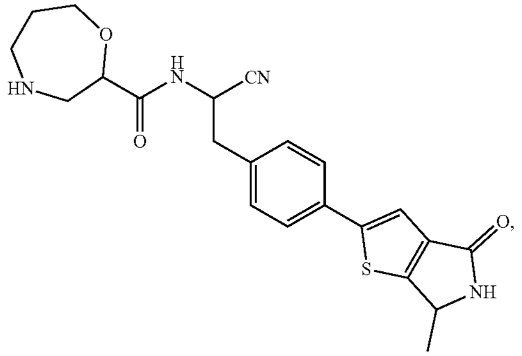
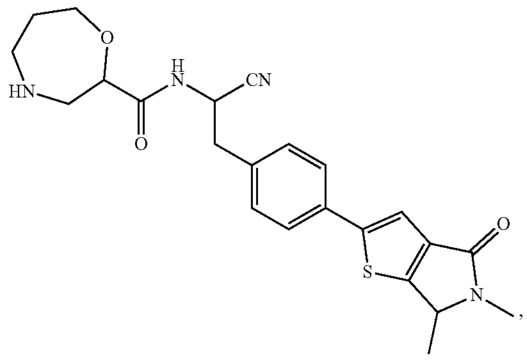
-continued
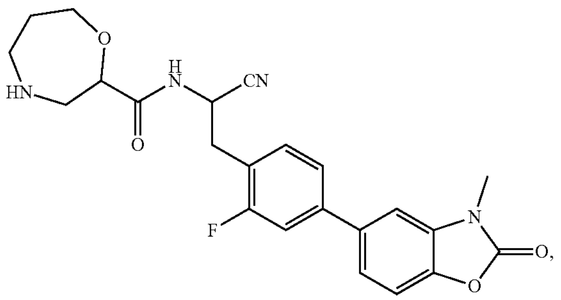
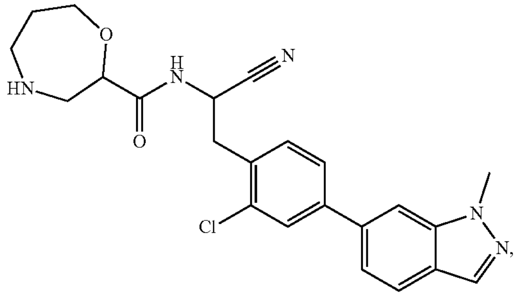
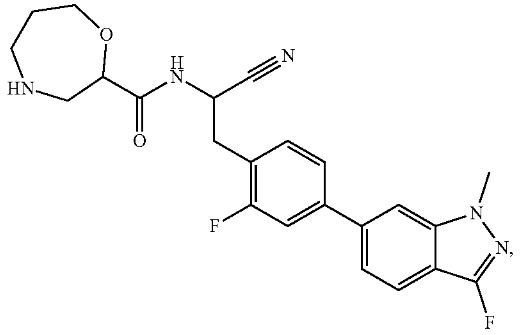
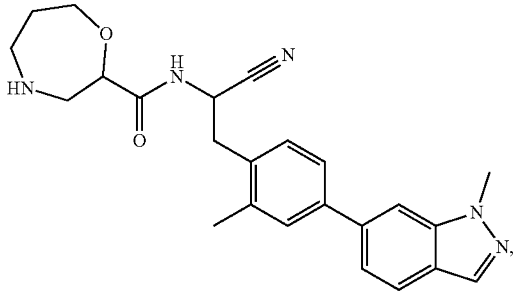
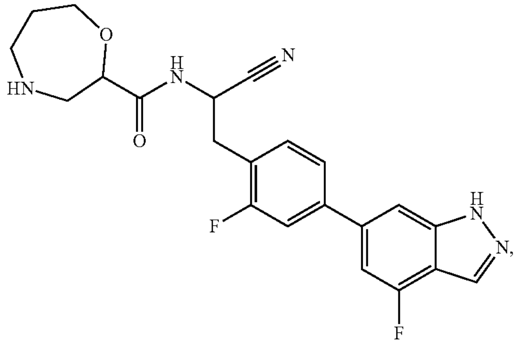

-continued
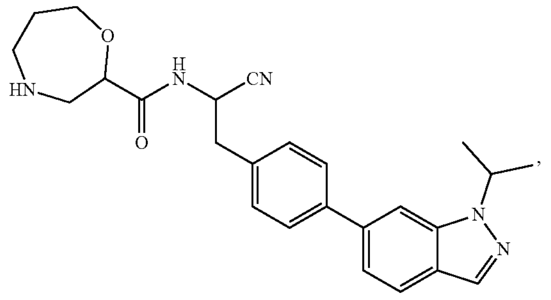
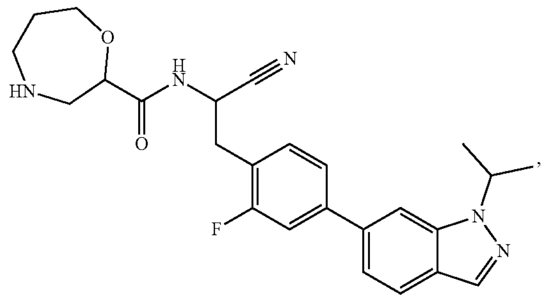
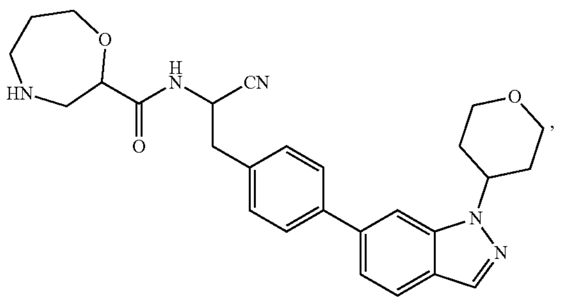
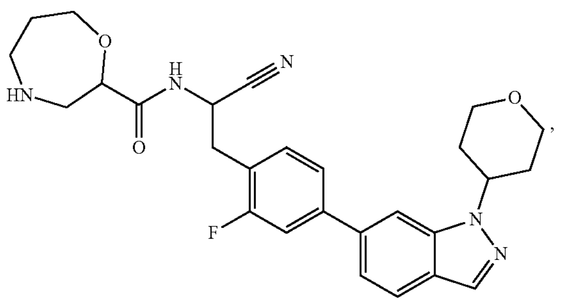
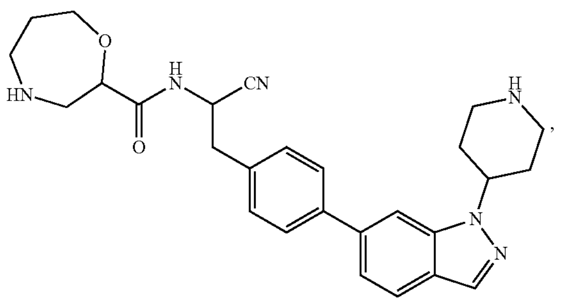
-continued
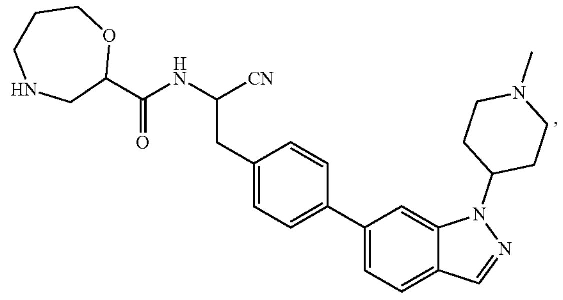
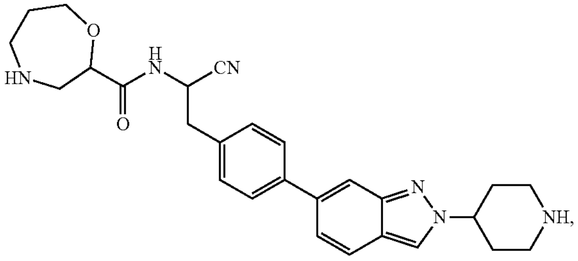
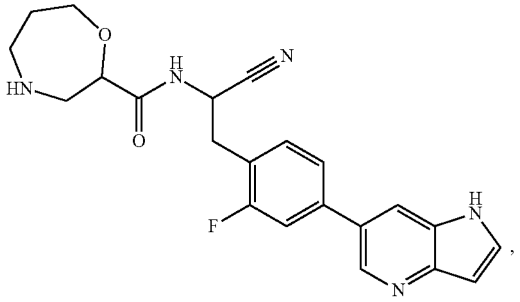
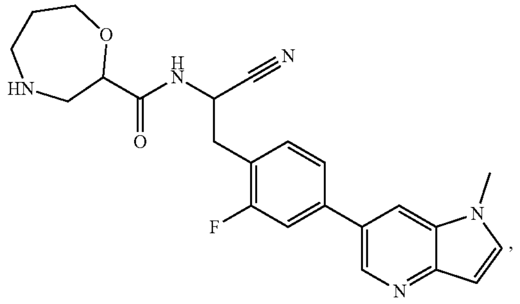
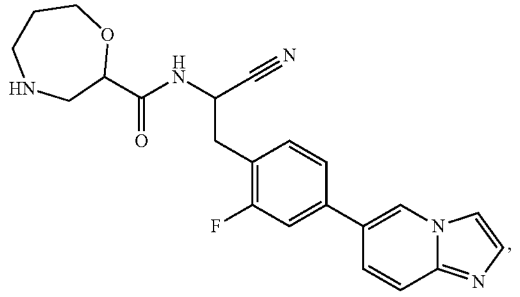

-continued
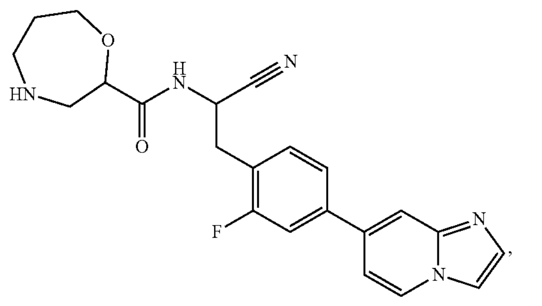
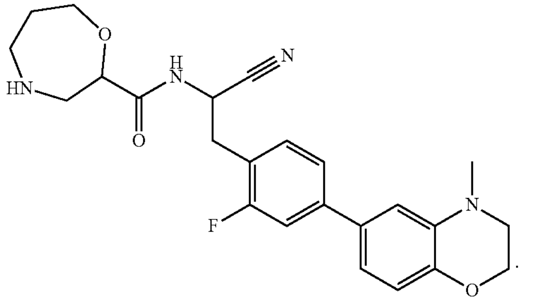
The present disclosure also provides a compound of the following formula or a pharmaceutically acceptable salt thereof,
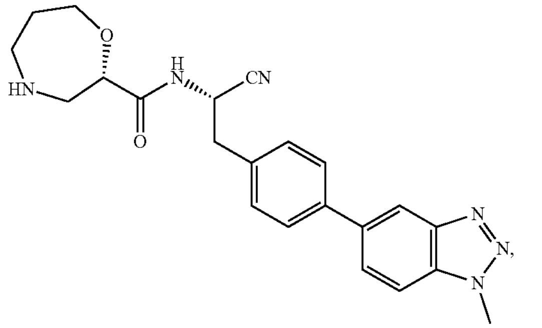
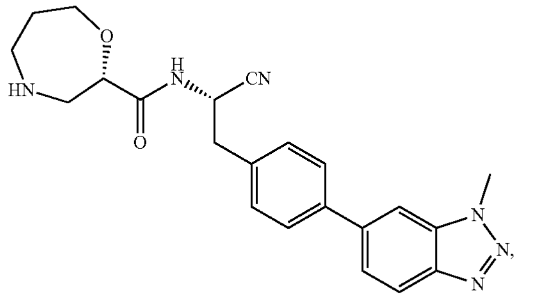
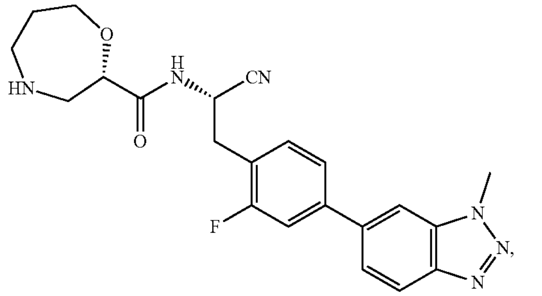
-continued
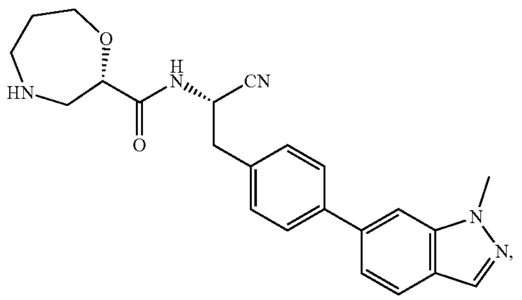
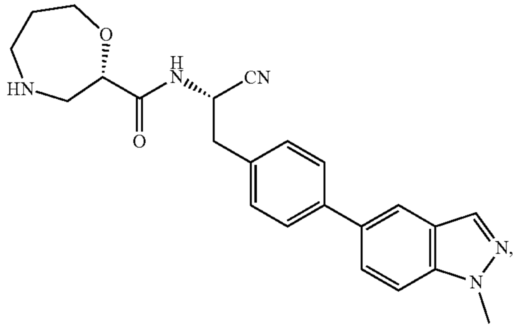
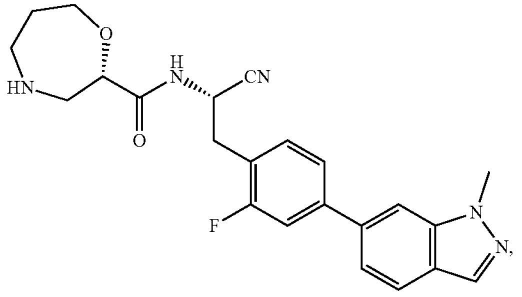
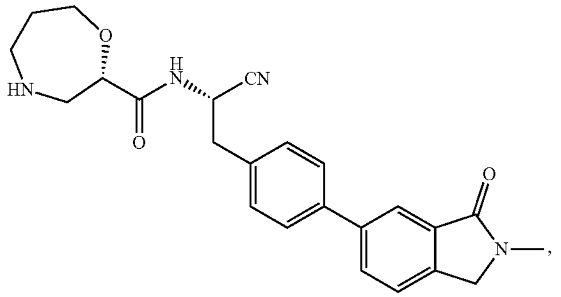
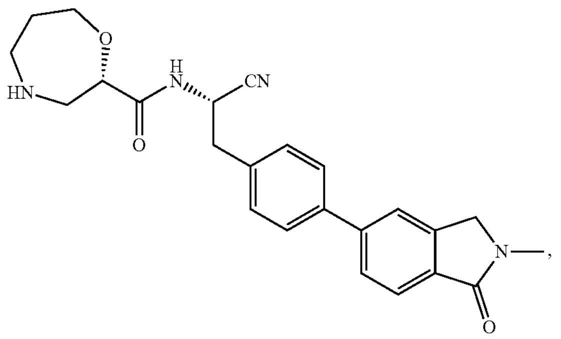

-continued
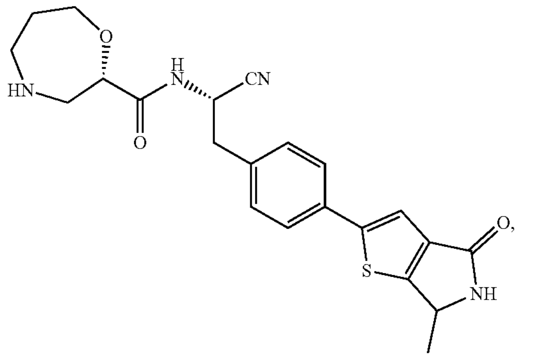
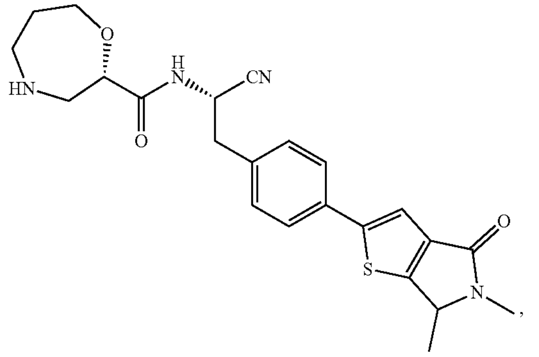
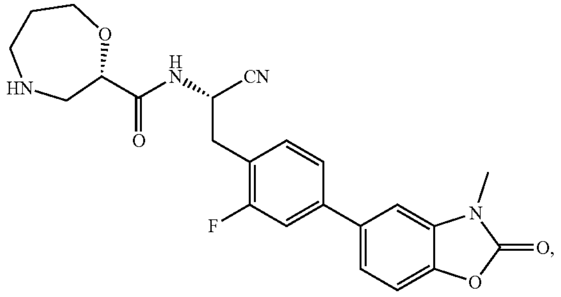
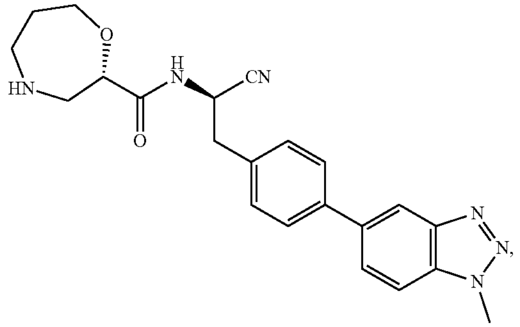
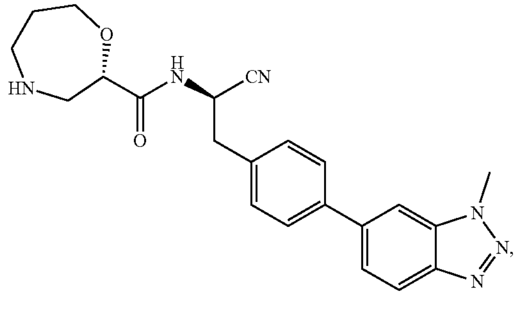
-continued
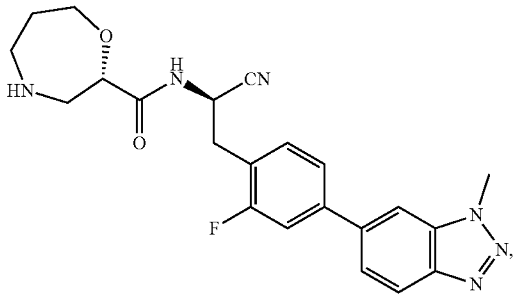
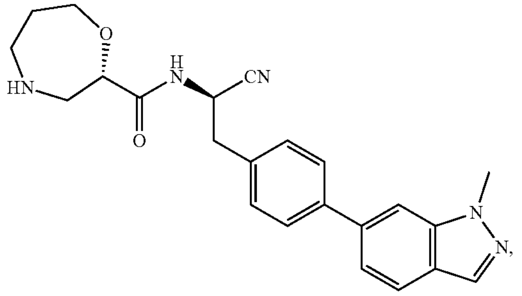
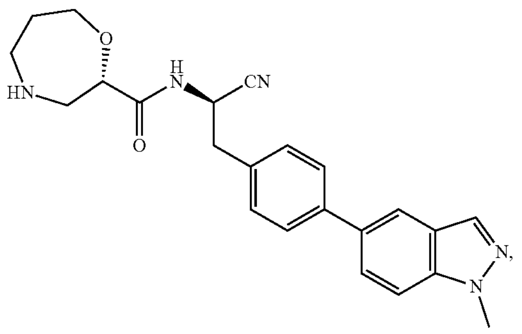
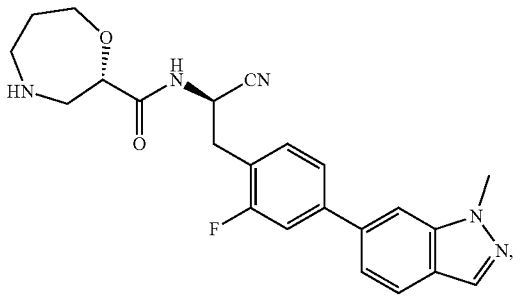
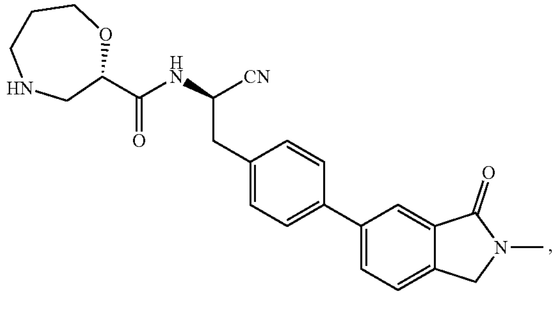

-continued
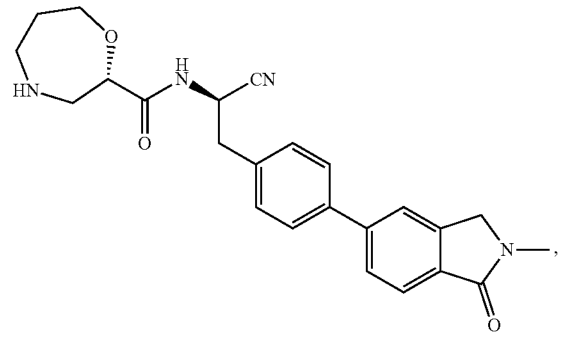
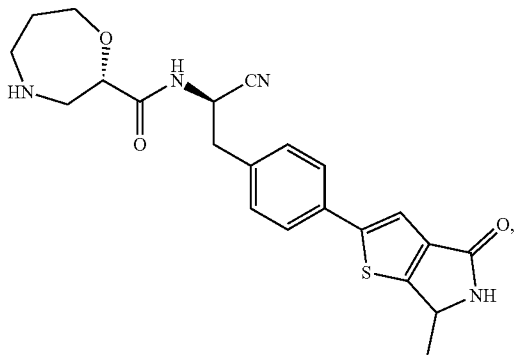
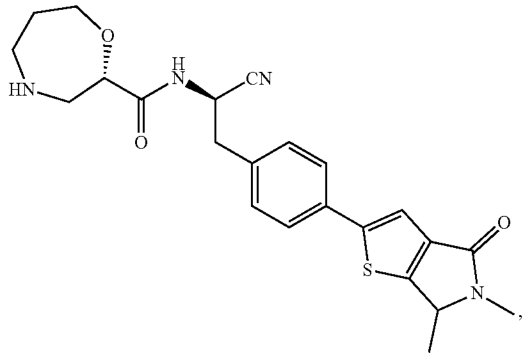
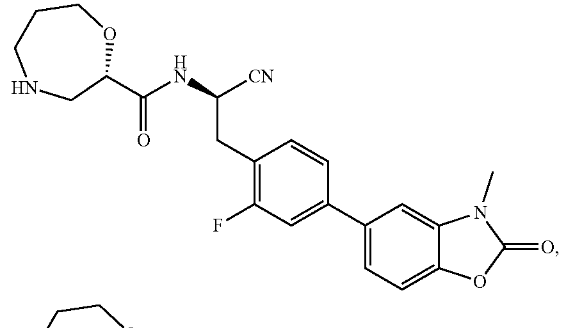
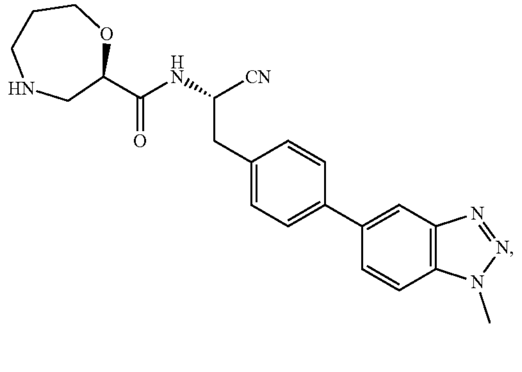
-continued
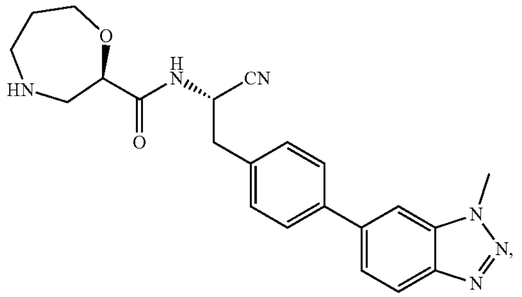
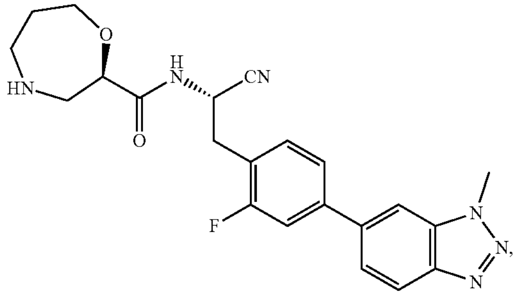
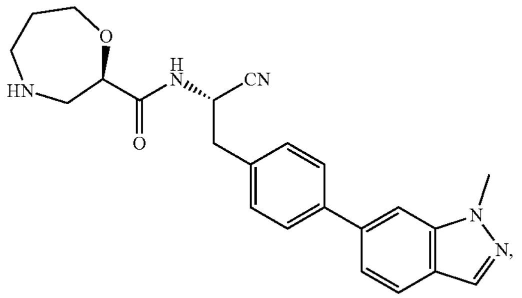
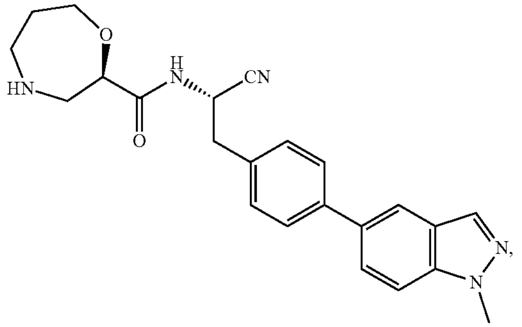
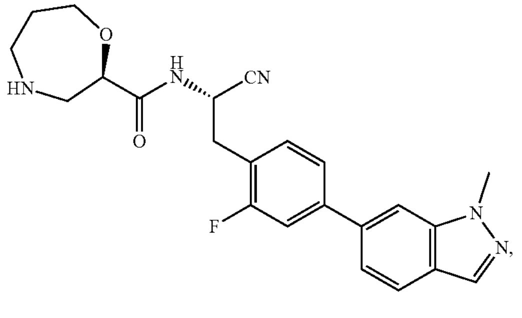

-continued
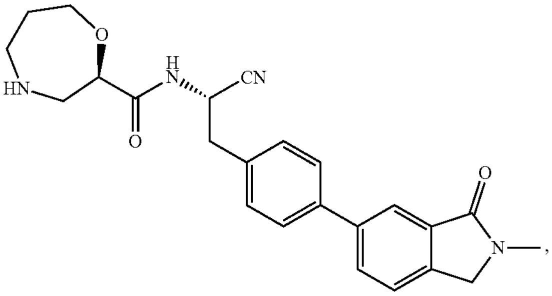
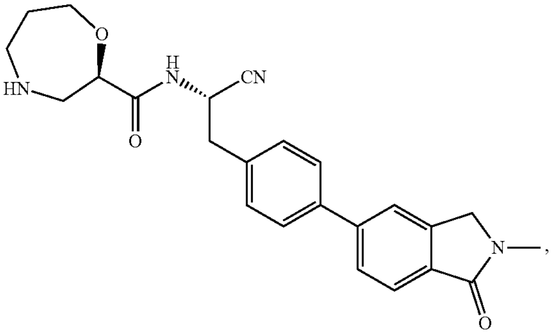
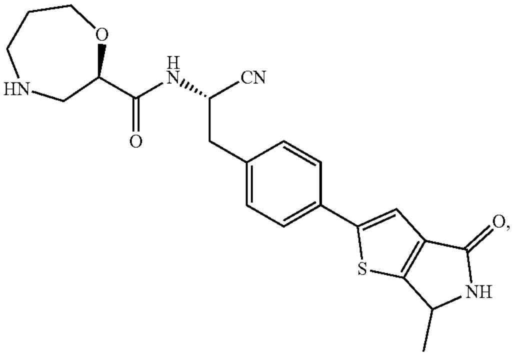
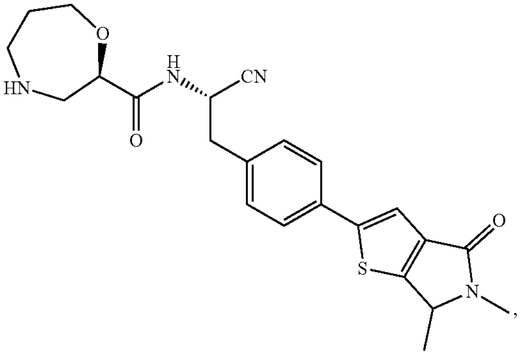
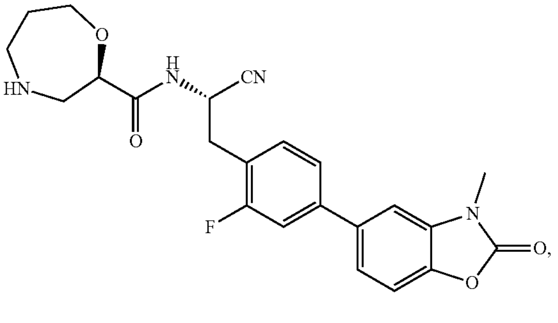
-continued
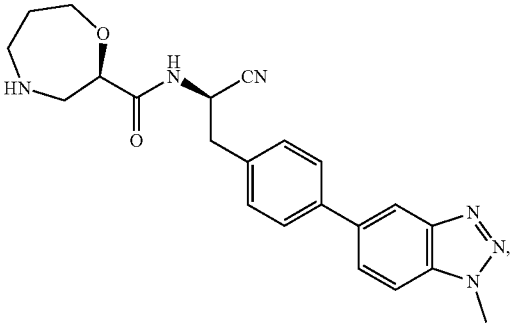
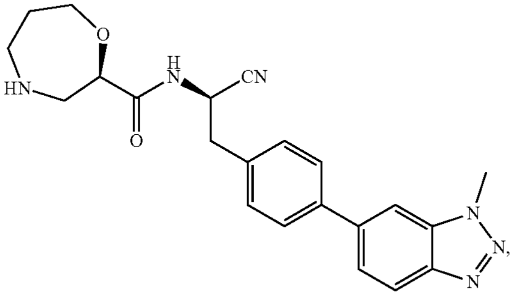
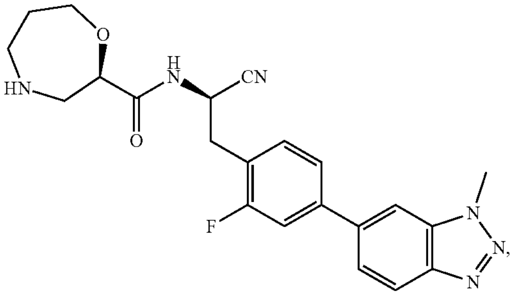
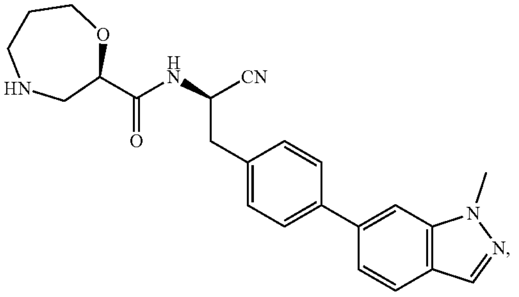
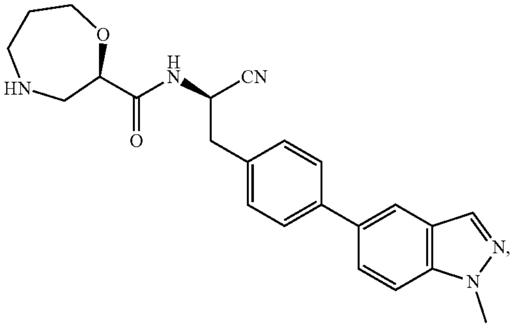

-continued
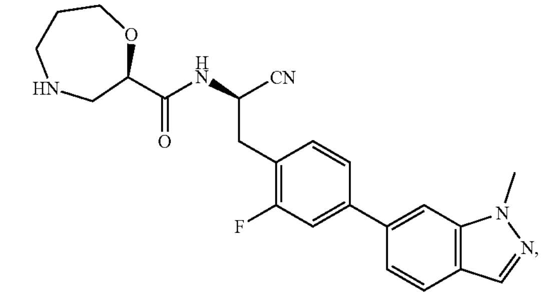
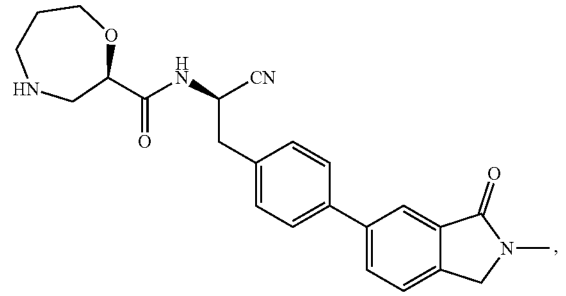
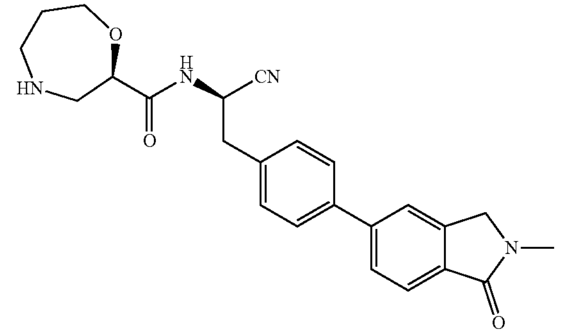
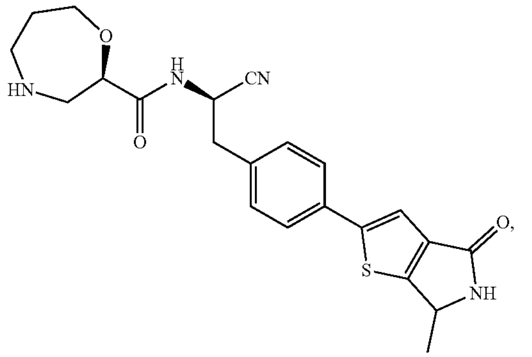
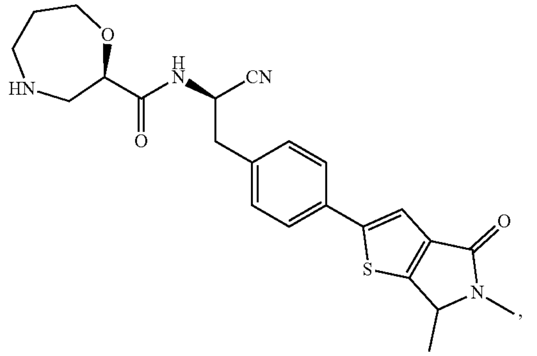
-continued
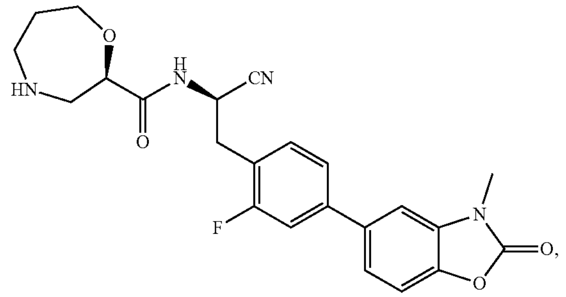
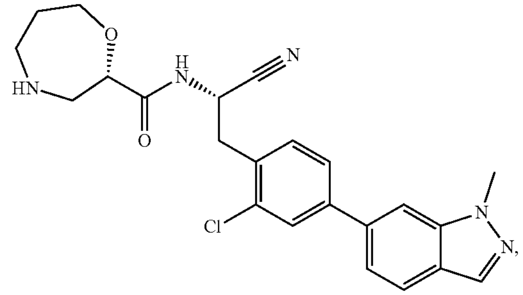
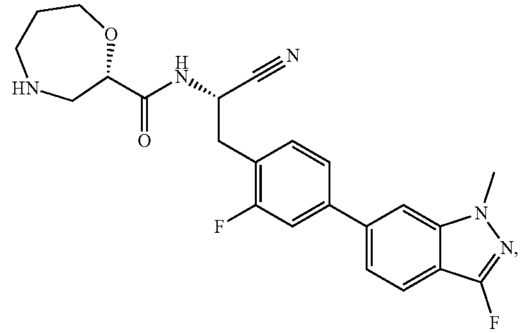
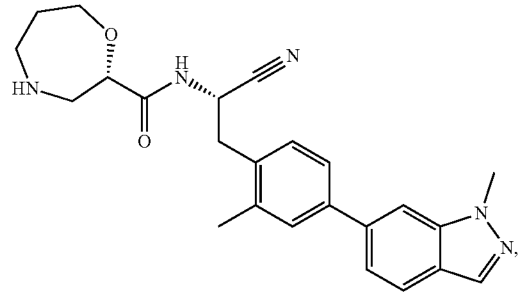
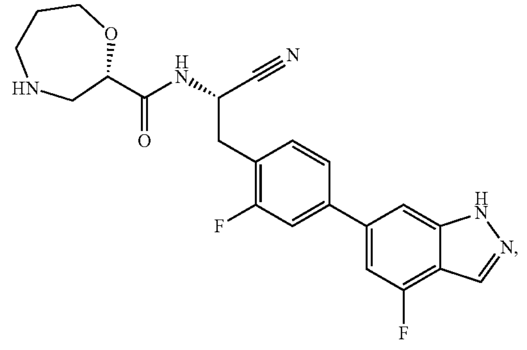

-continued
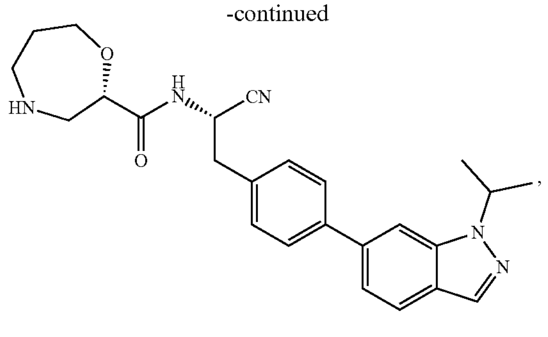
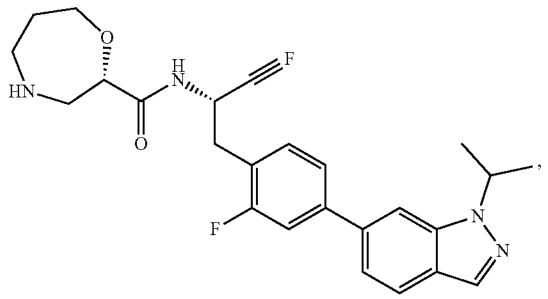
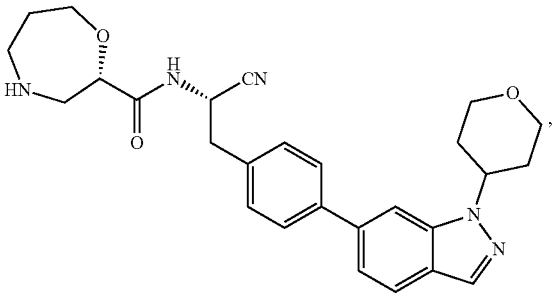
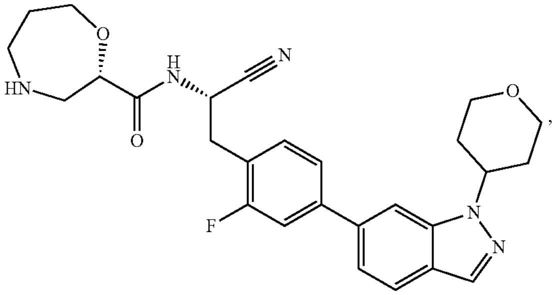
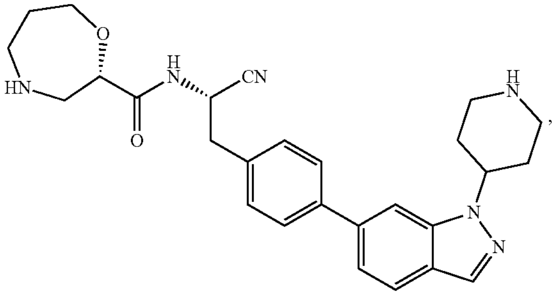
-continued
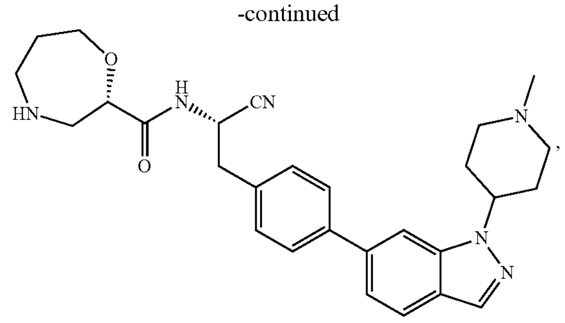
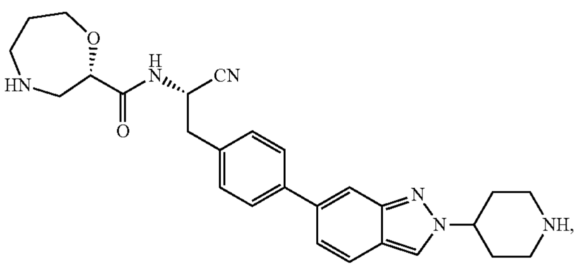
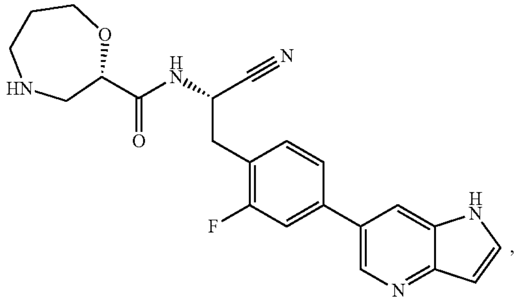
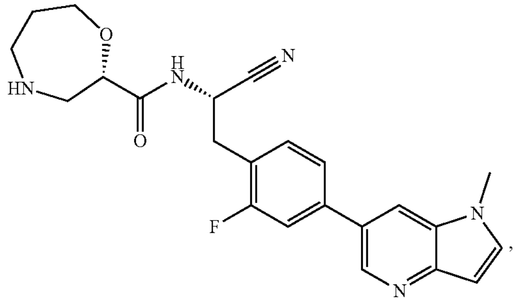
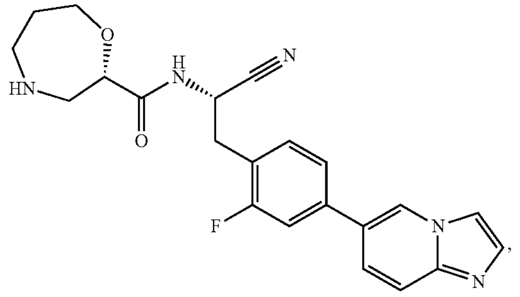

-continued
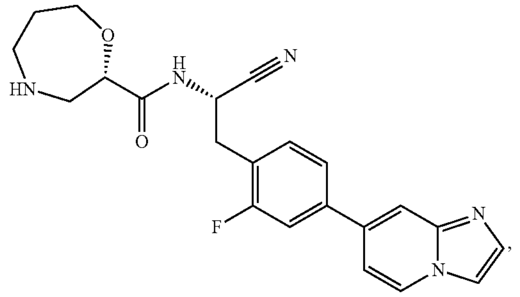
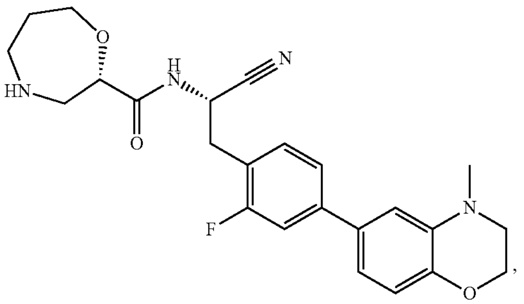
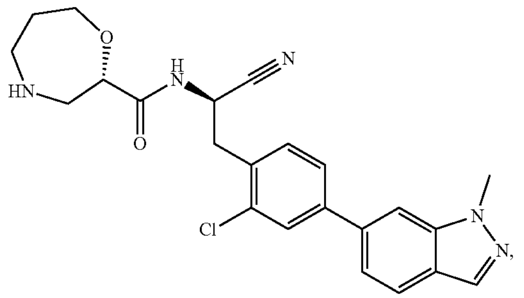
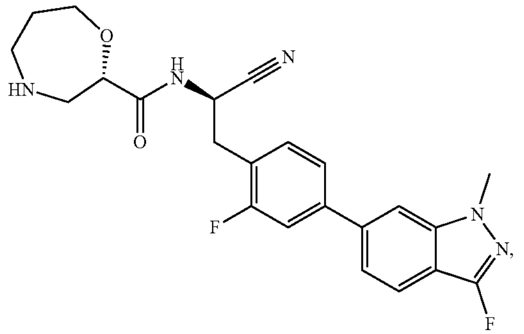
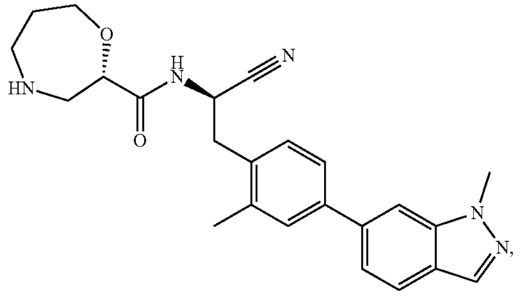
-continued
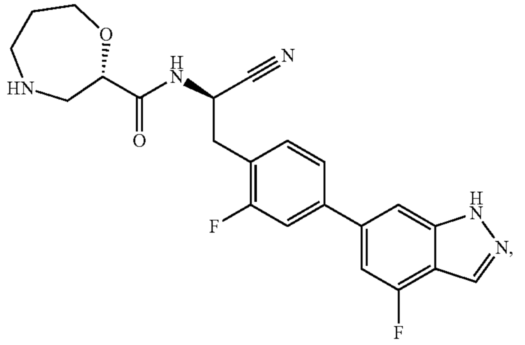
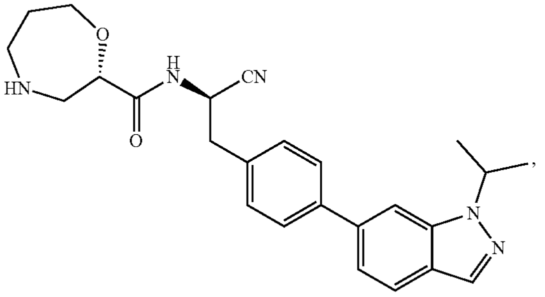
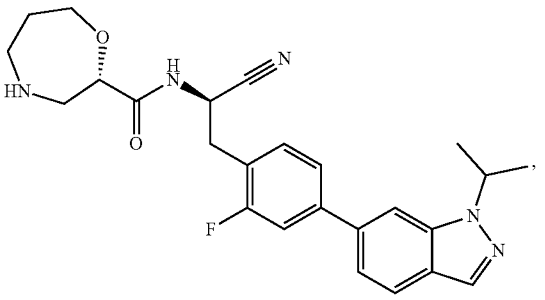
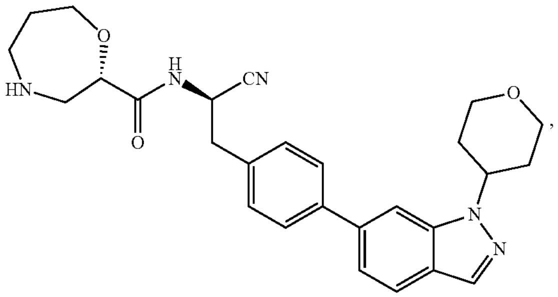
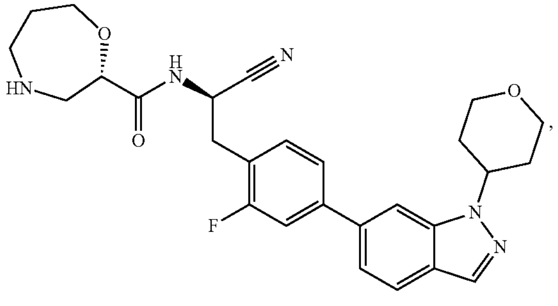

-continued

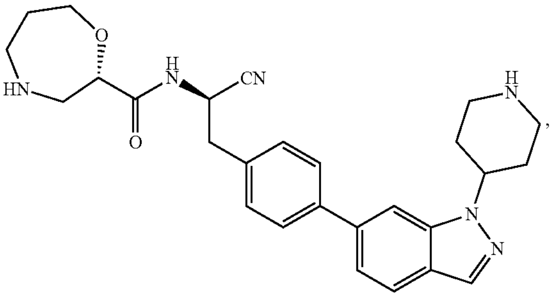

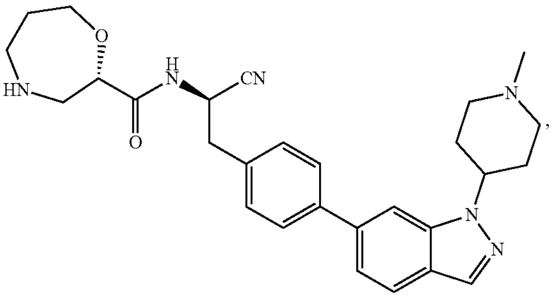

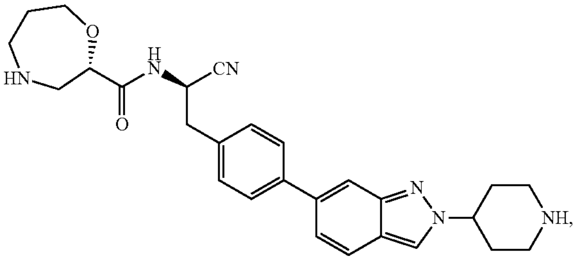

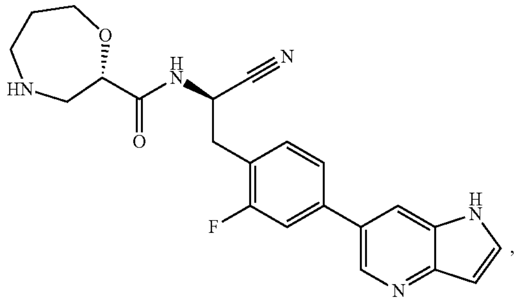

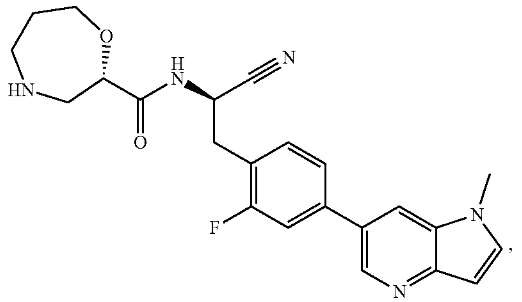

-continued

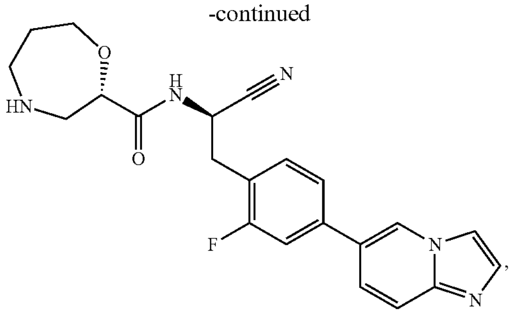

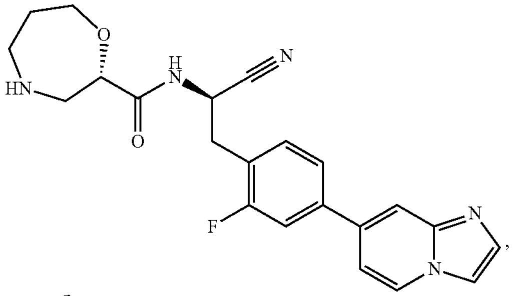

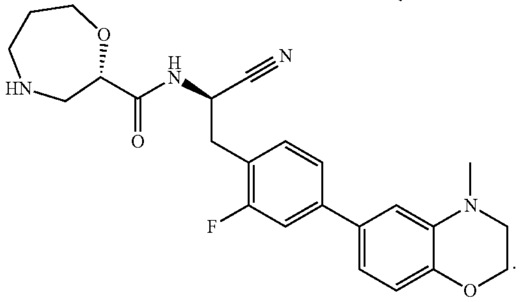

Technical Effect

The compounds provided by the present disclosure have significant inhibitory activity on DPP1 at the enzyme and cellular levels; the oral exposure dose in rats and mice in vivo is high, and the pharmacokinetic properties are good; the distribution ability in bone marrow is strong; the activity of rat bone marrow neutrophil elastase can be significantly inhibited.

Definition and Description

Unless otherwise specified, the following terms and phrases used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term “pharmaceutically acceptable” is used herein in terms of those compounds, materials, compositions, and/or dosage forms, which are suitable for use in contact with human and animal tissues within the scope of reliable medical judgment, with no excessive toxicity, irritation, an allergic reaction, or other problems or complications, commensurate with a reasonable benefit/risk ratio.

The term “pharmaceutically acceptable salt” refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by contacting the compound with a sufficient amount of a base in a pure solution or a suitable inert solvent. The pharmaceutically acceptable base addition salt includes a salt of sodium, potassium, calcium, ammonium, organic amine, magnesium, or similar salts. When the compound of the present disclosure contains a relatively basic functional group, an acid addition salt can be obtained by contacting the compound with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and salts of amino acid (such as arginine), and a salt of an organic acid such as glucuronic acid. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method.

Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, racemic, and other mixtures thereof, such as enantiomers or diastereomer enriched mixtures, all of which are within the scope of the present disclosure. Additional asymmetric carbon atoms may be present in substituents such as alkyl. All these isomers and their mixtures are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and "(±)" refers to racemic.

Unless otherwise specified, the absolute configuration of a stereogenic center is represented by a wedged solid bond ( ) and a wedged dashed bond ( ), and the relative configuration of a stereogenic center is represented by a straight solid bond ( ) an a straight dashed bond ( ), a wave line ( ) is used to represent a wedged solid bond ( ) or a wedged dashed bond ( ), or the wave line ( ) is used to represent a straight solid bond ( ) and a straight dashed bond ( ).

The compounds of the present disclosure may exist in specific. Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer", or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom that constitute the compound. For example, the compound can be radiolabeled with a radioactive isotope, such as tritium ($^3H$), iodine-125 ($^{125}I$), or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term “optional” or “optionally” means that the subsequently described event or circumstance may, but does not necessarily, occur, and the description includes instances where the event or circumstance occurs and instances where it does not.

The term “substituted” means one or more than one hydrogen atom(s) on a specific atom are substituted by the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term “optionally substituted” means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0 to 2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent is absent, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

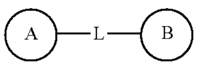

is -M-W—, then -M-W— can link ring A and ring B to form

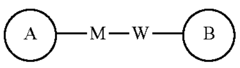

in the direction same as left-to-right reading order, and form

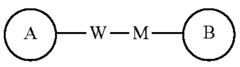

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (), a straight dashed bond (), a wavy line (  ).

For example, the straight solid bond in $-OCH_3$ means that it is linked to other groups through the oxygen atom in the group; the straight dashed bonds in

means that it is linked to other groups through the two ends of nitrogen atom in the group; the wave lines in

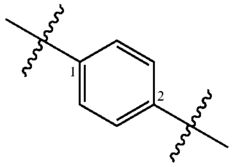 [SMILES: *c1ccc(*)cc1]

means that the phenyl group is linked to other groups through carbon atoms at position 1 and position 2.

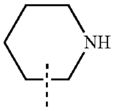

means that it can be linked to other groups through any linkable sites on the piperidinyl by one chemical bond, including at least four types of linkage, including

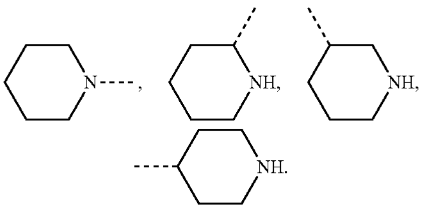

Even though the H atom is drawn on the —N—,

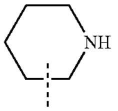

still includes the linkage of

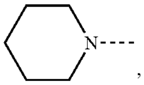

, merely when one chemical bond was connected, the H of this site will be reduced by one to the corresponding monovalent piperidinyl.

When the chemical bond of a substituent intersects with the chemical bond between two atoms in the ring, it means that the substituent can form a bond with any atom in the ring. When the atom connected to a substituent is not specified, the substituent can form a bond with any atom. If the atom to which the substituent is connected is in a bicyclic or tricyclic system, it means that the substituent can form a bond with any atom of any ring in the system. Combinations of substituents and/or variables are allowable only if such combinations result in stable compounds. For example, the structural moiety

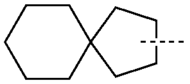

or

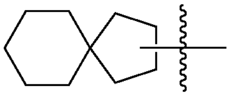

means that it can be substituted at any position on the cyclohexyl or cyclopentyl.

Unless otherwise specified, the term ring

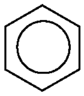

means an aromatic ring, including a benzene ring and a 5- to 6-membered heteroaryl ring, for example, ring

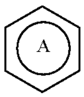

includes, but is not limited to,

,

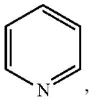

,

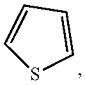

, etc.

Unless otherwise specified, the terms "5- to 6-membered heteroaryl ring" and "5- to 6-membered heteroaryl" in the present disclosure can be used interchangeably, and the term "5- to 6-membered heteroaryl" means a monocyclic group consisting of 5 to 6 ring atoms with a conjugated π-electron system, wherein 1, 2, 3, or 4 ring atoms are heteroatoms independently selected from O, S, and N, and the rest are carbon atoms. Where, the nitrogen atom is optionally quaternized, and the heteroatoms nitrogen and sulfur can be optionally oxidized (i.e., NO and $S(=O)_p$, wherein p is 1 or 2). The 5- to 6-membered heteroaryl can be linked to the rest of the molecule through a heteroatom or a carbon atom. The 5- to 6-membered heteroaryl includes 5- and 6-membered heteroaryl. Examples of the 5- to 6-membered heteroaryl include, but are not limited to, pyrrolyl (including N-pyrrolyl, 2-pyrrolyl, and 3-pyrrolyl, etc.), pyrazolyl (including 2-pyrazolyl and 3-pyrrolyl, etc.), imidazolyl (including N-imidazolyl, 2-imidazolyl, 4-imidazolyl, and 5-imidazolyl, etc.), oxazolyl (including 2-oxazolyl, 4-oxazolyl, and 5-oxazolyl, etc.), triazolyl (1H-1,2,3-triazolyl, 2H-1,2,3-triazolyl, 1H-1,2,4-triazolyl, and 4H-1,2,4-triazolyl, etc.), tetrazolyl, isoxazolyl (3-isoxazolyl, 4-isoxazolyl, and 5-isoxazolyl, etc.), thiazolyl (including 2-thiazolyl, 4-thiazolyl, and 5-thiazolyl, etc.), furyl (including 2-furyl and 3-furyl, etc.), thienyl (including 2-thienyl and 3-thienyl, etc.), pyridyl (including 2-pyridyl, 3-pyridyl, and 4-pyridyl, etc.), pyrazinyl, or pyrimidyl (including 2-pyrimidyl and 4-pyrimidyl, etc.).

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it can be monovalent (such as methyl), divalent (such as methylene), or multivalent (such as methine). Examples of $C_{1-3}$ alkyl include, but are not limited to, methyl (Me), ethyl (Et), propyl (including n-propyl and isopropyl), etc.

Unless otherwise specified, the number of atoms in a ring is usually defined as the number of ring members, for example, "5- to 6-membered ring" refers to a "ring" in which 5 to 6 atoms are arranged around.

Unless otherwise specified, the term "5- to 6-membered heterocycloalkyl" by itself or in combination with other terms refers to a saturated cyclic group consisting of 5 to 6 ring atoms, wherein 1, 2, 3, or 4 ring atoms are heteroatoms independently selected from O, S, and N, and the rest are carbon atoms, wherein nitrogen atoms are optionally quaternized, and carbon, nitrogen, and sulfur heteroatoms can be optionally oxidized (i.e., C(=O), NO, and $S(=O)_p$, p is 1 or 2). It includes monocyclic and bicyclic systems, wherein the bicyclic systems include a spiro ring, a fused ring, and a bridged ring. In addition, with regard to the "5- to 6-membered heterocycloalkyl", a heteroatom may occupy the connection position of the heterocycloalkyl with the rest of the molecule. The 5- to 6-membered heterocycloalkyl includes 5-membered and 6-membered heterocycloalkyl. Examples of 5- to 6-membered heterocycloalkyl include, but are not limited to, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl, and 3-piperidinyl, etc.), piperazinyl (including 1-piperazinyl and 2-piperazinyl, etc.), morpholinyl (including 3-morpholinyl and 4-morpholinyl, etc.), dioxinyl, dithianyl, isoxazolidinyl, isothiazolidinyl, 1,2-oxazinyl, 1,2-thiazinyl, hexahydropyridazinyl, etc. The term "leaving group" refers to a functional group or atom which can be replaced by another functional group or atom through a substitution reaction (such as nucleophilic substitution reaction). For example, representative leaving groups include triflate; chlorine, bromine, and iodine;

sulfonate group, such as mesylate, tosylate, p-bromobenzenesulfonate, p-toluenesulfonate; acyloxy, such as acetoxy, trifluoroacetoxy.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring.

The term "protecting group" includes, but is not limited to, "amino protecting group", "hydroxyl protecting group", or "mercapto protecting group". The term "amino protecting group" refers to a protecting group suitable for preventing the side reactions occurring at the nitrogen of an amino. Representative amino protecting groups include, but are not limited to: formyl; acyl, such as alkanoyl (e.g., acetyl, trichloroacetyl, or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for blocking the side reaction on hydroxyl. Representative hydroxyl protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the examples of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvents used in the present disclosure are commercially available.

The present disclosure adopts the following abbreviations: Alloc stands for allyloxycarbonyl; SEM stands for trimethylsilylethoxymethyl; OTs stands for 4-toluenesulfonyloxy; OMs stands for methanesulfonyloxy; Boc stands for tert-butoxycarbonyl; DCM stands for dichloromethane; DIEA stands for NN-diisopropylethylamine; MeI stands for iodomethane; PE stands for petroleum ether; EA stands for ethyl acetate; THF stands for tetrahydrofuran; EtOH stands for ethanol; MeOH stands for methanol; DMF stands for N,N-dimethylformamide; $Boc_2O$ stands for di-tert-butyl dicarbonate; $NH_4Cl$ stands for ammonium chloride; $T_3P$ stands for propylphosphonic anhydride; Pd/C stands for palladium/carbon catalyst; $TMSN_3$ stands for azidotrimethylsilane; NCS stands for N-chlorosuccinimide; HBr stands for hydrobromic acid; AcOH stands for acetic acid; HATU stands for 2-(7-azabenzotriazol-1-yl)-N,N,N',N'-tetramethyluronium hexafluorophosphate; DBU stands for 1,8-diazabicyclo[5.4.0]undec-7-ene; FA stands for formic acid; ACN stands for acetonitrile; TLC stands for thin layer chromatography; HPLC stands for high performance liquid chromatograph; LCMS stands for liquid chromatography-mass spectrometry; SFC stands for supercritical fluid chromatography. DMSO stands for dimethyl sulfoxide; DMSO-$d_6$ stands for deuterated dimethyl sulfoxide; $CD_3OD$ stands for deuterated methanol; $CDCl_3$ stands for deuterochloroform; $D_2O$ stands for deuterium oxide; solutol stands for polyethylene glycol (15)-hydroxystearate.

The compounds of the present disclosure are named according to the conventional naming principles in the art or by ChemDraw® software, and the commercially available compounds use the supplier catalog names.

BRIEF DESCRIPTION OF THE DRAWINGS

FIG. 1 is the in vivo efficacy test result of the compound of the present disclosure on the activity of neutrophil elastase in rat bone marrow.

DETAILED DESCRIPTION OF THE PREFERRED EMBODIMENT

The present disclosure is described in detail by the examples below, but it does not mean that there are any adverse restrictions on the present disclosure. The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the examples of the present disclosure. For one skilled in the art, it is obvious to make various modifications and improvements to the examples of the present disclosure without departing from the spirit and scope of the present disclosure.

Intermediate A

Synthetic Route:

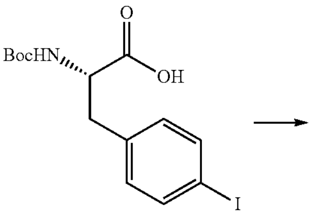

A-1

-continued

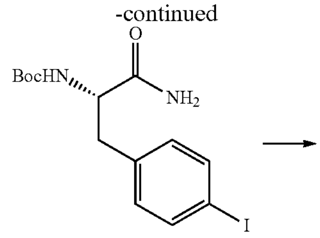

A-2

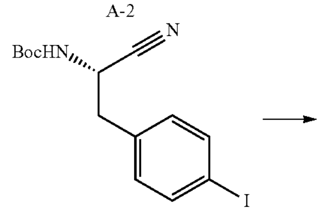

A-3

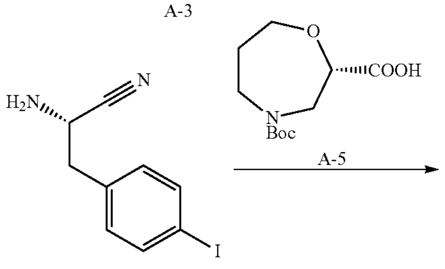

A-5

A-4

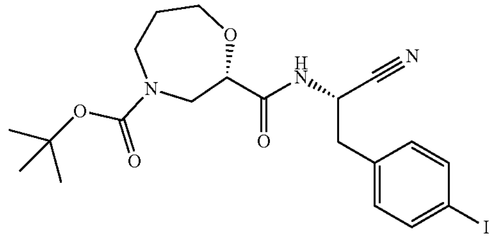

A

Step 1

Intermediate A-1 (12.5 g, 31.95 mmol) was dissolved in DMF (50 mL). DIEA (6.19 g, 47.93 mmol) and O-(benzotriazol-1-yl)-N,N,N',N'-tetramethyluronium tetrafluoroborate (10.26 g, 31.95 mmol) were sequentially added thereto. After stirring at 25° C. for 30 minutes, ammonia water (12 M, 4.79 mL, 57.52 mmol) was added thereto, and the reaction mixture was continued to stir at 25° C. for 12 hours. After the reaction was completed, water (50 mL) was added to the reaction mixture. The reaction mixture was stirred for 15 minutes and filtered. The filter cake was collected and dried to obtain intermediate A-2, which was directly used in the next reaction step. MS-ESI calculated for $[M+Na]^+$ 413, found 413.

Step 2

Intermediate A-2 (20.0 g, 50.11 mmol) was dissolved in dichloromethane (200 mL). Methyl N-(triethylammoniosulfonyl)carbamate (29.26 mg, 122.77 mmol) was added thereto. The reaction mixture was stirred at 25° C. for 12 hours. After the reaction was completed, the reaction mixture was added with water (200 mL) and extracted. The organic phase was dried over anhydrous sodium sulfate. The crude product obtained by concentration under reduced pressure was separated by silica gel column chromatography (petroleum ether/ethyl acetate, 15/1 to 1/1, V/V) to obtain intermediate A-3. MS-ESI calculated for $[M+H]^+$ 373, found 373.

Step 3

Intermediate A-3 (9.6 g, 25.79 mmol) was dissolved in THF (100 mL). Methanesulfonic acid (18.59 g, 193.44 mmol) was added thereto. The reaction mixture was stirred at 25° C. for 12 hours. After the reaction was completed, the reaction mixture was adjusted to pH>8 by saturated sodium bicarbonate aqueous solution and extracted with ethyl acetate (500 mL×3). The organic phases were combined, dried over anhydrous sodium sulfate, and concentrated under reduced pressure to obtain intermediate A-4, which was directly used in the next step. MS-ESI calculated for $[M+H]^+$ 273, found 273.

Step 4

The ethyl acetate solution of $T_3P$ (14.03 g, 22.05 mmol) was added to DMF (100 mL). Intermediate A-4 (4.0 g, 14.7 mmol), Intermediate A-5 (3.79 g, 15.44 mmol), and triethylamine (6.69 g, 66.2 mmol) were sequentially added thereto. The reaction mixture was stirred at 25° C. for 12 hours. After the reaction was completed, the reaction mixture was added with saturated brine (300 mL), extracted with ethyl acetate (250 mL×3). The organic phases were combined, washed with saturated brine (500 mL×3), and dried over anhydrous sodium sulfate. The crude product obtained by concentration under reduced pressure was separated by silica gel column chromatography (petroleum ether/ethyl acetate, 1/1 to 0/1, V/V) to obtain intermediate A. $^1H$ NMR (400 MHz, $CDCl_3$) δ 7.71 (d, J=8.0 Hz, 2H), 7.12-6.93 (m, 3H), 5.20-5.12 (m, 1H), 4.25-3.95 (m, 3H), 3.82-3.68 (m, 0.5H), 3.60-3.22 (m, 3H), 3.12-2.90 (m, 2.5H), 2.12-1.82 (m, 2H), 1.48 (s, 9H). MS-ESI calculated for $[M+Na]^+$ 522, found 522.

Intermediate B

Synthetic Route:

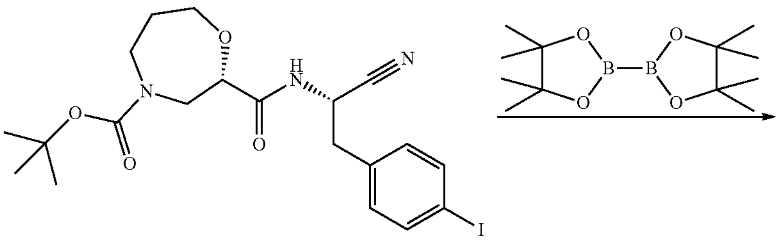

A

-continued

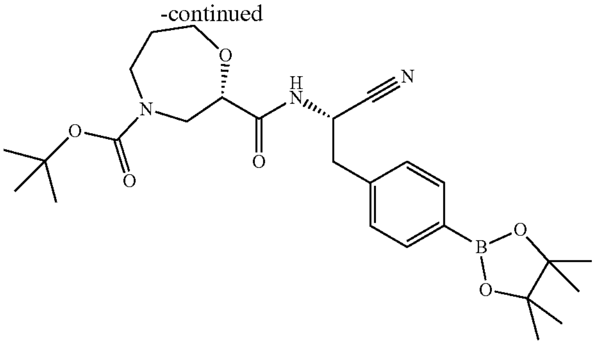

B

To dimethyl sulfoxide (6 mL) was added intermediate A (600 mg, 1200 μmol), potassium acetate (354 mg, 3600 μmol) and bis(pinacolato)diboron (397 mg, 1560 μmol), and then the reaction mixture was added with [1,1'-bis(diphenylphosphino)ferrocene]dichloropalladium(II) dichloromethane complex (49 mg, 60 μmol). The reaction mixture was heated to 85° C. and reacted for 5 hours under nitrogen atmosphere. The reaction mixture was concentrated under reduced pressure and separated by silica gel column chromatography (petroleum ether/ethyl acetate, 5/1 to 0/1, V/V) to obtain intermediate B. $^1$H NMR (400 MHz, $CDCl_3$) δ 7.82 (d, J=7.8 Hz, 2H), 7.40-7.25 (m, 2H), 7.08-6.98 (m, 1H), 5.25-5.05 (m, 1H), 4.25-3.98 (m, 3H), 3.78-3.68 (m, 0.5H), 3.52-2.96 (m, 5.5H), 2.15-1.80 (m, 2H), 1.47 (s, 9H), 1.25 (s, 12H). MS-ESI calculated for $[M+H]^+$ 500, found 500.

Intermediate C

Synthetic Route:

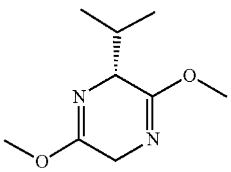

C-1a

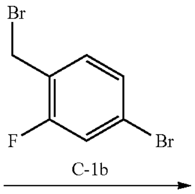

C-1b

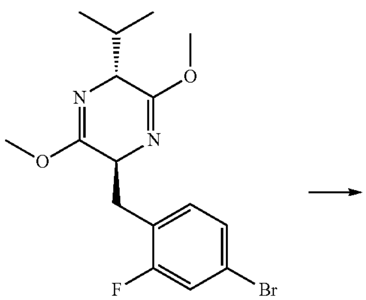

C-1c

-continued

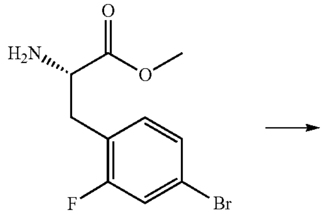

C-1d

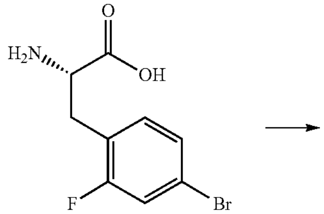

C-1e

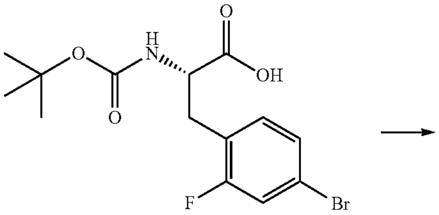

C-1f

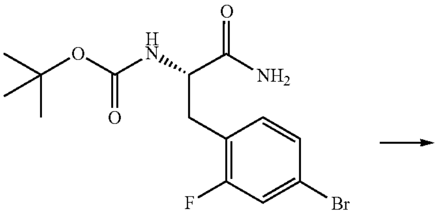

C-1

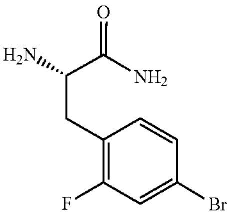

C-2

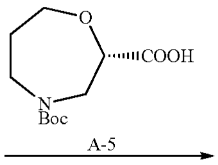

A-5

-continued

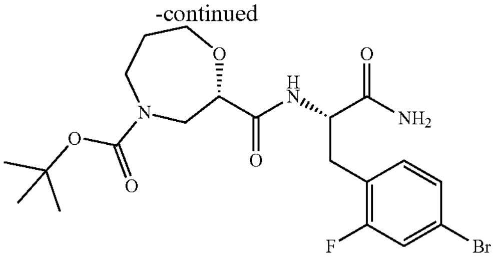

C

Step 1

Intermediate C-1a (15.0 g, 81.42 mmol) was dissolved in tetrahydrofuran (30 mL). n-Butyllithium (2.5 M, 40.71 mL, 102.8 mmol) was slowly added dropwise thereto at −78° C. and the mixture was reacted for half an hour. Then intermediate C-1b (21.81 g, 81.42 mmol) dissolved in tetrahydrofuran (150 mL) was slowly added at −78° C. The reaction mixture was stirred at 25° C. for 12 hours. The reaction mixture was quenched with saturated ammonium chloride solution (300 mL) and extracted with ethyl acetate (300 mL×2). The organic phases were combined, dried over anhydrous sodium sulfate, and concentrated under reduced pressure to obtain a crude product. The crude product was separated by silica gel column chromatography (petroleum ether/ethyl acetate, 10/1, V/V) to obtain intermediate C-1c. MS-ESI calculated for $[M+H]^+$ 371 and 373, found 371 and 373.

Step 2

Intermediate C-1c (24.85 g, 66.94 mmol) was dissolved in acetonitrile (200 mL). Hydrochloric acid (0.2 M, 840 mL, 167.34 mmol) was added thereto slowly. The reaction mixture was stirred at 25° C. for 12 hours. The reaction mixture was washed with tert-butyl methyl ether (200 mL). The pH of the aqueous phase was adjusted to 8 with saturated sodium bicarbonate aqueous solution. The mixture was extracted with ethyl acetate (1000 mL×2). The organic phases were combined, dried over anhydrous sodium sulfate and concentrated under reduced pressure to obtain intermediate C-1d, which was directly used in the next reaction step. MS-ESI calculated for $[M+H]^+$ 276 and 278, found 276 and 278.

Step 3

To intermediate C-1d (6.56 g, 23.76 mmol) was slowly added hydrochloric acid (3 M, 119 mL, 356 mmol), and the reaction mixture was reacted at 60° C. for 12 hours. The reaction mixture was cooled to room temperature. The pH of the solution was adjusted to 7 with sodium hydroxide aqueous solution. The reaction mixture was washed with water three times. The organic phases were combined, dried over anhydrous sodium sulfate, and concentrated under reduced pressure to obtain intermediate C-1e, which was directly used in the next reaction step. MS-ESI calculated for $[M+H]^+$ 262 and 264, found 262 and 264.

Step 4

Intermediate C-1e (3.38 g, 12.9 mmol) was dissolved in dioxane (50 mL) and water (100 mL). Sodium carbonate (1.50 g, 14.9 mmol) and $Boc_2O$ (3.27 g, 14.96 mmol) were added thereto. The reaction mixture was reacted at 25° C. for 4 hours. The pH of the reaction mixture was adjusted to 4 to 5 with saturated citric acid aqueous solution. The reaction mixture was extracted with ethyl acetate (100 mL×3). The organic phases were combined, dried over anhydrous sodium sulfate and then concentrated under reduced pressure to obtain intermediate C-1f, which was directly used in the next reaction step. MS-ESI calculated for $[M-56+1]^+$ 306 and 308, found 306 and 308.

Step 5

Intermediate C-1f (2.90 g, 8.01 mmol) was dissolved in DMF (50 mL). N-Methylmorpholine (1.21 g, 12.01 mmol) and O-(benzotriazol-1-yl)-N,N,N',N'-tetramethyluronium tetrafluoroborate (2.57 g, 8.01 mmol) were added thereto. The reaction mixture was stirred at 25° C. for 30 minutes. Then ammonium chloride aqueous solution (0.35 M, 45.75 mL, 16.01 mmol) was added thereto, and the reaction mixture was stirred at 25° C. for 12 hours. The reaction mixture was added with water (160 mL) and filtered, and the filter cake was collected and dried to obtain intermediate C-1, which was directly used in the next reaction step. MS-ESI calculated for $[M-56+1]^+$ 305 and 307, found 305 and 307.

Step 6

Intermediate C-1 (1810 mg, 5010 μmol) was dissolved in tetrahydrofuran (25 mL). Methanesulfonic acid (4820 mg, 50100 μmol) was added thereto, and the reaction mixture was reacted at 30° C. for 15 hours. The reaction mixture was added with saturated sodium bicarbonate solution (25 mL). The mixture was adjusted to pH=8 to 9 with saturated sodium bicarbonate solution and extracted with ethyl acetate (50 mL×2). The organic phases were combined and dried over anhydrous sodium sulfate. The crude product obtained by concentration under reduced pressure was separated by silica gel column chromatography (dichloromethane/methanol, 10/1 to 5/1, V/V) to obtain intermediate C-2. $^1H$ NMR (400 MHz, $CD_3OD$) δ 7.33-7.27 (m, 2H), 7.24-7.18 (m, 1H), 3.58 (t, J=6.8 Hz, 1H), 3.03-2.95 (m, 1H), 2.92-2.83 (m, 1H). MS-ESI calculated for $[M+H]^+$ 261 and 263, found 261 and 263.

Step 7

To DMF (10 mL) was added 50% ethyl acetate solution of $T_3P$ (1870 mg, 2940 μmol), and then intermediate C-2 (591 mg, 2260 μmol), intermediate A-5 (610 mg, 2490 μmol) and triethylamine (916 mg, 9050 μmol) were sequentially added thereto. The reaction mixture was reacted at 25° C. for 4 hours. The reaction mixture was added with saturated brine (50 mL) and extracted with ethyl acetate (50 mL×3). The organic phases were combined, washed with saturated brine (100 mL×3), dried over anhydrous sodium sulfate. The crude product obtained by concentration under reduced pressure was separated by silica gel column chromatography (dichloromethane/methanol, 100/1 to 10/1, V/V) to obtain intermediate C. $^1H$ NMR (400 MHz, $CDCl_3$) δ 7.26-7.19 (m, 2H), 7.16-7.10 (m, 1H), 4.70-4.55 (m, 1H), 4.25-3.94 (m, 3H), 3.88-3.75 (m, 0.5H), 3.57-3.28 (m, 2H), 3.27-2.95 (m, 3.5H), 2.07-1.78 (m, 2H), 1.46 (s, 9H). MS-ESI calculated for $[M+Na]^+$ 510 and 512, found 510 and 512.

Intermediate D

Synthetic Route:

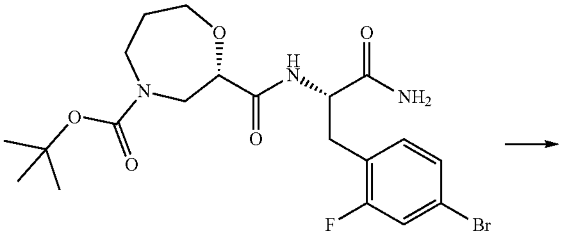

C

-continued

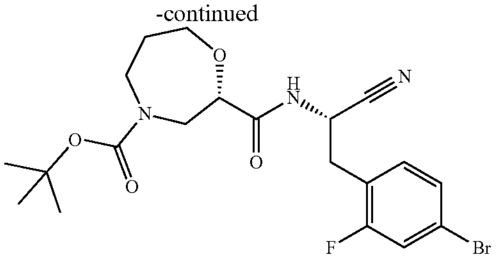

D

Intermediate C (52 mg, 106 μmol) was dissolved in dichloromethane (5 mL). Methyl N-(triethylammoniosulfonyl)carbamate (76 mg, 319 μmol) was added thereto. The reaction mixture was reacted at 25° C. for 18 hours. The reaction mixture was added with water (50 mL) and extracted with ethyl acetate (50 mL×2). The organic phases were combined and dried over anhydrous sodium sulfate. The crude product obtained by concentration under reduced pressure was separated by silica gel column chromatography (petroleum ether/ethyl acetate, 10/1 to 1/3, V/V) to obtain intermediate D. $^1$H NMR (400 MHz, $CDCl_3$) δ 7.34-7.25 (m, 2H), 7.22-7.14 (m, 1H), 5.42-5.10 (m, 1H), 4.23-3.96 (m, 3H), 3.83-3.70 (m, 0.5H), 3.59-2.96 (m, 5.5H), 2.03-1.72 (m, 2H), 1.46 (s, 9H). MS-ESI calculated for $[M+Na]^+$ 492 and 494, found 492 and 494.

Intermediate E

Synthetic Route:

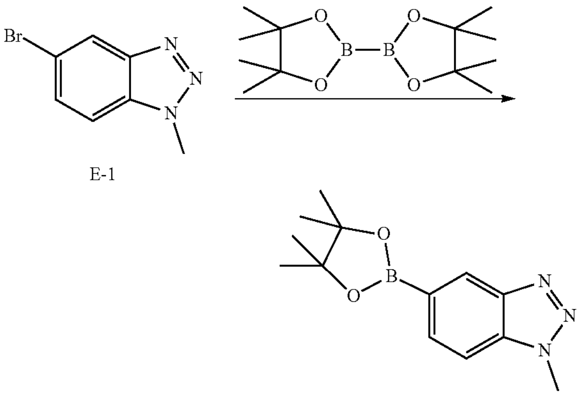

E-1

E

To 1,4-dioxane (8 mL) was added intermediate E-1 (300 mg, 1410 μmol), potassium phosphate (600 mg, 2830 μmol) and bis(pinacolato)diboron (539 mg, 2120 μmol), and the reaction mixture was added with [1,1'-bis(diphenylphosphino)ferrocene]dichloropalladium(II) (104 mg, 141 μmol). The reaction mixture was heated to 110° C. and reacted for 12 hours under nitrogen atmosphere. The reaction mixture was concentrated under reduced pressure and separated by silica gel column chromatography (petroleum ether/ethyl acetate, 10/1 to 3/2, V/V) to obtain intermediate E. $^1$H NMR (400 MHz, $CDCl_3$) δ 8.55 (s, 1H), 7.91 (d, J=8.4 Hz, 1H), 7.51 (d, J=8.4 Hz, 1H), 4.31 (s, 3H), 1.39 (s, 12H). MS-ESI calculated for $[M+H]^+$ 260, found 260.

Intermediate F

Synthetic Route:

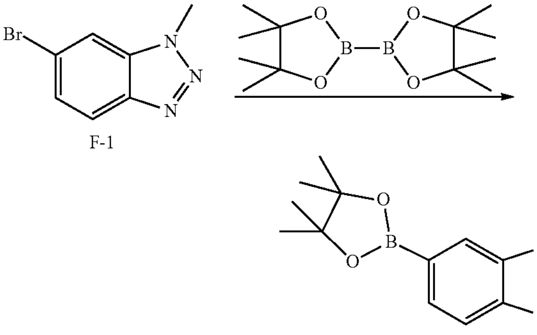

F-1

F

To 1,4-dioxane (8 mL) was added intermediate F-1 (300 mg, 1410 μmol), potassium acetate (277 mg, 2830 μmol) and bis(pinacolato)diboron (539 mg, 2120 μmol), and the reaction mixture was added with [1,1'-bis(diphenylphosphino)ferrocene]dichloropalladium(II) (207 mg, 282 μmol). The reaction mixture was heated to 110° C. and reacted for 12 hours under nitrogen atmosphere. The reaction mixture was concentrated under reduced pressure and separated by silica gel column chromatography (petroleum ether/ethyl acetate, 10/1 to 10/3, V/V) to obtain intermediate F. $^1$H NMR (400 MHz, $CDCl_3$) δ 8.06-8.02 (m, 2H), 7.83-7.77 (m, 1H), 4.33 (s, 3H), 1.40 (s, 12H). MS-ESI calculated for $[M+H]^+$ 260, found 260.

Intermediate G

Synthetic Route:

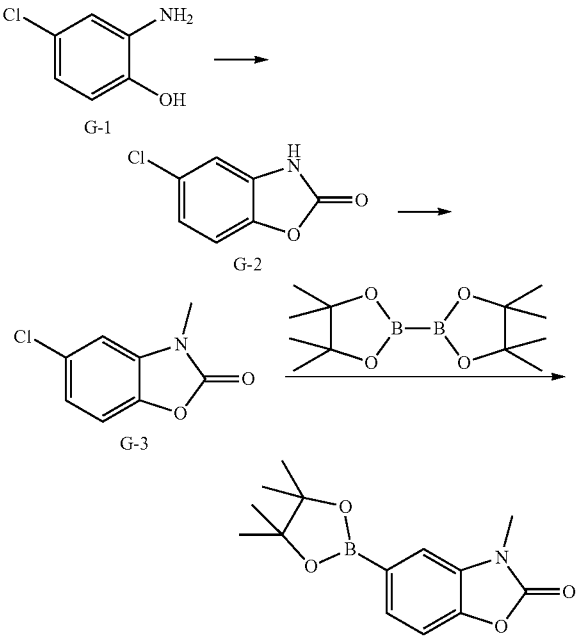

G-1

G-2

G-3

G

Step 1

Intermediate G-1 (20.0 g, 139.3 mmol) was dissolved in THF (100 mL). Carbonyldiimidazole (24.85 g, 153.23 mmol) was added thereto. The reaction mixture was stirred at 80° C. for 1 hour. The reaction mixture was adjusted to pH=6 with 1 M dilute hydrochloric acid and filtered. The filter cake was collected and dried to obtain intermediate G-2, which was directly used in the next reaction step. MS-ESI calculated for $[M+H]^+$ 170, found 170.

Step 2

To DMF (100 mL) was added intermediate G-2 (25.3 g, 149.2 mmol) and cesium carbonate (97.2 g, 298.41 mmol). After stirring at 25° C. for 20 minutes, iodomethane (25.4 g, 179.05 mmol) was added thereto, and the reaction mixture was continued to react at 25° C. for 2 hours. The reaction mixture was added with water (500 mL) and filtered, and the filter cake was collected and dried to obtain intermediate G-3, which was directly used in the next reaction step. MS-ESI calculated for $[M+H]^+$ 184, found 184.

Step 3

To 1,4-dioxane (20 mL) was added intermediate G-3 (1800 mg, 9800 μmol), potassium acetate (2890 mg, 29410 μmol) and bis(pinacolato)diboron (4980 mg, 19610 μmol). Then the reaction mixture was added with palladium acetate (132 mg, 588 μmol) and 2-dicyclohexylphosphino-2',4',6'-triisopropylbiphenyl (280 mg, 588 μmol). The reaction mixture was heated to 80° C. and reacted for 3 hours under nitrogen atmosphere. The reaction mixture was concentrated under reduced pressure and separated by silica gel column chromatography (petroleum ether/ethyl acetate, 20/1 to 3/1, V/V) to obtain intermediate G. $^1H$ NMR (400 MHz, $CDCl_3$) δ7.64 (d, J=8.0 Hz, 1H), 7.42 (s, 1H), 7.22 (d, J=8.0 Hz, 1H), 3.44 (s, 3H), 1.38 (s, 12H). MS-ESI calculated for $[M+H]^+$ 276, found 276.

Intermediate H

Synthetic Route:

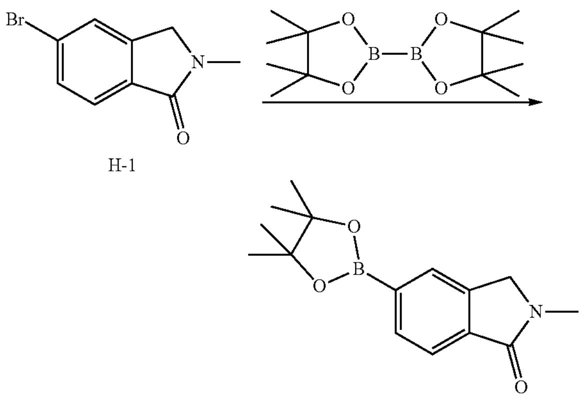

H-1

H

To 1,4-dioxane (10 mL) was added intermediate H-1 (995 mg, 4400 μmol), potassium acetate (1300 mg, 13200 μmol) and bis(pinacolato)diboron (2240 mg, 8800 μmol). Then the reaction mixture was added with palladium acetate (60 mg, 264 μmol) and 2-dicyclohexylphosphino-2',4',6'-triisopropylbiphenyl (126 mg, 264 μmol). The reaction mixture was heated to 80° C. and reacted for 3 hours under nitrogen atmosphere. The reaction mixture was concentrated under reduced pressure and separated by silica gel column chromatography (petroleum ether/ethyl acetate, 10/1 to 1/1, V/V) to obtain intermediate H. $^1H$ NMR (400 MHz, $CDCl_3$) δ7.96-7.86 (m, 2H), 7.86-7.81 (m, 1H), 4.41-4.34 (s, 2H), 3.21 (s, 3H), 1.32 (s, 12H). MS-ESI calculated for $[M+H]^+$ 274, found 274.

Intermediate I

Synthetic Route:

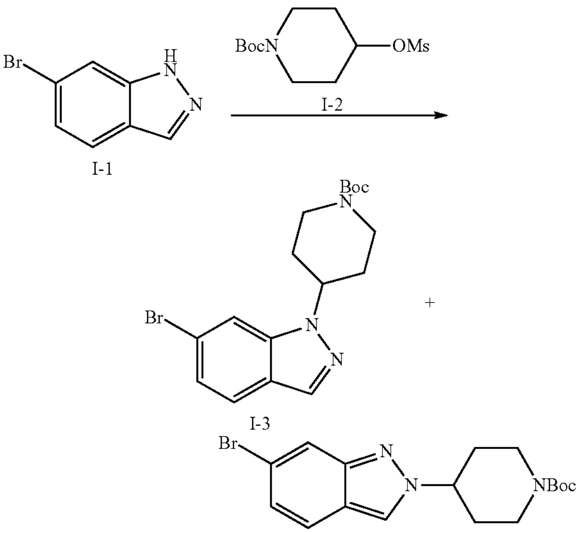

I-1

I-3

I-4

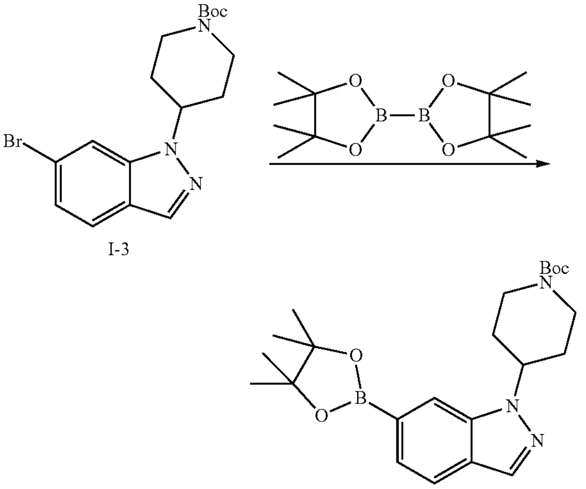

I-3

I

Step 1

To DMF (3 mL) was added intermediate I-1 (50 mg, 254 μmol), I-2 (106 mg, 381 μmol) and potassium carbonate (87 mg, 634 μmol). The reaction mixture was heated to 120° C. and reacted for 14 hours. The reaction mixture was added with saturated brine (50 mL) and extracted with ethyl acetate (50 mL×2). The organic phases were combined, dried over anhydrous sodium sulfate, and concentrated under reduced pressure to obtain a crude product. The crude product was separated by thin layer chromatography (developing solvent: petroleum ether/ethyl acetate, 3/1, V/V) to obtain intermediate I-3 and intermediate I-4.

Intermediate I-3: $^1H$ NMR (400 MHz, $CDCl_3$) δ 7.96 (s, 1H), 7.63 (s, 1H), 7.58 (d, J=8.5 Hz, 1H), 7.24 (d, J=8.5 Hz, 1H), 4.54-4.46 (m, 1H), 4.38-4.22 (m, 2H), 3.05-2.88 (m, 2H), 2.28-2.16 (m, 2H), 2.06-1.94 (m, 2H), 1.49 (s, 9H).

Intermediate I-4: $^1H$ NMR (400 MHz, $CDCl_3$) δ 7.85 (s, 1H), 7.80 (s, 1H), 7.44 (d, J=8.8 Hz, 1H), 7.08 (d, J=8.8 Hz, 1H), 4.52-4.40 (m, 1H), 4.35-4.14 (m, 2H), 2.94-2.76 (m, 2H), 2.20-2.12 (m, 2H), 2.09-1.92 (m, 2H), 1.41 (m, 9H).

Step 2

To 1,4-dioxane (3 mL) was added intermediate I-3 (50 mg, 131 μmol), potassium acetate (32 mg, 329 μmol), and bis(pinacolato)diboron (67 mg, 263 μmol), and the reaction mixture was added with [1,1'-bis(diphenylphosphino)ferrocene]dichloropalladium(II) (19 mg, 26 μmol). The reaction mixture was heated to 110° C. and reacted for 12 hours under nitrogen atmosphere. The reaction mixture was concentrated under reduced pressure and separated by silica gel column chromatography (petroleum ether/ethyl acetate, 100/1 to 4/1, V/V) to obtain intermediate I. $^1$H NMR (400 MHz, $CDCl_3$) δ 8.02 (s, 1H), 7.94 (s, 1H), 7.74 (d, J=8.1 Hz, 1H), 7.57 (d, J=8.1 Hz, 1H), 4.74-4.61 (m, 1H), 4.42-4.25 (m, 2H), 3.05-2.90 (m, 2H), 2.33-2.18 (m, 2H), 2.04-1.95 (m, 2H), 1.50 (s, 9H), 1.40 (s, 12H). MS-ESI calculated for $[M-56+1]^+$ 372, found 372.

Intermediate J

Synthetic Route:

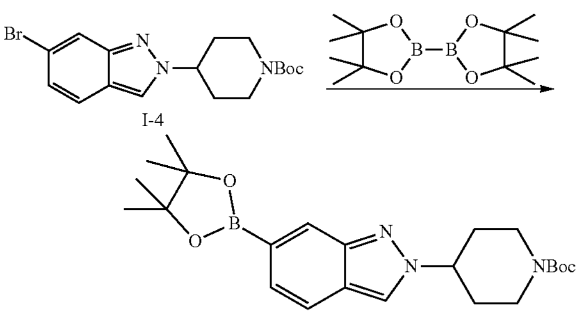

I-4

J

To 1,4-dioxane (3 mL) was added intermediate I-4 (50 mg, 131 μmol), potassium acetate (32 mg, 329 μmol), and bis(pinacolato)diboron (67 mg, 263 μmol), and the reaction mixture was added with [1,1'-bis(diphenylphosphino)ferrocene]dichloropalladium(II) (19 mg, 26 μmol). The reaction mixture was heated to 110° C. and reacted for 12 hours under nitrogen atmosphere. The reaction mixture was concentrated under reduced pressure and separated by silica gel column chromatography (petroleum ether/ethyl acetate, 100/1 to 4/1, V/V) to obtain intermediate J. $^1$H NMR (400 MHz, $CDCl_3$) δ 8.27 (s, 1H), 7.97-7.91 (m, 1H), 7.67-7.61 (m, 1H), 7.49-7.42 (m, 1H), 4.69-4.55 (m, 1H), 4.42-4.22 (m, 2H), 3.04-2.86 (m, 2H), 2.32-2.23 (m, 2H), 2.11-2.07 (m, 2H), 1.50 (s, 9H), 1.28 (s, 12H). MS-ESI calculated for $[M+H]^+$ 428, found 428.

Intermediate K

Synthetic Route:

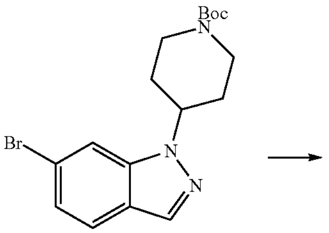

I-3

-continued

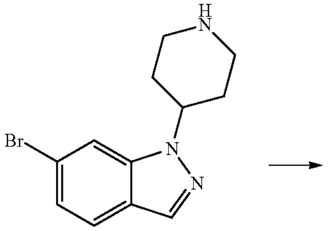

K-1

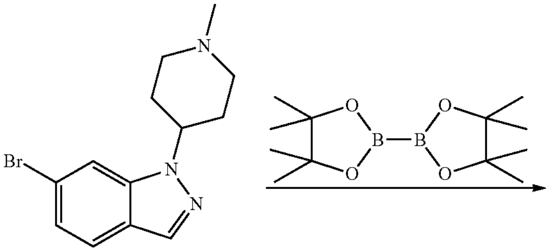

K-2

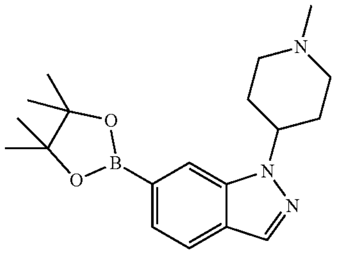

K

Step 1

Intermediate I-3 (500 mg, 1310 μmol) was dissolved in dichloromethane (5 mL). Trifluoroacetic acid (1540 mg, 13510 μmol) was added thereto. The reaction mixture was reacted at 25° C. for 1 hour. The reaction mixture was concentrated under reduced pressure to obtain a crude product containing intermediate K-1, which was directly used in the next reaction step. MS-ESI calculated for $[M+H]^+$ 280 and 282, found 280 and 282.

Step 2

Intermediate K-1 (364 mg, 1300 μmol) was dissolved in tetrahydrofuran (10 mL). Formaldehyde aqueous solution (37%, 0.67 mL, 9090 μmol) was added thereto. The reaction mixture was stirred at 25° C. for 30 minutes. Then sodium triacetoxyborohydride (550 mg, 2600 μmol) and acetic acid (117 mg, 1950 μmol) were added thereto. The reaction mixture was stirred at 25° C. for 2 hours. The reaction mixture was added with saturated sodium bicarbonate solution (100 mL) and extracted with ethyl acetate (100 mL×2). The organic phases were combined and dried over anhydrous sodium sulfate. The crude product obtained by concentration under reduced pressure was separated by silica gel column chromatography (dichloromethane/methanol, 20/1 to 10/1, V/V) to obtain intermediate K-2. $^1$H NMR (400 MHz, $CDCl_3$) δ 7.96 (s, 1H), 7.67 (s, 1H), 7.59 (d, J=8.5 Hz, 1H), 7.25 (d, J=8.5 Hz, 1H), 4.47-4.34 (m, 1H), 3.23-3.05 (m, 2H), 2.53-2.19 (m, 7H), 2.16-2.01 (m, 2H). MS-ESI calculated for $[M+H]^+$ 294 and 296, found 294 and 296.

Step 3

To 1,4-dioxane (3 mL) was added intermediate K-2 (320 mg, 1090 μmol), potassium acetate (267 mg, 2720 μmol), and bis(pinacolato)diboron (414 mg, 1630 μmol), and the reaction mixture was added with [1,1'-bis(diphenylphosphino)ferrocene]dichloropalladium(II) (80 mg, 109 μmol).

The reaction mixture was heated to 110° C. and reacted for 12 hours under nitrogen atmosphere. The reaction mixture was concentrated under reduced pressure and separated by silica gel column chromatography (dichloromethane/methanol, 10/1 to 20/3, V/V) to obtain intermediate K. $^1$H NMR (400 MHz, $CDCl_3$) δ 8.00 (s, 1H), 7.92 (s, 1H), 7.74 (d, J=8.0 Hz, 1H), 7.58 (d, J=8.3 Hz, 1H), 4.80-4.71 (m, 1H), 3.46-3.36 (m, 2H), 2.90-2.76 (m, 2H), 2.62 (s, 3H), 2.52-2.28 (m, 4H), 1.39 (m, 12H). MS-ESI calculated for $[M+H]^+$ 342, found 342.

Intermediate L

Synthetic Route:

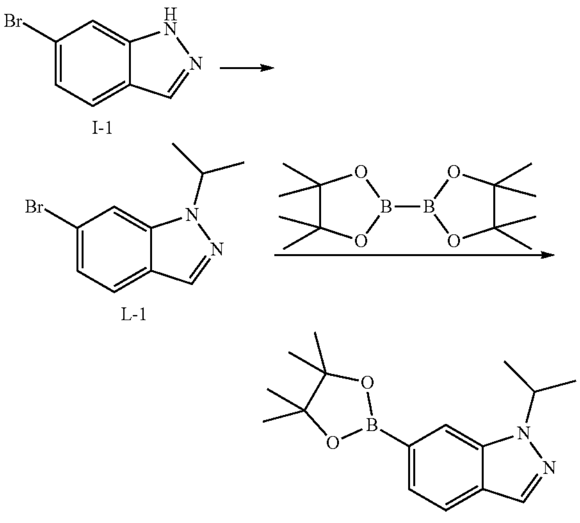

L

Step 1

Intermediate I-1 (500 mg, 2.54 mmol) was dissolved in dimethyl sulfoxide (5 mL). Potassium carbonate (491 mg, 3.55 mmol), 2-iodopropane (518 mg, 3.05 mmol) were slowly added thereto. The reaction mixture was reacted at 15° C. for 12 hours. The reaction mixture was extracted with ethyl acetate (10 mL×3). The organic phases were combined, washed with saturated brine (20 mL×2), dried over anhydrous sodium sulfate, and concentrated under reduced pressure to obtain a crude product. The crude product was separated by silica gel column chromatography (petroleum ether/ethyl acetate, 10/1, V/V) to obtain intermediate L-1. MS-ESI calculated for $[M+H]^+$ 239 and 241, found 239 and 241.

Step 2

To 1,4-dioxane (3 mL) was added intermediate L-1 (233 mg, 974 μmol), potassium acetate (191 mg, 1.95 mmol) and bis(pinacolato)diboron (371 mg, 1.46 mmol), and the reaction mixture was added with [1,1'-bis(diphenylphosphino) ferrocene]dichloropalladium(II) (143 mg, 195 μmol). The reaction mixture was heated to 110° C. and reacted for 12 hours under nitrogen atmosphere. The reaction mixture was concentrated under reduced pressure to obtain intermediate L, which was directly used in the next reaction step. MS-ESI calculated for $[M+H]^+$ 287, found 287.

Intermediate M

Synthetic Route:

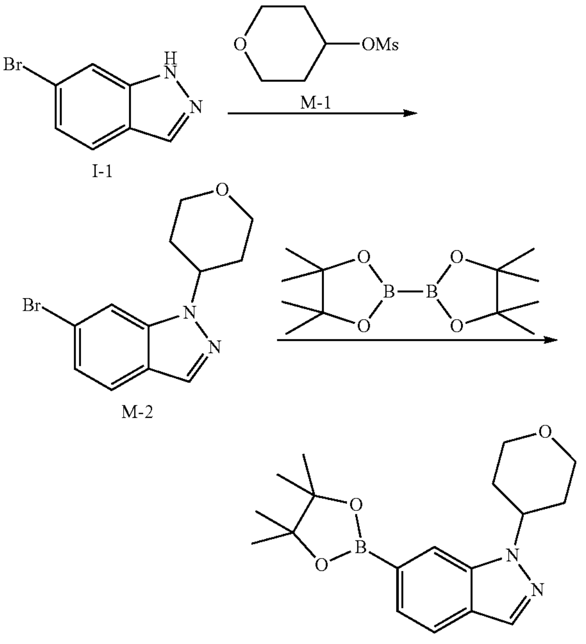

M

Step 1

Intermediate I-1 (500 mg, 2.54 mmol), intermediate M-1 (686 mg, 3.81 mmol) were dissolved in DMF (5 mL). Potassium carbonate (879 mg, 6.34 mmol), tetrabutylammonium iodide (94 mg, 254 μmol) were slowly added thereto. The reaction mixture was reacted at 120° C. for 14 hours under nitrogen atmosphere. The reaction mixture was extracted with water (20 mL×3). The organic phases were combined, washed with saturated brine (20 mL×2), dried over anhydrous sodium sulfate, and concentrated under reduced pressure to obtain a crude product. The crude product was separated by silica gel column chromatography (petroleum ether/ethyl acetate, 2/1, V/V) to obtain intermediate M-2. $^1$H NMR (400 MHz, $CDCl_3$) δ 8.00 (s, 1H), 7.68 (s, 1H), 7.62 (d, J=8.5 Hz, 1H), 7.34-7.21 (m, 1H), 4.67-4.54 (m, 1H), 4.27-4.13 (m, 2H), 3.72-3.57 (m, 2H), 2.51-2.28 (m, 2H), 2.09-1.92 (m, 2H). MS-ESI calculated for $[M+H]^+$ 281 and 283, found 281 and 283.

Step 2

Intermediate M-2 (237 mg, 843 μmol), potassium acetate (248 mg, 2.53 mmol), and bis(pinacolato)diboron (321.09 mg, 1.26 mmol) were added to 1,4-dioxane (3 mL), and then the reaction mixture was added with [1,1'-bis(diphenylphosphino)ferrocene]dichloropalladium(II) (62 mg, 84 μmol). The reaction mixture was heated to 110° C. and reacted for 12 hours under nitrogen atmosphere. The reaction mixture was concentrated under reduced pressure to obtain intermediate M, which was directly used in the next reaction step. MS-ESI calculated for $[M+H]^+$ 329, found 329.

Intermediate N

Synthetic Route:

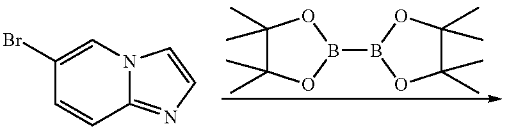

N-1

-continued

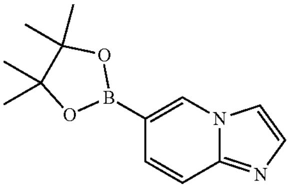

N

To 1,4-dioxane (2 mL) was added intermediate N-1 (201 mg, 1.02 mmol), potassium acetate (298 mg, 3.04 mmol), and bis(pinacolato)diboron (385 mg, 1.52 mmol), and then the reaction mixture was added with [1,1'-bis(diphenylphosphino)ferrocene]dichloropalladium(II) (74 mg, 101 μmol). The reaction mixture was heated to 90° C. and reacted for 12 hours under nitrogen atmosphere. The reaction mixture was extracted with ethyl acetate (10 mL×3). The organic phase was dried over anhydrous sodium sulfate, and then concentrated under reduced pressure to obtain intermediate N, which was directly used in the next reaction step. MS-ESI calculated for $[M+H]^+$ 245, found 245.

Intermediate O

Synthetic Route:

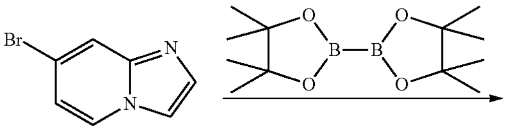

O-1

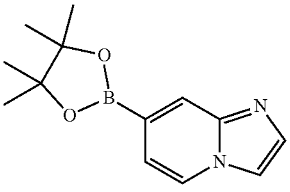

O

To 1,4-dioxane (2 mL) was added intermediate O-1 (200 mg, 1.02 mmol), potassium acetate (297 mg, 3.03 mmol), and bis(pinacolato)diboron (385 mg, 1.52 mmol), and then the reaction mixture was added with [1,1'-bis(diphenylphosphino)ferrocene]dichloropalladium(II) (74 mg, 101 μmol). The reaction mixture was heated to 90° C. and reacted for 12 hours under nitrogen atmosphere. The reaction mixture was extracted with ethyl acetate (10 mL×3). The organic phase was dried over anhydrous sodium sulfate, and then concentrated under reduced pressure to obtain intermediate O, which was directly used in the next reaction step. MS-ESI calculated for $[M+H]^+$ 245, found 245.

Intermediate P

Synthetic Route:

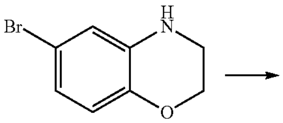

P-1

-continued

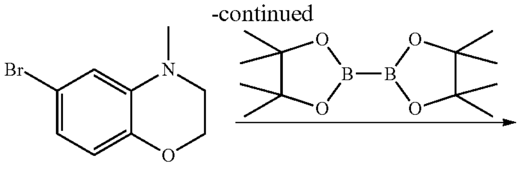

P-2

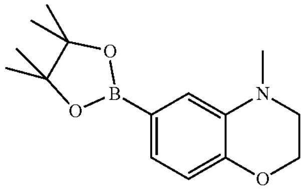

P

Step 1

Intermediate P-1 (500 mg, 2.34 mmol) was dissolved in acetonitrile (5 mL). Potassium carbonate (516 mg, 3.74 mmol), iodomethane (1.66 g, 3.05 mmol) were slowly added thereto. The reaction mixture was reacted at 50° C. for 12 hours. The reaction mixture was extracted with ethyl acetate (20 mL×3). The organic phases were combined, dried over anhydrous sodium sulfate, and concentrated under reduced pressure to obtain a crude product. The crude product was separated by silica gel column chromatography (petroleum ether/ethyl acetate, 5/1, V/V) to obtain intermediate P-2. MS-ESI calculated for $[M+H]^+$ 228 and 230, found 228 and 230.

Step 2

To 1,4-dioxane (2 mL) was added intermediate P-2 (174 mg, 762.87 μmol), potassium acetate (225 mg, 2.29 mmol), and bis(pinacolato)diboron (291 mg, 1.14 mmol), and then the reaction mixture was added with [1,1'-bis(diphenylphosphino)ferrocene]dichloropalladium(II) (56 mg, 76.29 μmol). The reaction mixture was heated to 90° C. and reacted for 12 hours under nitrogen atmosphere. The reaction mixture was concentrated under reduced pressure to obtain intermediate P, which was directly used in the next reaction step. MS-ESI calculated for $[M+H]^+$ 276, found 276.

Intermediate Q

Synthetic Route:

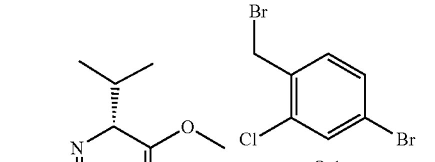

C-1a

Q-1

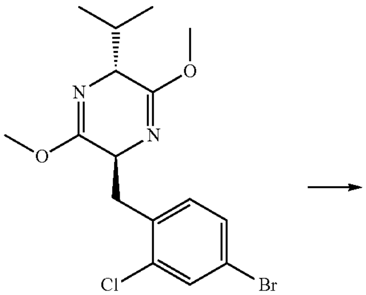

Q-2

-continued

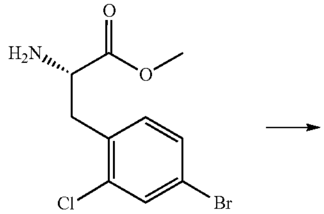

Q-3

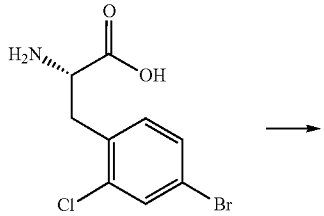

Q-4

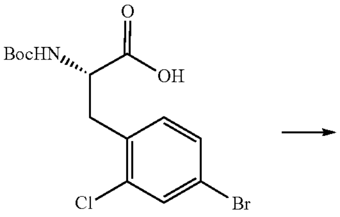

Q-5

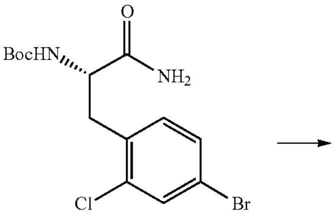

Q-6

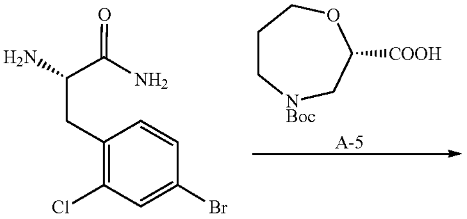

Q-7 lp;2p

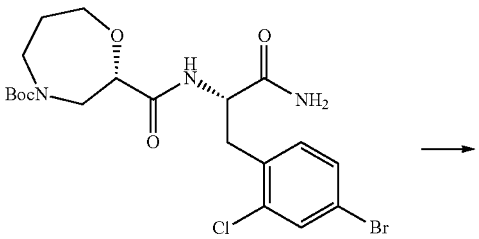

Q-8

-continued

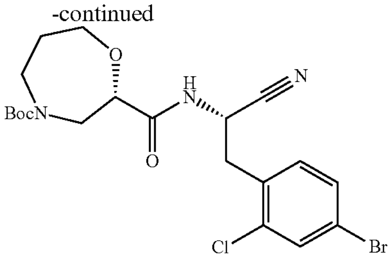

Q

Step 1

Intermediate C-1a (3 g, 16.28 mmol) was dissolved in tetrahydrofuran (30 mL). n-Butyllithium (2.5 M, 13.03 mL) was slowly added thereto at −78° C. The reaction mixture was reacted for half an hour, and then intermediate Q-1 (4.86 g, 17.1 mmol) dissolved in tetrahydrofuran (10 mL) was slowly added thereto at −78° C. The reaction mixture was reacted at 25° C. for 12 hours. The reaction mixture was quenched with ammonium chloride solution (30 mL) and extracted with ethyl acetate (30 mL×3). The organic phases were combined, washed with saturated brine (20 mL×2), dried over anhydrous sodium sulfate, and concentrated under reduced pressure to obtain a crude product. The crude product was separated by silica gel column chromatography (petroleum ether/ethyl acetate, 1/0 to 100/1, V/V) to obtain intermediate Q-2. $^1$H NMR (400 MHz, $CDCl_3$) δ 7.51 (d, J=2.0 Hz, 1H), 7.31-7.28 (m, 1H), 7.09 (d, J=8.3 Hz, 1H), 4.26-4.33 (m, 1H), 3.74 (s, 3H), 3.68-3.60 (m, 4H), 3.45-3.37 (m, 1H), 2.94-2.86 (m, 1H), 2.25-2.17 (m, 1H), 1.01 (m, J=6.8 Hz, 3H), 0.65 (d, J=6.8 Hz, 3H). MS-ESI calculated for $[M+H]^+$ 387 and 389, found 387 and 389.

Step 2

Intermediate Q-2 (6.4 g, 16.51 mmol) was dissolved in acetonitrile (30 mL). Hydrochloric acid (0.2 M, 173 mL) was slowly added thereto. The reaction mixture was reacted at 25° C. for 12 hours. The reaction mixture was washed with n-heptane (30 mL×2). The pH of the aqueous phase was adjusted to 8 with saturated sodium bicarbonate aqueous solution. The reaction mixture was extracted with ethyl acetate (30 mL×3). The organic phases were combined, dried over anhydrous sodium sulfate and concentrated under reduced pressure to obtain intermediate Q-3, which was directly used in the next reaction step. $^1$H NMR (400 MHz, $CDCl_3$) δ 7.57-7.52 (m, 1H), 7.37-7.32 (m, 1H), 7.12 (d, J=8.2 Hz, 1H), 3.82-3.76 (m, 1H), 3.71 (s, 3H), 3.22-3.15 (m, 1H), 2.92-2.85 (m, 1H). MS-ESI calculated for $[M+H]^+$ 292 and 294, found 292 and 294.

Step 3

To intermediate Q-3 (3.42 g, 11.69 mmol) was slowly added hydrochloric acid (3 M, 55 mL), and the reaction mixture was reacted at 60° C. for 16 hours. The reaction mixture was cooled to room temperature. The pH of the solution was adjusted to 7 with sodium hydroxide aqueous solution. The reaction mixture was washed with water three times. The organic phases were combined, dried over anhydrous sodium sulfate, and concentrated under reduced pressure to obtain intermediate Q-4, which was directly used in the next reaction step. MS-ESI calculated for $[M+H]^+$ 278 and 280, found 278 and 280.

Step 4

Intermediate Q-4 (4 g, 14.36 mmol) was dissolved in dioxane (40 mL). Sodium carbonate (2 M, 7.90 mL) and $Boc_2O$ (3.64 g, 16.66 mmol) were added thereto. The reaction mixture was reacted at 25° C. for 4 hours. The pH of the reaction mixture was adjusted to 4 to 5 with saturated citric acid aqueous solution and extracted with ethyl acetate (50 mL×3). The organic phases were combined, washed with saturated brine (50 mL×2), dried over anhydrous sodium sulfate and then concentrated under reduced pressure. n-Heptane (15 mL) was added thereto, and the mixture was stirred for 15 minutes and filtered. The filter cake was collected, and dried to obtain intermediate Q-5, which was directly used in the next reaction step. $^1H$ NMR (400 MHz, MeOD-$d_4$) δ 7.68-7.54 (m, 1H), 7.48-7.37 (m, 1H), 7.24 (d, J=8.2 Hz, 1H), 4.59-4.40 (m, 1H), 3.43-3.36 (m, 1H), 3.02-2.83 (m, 1H), 1.37 (s, 9H). MS-ESI calculated for $[M+H]^+$ 378 and 380, found 378 and 380.

Step 5

Intermediate Q-5 (1.06 g, 2.79 mmol) was dissolved in DMF (5 mL). Ammonia water (12 M, 696.56 μL), N-methylmorpholine (423 mg, 4.18 mmol) were slowly added thereto. The reaction mixture was stirred at 25° C. for 30 minutes. Then HATU (1.06 g, 2.79 mmol) was added thereto at 0° C., and the reaction mixture was reacted at 25° C. for 12 hours. The reaction mixture was added with water (20 mL) and filtered. The filter cake was washed three times with water. The filter cake was collected and dried to obtain intermediate Q-6, which was directly used in the next reaction step. $^1H$ NMR (400 MHz, DMSO-$d_6$) δ 7.66 (d, J=1.8 Hz, 1H), 7.53-7.44 (m, 1H), 6.90 (d, J=9.0 Hz, 1H), 4.22-4.15 (m, 1H), 3.18-3.07 (m, 1H), 2.85-2.74 (m, 1H), 1.28 (s, 9H). MS-ESI calculated for $[M+Na]^+$ 399 and 401, found 399 and 401.

Step 6

Intermediate Q-6 (1 g, 2.65 mmol) was dissolved in dichloromethane (10 mL). Trifluoroacetic acid (12.13 g, 106.35 mmol) was slowly added thereto, and the reaction mixture was reacted at 25° C. for 12 hours. The reaction mixture was adjusted to pH greater than 8 with saturated sodium bicarbonate aqueous solution. The reaction mixture was extracted with ethyl acetate (10 mL×3). The organic phases were washed with saturated brine (10 mL×3), combined, dried over anhydrous sodium sulfate, and concentrated under reduced pressure to obtain intermediate Q-7, which was directly used in the next reaction step. MS-ESI calculated for $[M+H]^+$ 277 and 279, found 277 and 279.

Step 7

$T_3P$ (50% ethyl acetate solution, 278.58 mg, 876 μmol) was dissolved in DMF (3 mL), and then intermediate Q-7 (243 mg, 876 μmol), intermediate A-5 (143 mg, 584 μmol) were added thereto, and then triethylamine (266 mg, 2.63 mmol) was added thereto. The reaction mixture was reacted at 25° C. for 12 hours. The reaction mixture was added with water (50 mL) and extracted with ethyl acetate (50 mL×3). The organic phases were washed with saturated brine (10 mL×3), combined, dried over anhydrous sodium sulfate, and concentrated under reduced pressure. The crude product was separated by silica gel column chromatography (dichloromethane/methanol, 10/1, V/V) to obtained intermediate Q-8. MS-ESI calculated for $[M+Na]^+$ 526 and 528, found 526 and 528.

Step 8

To dichloromethane (3 mL) was added intermediate Q-8 (350 mg, 693 μmol) and methyl N-(triethylammoniumsulphonyl)carbamate (826 mg, 3.47 mmol). The reaction mixture was reacted at 25° C. for 12 hours. The reaction mixture was added with water (20 mL), extracted with ethyl acetate (10 mL×2). The organic phase was dried over anhydrous sodium sulfate, and concentrated under reduced pressure to obtain intermediate Q, which was directly used in the next reaction step. MS-ESI calculated for $[M+Na]^+$ 508 and 510, found 508 and 510.

Intermediate R

Synthetic Route:

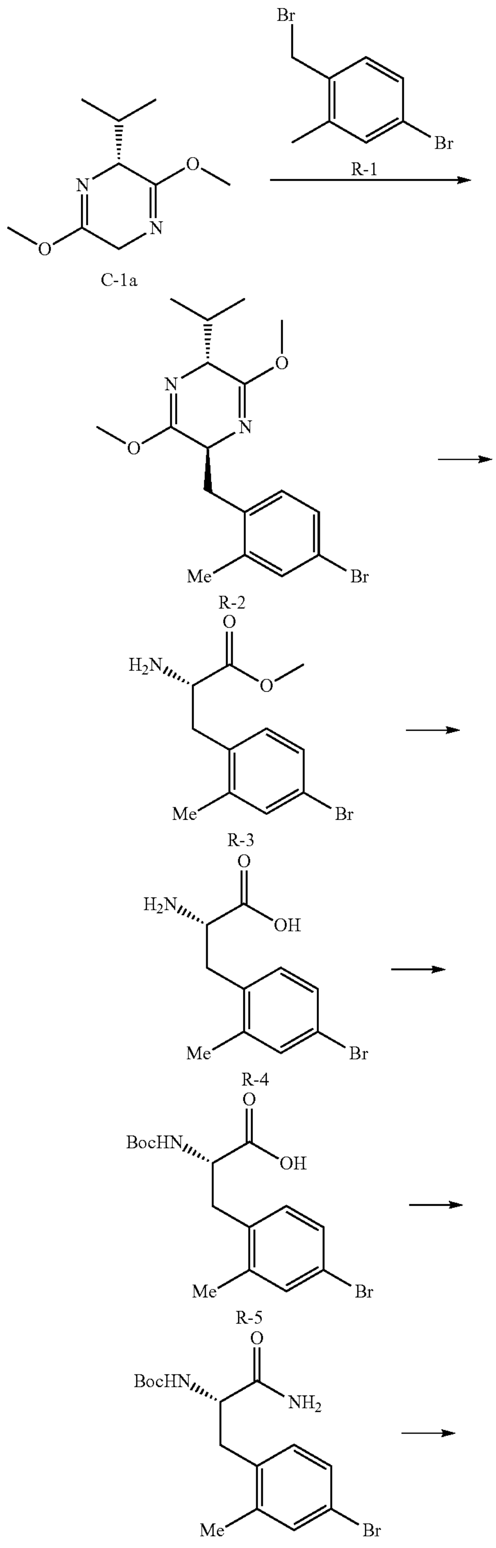

C-1a

R-2

R-3

R-4

R-5

R-6

-continued

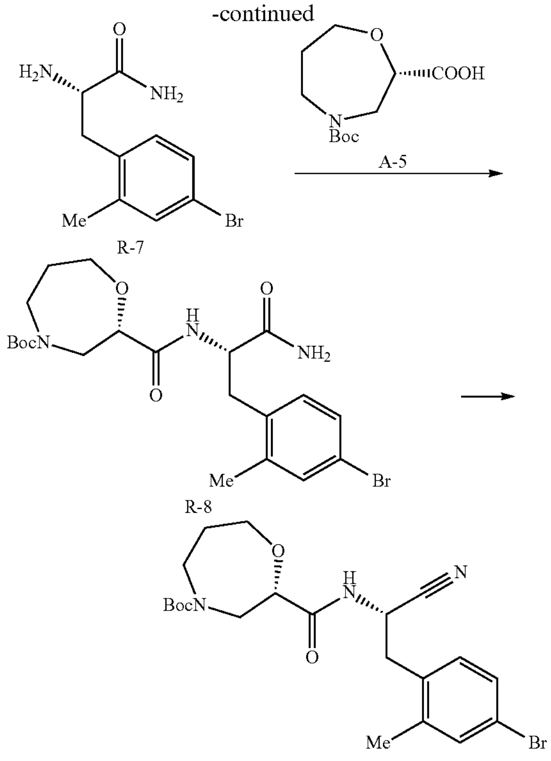

R-7

R-8

R

Step 1

Intermediate C-1a (2.0 g, 10.86 mmol) was dissolved in tetrahydrofuran (30 mL). n-Butyllithium (2.5 M, 6.08 mL, 15.20 mmol) was slowly dropwise added thereto at −78° C. The reaction mixture was reacted for half an hour, and then intermediate R-1 (2.87 g, 10.86 mmol) dissolved in tetrahydrofuran (15 mL) was slowly added thereto at −78° C. The reaction mixture was reacted at 25° C. for 12 hours. The reaction mixture was quenched with saturated ammonium chloride solution (50 mL) and extracted with ethyl acetate (50 mL×2). The organic phases were combined, dried over anhydrous sodium sulfate, and concentrated under reduced pressure to obtain a crude product. The crude product was separated by silica gel column chromatography (petroleum ether/ethyl acetate, 1/0 to 10/1, V/V) to obtain intermediate R-2. $^1$H NMR (400 MHz, $CDCl_3$) δ 7.27 (s, 1H), 7.21 (d, J=8.0 Hz, 1H), 6.97 (d, J=8.3 Hz, 1H), 4.30-4.21 (m, 1H), 3.73 (s, 3H), 3.64 (s, 3H), 3.59-3.54 (m, 1H), 3.26-3.17 (m, 1H), 2.92-2.83 (m, 1H), 2.33 (s, 3H), 2.26-2.15 (m, 1H), 1.00 (d, J=6.8 Hz, 3H), 0.64 (d, J=6.8 Hz, 3H). MS-ESI calculated for $[M+H]^+$ 367 and 369, found 367 and 369.

Step 2

Intermediate R-2 (2.7 g, 7.35 mmol) was dissolved in acetonitrile (9 mL). Hydrochloric acid (0.2 M, 77 mL, 15.44 mmol) was slowly added thereto. The reaction mixture was stirred at 25° C. for 12 hours. The reaction mixture was washed with tert-butyl methyl ether (20 mL). The pH of the aqueous phase was adjusted to 8 with saturated sodium bicarbonate aqueous solution. The reaction mixture was extracted with ethyl acetate (100 mL×3). The organic phases were combined, dried over anhydrous sodium sulfate and concentrated under reduced pressure to obtain intermediate R-3, which was directly used in the next reaction step. $^1$H NMR (400 MHz, $CDCl_3$) δ 7.33 (s, 1H), 7.29-7.27 (m, 1H), 7.02 (d, J=8.0 Hz, 1H), 3.71 (s, 3H), 3.70-3.66 (m, 1H), 3.12-3.03 (m, 1H), 2.81-2.72 (m, 1H), 2.33 (s, 3H). MS-ESI calculated for $[M+H]^+$ 272 and 274, found 272 and 274.

Step 3

To intermediate R-3 (2.0 g, 7.35 mmol) was slowly added hydrochloric acid (3 M, 37 mL, 110 mmol), and the reaction mixture was reacted at 60° C. for 16 hours. The reaction mixture was cooled to room temperature. The pH of the solution was adjusted to 7 with sodium hydroxide aqueous solution. The reaction mixture was washed with water three times. The organic phases were combined, dried over anhydrous sodium sulfate, and concentrated under reduced pressure to obtain intermediate R-4, which was directly used in the next reaction step. MS-ESI calculated for $[M+H]^+$ 258 and 260, found 258 and 260.

Step 4

Intermediate R-4 (1.93 g, 7.48 mmol) was dissolved in dioxane (20 mL) and water (80 mL). Sodium carbonate (1.59 g, 14.95 mmol) and $Boc_2O$ (1.71 g, 7.85 mmol) were added thereto. The reaction mixture was reacted at 25° C. for 4 hours. The pH of the reaction mixture was adjusted to 4 to 5 with saturated citric acid aqueous solution. The reaction mixture was extracted with ethyl acetate (200 mL×3). The organic phases were combined, dried over anhydrous sodium sulfate and then concentrated under reduced pressure to obtain intermediate R-5, which was directly used in the next reaction step. MS-ESI calculated for $[M-H]^-$ 356 and 358, found 356 and 358.

Step 5

Intermediate R-5 (2.68 g, 7.48 mmol) was dissolved in DMF (15 mL). N-Methylmorpholine (1.14 g, 11.22 mmol) and HATU (2.84 g, 7.48 mmol) were added thereto. The reaction mixture was stirred at 0° C. for 30 minutes. Then ammonia water (865 μL, 22.44 mmol) was added thereto, and the reaction mixture was stirred at 25° C. for 12 hours. The reaction mixture was added with water (100 mL) and extracted with ethyl acetate (100 mL×3). The organic phases were combined, washed with saturated brine (200 mL×3), dried over anhydrous sodium sulfate, and concentrated under reduced pressure. The crude product was separated by silica gel column chromatography (petroleum ether/ethyl acetate, 1/4 to 1/3, V/V) to obtain intermediate R-6. $^1$H NMR (400 MHz, MeOD-$d_4$) δ7.31 (s, 1H), 7.23 (d, J=8.0 Hz, 1H), 7.08 (s, 1H), 4.34-4.20 (m, 1H), 3.17-3.08 (m, 1H), 2.81-2.73 (m, 1H), 2.35 (s, 3H), 1.35 (s, 9H). MS-ESI calculated for $[M-100]^+$ 257 and 259, found 257 and 259.

Step 6

Intermediate R-6 (2.3 g, 6.44 mmol) was dissolved in THF (40 mL). Methanesulfonic acid (6.19 g, 64.38 mmol) was slowly added thereto, and the reaction mixture was reacted at 25° C. for 12 hours. The reaction mixture was adjusted to pH greater than 8 with saturated sodium bicarbonate aqueous solution and extracted with ethyl acetate (10 mL×3). The organic phases were combined, dried over anhydrous sodium sulfate, concentrated under reduced pressure. The crude product was separated by silica gel column chromatography (dichloromethane/methanol, 20/to 10/1, V/V) to obtain intermediate R-7. $^1$H NMR (400 MHz, MeOD-$d_4$) δ 7.37-7.34 (m, 1H), 7.29-7.25 (m, 1H), 7.12 (d, J=8.0 Hz, 1H), 3.31-3.26 (m, 1H), 2.92-2.81 (m, 1H), 2.59-2.52 (m, 1H), 2.29 (s, 3H). MS-ESI calculated for $[M+H]^+$ 257 and 259, found 257 and 259.

Step 7

$T_3P$ (50% ethyl acetate solution, 389 mg, 612 μmol) was dissolved in DMF (5 mL), and then intermediate R-7 (115 mg, 448 μmol), intermediate A-5 (100 mg, 407 μmol) were added thereto, and then triethylamine (187 mg, 1.83 mmol) was added thereto. The reaction mixture was reacted at 25° C. for 12 hours. The reaction mixture was added with water (50 mL) and extracted with ethyl acetate (50 mL×3). The organic phases were washed with saturated brine (100 mL×3), combined, dried over anhydrous sodium sulfate, and concentrated under reduced pressure to obtain a crude product. The crude product was separated by silica gel column chromatography (petroleum ether/ethyl acetate, 1/4, V/V) to obtain intermediate R-8. $^{1}$H NMR (400 MHz, $CDCl_3$) δ 7.29-7.11 (m, 3H), 6.95 (d, J=8.4 Hz, 1H), 4.67-4.50 (m, 1H), 4.13-3.81 (m, 3H), 3.80-3.68 (m, 0.5H), 3.54-3.33 (m, 1.5H), 3.28-3.15 (m, 0.5H), 3.12-2.82 (m, 3.5H), 2.26 (s, 3H), 1.94-1.71 (m, 2H), 1.38 (s, 9H). MS-ESI calculated for $[M+Na]^+$ 506 and 508, found 506 and 508.

Step 8

To dichloromethane (5 mL) was added intermediate R-8 (190 mg, 393 μmol), methyl N-(triethylammoniumsulphonyl)carbamate (280 mg, 1.18 mmol). The reaction mixture was reacted at 25° C. for 12 hours. The reaction mixture was added with water (50 mL), extracted with ethyl acetate (50 mL×2), dried over anhydrous sodium sulfate, and concentrated under reduced pressure. The crude product obtained was separated by silica gel column chromatography (petroleum ether/ethyl acetate, 10/3, V/V) to obtain intermediate R. $^{1}$H NMR (400 MHz, $CDCl_3$) δ 7.37-7.34 (s, 1H), 7.33-7.28 (m, 1H), 7.23-7.12 (m, 1H), 7.11-7.05 (m, 1H), 5.13-4.98 (m, 1H), 4.25-3.97 (m, 3H), 3.82-3.70 (m, 0.5H), 3.56-3.17 (m, 3H), 3.15-2.94 (m, 2.5H), 2.36 (s, 3H), 2.01-1.80 (m, 2H), 1.45 (m, 9H). MS-ESI calculated for $[M+Na]^+$ 488 and 490, found 488 and 490.

Intermediate S

Synthetic Route:

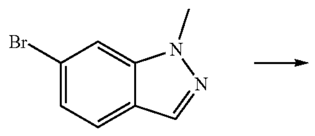

S-1

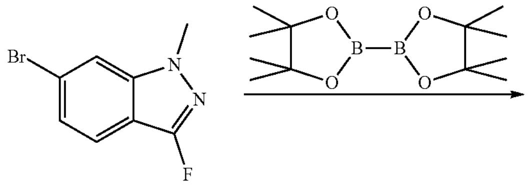

S-2

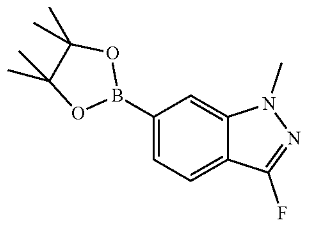

S

Step 1

Intermediate S-1 (200 mg, 948 μmol) was dissolved in acetonitrile (10 mL). 1-Chloromethyl-4-fluoro-1,4-diazoniabicyclo[2.2.2]octane ditetrafluoroborate (419 mg, 1.18 mmol) was added thereto, and the reaction mixture was reacted at 90° C. for 2 hours. The reaction mixture was poured into water (50 mL) and extracted with ethyl acetate (30 mL×2). The organic phases were combined, dried over anhydrous sodium sulfate, and concentrated under reduced pressure to obtain a crude product. The crude product was separated by thin-layer chromatography (petroleum ether/ethyl acetate, 20/3, V/V) to obtain intermediate S-2. $^{1}$H NMR (400 MHz, $CDCl_3$) δ 7.53-7.47 (m, 2H), 7.24 (d, J=8.8 Hz, 1H), 3.89 (s, 3H). MS-ESI calculated for $[M+H]^+$ 229 and 231, found 229 and 231.

Step 2

To 1,4-dioxane (3 mL) was added intermediate S-2 (33 mg, 144 μmol), potassium acetate (35 mg, 369 μmol), and bis(pinacolato)diboron (55 mg, 216 μmol), and then the reaction mixture was added with [1,1'-bis(diphenylphosphino)ferrocene]dichloropalladium(II) (21 mg, 29 μmol). The reaction mixture was heated to 90° C. and reacted for 12 hours under nitrogen atmosphere. The reaction mixture was concentrated under reduced pressure and separated by silica gel column chromatography (petroleum ether/ethyl acetate, 20/3, V/V) to obtain intermediate S. $^{1}$H NMR (400 MHz, $CDCl_3$) δ 7.73 (d, J=1.8 Hz, 1H), 7.56 (d, J=8.0 Hz, 1H), 7.49-7.43 (m, 1H), 3.87 (s, 3H), 1.31 (s, 12H). MS-ESI calculated for $[M+H]^+$ 277, found 277.

Intermediate T

Synthetic Route:

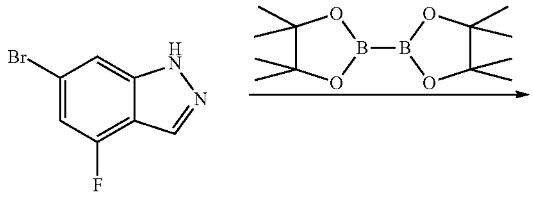

T-1

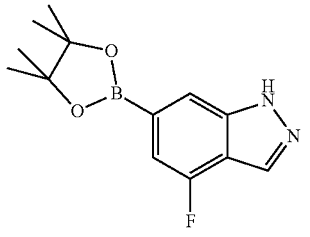

T

To 1,4-dioxane (6 mL) was added intermediate T-1 (500 mg, 2.33 mmol), potassium acetate (571 mg, 5.81 mmol), and bis(pinacolato)diboron (886 mg, 3.49 mmol), and then the reaction mixture was added with [1,1'-bis(diphenylphosphino)ferrocene]dichloropalladium(II) (170 mg, 232 μmol). The reaction mixture was heated to 100° C. and reacted for 12 hours under nitrogen atmosphere. The reaction mixture was concentrated under reduced pressure and separated by silica gel column chromatography (petroleum ether/ethyl acetate, 3/2, V/V) to obtain intermediate T. $^{1}$H NMR (400 MHz, $CDCl_3$) δ 8.28-8.10 (m, 1H), 7.79 (s, 1H), 7.24-7.18 (m, 1H), 1.38 (s, 12H). MS-ESI calculated for $[M+H]^+$ 263, found 263.

Intermediate U

Synthetic Route:

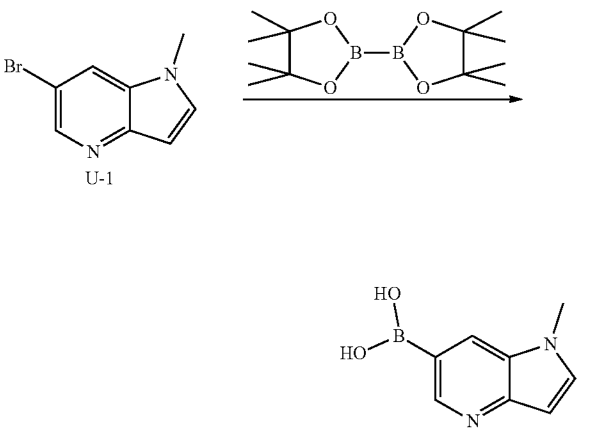

U-1

U

To 1,4-dioxane (3 mL) was added intermediate U-1 (50 mg, 237 μmol), potassium acetate (58 mg, 593 μmol), and bis(pinacolato)diboron (90 mg, 355 μmol), and then the reaction mixture was added with [1,1'-bis(diphenylphosphino)ferrocene]dichloropalladium(II) (35 mg, 47 μmol). The reaction mixture was heated to 100° C. and reacted for 12 hours under nitrogen atmosphere. The reaction mixture was concentrated under reduced pressure to obtain intermediate U, which was directly used in the next step. MS-ESI calculated for $[M+H]^+$ 177, found 177.

Intermediate V

Synthetic Route:

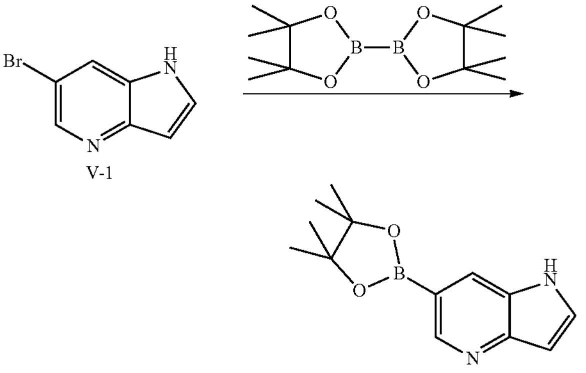

V-1

V

To 1,4-dioxane (3 mL) was added intermediate V-1 (100 mg, 507 μmol), potassium acetate (125 mg, 1.27 mmol), and bis(pinacolato)diboron (193 mg, 761 μmol), and then the reaction mixture was added with [1,1'-bis(diphenylphosphino)ferrocene]dichloropalladium(II) (74 mg, 101 μmol). The reaction mixture was heated to 100° C. and reacted for 12 hours under nitrogen atmosphere. The reaction mixture was concentrated under reduced pressure to obtain intermediate V, which was directly used in the next reaction step. MS-ESI calculated for $[M+Na]^+$ 267, found 267.

Example 1

Synthetic Route:

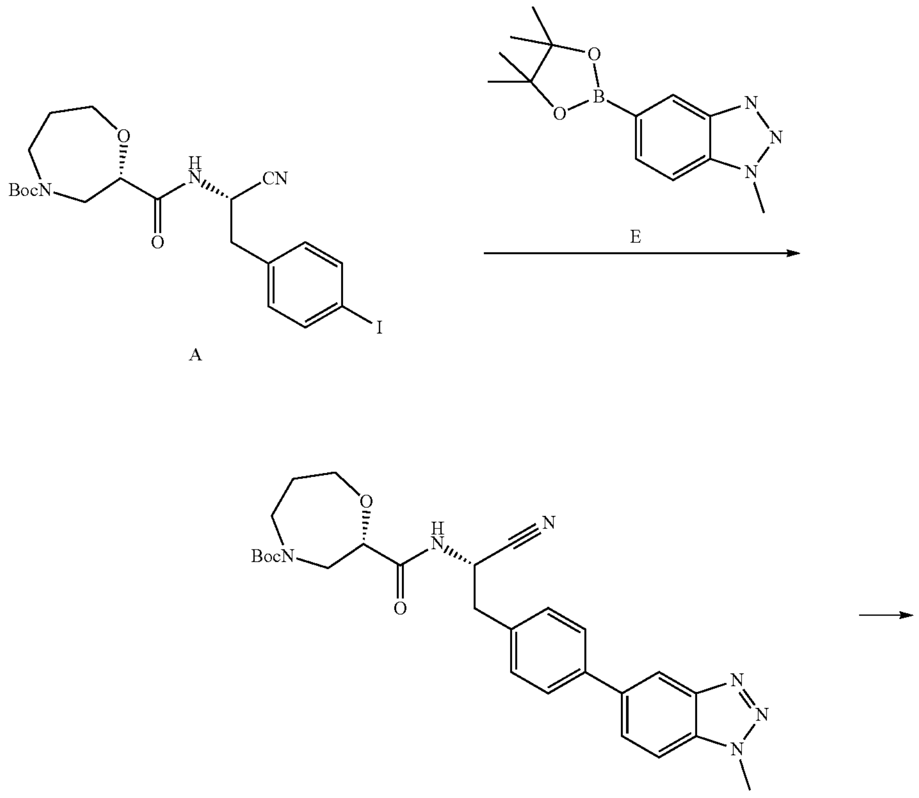

A 1-1

-continued

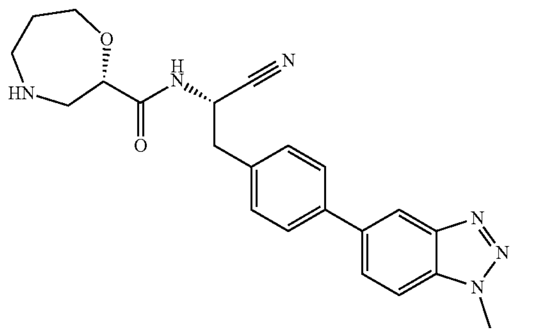

or

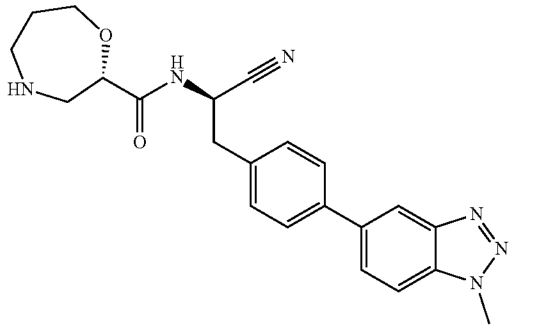

1

Step 1

To acetonitrile (8 mL) and water (2 mL) were added intermediate A (60 mg, 120 μmol), intermediate E (41 mg, 156 μmol), and potassium carbonate (50 mg, 360 μmol). Under nitrogen atmosphere, the reaction mixture was added with [1,1'-bis(diphenylphosphino)ferrocene]dichloropalladium(II) dichloromethane complex (20 mg, 24 μmol). The reaction mixture was heated to 80° C. and reacted for 2 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by silica gel column chromatography (petroleum ether/ethyl acetate, 10/1 to 1/4, V/V) to obtain compound 1-1. MS-ESI calculated for $[M+Na]^+$ 527, found 527.

Step 2

To formic acid (2 mL) was added compound 1-1 (60 mg, 119 μmol), and the reaction mixture was reacted at 50° C. for 10 minutes. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by SFC (separation column: DAICEL CHIRALPAK AD 250 mm×30 mm×10 μm; mobile phase: phase A was supercritical $CO_2$, and phase B was ethanol solution containing 0.1% ammonia water; gradient: phase B 50% to 50%) to obtain compound 1. Then the e.e. values were determined by SFC (chromatographic column: Chiralcel AD-3 50 mm×4.6 mm×3 μm; mobile phase: phase A was supercritical $CO_2$, phase B was ethanol solution containing 0.05% diethylamine; gradient: phase B 5% to 40%).

Compound 1: e.e. %=100.00%, RT=2.547 min. $^1$H NMR (400 MHz, $CDCl_3$) δ 8.23 (s, 1H), 7.77 (d, J=8.4 Hz, 1H), 7.66 (d, J=8.0 Hz, 2H), 7.60 (d, J=8.4 Hz, 1H), 7.45 (d, J=8.0 Hz, 2H), 7.22 (d, J=8.8 Hz, 1H), 5.27-5.19 (m, 1H), 4.35 (s, 3H), 4.13-4.10 (m, 1H), 4.03-3.96 (m, 1H), 3.79-3.71 (m, 1H), 3.34-3.26 (m, 1H), 3.22-3.15 (m, 2H), 3.10-3.03 (m, 1H), 3.02-2.93 (m, 1H), 2.92-2.84 (m, 1H), 1.93-1.77 (m, 2H). MS-ESI calculated for $[M+H]^+$ 405, found 405.

Example 2

Synthetic Route:

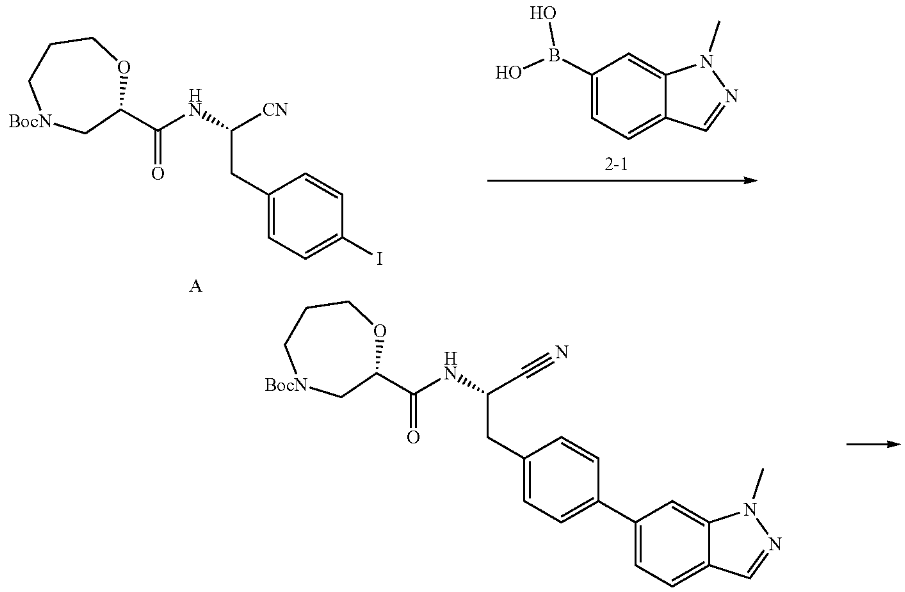

A 2-1

2-2

-continued

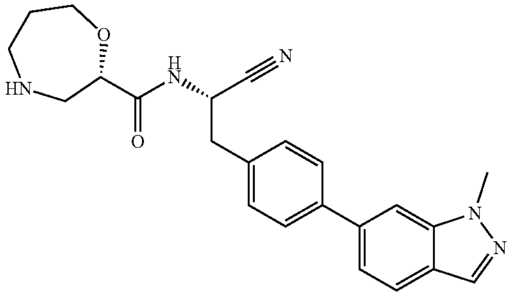

or

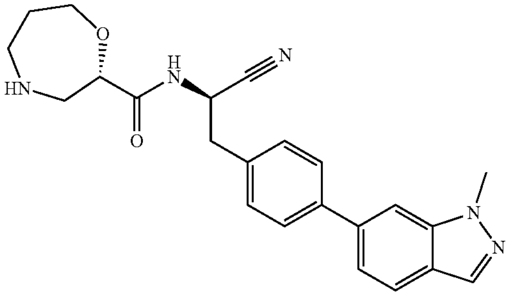

2

Step 1

To acetonitrile (6 mL) and water (2 mL) were added intermediate A (80 mg, 160 μmol), compound 2-1 (42 mg, 240 μmol), and potassium carbonate (66 mg, 480 μmol). Under nitrogen atmosphere, the reaction mixture was added with [1,1'-bis(diphenylphosphino)ferrocene]dichloropalladium(II) dichloromethane complex (26 mg, 32 μmol). The reaction mixture was heated to 80° C. and reacted for 2 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by silica gel column chromatography (petroleum ether/ethyl acetate, 10/1 to 3n, V/V) to obtain compound 2-2. MS-ESI calculated for $[M+Na]^+$ 526, found 526.

Step 2

To formic acid (1.5 mL) and water (0.15 mL) were added compound 2-2 (80 mg, 158 μmol), and the reaction mixture was reacted at 25° C. for 2 hours. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by SFC (separation column: DAICEL CHIRALPAK AD 250 mm×30 mm×10 μm; mobile phase: phase A was supercritical $CO_2$, and phase B was ethanol solution containing 0.1% ammonia water; gradient: phase B 60% to 60%) to obtain compound 2. Then the e.e. values were determined by SFC (chromatographic column: Chiralcel IG-3 50 mm×4.6 mm×3 μm; mobile phase: phase A was supercritical $CO_2$, phase B was ethanol solution containing 0.05% diethylamine; gradient: phase B 5% to 40%).

Compound 2: e.e. %=100.00%, RT=2.759 min. $^1H$ NMR (400 MHz, $CD_3OD$) δ 8.00 (s, 1H), 7.81 (d, J=8.4 Hz, 1H), 7.78-7.68 (m, 3H), 7.48-7.37 (m, 3H), 5.38-5.20 (m, 1H), 4.19-4.11 (m, 1H), 4.10 (s, 3H), 4.02-3.96 (m, 1H), 3.83-3.74 (m, 1H), 3.32-3.15 (m, 3H), 2.98-2.88 (m, 1H), 2.86-2.77 (m, 1H), 2.74-2.65 (m, 1H), 1.99-1.77 (m, 2H). MS-ESI calculated for $[M+H]^+$ 404, found 404.

Example 3

Synthetic Route:

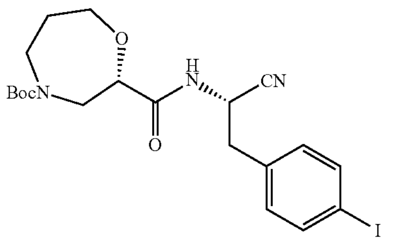

A

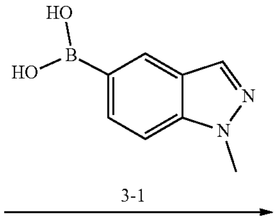

3-1

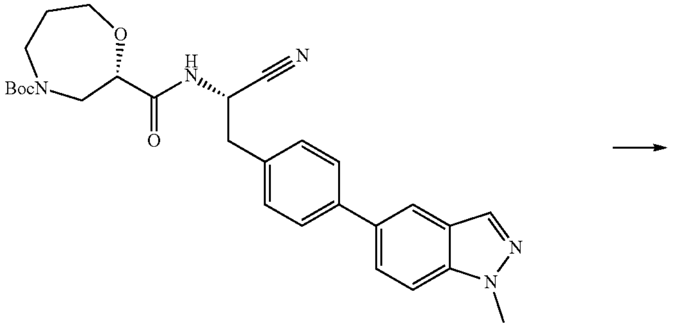

3-1

-continued

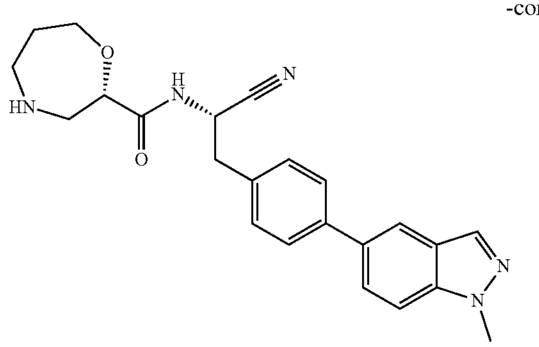

or

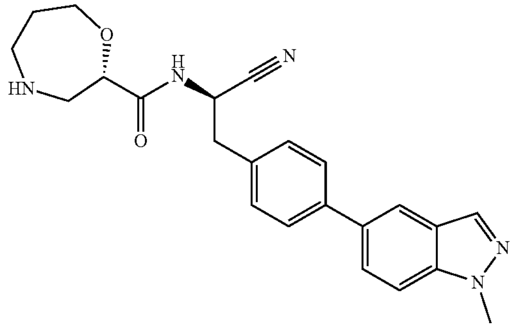

3

Step 1

To acetonitrile (8 mL) and water (2 mL) were added intermediate A (80 mg, 160 μmol), compound 3-1 (42 mg, 240 μmol), and potassium carbonate (66 mg, 480 μmol). Under nitrogen atmosphere, the reaction mixture was added with [1,1'-bis(diphenylphosphino)ferrocene]dichloropalladium(II) dichloromethane complex (26 mg, 32 μmol). The reaction mixture was heated to 80° C. and reacted for 2 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by silica gel column chromatography (dichloromethane/methanol, 100/1 to 20/1, V/V) to obtain compound 3-2. MS-ESI calculated for $[M+Na]^+$ 526, found 526.

Step 2

To formic acid (1.5 mL) and water (0.15 mL) were added compound 3-2 (74 mg, 147 μmol), and the reaction mixture was reacted at 25° C. for 2 hours. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by SFC (separation column: DAICEL CHIRALPAK AD 250 mm×30 mm×10 μm; mobile phase: phase A was supercritical $CO_2$, and phase B was ethanol solution containing 0.1% ammonia water; gradient: phase B 50% to 50%) to obtain compound 3. Then the e.e. values were determined by SFC (chromatographic column: Chiralcel AD-3 50 mm×4.6 mm×3 μm; mobile phase: phase A was supercritical $CO_2$, phase B was ethanol solution containing 0.05% diethylamine; gradient: phase B 5% to 40%).

Compound 3: e.e. %=100.00%, RT=2.456 min. $^1$H NMR (400 MHz, $CD_3OD$) δ 8.05 (s, 1H), 7.97 (s, 1H), 7.74-7.69 (m, 1H), 7.68-7.60 (m, 3H), 7.39 (d, J=8.0 Hz, 2H), 5.14-5.08 (m, 1H), 4.14-4.10 (m, 1H), 4.09 (s, 3H), 4.02-3.93 (m, 1H), 3.82-3.74 (m, 1H), 3.31-3.26 (m, 1H), 3.23-3.15 (m, 2H), 2.93-2.85 (m, 1H), 2.82-2.72 (m, 1H), 2.68-2.61 (m, 1H), 1.95-1.77 (m, 2H). MS-ESI calculated for $[M+H]^+$ 404, found 404.

Example 4

Synthetic Route:

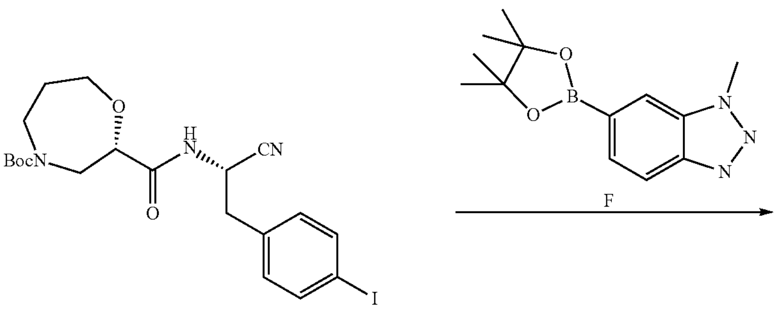

A

-continued

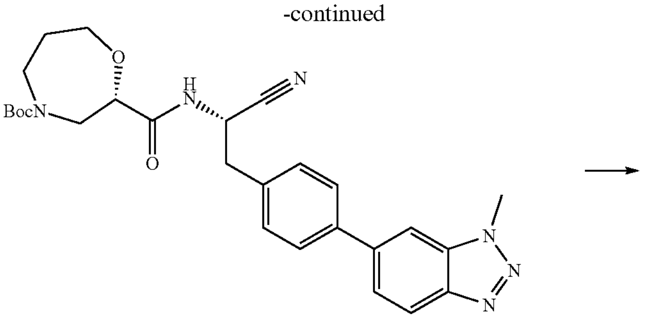

4-1

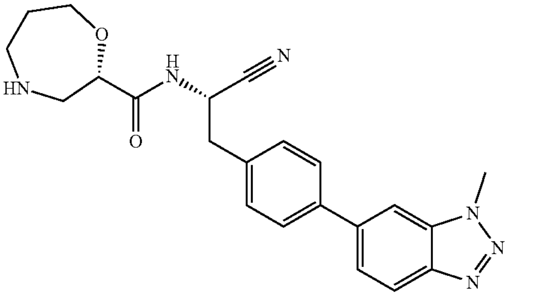

or

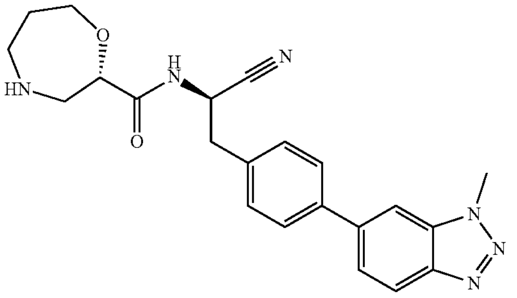

4

Step 1

To acetonitrile (8 mL) and water (2 mL) were added intermediate A (60 mg, 120 μmol), intermediate F (47 mg, 180 μmol), and potassium carbonate (33 mg, 240 μmol). Under nitrogen atmosphere, the reaction mixture was added with [1,1'-bis(diphenylphosphino)ferrocene]dichloropalladium(II) dichloromethane complex (20 mg, 24 μmol). The reaction mixture was heated to 80° C. and reacted for 2 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by silica gel column chromatography (petroleum ether/ethyl acetate, 10/1 to 1/3, V/V) to obtain compound 4-1. MS-ESI calculated for $[M+Na]^+$ 527, found 527.

Step 2

To formic acid (1.5 mL) and water (0.15 mL) were added compound 4-1 (58 mg, 115 μmol), and the reaction mixture was reacted at 25° C. for 2 hours. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by SFC (separation column: DAICEL CHIRALPAK AD 250 mm×30 mm×10 μm; mobile phase: phase A was supercritical $CO_2$, and phase B was ethanol solution containing 0.1% ammonia water; gradient: phase B 50% to 50%) to obtain compound 4. Then the e.e. values were determined by SFC (chromatographic column: Chiralcel AD-3 50 mm×4.6 mm×3 μm; mobile phase: phase A was supercritical $CO_2$, phase B was ethanol solution containing 0.05% diethylamine; gradient: phase B 5% to 40%).

Compound 4: e.e. %=100.00%, RT=2.247 min. $^1H$ NMR (400 MHz, $CDCl_3$) δ 8.12 (d, J=8.8 Hz, 1H), 7.73-7.65 (m, 3H), 7.62 (d, J=8.8 Hz, 1H), 7.46 (d, J=8.0 Hz, 1H), 7.25-7.19 (m, 1H), 5.30-5.18 (m, 1H), 4.36 (s, 3H), 4.15-4.08 (m, 1H), 4.05-3.96 (m, 1H), 3.83-3.72 (m, 1H), 3.38-3.28 (m, 1H), 3.24-3.12 (m, 2H), 3.11-3.03 (m, 1H), 3.02-2.93 (m, 1H), 2.93-2.83 (m, 1H), 1.95-1.77 (m, 2H). MS-ESI calculated for $[M+H]^+$ 405, found 405.

Example 5

Synthetic Route:

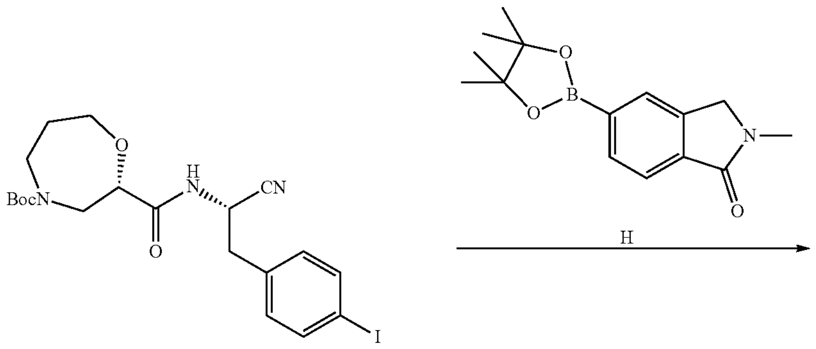

A

-continued

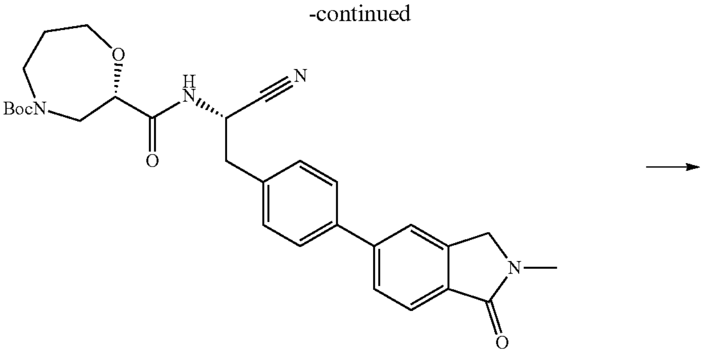

5-1

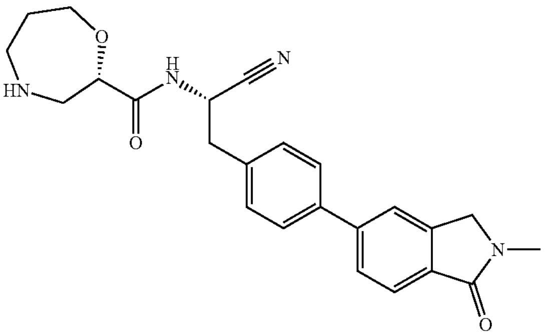

or

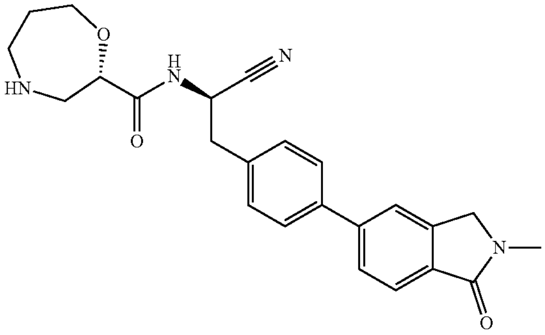

5

Step 1

To acetonitrile (8 mL) and water (2 mL) were added intermediate A (100 mg, 200 μmol), intermediate H (76 mg, 280 μmol), and potassium carbonate (55 mg, 400 μmol). Under nitrogen atmosphere, the reaction mixture was added with [1,1'-bis(diphenylphosphino)ferrocene]dichloropalladium(II) dichloromethane complex (32 mg, 40 μmol). The reaction mixture was heated to 80° C. and reacted for 3 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by thin-layer chromatography (petroleum ether/ethyl acetate, 0/1, V/V) to obtain compound 5-1. MS-ESI calculated for [M+Na]+541, found 541.

Step 2

To formic acid (1.0 mL) and water (0.1 mL) were added compound 5-1 (56 mg, 108 μmol), and the reaction mixture was reacted at 25° C. for 2 hours. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by preparative high performance liquid chromatography (chromatographic column: Waters Xbridge 150 mm×25 mm×5 μm; mobile phase: phase A was an aqueous solution containing 0.05% ammonia monohydrate, and phase B was acetonitrile; gradient: phase B 16% to 46%, 10 min) to obtain compound 5. Then the e.e. values were determined by SFC (chromatographic column: Chiralcel AD-3 50 mm×4.6 mm×3 μm; mobile phase: phase A was supercritical $CO_2$, phase B was isopropanol solution containing 0.05% diethylamine; gradient: phase B 40%).

Compound 5: e.e. %=100.00%, RT=0.747 min. $^1H$ NMR (400 MHz, $CDCl_3$) δ7.91 (d, J=8.0 Hz, 1H), 7.70-7.65 (m, 1H), 7.65-7.60 (m, 3H), 7.43 (d, J=8.0 Hz, 2H), 7.24-7.17 (m, 1H), 5.28-5.16 (m, 1H), 4.45 (s, 2H), 4.14-4.08 (m, 1H), 4.04-3.96 (m, 1H), 3.82-3.71 (m, 1H), 3.37-3.28 (m, 1H), 3.24 (s, 3H), 3.19-3.14 (m, 2H), 3.09-3.03 (m, 1H), 3.01-2.85 (m, 2H), 1.95-1.79 (m, 2H). MS-ESI calculated for $[M+H]^+$ 419, found 419.

Example 6

Synthetic Route:

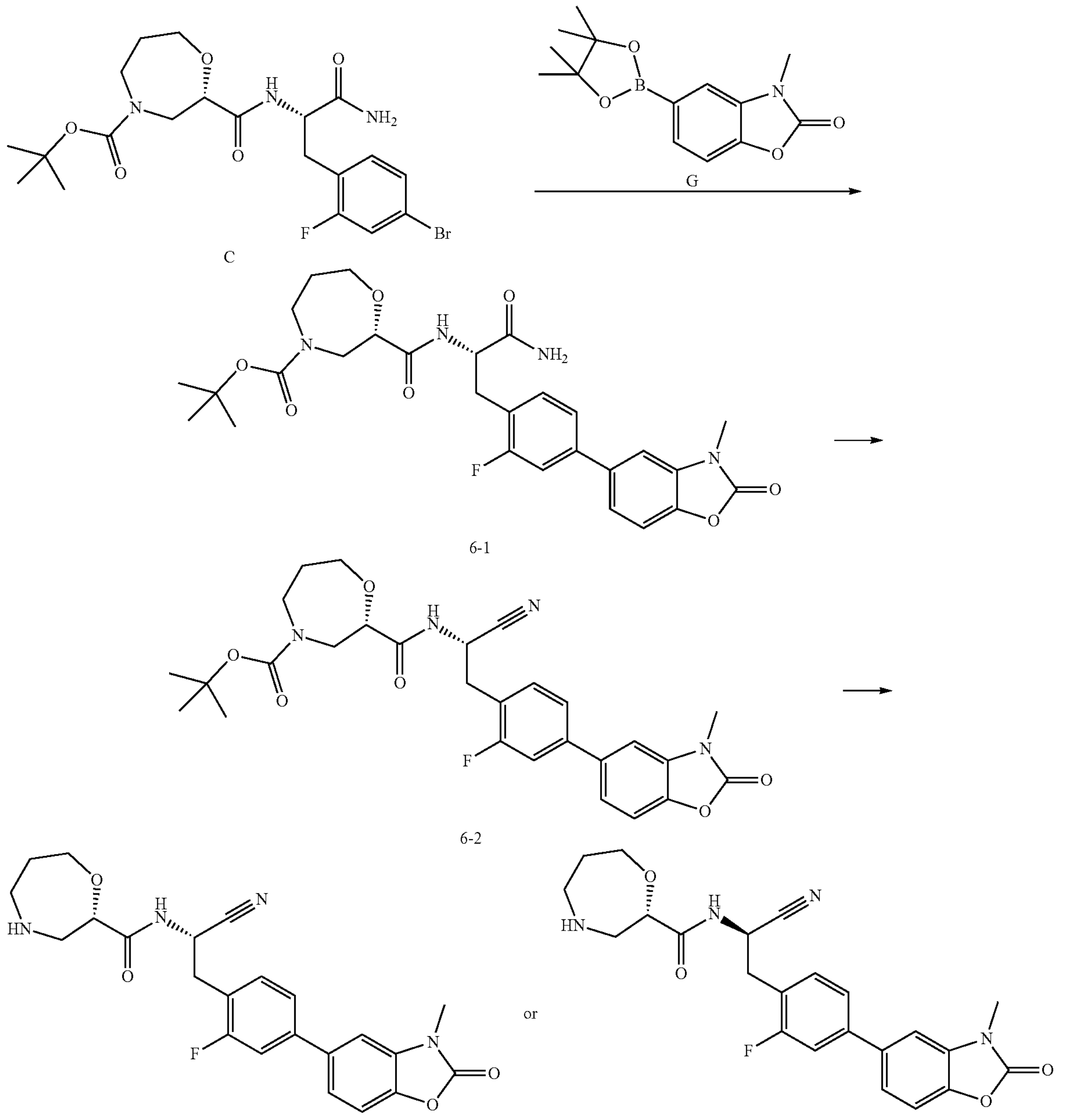

C

G 6-1

6-2 or

6

Step 1

To tetrahydrofuran (8 mL) and water (3 mL) were added intermediate C (80 mg, 164 μmol), intermediate G (90 mg, 328 μmol), and potassium phosphate (104 mg, 491 μmol). Under nitrogen atmosphere, the reaction mixture was added with 1,1'-bis(di-tert-butylphosphino)ferrocene palladium dichloride (21 mg, 32 μmol). The reaction mixture was heated to 60° C. and reacted for 6 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by thin-layer chromatography (developing solvent: dichloromethane/methanol, 20/1, V/V) to obtain compound 6-1. MS-ESI calculated for $[M+H]^+$ 557, found 557.

Step 2

Compound 6-1 (104 mg, 187 μmol) was dissolved in dichloromethane (10 mL). Methyl N-(triethylammoniosulfonyl)carbamate (67 mg, 280 μmol) was added thereto. The reaction mixture was reacted at 25° C. for 12 hours. The reaction mixture was added with water (50 mL) and extracted with ethyl acetate (50 mL×2). The organic phases were combined, dried over anhydrous sodium sulfate, and concentrated under reduced pressure. The obtained crude product containing compound 6-2 was directly used in the next reaction step. MS-ESI calculated for $[M+Na]^+$ 561, found 561.

Step 3

To formic acid (1.7 mL) and water (0.5 mL) were added compound 6-2 (95 mg, 177 μmol), and the reaction mixture was reacted at 25° C. for 2 hours. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by preparative high performance liquid chromatography (chromatographic column: Waters Xbridge 150 mm×25 mm×5 μm; mobile phase: phase A was an aqueous solution containing 0.05% ammonia monohydrate, and phase B was acetonitrile; gradient: phase B 22% to 52%, 10 min) to obtain compound 6. Then the e.e. values were determined by SFC (chromatographic column: Chiralcel OJ-3 50 mm×4.6 mm×3 μm; mobile phase: phase A was supercritical $CO_2$, phase B was ethanol solution containing 0.05% diethylamine; gradient: phase B 5% to 40%).

Compound 6: e.e. %=100.00%, RT=2.123 min. $^1H$ NMR (400 MHz, $CD_3OD$) δ7.51-7.39 (m, 5H), 7.32 (d, J=8.2 Hz, 1H), 5.19-5.14 (m, 1H), 4.15-4.08 (m, 1H), 4.05-3.95 (m, 1H), 3.84-3.74 (m, 1H), 3.46 (s, 3H), 3.29-3.16 (m, 3H), 2.97-2.88 (m, 1H), 2.85-2.75 (m, 1H), 2.70-2.62 (m, 1H), 1.98-1.79 (m, 2H). MS-ESI calculated for $[M+H]^+$ 439, found 439.

Example 7

Synthetic Route:

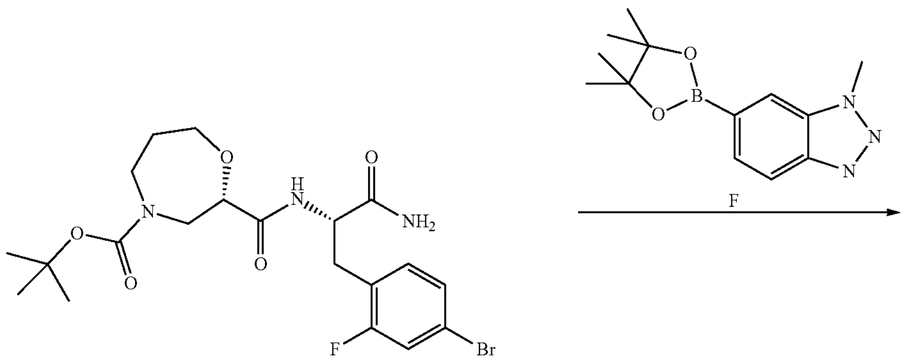

C

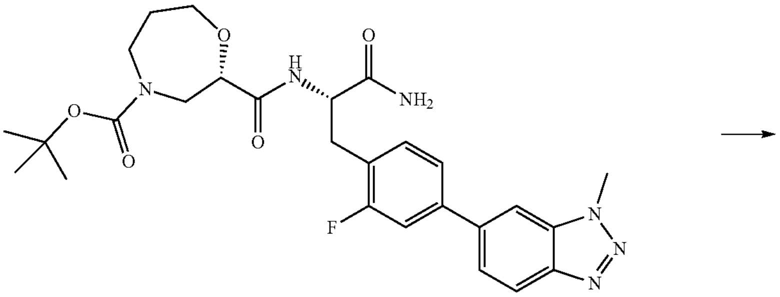

7-1

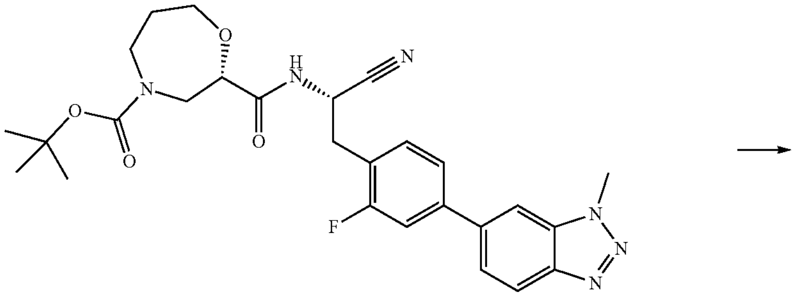

7-2

-continued

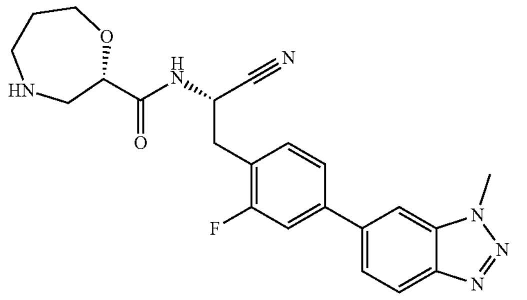

or

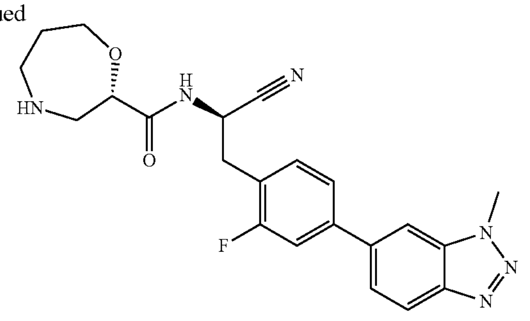

7

Step 1

To tetrahydrofuran (8 mL) and water (3 mL) were added intermediate C (100 mg, 205 μmol), intermediate F (69 mg, 266 μmol), and potassium phosphate (130 mg, 614 μmol). Under nitrogen atmosphere, the reaction mixture was added with 1,1'-bis(di-tert-butylphosphino)ferrocene palladium dichloride (27 mg, 41 μmol). The reaction mixture was heated to 70° C. and reacted for 5 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by silica gel column chromatography (dichloromethane/methanol, 100/1 to 20/1, V/V) to obtain compound 7-1. MS-ESI calculated for $[M+Na]^+$ 563, found 563.

Step 2

Compound 7-1 (110 mg, 203 μmol) was dissolved in dichloromethane (5 mL). Methyl N-(triethylammoniosulfonyl)carbamate (122 mg, 512 μmol) was added thereto. The reaction mixture was reacted at 25° C. for 22 hours. The reaction mixture was added with water (50 mL) and extracted with ethyl acetate (50 mL×2). The organic phases were combined and dried over anhydrous sodium sulfate. The crude product obtained by concentration under reduced pressure was separated by silica gel column chromatography (petroleum ether/ethyl acetate, 10/1 to 1/4, V/V) to obtain compound 7-2. MS-ESI calculated for $[M+Na]^+$ 545, found 545.

Step 3

To formic acid (1.5 mL) and water (0.3 mL) were added compound 7-2 (101 mg, 193 μmol), and the reaction mixture was reacted at 25° C. for 2 hours. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by preparative high performance liquid chromatography (chromatographic column: Phenomenex Gemini-NX 80 mm×40 mm×3 μm; mobile phase: phase A was an aqueous solution containing 0.05% ammonia monohydrate, and phase B was acetonitrile; gradient: phase B 26% to 56%, 8 min) to obtain compound 7. Then the e.e. values were determined by SFC (chromatographic column: Chiralcel AD-3 150 mm×4.6 mm×3 μm; mobile phase: phase A was supercritical $CO_2$, phase B was ethanol solution containing 0.05% diethylamine; gradient: phase B 5% to 40%).

Compound 7: e.e. %=91.78%, RT=6.090 min. $^1H$ NMR (400 MHz, $CD_3OD$) δ 8.10-7.98 (m, 2H), 7.74 (d, J=8.8 Hz, 1H), 7.63-7.53 (m, 2H), 7.48 (t, J=8.0 Hz, 1H), 5.21-5.16 (m, 1H), 4.38 (s, 3H), 4.16-4.09 (m, 1H), 4.06-3.97 (m, 1H), 3.84-3.74 (m, 1H), 3.40-3.24 (m, 2H), 3.23-3.16 (m, 1H), 2.99-2.88 (m, 1H), 2.85-2.74 (m, 1H), 2.70-2.62 (m, 1H), 1.99-1.78 (m, 2H). MS-ESI calculated for $[M+H]^+$ 423, found 423.

Example 8

Synthetic Route:

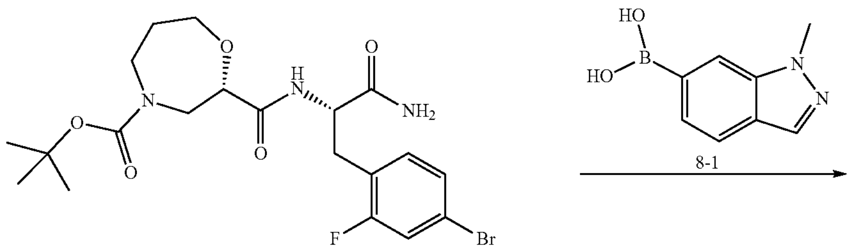

C

-continued

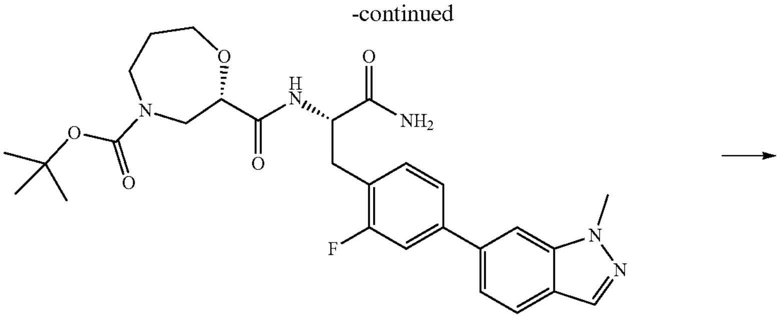

8-2

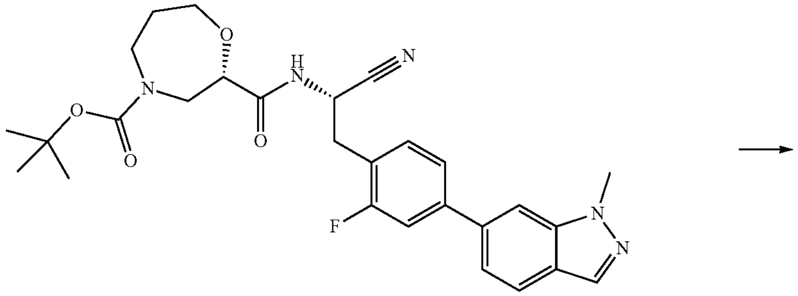

8-3

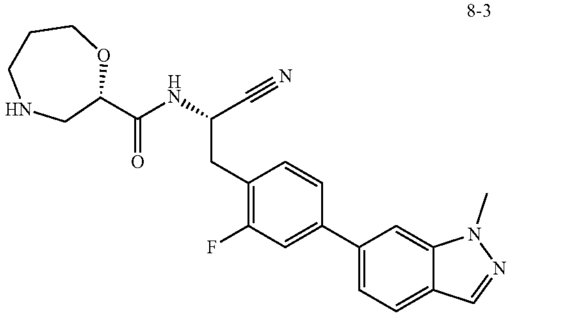

or

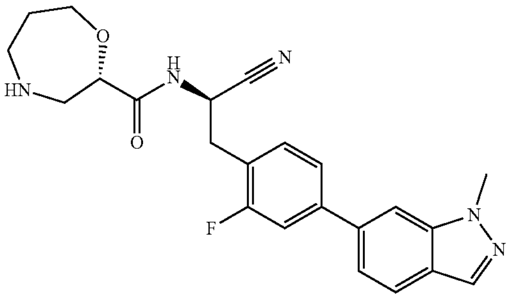

8

Step 1

To acetonitrile (4 mL) and water (1 mL) were added intermediate C (100 mg, 205 μmol), compound 8-1 (43 mg, 245 μmol), and potassium carbonate (85 mg, 614 μmol). Under nitrogen atmosphere, the reaction mixture was added with [1,1'-bis(diphenylphosphino)ferrocene]dichloropalladium(II) dichloromethane complex (33 mg, 41 μmol). The reaction mixture was heated to 80° C. and reacted for 12 hours under nitrogen atmosphere. The reaction mixture was added with water (20 mL) and extracted with ethyl acetate (20 mL×2). The organic phases were combined and dried over anhydrous sodium sulfate. The crude product obtained by concentration under reduced pressure was separated by thin-layer chromatography (developing solvent: petroleum ether/ethyl acetate, 1/1, V/V) to obtain compound 8-2. MS-ESI calculated for $[M+H]^+$ 540, found 540.

Step 2

Compound 8-2 (100 mg, 185 μmol) was dissolved in dichloromethane (6 mL). Methyl N-(triethylammoniosulfonyl)carbamate (66 mg, 278 μmol) was added thereto. The reaction mixture was reacted at 25° C. for 12 hours. The reaction mixture was added with water (50 mL) and extracted with ethyl acetate (50 mL×2). The organic phases were combined and dried over anhydrous sodium sulfate. The crude product obtained by concentration under reduced pressure was separated by silica gel column chromatography (developing solvent: dichloromethane/methanol, 20/1, V/V) to obtain compound 8-3. MS-ESI calculated for $[M-56+H]^+$ 466, found 466.

Step 3

To formic acid (1.5 mL) and water (0.1 mL) were added compound 8-3 (95 mg, 182 μmol), and the reaction mixture was reacted at 40° C. for 12 hours. The reaction mixture was added with saturated sodium bicarbonate solution (30 mL), adjusted to pH=8 to 9 with saturated sodium bicarbonate solution and extracted with dichloromethane (20 mL×2). The organic phases were combined and dried over anhydrous sodium sulfate. The crude product was obtained by concentration under reduced pressure. The crude product was separated by preparative high performance liquid chromatography (chromatographic column: Phenomenex Gemini-NX C18 75 mm×30 mm×3 μm; mobile phase: phase A was an aqueous solution containing 0.05% ammonia monohydrate, and phase B was acetonitrile; gradient: phase B 23% to 53%, 7 min) to obtain compound 8. Then the e.e. values were determined by SFC (chromatographic column: Chiralcel AD-3 50 mm×4.6 mm×3 μm; mobile phase: phase A was supercritical $CO_2$, phase B was ethanol solution containing 0.05% diethylamine; gradient: phase B 5% to 40%).

Compound 8: e.e. %=84.21%, RT=2.200 min. $^1H$ NMR (400 MHz, $CD_3OD$) δ8.00 (s, 1H), 7.87-7.71 (m, 2H), 7.58-7.31 (m, 4H), 5.23-5.15 (m, 1H), 4.16-4.10 (m, 1H), 4.09 (s, 3H), 4.03-3.94 (m, 1H), 3.82-3.73 (m, 1H), 3.39-3.15 (m, 3H), 2.94-2.86 (m, 1H), 2.84-2.73 (m, 1H), 2.69-2.61 (m, 1H), 1.98-1.77 (m, 2H). MS-ESI calculated for $[M+H]^+$ 422, found 422.

Example 9

Synthetic Route:

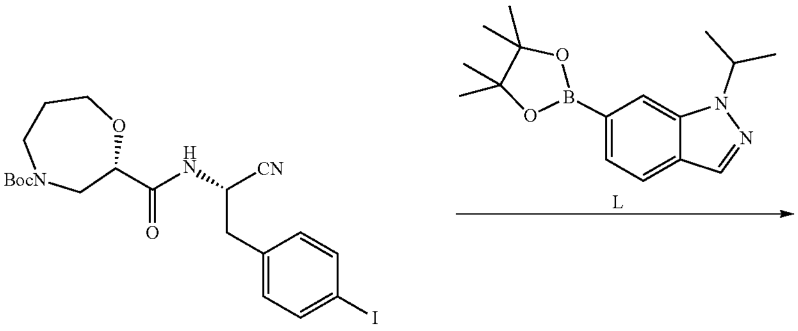

A

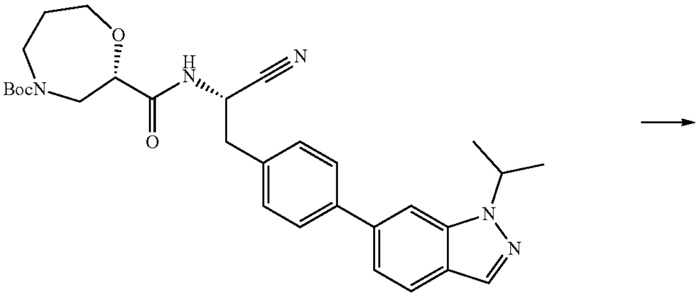

9-1

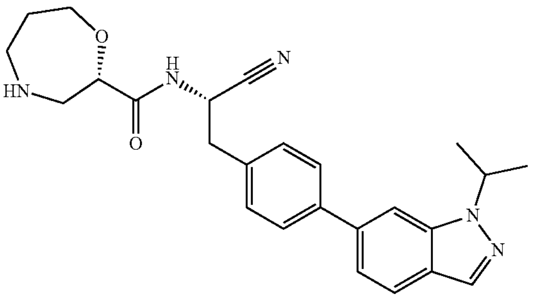

or

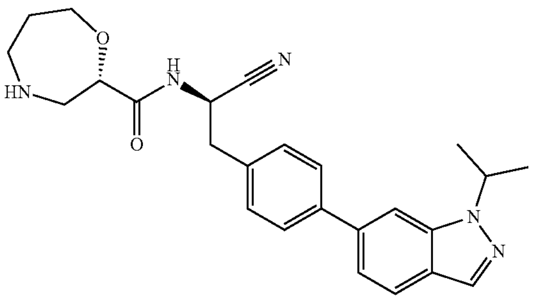

9

Step 1

To acetonitrile (2 mL) and water (0.5 mL) were added intermediate A (250 mg, 874 μmol), intermediate L (392.6 mg, 786 μmol), and potassium carbonate (241 mg, 1.75 mmol). Under nitrogen atmosphere, the reaction mixture was added with [1,1'-bis(diphenylphosphino)ferrocene]dichloropalladium(II) dichloromethane complex (143 mg, 175 μmol). The reaction mixture was heated to 80° C. and reacted for 3 hours under nitrogen atmosphere. The crude product obtained by concentrating the reaction mixture under reduced pressure was separated by silica gel column chromatography (dichloromethane/methanol, 10/1, V/V) to obtain compound 9-1. MS-ESI calculated for $[M+H]^+$ 532, found 532.

Step 2

To formic acid (2.0 mL) and water (0.2 mL) were added compound 9-1 (169 mg, 318 μmol), and the reaction mixture was reacted at 25° C. for 3 hours. The reaction mixture was added with saturated sodium bicarbonate solution (20 mL), adjusted to pH=8 to 9 with saturated sodium bicarbonate solution and extracted with ethyl acetate (10 mL×3). The organic phases were combined, washed with saturated brine (20 mL×2), dried over anhydrous sodium sulfate, and concentrated under reduced pressure to obtain a crude product. The crude product was separated by preparative high performance liquid chromatography (chromatographic column: Welch Ultimate XB-CN 250 mm×50 mm×10 μm; mobile phase: phase A was n-hexane, and phase B was ethanol solution containing 0.1% ammonia monohydrate; gradient: phase B 25% to 65%, 15 min) to obtain compound 9. Then the e.e. values of compound 9 were determined by SFC (chromatographic column: Chiralcel OJ-3 50 mm×4.6 mm I.D., 3 μm; mobile phase: phase A was supercritical $CO_2$, phase B was methanol solution containing 0.05% diethylamine; gradient: phase B 5% to 40%).

Compound 9: e.e. %=93.00%, RT=1.896 min. $^1H$ NMR (400 MHz, $CD_3OD$) δ 8.05 (s, 1H), 7.85-7.77 (m, 2H), 7.73 (d, J=8.3 Hz, 2H), 7.51-7.39 (m, 3H), 5.20-5.13 (m, 1H), 5.12-5.03 (m, 1H), 4.20-4.13 (m, 1H), 4.05-3.95 (m, 1H), 3.85-3.76 (m, 1H), 3.32-3.28 (m, 1H), 3.27-3.18 (m, 2H), 2.98-2.89 (m, 1H), 2.87-2.78 (m, 1H), 2.76-2.67 (m, 1H), 1.98-1.83 (m, 2H), 1.60 (d, J=6.6 Hz, 6H). MS-ESI calculated for $[M+H]^+$ 432, found 432.

Example 10

Synthetic Route:

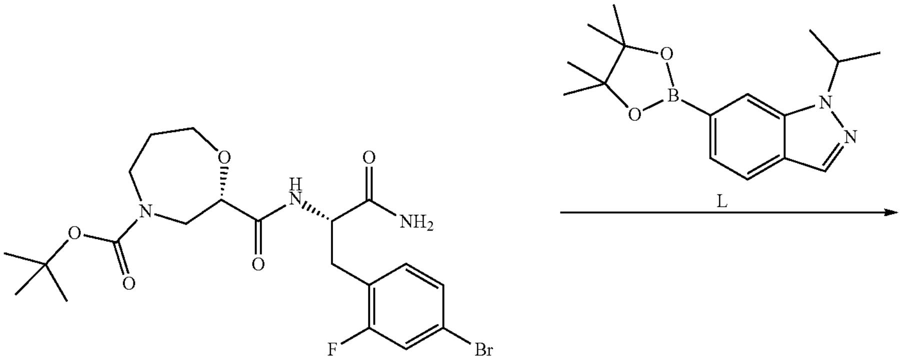

C

L

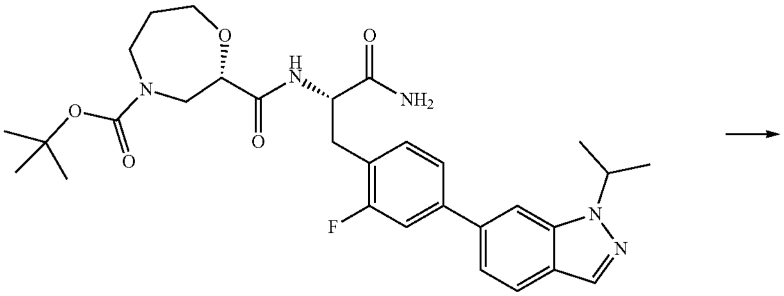

10-1

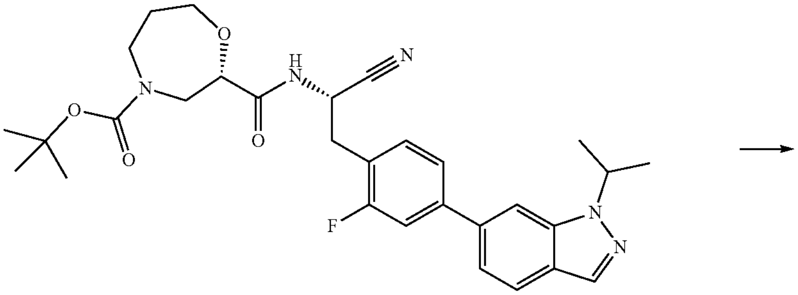

10-2

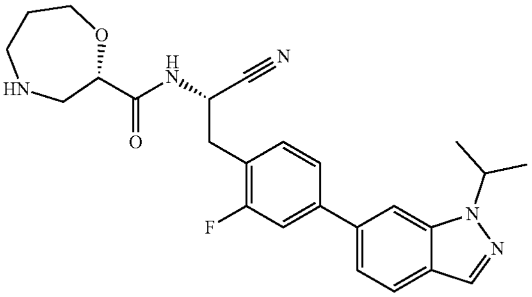

or

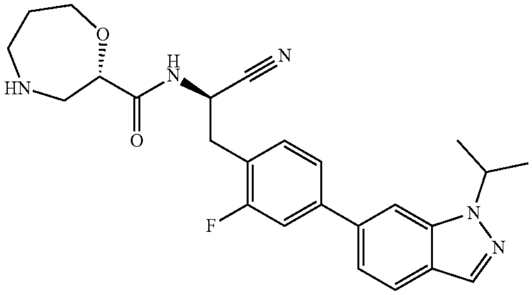

10

Step 1

To tetrahydrofuran (3 mL) and water (1 mL) were added intermediate C (200 mg, 699 μmol), intermediate L (341 mg, 699 μmol), and potassium phosphate (371 mg, 1.75 mmol). Under nitrogen atmosphere, the reaction mixture was added with [1,1'-bis(diphenylphosphino)ferrocene]dichloropalladium(II) dichloromethane complex (143 mg, 175 μmol). The reaction mixture was heated to 80° C. and reacted for 3 hours under nitrogen atmosphere. The crude product obtained by concentrating the reaction mixture under reduced pressure was separated by silica gel column chromatography (dichloromethane/methanol, 10/1, V/V) to obtain compound 10-1. MS-ESI calculated for $[M-56+1]^+$ 512, found 512.

Step 2

To dichloromethane (3 mL) was added compound 10-1 (300 mg, 528 μmol), methyl N-(triethylammoniumsulphonyl)carbamate (309 mg, 1.29 mmol). The reaction mixture was reacted at 25° C. for 12 hours. The reaction mixture was washed with water (10×3 mL) and saturated brine (10×3 mL), dried over anhydrous sodium sulfate, and concentrated under reduced pressure to obtain compound 10-2, which was directly used in the next reaction step. MS-ESI calculated for $[M+H]^+$ 550, found 550.

Step 3

To formic acid (2.0 mL) and water (0.2 mL) were added compound 10-2 (200 mg, 364 μmol), and the reaction mixture was reacted at 25° C. for 3 hours. The reaction mixture was extracted with dichloromethane (5 mL×3). The organic phases were combined, washed with saturated brine (5 mL×2), dried over anhydrous sodium sulfate, and concentrated under reduced pressure to obtain a crude product. The crude product was separated by preparative high performance liquid chromatography (chromatographic column: Unisil 3-100 C18 Ultra 150 mm×50 mm×3 μm; mobile phase: phase A was an aqueous solution containing 0.225% formic acid, and phase B was acetonitrile; gradient: phase B 15% to 45%, 10 min) to obtain the formate of compound 10. Then the e.e. values of the formate of compound 10 were determined by SFC (chromatographic column: Chiralpak AD-3 50 mm×4.6 mm I.D., 3 μm; mobile phase: phase A was supercritical $CO_2$, phase B was methanol solution containing 0.05% diethylamine; gradient: phase B 5% to 40%).

Compound 10: e.e. %=83.46%, RT=1.879 min. $^1H$ NMR (400 MHz, $CD_3OD$) δ 8.10-8.03 (m, 1H), 7.91-7.81 (m, 2H), 7.65-7.43 (m, 4H), 5.24-5.15 (m, 1H), 5.13-5.04 (m, 1H), 4.46-4.35 (m, 1H), 4.16-4.04 (m, 1H), 3.92-3.81 (m, 1H), 3.60-3.47 (m, 1H), 3.42-3.36 (m, 1H), 3.30-3.24 (m, 1H), 3.23-3.13 (m, 1H), 3.08-2.95 (m, 1H), 2.20-1.99 (m, 2H), 1.60 (d, J=6.7 Hz, 6H). MS-ESI calculated for $[M+H]^+$ 450, found 450.

Example 11

Synthetic Route:

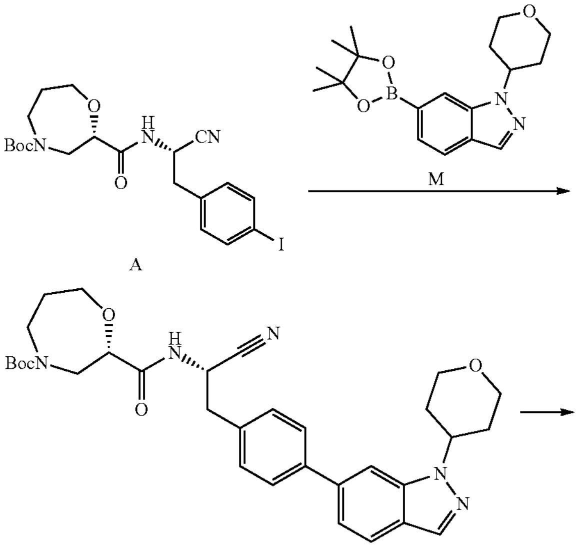

A 11-1

-continued

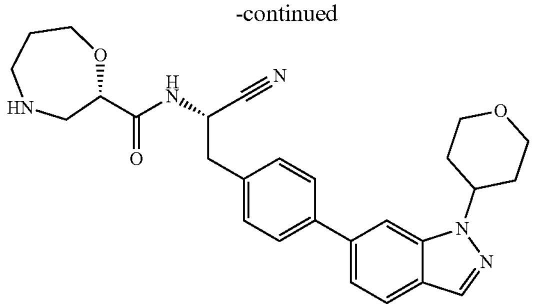

or

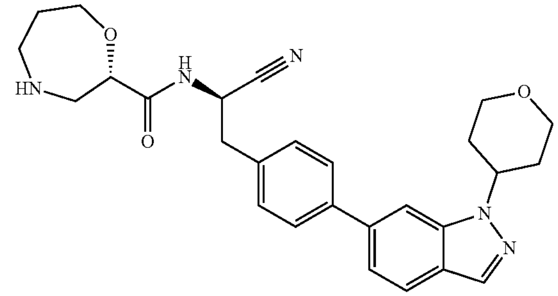

11

Step 1

To acetonitrile (2 mL) and water (0.5 mL) were added intermediate A (250 mg, 762 μmol), intermediate M (342 mg, 685 μmol), and potassium carbonate (210 mg, 1.52 mmol). Under nitrogen atmosphere, the reaction mixture was added with [1,1'-bis(diphenylphosphino)ferrocene]dichloropalladium(II) dichloromethane complex (124 mg, 152 μmol). The reaction mixture was heated to 80° C. and reacted for 3 hours under nitrogen atmosphere. The crude product obtained by concentrating the reaction mixture under reduced pressure was separated by silica gel column chromatography (dichloromethane/methanol, 20/1, V/V) to obtain compound 11-1. MS-ESI calculated for $[M+H]^+$ 574, found 574.

Step 2

To formic acid (2.0 mL) and water (0.2 mL) were added compound 11-1 (100 mg, 174 μmol), and the reaction mixture was reacted at 25° C. for 3 hours. The reaction mixture was quenched with sodium bicarbonate solution (10 mL) and extracted with ethyl acetate (10 mL×3). The organic phases were combined, washed with saturated brine (20 mL×2), dried over anhydrous sodium sulfate and concentrated under reduced pressure to obtain a crude product. The crude product was separated by preparative high performance liquid chromatography (chromatographic column: Waters Xbridge 150 mm×25 mm×5 μm; mobile phase: phase A was an aqueous solution containing 0.05% ammonia monohydrate, and phase B was acetonitrile; gradient: phase B 25% to 55%, 9 min) to obtain compound 11. Then the e.e. values of compound 11 were determined by SFC (chromatographic column: Chiralcel OD-3 50 mm×4.6 mm I.D., 3 μm; mobile phase: phase A was supercritical $CO_2$, phase B was methanol solution containing 0.05% diethylamine; gradient: phase B 5% to 40%).

Compound 11: e.e. %=95.846%, RT=2.026 min. $^1H$ NMR (400 MHz, $CD_3OD$) δ 8.06 (s, 1H), 7.91-7.79 (m, 2H), 7.75 (d, J=7.2 Hz, 2H), 7.54-7.42 (m, 3H), 5.24-5.08 (m, 1H), 4.26-4.08 (m, 3H), 4.06-3.95 (m, 1H), 3.85-3.60 (m, 5H), 3.09-2.66 (m, 5H), 2.50-2.26 (m, 2H), 2.10-1.79 (m, 4H). MS-ESI calculated for $[M+H]^+$ 474, found 474.

Example 12

Synthetic Route:

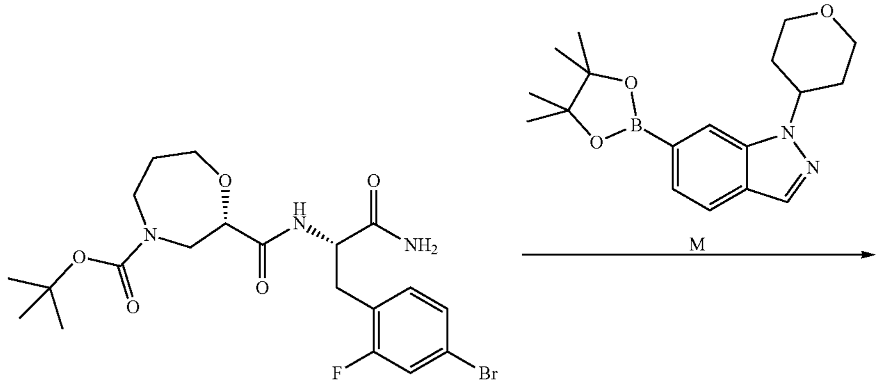

M

C

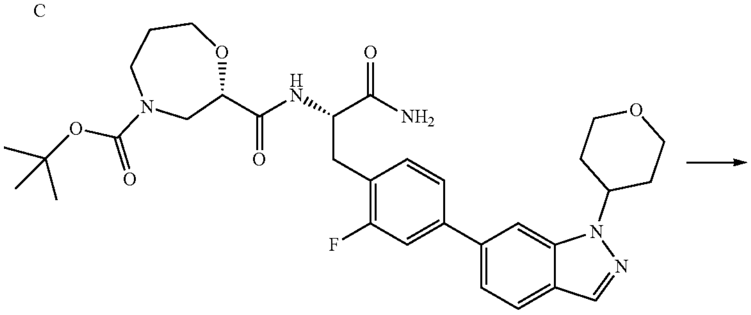

12-1

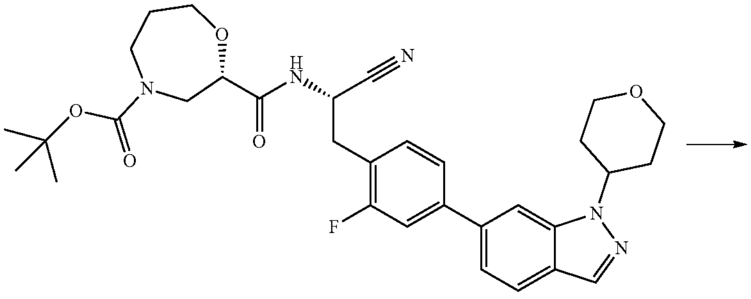

12-2

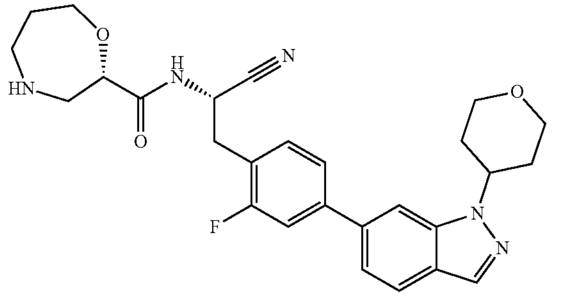

or

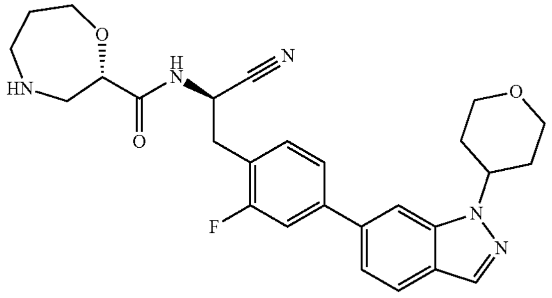

12

Step 1

To tetrahydrofuran (3 mL) and water (1 mL) were added intermediate C (200 mg, 609 μmol), intermediate M (297.58 mg, 609 μmol), and potassium phosphate (323 mg, 1.52 mmol). Under nitrogen atmosphere, the reaction mixture was added with 1,1'-bis(di-tert-butylphosphino)ferrocene palladium dichloride (79 mg, 122 μmol). The reaction mixture was heated to 60° C. and reacted for 12 hours under nitrogen atmosphere. The crude product obtained by concentrating the reaction mixture under reduced pressure was separated by silica gel column chromatography (petroleum ether/ethyl acetate, 5/1 to 0/1, V/V) to obtain compound 12-1. MS-ESI calculated for $[M+H]^+$ 610, found 610.

Step 2

To dichloromethane (3 mL) was added compound 12-1 (107 mg, 176 μmol), methyl N-(triethylammoniumsulphonyl)carbamate (102 mg, 430 μmol). The reaction mixture was reacted at 25° C. for 12 hours. The reaction mixture was washed with water (10x3 mL) and saturated brine (10x3 mL), dried over anhydrous sodium sulfate, and concentrated under reduced pressure to obtain compound 12-2, which was directly used in the next reaction step. MS-ESI calculated for $[M+H]^+$ 592, found 592.

Step 3

To formic acid (2.0 mL) and water (0.2 mL) were added compound 12-2 (90 mg, 152 μmol), and the reaction mixture was reacted at 25° C. for 3 hours. The reaction mixture was quenched with sodium bicarbonate solution (30 mL) and extracted with dichloromethane (20 mLx3). The organic phases were combined, washed with saturated brine (20 mLx2), dried over anhydrous sodium sulfate and concentrated under reduced pressure to obtain a crude product. The crude product was separated by preparative high performance liquid chromatography (chromatographic column: Welch Ultimate XB-CN 250 mmx50 mmx10 μm; mobile phase: phase A was n-hexane, and phase B was ethanol solution containing 0.1% ammonia monohydrate; gradient: phase B 25% to 65%, 15 min) to obtain compound 12. Then the e.e. values of compound 12 were determined by SFC (chromatographic column: Chiralcel OJ-3 50 mmx4.6 mm I.D., 3 μm; mobile phase: phase A was supercritical $CO_2$, phase B was methanol solution containing 0.05% diethylamine; gradient: phase B 5% to 40%).

Compound 12: e.e. %=96.59%, RT=2.110 min. $^1H$ NMR (400 MHz, $CD_3OD$) δ 8.07 (s, 1H), 7.92 (s, 1H), 7.84 (d, J=8.4 Hz, 1H), 7.62-7.52 (m, 2H), 7.50-7.44 (m, 2H), 5.23-5.17 (m, 1H), 5.02-4.92 (m, 1H), 4.20-4.10 (m, 3H), 4.07-3.96 (m, 1H), 3.86-3.68 (m, 3H), 3.41-3.35 (m, 1H), 3.30-3.18 (m, 2H), 2.98-2.89 (m, 1H), 2.86-2.77 (m, 1H), 2.72-2.63 (m, 1H), 2.42-2.27 (m, 2H), 2.03-1.81 (m, 4H). MS-ESI calculated for $[M+H]^+$ 492, found 492.

Example 13

Synthetic Route:

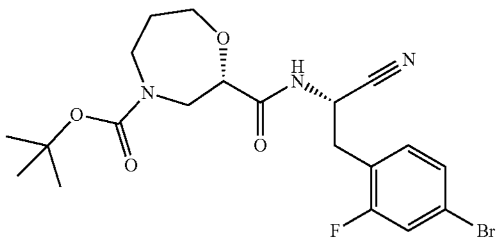

D

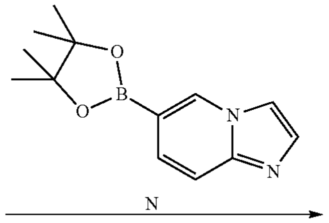

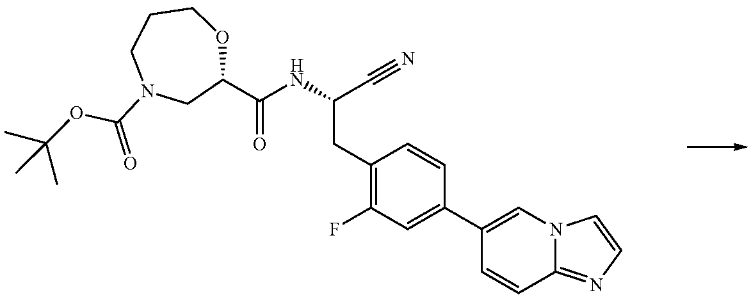

13-1

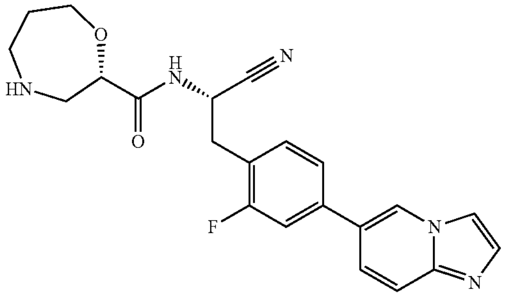

or

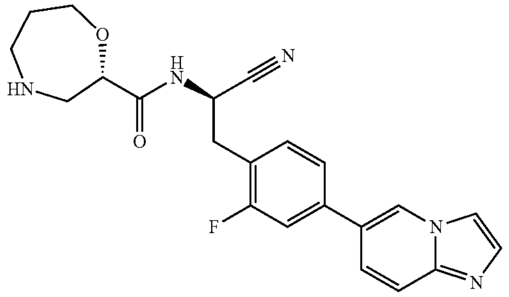

13

Step 1

To tetrahydrofuran (3 mL) and water (1 mL) were added intermediate D (58 mg, 236 μmol), intermediate N (100 mg, 213 μmol), and potassium phosphate (125 mg, 591 μmol). Under nitrogen atmosphere, the reaction mixture was added with 1,1'-bis(di-tert-butylphosphino)ferrocene palladium dichloride (31 mg, 47 μmol). The reaction mixture was heated to 60° C. and reacted for 12 hours under nitrogen atmosphere. The reaction mixture was extracted with ethyl acetate (10 mL×3), washed with saturated brine (10 mL×3), dried over anhydrous sodium sulfate, and then concentrated under reduced pressure. The crude product obtained by concentration under reduced pressure was separated by silica gel column chromatography (dichloromethane/methanol, 10/1, V/V) to obtain compound 13-1. MS-ESI calculated for $[M+H]^+$ 508, found 508.

Step 2

To formic acid (0.5 mL) and water (0.1 mL) were added compound 13-1 (95 mg, 187 μmol), and the reaction mixture was reacted at 25° C. for 3 hours. The reaction mixture was quenched with sodium bicarbonate solution (20 mL) and extracted with dichloromethane (20 mL×3). The organic phases were combined, dried over anhydrous sodium sulfate and concentrated under reduced pressure to obtain a crude product. The crude product was separated by preparative high performance liquid chromatography (chromatographic column: Waters Xbridge 150 mm×25 mm×5 μm; mobile phase: phase A was an aqueous solution containing 0.05% ammonia monohydrate, and phase B was acetonitrile; gradient: phase B 18% to 48%, 9 min) to obtain compound 13. Then the e.e. values of compound 13 were determined by SFC (chromatographic column: Chiralcel OJ-3 50 mm×4.6 mm I.D., 3 μm; mobile phase: phase A was supercritical $CO_2$, phase B was methanol solution containing 0.05% diethylamine; gradient: phase B 5% to 40%).

Compound 13: e.e. %=88.24%, RT=1.769 min. $^1H$ NMR (400 MHz, $CD_3OD$) δ 8.58-8.48 (m, 1H), 7.90 (s, 1H), 7.83 (s, 1H), 7.66-7.55 (m, 3H), 7.50 (t, J=8.0 Hz, 1H), 7.35-7.25 (m, 1H), 5.23-5.17 (m, 1H), 4.22-4.13 (m, 1H), 4.06-3.98 (m, 1H), 3.87-3.78 (m, 1H), 3.50-3.41 (m, 1H), 3.29-3.20 (m, 2H), 3.02-2.78 (m, 2H), 2.75-2.62 (m, 1H), 2.01-1.82 (m, 2H). MS-ESI calculated for $[M+H]^+$ 408, found 408.

Example 14

Synthetic Route:

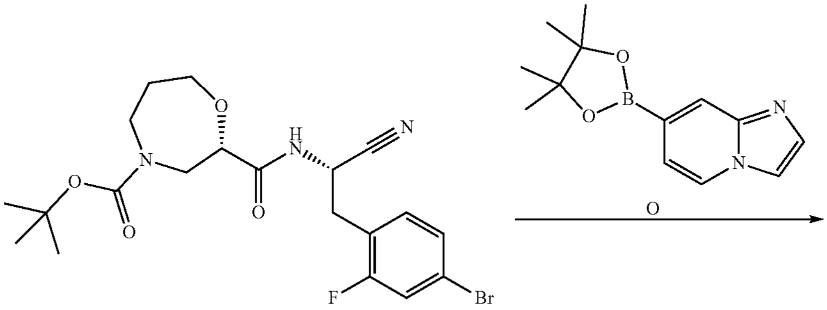

D

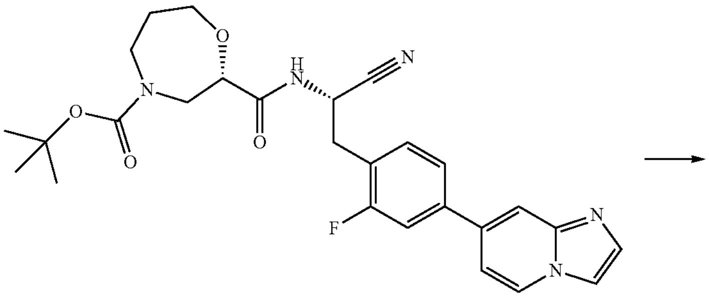

14-1

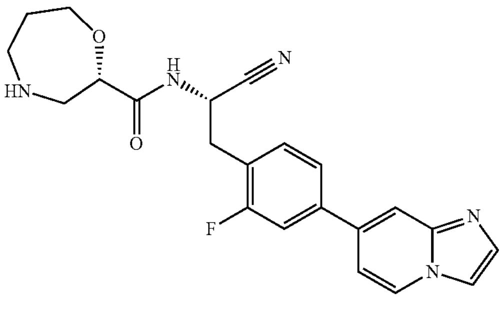

or

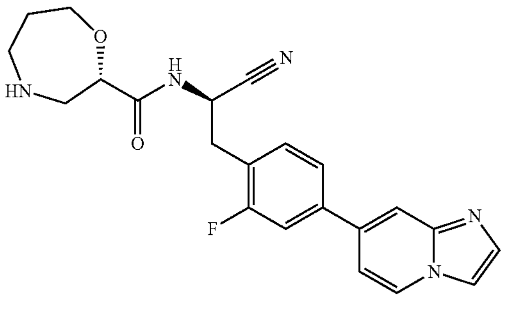

14

Step 1

To tetrahydrofuran (3 mL) and water (1 mL) were added intermediate D (58 mg, 236 μmol), intermediate O (100 mg, 213 μmol), and potassium phosphate (125 mg, 591 μmol). Under nitrogen atmosphere, the reaction mixture was added with 1,1'-bis(di-tert-butylphosphino)ferrocene palladium dichloride (31 mg, 47.25 μmol). The reaction mixture was heated to 60° C. and reacted for 12 hours under nitrogen atmosphere. The reaction mixture was extracted with ethyl acetate (10 mL×3), washed with saturated brine (10 mL×3), dried over anhydrous sodium sulfate, and then concentrated under reduced pressure. The crude product obtained by concentration under reduced pressure was separated by silica gel column chromatography (dichloromethane/methanol, 10/1, V/V) to obtain compound 14. MS-ESI calculated for $[M+H]^+$ 508, found 508.

Step 2

To formic acid (0.5 mL) and water (0.1 mL) were added compound 14-1 (100 mg, 197 μmol), and the reaction mixture was reacted at 25° C. for 3 hours. The reaction mixture was quenched with sodium bicarbonate solution (10 mL) and extracted with ethyl acetate (10 mL×3). The organic phases were washed with saturated brine (20 mL×2), combined, dried over anhydrous sodium sulfate, and concentrated under reduced pressure to obtain a crude product. The crude product was separated by preparative high performance liquid chromatography (chromatographic column: Waters Xbridge 150 mm×25 mm×5 μm; mobile phase: phase A was an aqueous solution containing 0.05% ammonia monohydrate, and phase B was acetonitrile; gradient: phase B 18% to 48%, 9 min) to obtain compound 14. Then the e.e. values of compound 14 were determined by SFC (chromatographic column: Chiralcel OJ-3 50 mm×4.6 mm I.D., 3 μm; mobile phase: phase A was supercritical $CO_2$, phase B was methanol solution containing 0.05% diethylamine; gradient: phase B 5% to 40%).

Compound 14: e.e. %=67%, RT=1.956 min. $^1H$ NMR (400 MHz, $CD_3OD$) δ 8.89-8.76 (m, 1H), 7.93 (d, J=1.3 Hz, 1H), 7.71-7.60 (m, 3H), 7.57-7.44 (m, 3H), 5.25-5.11 (m, 1H), 4.30-4.21 (m, 1H), 4.11-4.00 (m, 1H), 3.88-3.77 (m, 1H), 3.41-3.35 (m, 1H), 3.29-3.23 (m, 2H), 3.17-2.95 (m, 2H), 2.88-2.74 (m, 1H), 2.11-1.87 (m, 2H). MS-ESI calculated for $[M+H]^+$ 408, found 408.

Example 15

Synthetic Route:

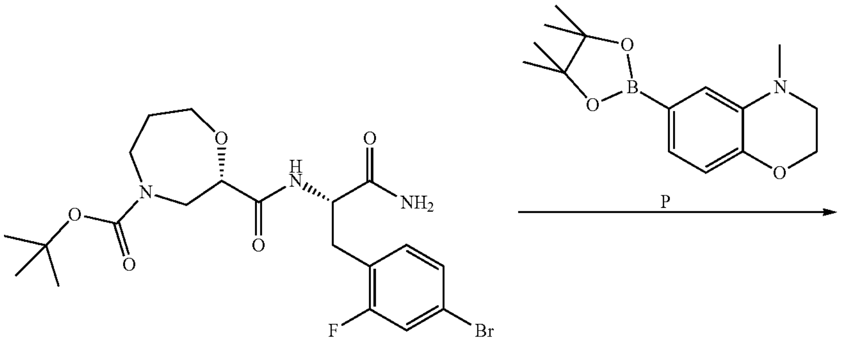

C

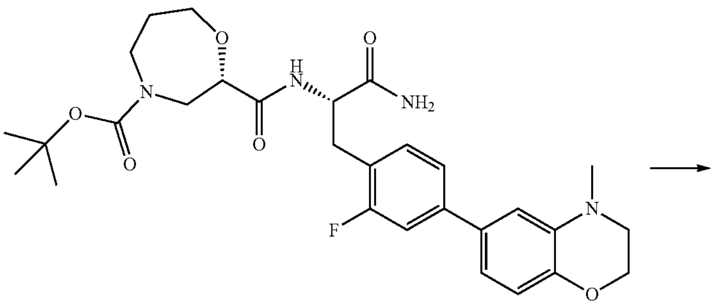

15-1

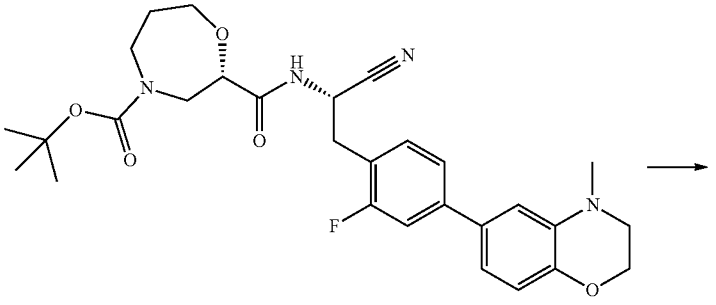

15-2

-continued

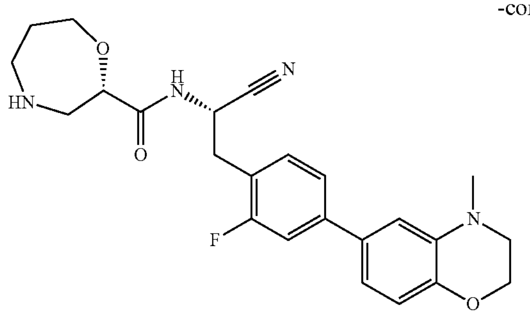

or

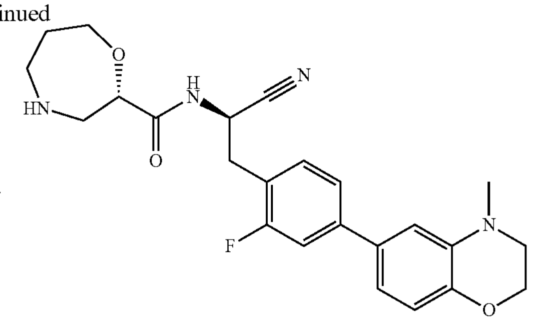

15

Step 1

To tetrahydrofuran (3 mL) and water (1 mL) were added intermediate C (180 mg, 654 μmol), intermediate P (288 mg, 589 μmol), and potassium phosphate (347 mg, 1.64 mmol). Under nitrogen atmosphere, the reaction mixture was added with 1,1'-bis(di-tert-butylphosphino)ferrocene palladium dichloride (85 mg, 131 μmol). The reaction mixture was heated to 60° C. and reacted for 12 hours under nitrogen atmosphere. The crude product obtained by concentrating the reaction mixture under reduced pressure was separated by silica gel column chromatography (dichloromethane/methanol, 10/1, V/V) to obtain compound 15-1. MS-ESI calculated for $[M+H]^+$ 557, found 557.

Step 2

To dichloromethane (3 mL) was added compound 15-1 (196 mg, 351 μmol), methyl N-(triethylammoniumsulphonyl)carbamate (206 mg, 862 μmol). The reaction mixture was reacted at 15° C. for 12 hours. The reaction mixture was washed with water (20×3 mL) and saturated brine (20×3 mL), dried over anhydrous sodium sulfate, and concentrated under reduced pressure to obtain compound 15-2, which was directly used in the next reaction step. MS-ESI calculated for $[M+H]^+$ 539, found 539.

Step 3

To formic acid (0.5 mL) and water (0.1 mL) were added compound 15-2 (100 mg, 186 μmol), and the reaction mixture was reacted at 25° C. for 3 hours. The reaction mixture was added with saturated sodium bicarbonate solution (25 mL) and extracted with dichloromethane (20 mL×3). The organic phases were combined, dried over anhydrous sodium sulfate, and concentrated under reduced pressure to obtain a crude product. The crude product was separated by preparative high performance liquid chromatography (chromatographic column: Phenomenex Synergi C18 150 mm×25 mm×10 μm; mobile phase: phase A was an aqueous solution containing 0.225% formic acid, and phase B was acetonitrile; gradient: phase B 10% to 40%, 10 min) to obtain the formate of compound 15. Then the e.e. values of the formate of compound 15 were determined by SFC (chromatographic column: Chiralpak AD-3 50 mm×4.6 mm I.D., 3 μm; mobile phase: phase A was supercritical $CO_2$, phase B was methanol solution containing 0.05% diethylamine; gradient: phase B 40%).

Compound 15: e.e. %=82.26%, RT=0.879 min. $^1H$ NMR (400 MHz, $CD_3OD$) δ 7.55-7.25 (m, 3H), 6.97-6.83 (m, 2H), 6.76 (d, J=8.3 Hz, 1H), 5.24-5.04 (m, 1H), 4.32-4.26 (m, 2H), 4.24-4.14 (m, 1H), 4.05-3.96 (m, 1H), 3.85-3.77 (m, 1H), 3.32-3.19 (m, 5H), 3.08-2.97 (m, 1H), 2.95 (s, 3H), 2.94-2.88 (m, 1H), 2.82-2.69 (m, 1H), 2.09-1.80 (m, 2H). MS-ESI calculated for $[M+H]^+$ 439, found 439.

Example 16

Synthetic Route:

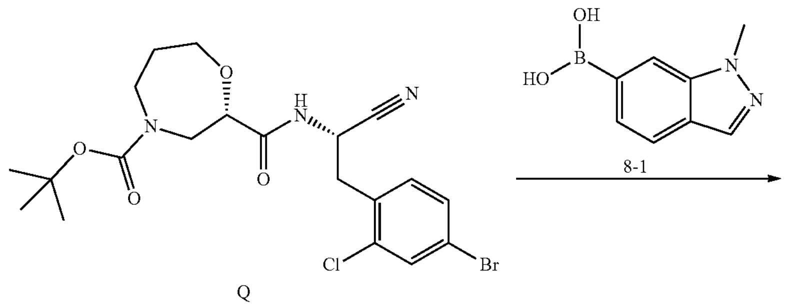

Q

-continued

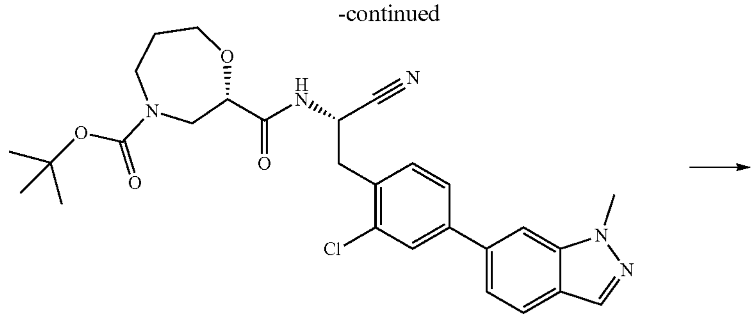

16-1

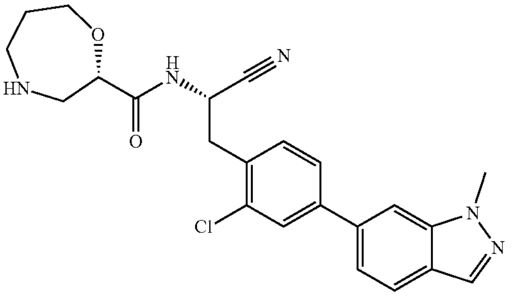

or

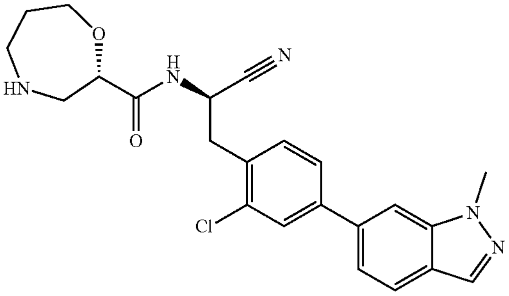

16

Step 1

To tetrahydrofuran (3 mL) and water (1 mL) were added intermediate Q (239 mg, 491 μmol), compound 8-1 (87 mg, 491 μmol), and potassium phosphate (261 mg, 1.23 mmol). Under nitrogen atmosphere, the reaction mixture was added with 1,1'-bis(di-tert-butylphosphino)ferrocene palladium dichloride (64 mg, 98 μmol). The reaction mixture was heated to 70° C. and reacted for 12 hours under nitrogen atmosphere. The reaction mixture was extracted with ethyl acetate (10 mL×3). The organic phases were washed with saturated brine (10 mL×3), combined, dried over anhydrous sodium sulfate. The crude product obtained by concentrating under reduced pressure was separated by silica gel column chromatography (dichloromethane/methanol, 10/1, V/V) to obtained compound 16-1. MS-ESI calculated for $[M-55]^+$ 482, found 482.

Step 2

To formic acid (0.5 mL) and water (0.1 mL) were added compound 16-1 (167 mg, 310 μmol), and the reaction mixture was stirred at 25° C. for 3 hours. The reaction mixture was quenched with sodium bicarbonate solution (10 mL) and extracted with ethyl acetate (10 mL×3). The organic phases were combined, washed with saturated brine (20 mL×2), dried over anhydrous sodium sulfate, and concentrated under reduced pressure to obtain a crude product. The crude product was separated by preparative high performance liquid chromatography (chromatographic column: Waters Xbridge 150 mm×25 mm×5 μm; mobile phase: phase A was an aqueous solution containing 0.05% ammonia monohydrate, and phase B was acetonitrile; gradient: phase B 27% to 57%, 9 min) to obtain compound 16. Then the e.e. values of compound 16 were determined by SFC (chromatographic column: Chiralpak AD-3 50 mm×4.6 mm I.D., 3 μm; mobile phase: phase A was supercritical $CO_2$, phase B was methanol solution containing 0.05% diethylamine; gradient: phase B 40%).

Compound 16: e.e. %=100%, RT=0.790 min. $^1H$ NMR (400 MHz, $CDCl_3$) δ 8.03 (s, 1H), 7.81 (d, J=8.4 Hz, 1H), 7.74 (d, J=1.5 Hz, 1H), 7.63-7.53 (m, 2H), 7.47 (d, J=8.0 Hz, 1H), 7.42-7.31 (m, 2H), 5.32-5.22 (m, 1H), 4.23-4.12 (s, 4H), 4.10-4.03 (m, 1H), 3.85-3.76 (m, 1H), 3.45-3.32 (m, 3H), 3.02-2.92 (m, 3H), 2.07-1.79 (m, 2H). MS-ESI calculated for $[M+H]^+$ 438, found 438.

Example 17

Synthetic Route:

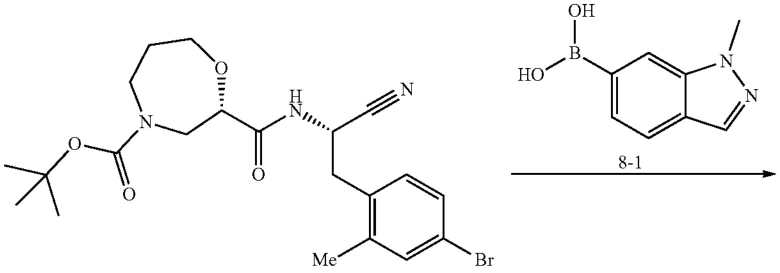

R

-continued

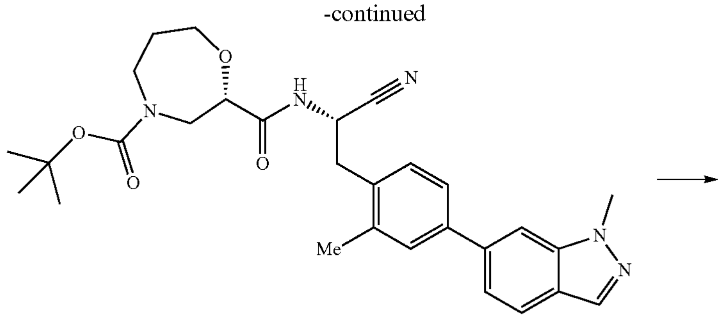

17-1

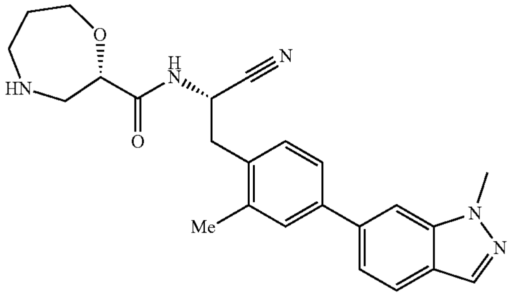

or

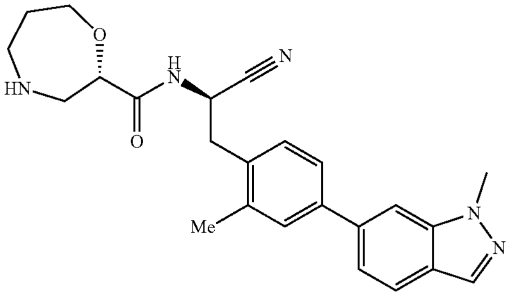

17

Step 1

To tetrahydrofuran (6 mL) and water (3 mL) were added intermediate R (100 mg, 214 μmol), compound 8-1 (75 mg, 428 μmol), and potassium phosphate (159 mg, 751 μmol). Under nitrogen atmosphere, the reaction mixture was added with 1,1'-bis(di-tert-butylphosphino)ferrocene palladium dichloride (28 mg, 43 μmol). The reaction mixture was heated to 70° C. and reacted for 5 hours under nitrogen atmosphere. The reaction mixture was added with water (30 mL) and extracted with ethyl acetate (30 mL×2). The organic phases were combined and dried over anhydrous sodium sulfate. The crude product obtained by concentration under reduced pressure was separated by silica gel column chromatography (petroleum ether/ethyl acetate, 3/2, V/V) to obtain compound 17-1. $^1$H NMR (400 MHz, $CDCl_3$) δ 7.98 (s, 1H), 7.75 (d, J=8.5 Hz, 1H), 7.56-7.46 (m, 3H), 7.39-7.25 (m, 3H), 5.25-5.10 (m, 1H), 4.24-4.00 (m, 6H), 3.83-3.70 (m, 0.5H), 3.58-3.48 (m, 1H), 3.47-3.00 (m, 4.5H), 2.48 (s, 3H), 2.01-1.78 (m, 2H), 1.46 (s, 9H). MS-ESI calculated for $[M+Na]^+$ 540, found 540.

Step 2

To formic acid (1.5 mL) and water (0.15 mL) were added compound 17-1 (80 mg, 154 μmol), and the reaction mixture was stirred at 25° C. for 2 hours. The reaction mixture was quenched with sodium bicarbonate solution (50 mL) and extracted with dichloromethane (50 mL×2). The organic phases were combined, dried over anhydrous sodium sulfate and concentrated under reduced pressure to obtain a crude product. The crude product was separated by preparative high performance liquid chromatography (chromatographic column: Phenomenex C18 80 mm×40 mm×3 μm; mobile phase: phase A was an aqueous solution containing 0.05% ammonia monohydrate, and phase B was acetonitrile; gradient: phase B 37% to 67%, 8 min) to obtain compound 17. Then the e.e. values of compound 17 were determined by SFC (chromatographic column: Chiralpak AD-3 150 mm×4.6 mm I.D., 3 μm; mobile phase: phase A was supercritical $CO_2$, phase B was ethanol solution containing 0.05% diethylamine; gradient: phase B 40%).

Compound 17: e.e. %=100%, RT=2.581 min. $^1$H NMR (400 MHz, MeOD-$d_4$) δ 7.99 (s, 1H), 7.78 (d, J=8.5 Hz, 1H), 7.72 (s, 1H), 7.56 (s, 1H), 7.52 (d, J=7.8 Hz, 1H), 7.45-7.39 (m, 1H), 7.33 (d, J=7.8 Hz, 1H), 5.18-5.13 (m, 1H), 4.14-4.10 (m, 1H), 4.09 (s, 3H), 4.05-3.96 (m, 1H), 3.84-3.75 (m, 1H), 3.39-3.32 (m, 1H), 3.24-3.15 (m, 2H), 2.96-2.85 (m, 1H), 2.83-2.73 (m, 1H), 2.79-2.60 (m, 1H), 2.48 (s, 3H), 1.98-1.79 (m, 2H). MS-ESI calculated for $[M+H]^+$ 418, found 418.

Example 18

Synthetic Route:

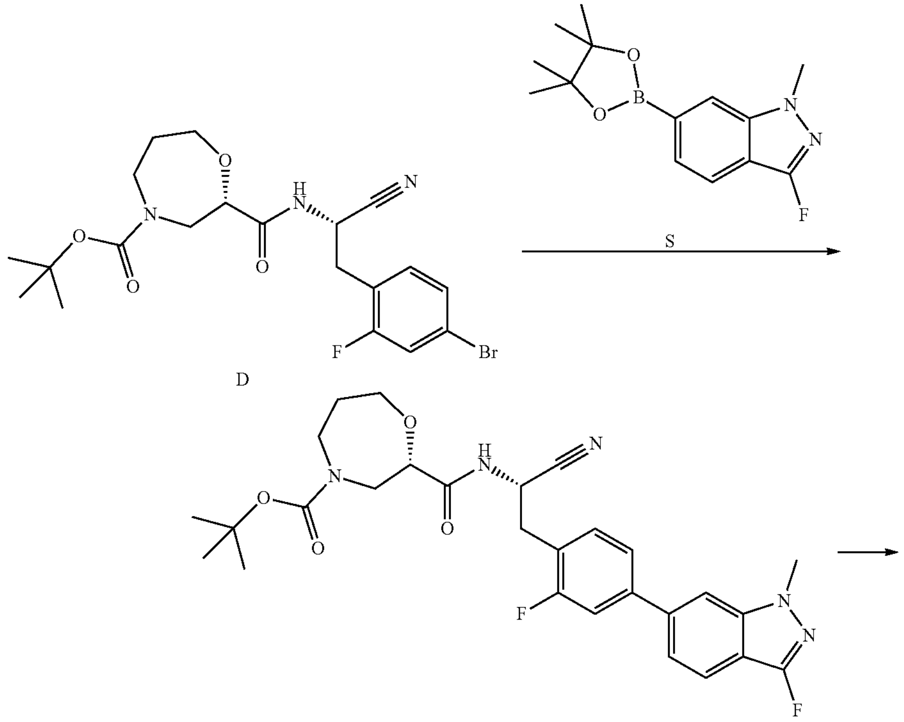

D 18-1

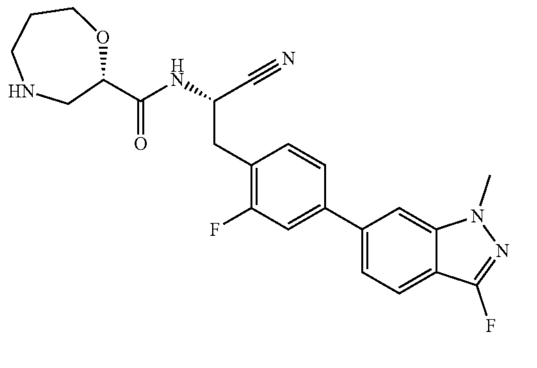

or

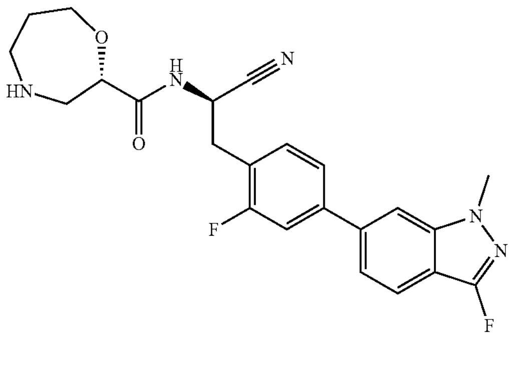

18

Step 1

To THF (6 mL) and water (3 mL) were added intermediate D (50 mg, 106 μmol), intermediate S (33 mg, 117 μmol), and potassium phosphate (56 mg, 266 μmol). Under nitrogen atmosphere, the reaction mixture was added with 1,1'-bis(di-tert-butylphosphino)ferrocene palladium dichloride (14 mg, 22 μmol). The reaction mixture was heated to 70° C. and reacted for 5 hours under nitrogen atmosphere. The crude product obtained by concentrating the reaction mixture under reduced pressure was separated by silica gel column chromatography (petroleum ether/ethyl acetate, 1/1, V/V) to obtain compound 18-1. $^1$H NMR (400 MHz, $CDCl_3$) δ 7.70 (d, J=8.3 Hz, 1H), 7.49-7.31 (m, 5H), 7.26 (d, J=7.5 Hz, 1H), 5.27-5.11 (m, 1H), 4.22-4.00 (m, 3.5H), 3.96 (s, 3H), 3.81-3.70 (m, 0.5H), 3.61-3.42 (m, 1.5H), 3.32-3.05 (m, 3.5H), 2.04-1.85 (m, 2H), 1.45 (s, 9H). MS-ESI calculated for $[M+Na]^+$ 562, found 562.

Step 2

To formic acid (1.5 mL) and water (0.15 mL) were added compound 18-1 (84 mg, 155 μmol), and the reaction mixture was reacted at 25° C. for 2 hours. The reaction mixture was added with saturated sodium bicarbonate solution (20 mL), adjusted to pH=8 with saturated sodium bicarbonate solution and extracted with dichloromethane (70 mL×3). The organic phases were combined and dried over anhydrous sodium sulfate. The crude product was obtained by concentration under reduced pressure. The crude product was separated by preparative high performance liquid chromatography (chromatographic column: Phenomenex C18 80 mm×40 mm×3 μm; mobile phase: phase A was an aqueous solution containing 0.05% ammonia monohydrate, and phase B was acetonitrile; gradient: phase B 42% to 72%, 8 min) to obtain compound 18. Then the e.e. values of compound 18 were determined by SFC (chromatographic column: Chiralcel OJ-3 50 mm×4.6 mm I.D., 3 μm; mobile phase: phase A was supercritical $CO_2$, phase B was ethanol solution containing 0.05% diethylamine; gradient: phase B 5% to 40%).

Compound 18: e.e. %=100.00%, RT=3.989 min. $^1$H NMR (400 MHz, $CD_3OD$) δ 7.72 (d, J=11.0 Hz, 2H), 7.58-7.49 (m, 2H), 7.49-7.42 (m, 2H), 5.22-5.14 (m, 1H), 4.17-4.09 (m, 1H), 4.05-3.90 (m, 4H), 3.84-3.75 (m, 1H), 3.39-3.33 (m, 1H), 3.30-3.24 (m, 1H), 3.23-3.15 (m, 1H), 2.98-2.86 (m, 1H), 2.84-2.73 (m, 1H), 2.70-2.60 (m, 1H), 1.99-1.78 (m, 2H). MS-ESI calculated for $[M+H]^+$ 440, found 440.

Example 19

Synthetic Route:

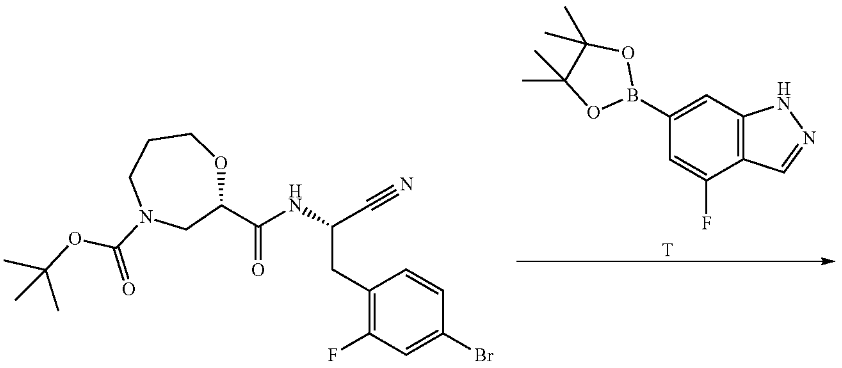

D

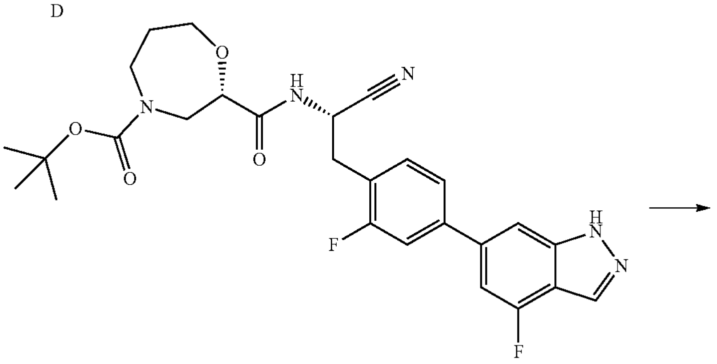

19-1

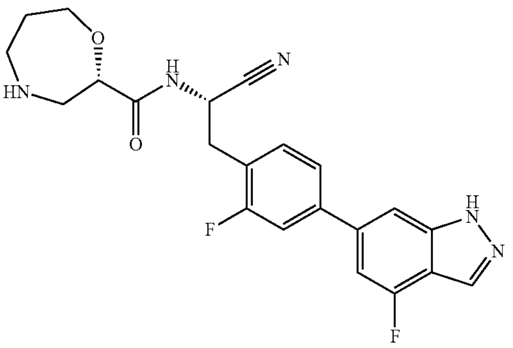

or

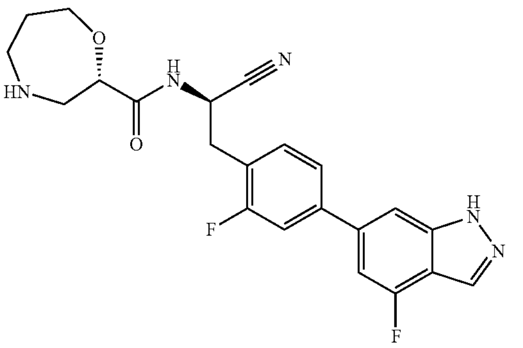

19

Step 1

To THF (6 mL) and water (3 mL) were added intermediate D (50 mg, 106 μmol), intermediate T (56 mg, 212 μmol), and potassium phosphate (68 mg, 319 μmol). Under nitrogen atmosphere, the reaction mixture was added with 1,1'-bis(di-tert-butylphosphino)ferrocene palladium dichloride (14 mg, 22 μmol). The reaction mixture was heated to 70° C. and reacted for 3 hours under nitrogen atmosphere. The crude product obtained by concentrating the reaction mixture under reduced pressure was separated by silica gel column chromatography (petroleum ether/ethyl acetate, 10/7, V/V) to obtain compound 19-1. $^1$H NMR (400 MHz, $CDCl_3$) δ 8.16 (s, 1H), 7.47-7.30 (m, 5H), 7.00 (d, J=10.8 Hz, 1H), 5.30-5.13 (m, 1H), 4.18-4.09 (m, 3H), 3.83-3.71 (m, 0.5H), 3.61-3.47 (m, 1.5H), 3.44-3.07 (m, 4H), 2.00-1.89 (m, 2H), 1.46 (s, 9H). MS-ESI calculated for $[M+Na]^+$ 548, found 548.

Step 2

To formic acid (1.5 mL) and water (0.15 mL) were added compound 19-1 (30 mg, 57 μmol), and the reaction mixture was reacted at 25° C. for 2 hours. The reaction mixture was added with saturated sodium bicarbonate solution (20 mL), adjusted to pH=8 with saturated sodium bicarbonate solution and extracted with dichloromethane (30 mL×2). The organic phases were combined, dried over anhydrous sodium sulfate, and concentrated under reduced pressure to obtain a crude product. The crude product was separated by preparative high performance liquid chromatography (chromatographic column: Phenomenex C18 80×40 mm×3 μm; mobile phase: phase A was an aqueous solution containing 0.05% ammonia monohydrate, and phase B was acetonitrile; gradient: phase B 36% to 66%, 8 min) to obtain compound 19. Then the e.e. values of compound 19 were determined by SFC (chromatographic column: Chiralcel OJ-3 100 mm×4.6 mm I.D., 3 μm; mobile phase: phase A was supercritical $CO_2$, phase B was ethanol solution containing 0.05% diethylamine; gradient: phase B 5% to 40%).

Compound 19: e.e. %=100.00%, RT=3.563 min. $^1H$ NMR (400 MHz, $CD_3OD$) δ 8.13 (s, 1H), 7.59 (s, 1H), 7.54-7.42 (m, 3H), 7.14 (d, J=11.3 Hz, 1H), 5.23-5.13 (m, 1H), 4.16-4.08 (m, 1H), 4.04-3.94 (m, 1H), 3.84-3.74 (m, 1H), 3.39-3.33 (m, 1H), 3.29-3.22 (m, 1H), 3.21-3.15 (m, 1H), 2.97-2.86 (m, 1H), 2.84-2.74 (m, 1H), 2.68-2.60 (m, 1H), 1.98-1.79 (m, 2H). MS-ESI calculated for $[M+H]^+$ 426, found 426.

Example 20

Synthetic Route:

Step 1

To dioxane (6 mL) and water (3 mL) were added intermediate D (47 mg, 100 μmol), intermediate U (51 mg, 200 μmol), and potassium carbonate (35 mg, 250 μmol). Under nitrogen atmosphere, the reaction mixture was added with [1,1'-bis(diphenylphosphino)ferrocene]dichloropalladium (II) dichloromethane complex (16 mg, 20 μmol). The reaction mixture was heated to 80° C. and reacted for 8 hours under nitrogen atmosphere. The crude product obtained by concentrating the reaction mixture under reduced pressure was separated by silica gel column chromatography (petroleum ether/ethyl acetate, 0/1, V/V) to obtain compound 20-1. MS-ESI calculated for $[M+H]^+$ 522, found 522.

Step 2

To formic acid (1.5 mL) and water (0.15 mL) were added compound 20-1 (31 mg, 59 μmol), and the reaction mixture was reacted at 25° C. for 5 hours. The reaction mixture was added with saturated sodium bicarbonate solution (20 mL), adjusted to pH=8 with saturated sodium bicarbonate solution and extracted with dichloromethane (30 mL×2). The organic phases were combined, dried over anhydrous sodium sulfate, and concentrated under reduced pressure to obtain a crude product. The crude product was separated by preparative high performance liquid chromatography (chromatographic column: Phenomenex Gemini-NX 80 mm×40 mm×3 μm; mobile phase: phase A was an aqueous solution

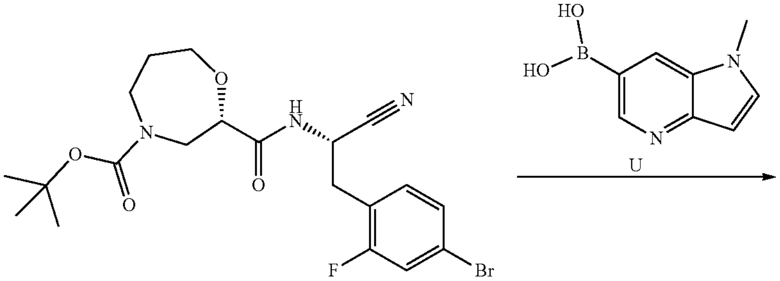

D

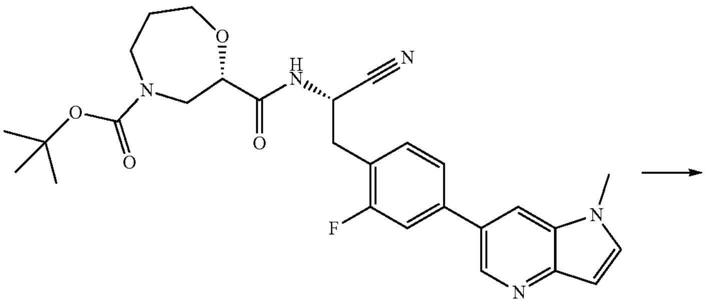

20-1

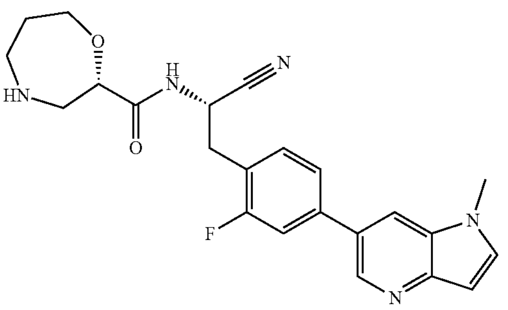

or

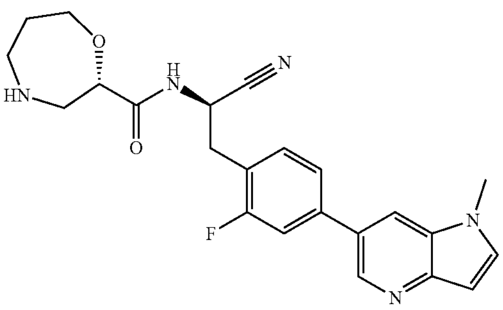

20 containing 0.05% ammonia monohydrate, and phase B was acetonitrile; gradient: phase B 33% to 63%, 8 min) to obtain compound 20. Then the e.e. values of compound 20 were determined by SFC (chromatographic column: Chiralcel AD-3 50 mm×4.6 mm I.D., 3 μm; mobile phase: phase A was supercritical $CO_2$, phase B was ethanol solution containing 0.05% diethylamine; gradient: phase B 40%).

Compound 20: e.e. %=99.46%, RT=0.598 min. $^1$H NMR (400 MHz, $CD_3OD$) δ 8.60 (d, J=1.5 Hz, 1H), 8.15 (s, 1H), 7.63-7.42 (m, 4H), 6.62 (d, J=3.0 Hz, 1H), 5.16-5.08 (m, 1H), 4.13-3.99 (m, 2H), 3.93 (s, 3H), 3.83-3.74 (m, 1H), 3.38-3.32 (m, 1H), 3.30-3.23 (m, 2H), 3.01-2.91 (m, 1H), 2.91-2.79 (m, 2H), 1.98-1.79 (m, 2H). MS-ESI calculated for [M+H]*422, found 422.

Example 21

Synthetic Route:

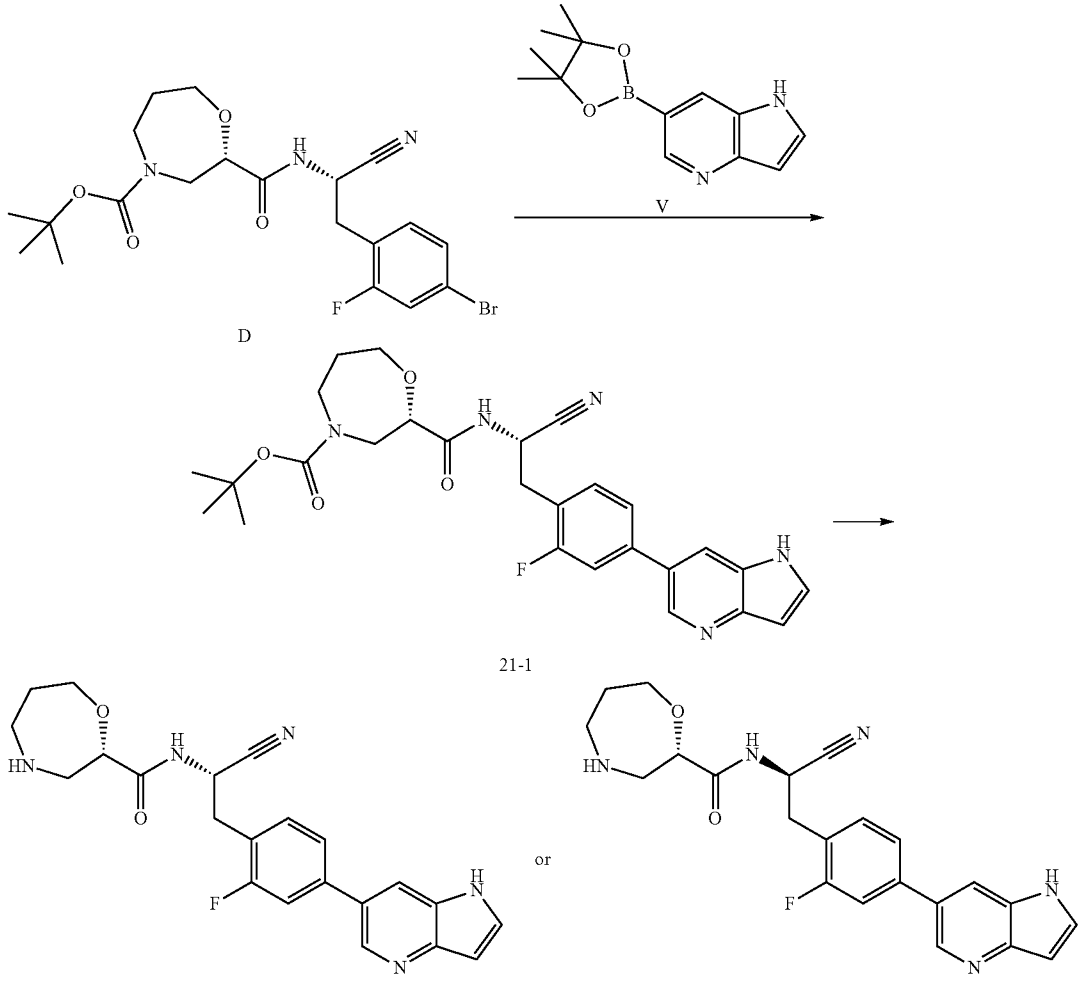

D 21-1 or

21

Step 1

To dioxane (10 mL) and water (5 mL) were added intermediate D (50 mg, 105 μmol), intermediate V (49 mg, 200 μmol), and potassium carbonate (58 mg, 421 μmol). Under nitrogen atmosphere, the reaction mixture was added with [1,1'-bis(diphenylphosphino)ferrocene]dichloropalladium(II) dichloromethane complex (17 mg, 21 μmol). The reaction mixture was heated to 85° C. and reacted for 12 hours under nitrogen atmosphere. The crude product obtained by concentrating the reaction mixture under reduced pressure was separated by silica gel column chromatography (dichloromethane/methanol, 20/1 to 10/1, V/V) to obtain compound 21-1. MS-ESI calculated for $[M+H]^+$ 508, found 508.

Step 2

To formic acid (1.5 mL) and water (0.15 mL) were added compound 21-1 (180 mg, 354 μmol), and the reaction mixture was reacted at 25° C. for 2 hours. The reaction mixture was added with saturated sodium bicarbonate solution (20 mL), adjusted to pH=8 with saturated sodium bicarbonate solution and extracted with dichloromethane (30 mL×2). The organic phases were combined, dried over anhydrous sodium sulfate, and concentrated under reduced pressure to obtain a crude product. The crude product was separated by preparative high performance liquid chromatography (chromatographic column: Phenomenex Gemini-NX 80 mm×40 mm×3 μm; mobile phase: phase A was an aqueous solution containing 0.05% ammonia monohydrate, and phase B was acetonitrile; gradient: phase B 32% to 62%, 8 min) to obtain compound 21. Then the e.e. values of compound 21 were determined by SFC (chromatographic column: Chiralcel OJ-3 100 mm×4.6 mm I.D., 3 μm; mobile phase: phase A was supercritical $CO_2$, phase B was ethanol solution containing 0.05% diethylamine; gradient: phase B 5% to 40%).

Compound 21: e.e. %=98.58%, RT=3.576 min. $^1$H NMR (400 MHz, $CD_3OD$) δ8.58 (d, J=1.8 Hz, 1H), 8.06 (d, J=1.0 Hz, 1H), 7.64 (d, J=3.3 Hz, 1H), 7.54-7.43 (m, 3H), 6.64 (d, J=3.3 Hz, 1H), 5.23-5.15 (m, 1H), 4.14-4.09 (m, 1H), 4.04-3.96 (m, 1H), 3.84-3.75 (m, 1H), 3.39-3.33 (m, 1H), 3.30-3.23 (m, 1H), 3.22-3.15 (m, 1H), 2.97-2.88 (m, 1H), 2.83-2.74 (m, 1H), 2.68-2.60 (m, 1H), 1.98-1.79 (m, 2H). MS-ESI calculated for $[M+H]^+$ 408, found 408.

Example 22

Synthetic Route:

The crude product obtained by concentrating the reaction mixture under reduced pressure was separated by silica gel column chromatography (petroleum ether/ethyl acetate, 10/7, V/V) to obtain compound 22-1. $^1$H NMR (400 MHz, $CDCl_3$) δ 8.03 (s, 1H), 7.79 (d, J=8.3 Hz, 1H), 7.58 (s, 1H), 7.50-7.43 (m, 1H), 7.43-7.33 (m, 3H), 7.23 (d, J=8.5 Hz, 1H), 5.27-5.13 (m, 1H), 4.69-4.58 (m, 1H), 4.43-4.21 (m, 2H), 4.21-4.13 (m, 1H), 4.09-4.01 (m, 1H), 3.78-3.69 (m, 0.5H), 3.60-3.44 (m, 1.5H), 3.42-3.19 (m, 3.5H), 3.17-3.08 (m, 0.5H), 3.06-2.90 (m, 2H), 2.35-2.19 (m, 2H), 2.09-2.04 (m, 2H), 2.03-1.99 (m, 1H), 1.99-1.87 (m, 2H), 1.49 (s, 9H), 1.45 (s, 9H). MS-ESI calculated for $[M+Na]^+$ 713, found 713.

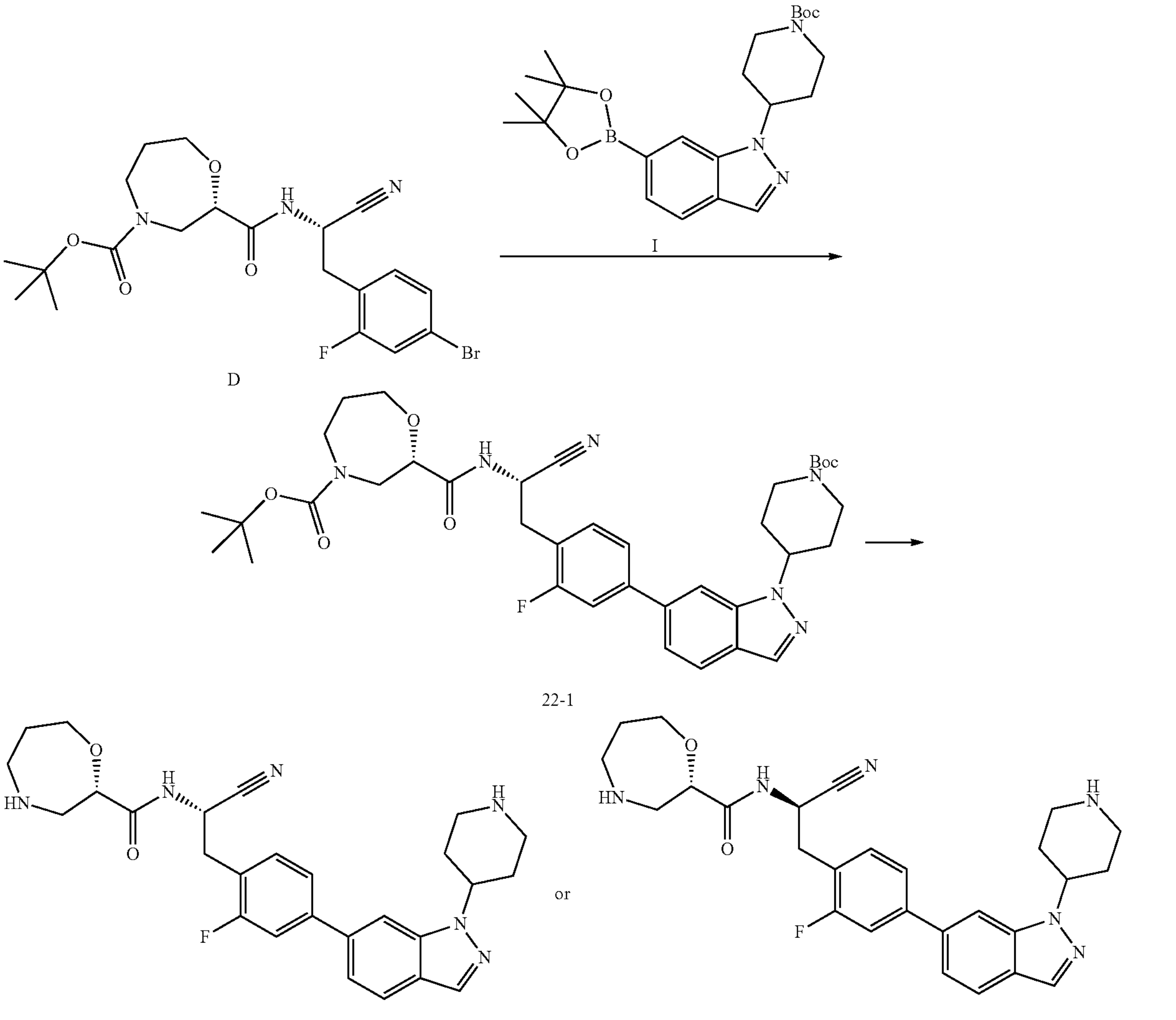

D
22-1
or
22

Step 1

To THF (5 mL) and water (2 mL) were added intermediate D (70 mg, 149 μmol), intermediate I (95 mg, 223 μmol), and potassium phosphate (95 mg, 447 μmol). Under nitrogen atmosphere, the reaction mixture was added with 1,1'-bis(di-tert-butylphosphino)ferrocene palladium dichloride (19 mg, 30 μmol). The reaction mixture was heated to 70° C. and reacted for 2 hours under nitrogen atmosphere.

Step 2

To formic acid (1.5 mL) and water (0.3 mL) were added compound 22-1 (70 mg, 101 μmol), and the reaction mixture was reacted at 25° C. for 2 hours. The reaction mixture was added with saturated sodium bicarbonate solution (50 mL), adjusted to pH=8 with saturated sodium bicarbonate solution and extracted with dichloromethane/methanol (4/1, V/V, 50 mL×2). The organic phases were combined, dried over anhydrous sodium sulfate, and concentrated under reduced pressure to obtain a crude product. The crude product was separated by preparative high performance liquid chromatography (chromatographic column: Phenomenex Gemini-NX C18 75 mm×30 mm×3 μm; mobile phase: phase A was an aqueous solution containing 0.025% formic acid, and phase B was acetonitrile; gradient: phase B 0% to 30%, 7 min) to obtain the formate of compound 22. Then the e.e. values of the formate of compound 22 were determined by SFC (chromatographic column: Chiralcel AD-3 50 mm×4.6 mm I.D., 3 μm; mobile phase: phase A was supercritical $CO_2$, phase B was ethanol solution containing 0.05% diethylamine; gradient: phase B 5% to 40%).

Compound 22: e.e. %=75.40%, RT=2.230 min. $^1H$ NMR (400 MHz, $CD_3OD$) δ 8.09 (s, 1H), 7.92 (s, 1H), 7.84 (d, J=8.4 Hz, 1H), 7.62-7.52 (m, 2H), 7.52-7.42 (m, 2H), 5.19-5.13 (m, 1H), 5.13-5.02 (m, 1H), 4.44-4.34 (m, 1H), 4.16-4.03 (m, 1H), 3.88-3.80 (m, 1H), 3.67-3.58 (m, 2H), 3.57-3.48 (m, 1H), 3.40-3.32 (m, 2H), 3.30-3.13 (m, 4H), 3.07-2.97 (m, 1H), 2.54-2.39 (m, 2H), 2.35-2.24 (m, 2H), 2.17-1.98 (m, 2H). MS-ESI calculated for $[M+H]^+$ 491, found 491.

Example 23

Synthetic Route:

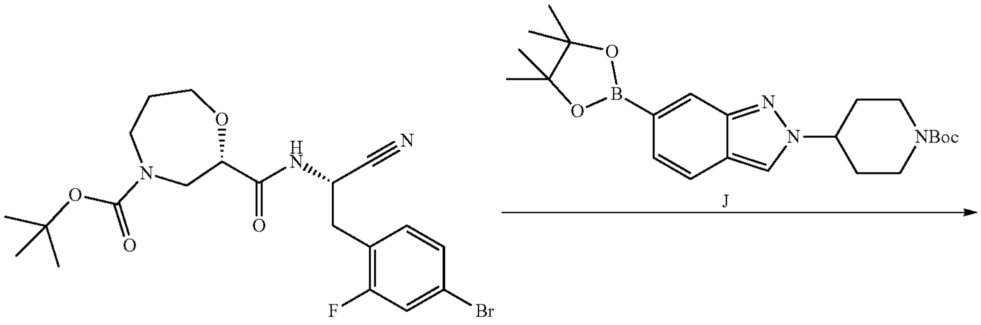

J

D

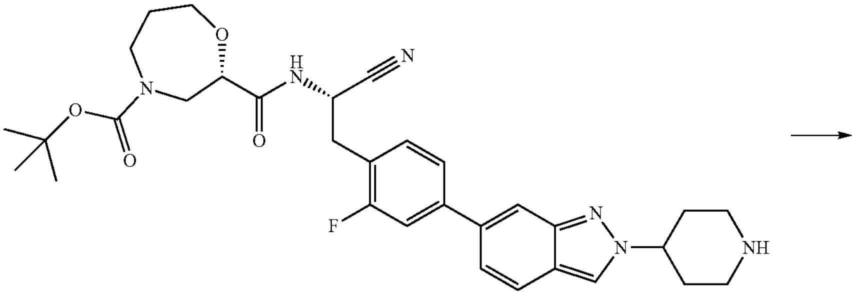

23-1

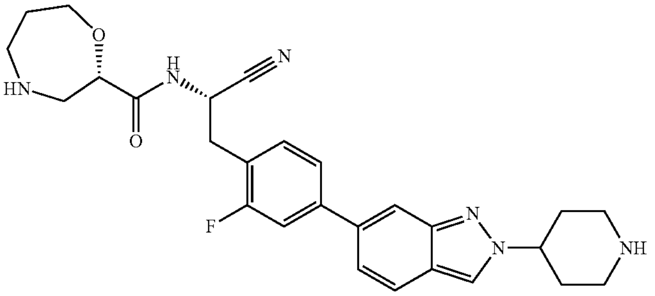

or

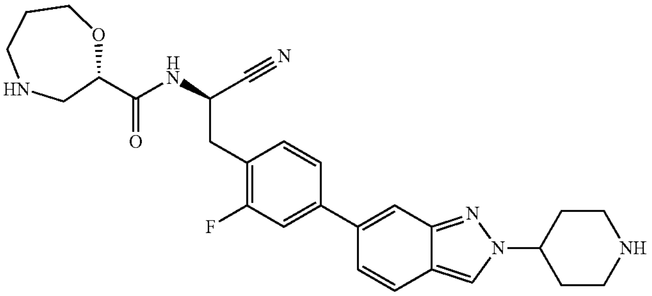

23

Step 1

To THF (5 mL) and water (2 mL) were added intermediate D (50 mg, 106 μmol), intermediate J (91 mg, 212 μmol), and potassium phosphate (68 mg, 319 μmol). Under nitrogen atmosphere, the reaction mixture was added with 1,1'-bis(di-tert-butylphosphino)ferrocene palladium dichloride (14 mg, 21 μmol). The reaction mixture was heated to 70° C. and reacted for 2 hours under nitrogen atmosphere. The crude product obtained by concentrating the reaction mixture under reduced pressure was separated by silica gel column chromatography (petroleum ether/ethyl acetate, 1/3, V/V) to obtain compound 23-1. $^1$H NMR (400 MHz, $CDCl_3$) δ 8.05-7.93 (m, 1H), 7.88 (s, 1H), 7.73 (d, J=8.8 Hz, 1H), 7.50-7.15 (m, 6H), 5.25-5.13 (m, 1H), 4.66-4.53 (m, 1H), 4.43-4.25 (m, 2H), 4.21-3.98 (m, 3H), 3.83-3.73 (m, 0.5H), 3.61-3.49 (m, 1H), 3.44-3.15 m, 3.5H), 3.13-2.87 (m, 3H), 2.33-2.21 (m, 2H), 2.20-2.07 (m, 2H), 2.00-1.85 (m, 2H), 1.50 (s, 9H), 1.46 (s, 9H). MS-ESI calculated for $[M+Na]^+$ 713, found 713.

Step 2

To formic acid (1.5 mL) and water (0.15 mL) were added compound 23-1 (60 mg, 87 μmol), and the reaction mixture was reacted at 25° C. for 2 hours. The reaction mixture was added with saturated sodium bicarbonate solution (50 mL), adjusted to pH>8 with saturated sodium bicarbonate solution and extracted with dichloromethane/methanol (4/1, V/V, 50 mL×2). The organic phases were combined, dried over anhydrous sodium sulfate, and concentrated under reduced pressure to obtain a crude product. The crude product was separated by preparative high performance liquid chromatography (chromatographic column: Phenomenex Gemini-NX C18 75 mm×30 mm×3 μm; mobile phase: phase A was an aqueous solution containing 0.025% formic acid, and phase B was acetonitrile; gradient: phase B 0% to 20%, 7 min) to obtain the formate of compound 23. Then the e.e. values of the formate of compound 23 were determined by SFC (chromatographic column: Chiralcel IA 100 mm×4.6 mm I.D., 3 μm; mobile phase: phase A was n-hexane containing 0.1% diethylamine, phase B was ethanol solution containing 0.1% diethylamine; gradient: phase B 80%).

Compound 23: e.e. %=90.87%, RT=6.608 min. $^1$H NMR (400 MHz, $CD_3OD$) δ 8.41-8.29 (m, 1H), 7.90-7.75 (m, 2H), 7.56-7.38 (m, 4H), 5.25-5.10 (m, 1H), 4.45-4.35 (m, 1H), 4.15-4.02 (m, 1H), 3.92-3.78 (m, 1H), 3.70-3.47 (m, 3H), 3.44-3.36 (m, 1H), 3.28-3.10 (m, 5H), 3.08-2.95 (m, 1H), 2.52-2.38 (m, 4H), 2.15-1.97 (m, 2H). MS-ESI calculated for $[M+H]^+$ 491, found 491.

Example 24

Synthetic Route:

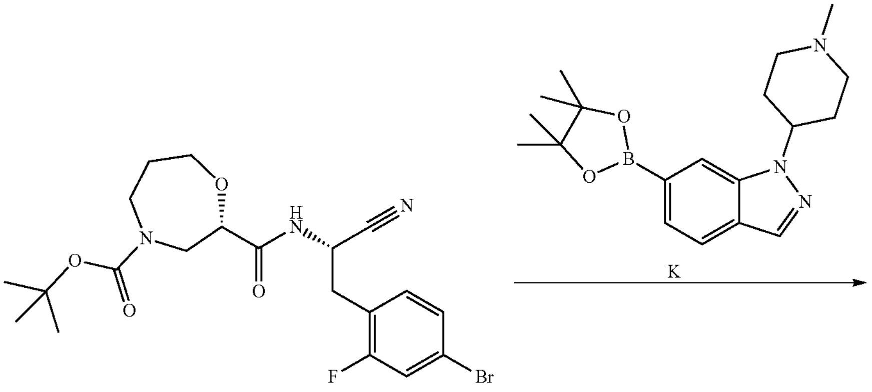

D

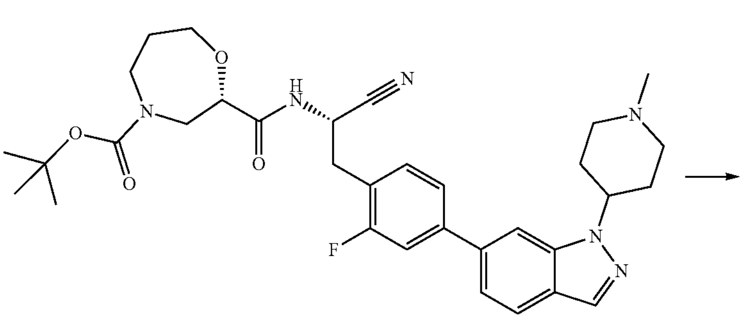

24-1

-continued

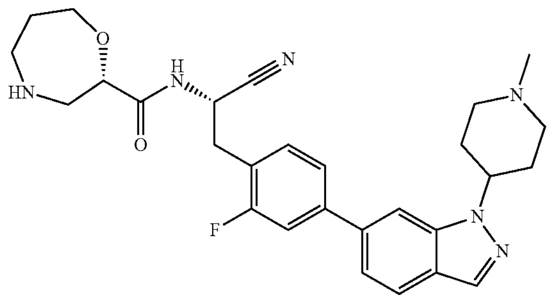

or

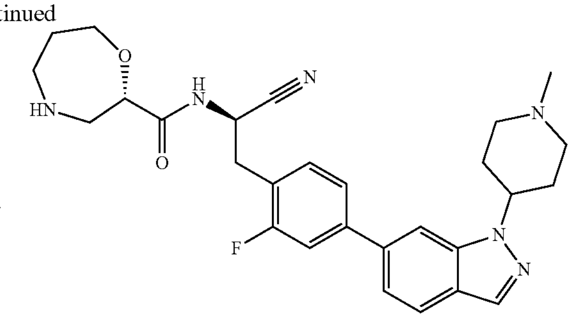

24

Step 1

To THF (5 mL) and water (2 mL) were added intermediate D (70 mg, 149 μmol), intermediate K (101 mg, 298 μmol), and potassium phosphate (95 mg, 447 μmol). Under nitrogen atmosphere, the reaction mixture was added with 1,1'-bis(di-tert-butylphosphino)ferrocene palladium dichloride (19 mg, 30 μmol). The reaction mixture was heated to 70° C. and reacted for 2 hours under nitrogen atmosphere. The crude product obtained by concentrating the reaction mixture under reduced pressure was separated by silica gel column chromatography (dichloromethane/methanol, 20/1 to 10/1, V/V) to obtain compound 24-1. $^1$H NMR (400 MHz, $CDCl_3$) δ 8.01 (s, 1H), 7.78 (d, J=8.3 Hz, 1H), 7.60 (s, 1H), 7.51-7.23 (m, 5H), 5.28-5.10 (m, 1H), 4.58-4.42 (m, 1H), 4.25-3.98 (m, 3H), 3.81-3.68 (m, 0.5H), 3.60-3.46 (m, 1H), 3.41-2.80 (m, 7H), 2.58-2.39 (m, 1.5H), 2.38 (s, 3H), 2.34-2.22 (m, 2H), 2.14-2.02 (m, 2H), 2.00-1.81 (m, 2H), 1.45 (s, 9H). MS-ESI calculated for $[M+H]^+$ 605, found 605.

Step 2

To formic acid (1.5 mL) and water (0.15 mL) were added compound 24-1 (110 mg, 182 μmol), and the reaction mixture was reacted at 25° C. for 2 hours. The reaction mixture was added to saturated sodium bicarbonate solution (50 mL), adjusted to pH=8 with saturated sodium bicarbonate solution and extracted with dichloromethane/methanol (4/1, V/V, 50 mL×2). The organic phases were combined, dried over anhydrous sodium sulfate, and concentrated under reduced pressure to obtain a crude product. The crude product was separated by preparative high performance liquid chromatography (chromatographic column: Phenomenex Gemini-NX 80 mm×40 mm×3 μm; mobile phase: phase A was an aqueous solution containing 0.05% ammonia monohydrate, and phase B was acetonitrile; gradient: phase B 36% to 66%, 8 min) to obtain compound 24. Then the e.e. values of compound 24 were determined by SFC (chromatographic column: Chiralcel IG-3 100 mm×4.6 mm I.D., 3 μm; mobile phase: phase A was supercritical $CO_2$, phase B was ethanol solution containing 0.05% diethylamine; gradient: phase B 40%).

Compound 24: e.e. %=84.10%, RT=3.362 min. $^1$H NMR (400 MHz, $CD_3OD$) δ 8.04 (s, 1H), 7.91 (s, 1H), 7.83 (d, J=8.5 Hz, 1H), 7.62-7.52 (m, 2H), 7.51-7.41 (m, 2H), 5.24-5.17 (m, 1H), 4.82-4.74 (m, 1H), 4.21-4.13 (m, 1H), 4.07-3.99 (m, 1H), 3.86-3.77 (m, 1H), 3.41-3.41 (m, 1H), 3.39-3.35 (m, 1H), 3.31-3.23 (m, 2H), 3.18-3.11 (m, 2H), 3.03-2.94 (m, 1H), 2.91-2.83 (m, 1H), 2.77-2.68 (m, 1H), 2.54-2.47 (m, 2H), 2.45 (s, 3H), 2.45-2.37 (m, 2H), 2.12-2.04 (m, 2H), 2.02-1.85 (m, 2H). MS-ESI calculated for $[M+H]^+$ 505, found 505.

Biological Activity Assessment:

Experimental Example 1: Inhibition Effect Test of DPP1 Enzyme Activity

Experimental Materials:

Recombinant human cathepsin C/DPP1 was purchased from R&D Systems;

Recombinant human cathepsin L (rhCathepsin L) was purchased from R&D Systems;

Gly-Arg-AMC (hydrochloride) was purchased from CAYMAN CHEMICAL COMPANY.

Experimental Methods:

1× activation buffer: 5 mM DTT 0.01% (V/V) Triton X-100 (preparation for current use);

1× assay buffer: 50 mM NaCl 5 mM DTT 0.01% (V/V) Triton X-100 (preparation for current use);

1× activation buffer was used to dilute recombinant human cathepsin C/DPP1 enzyme and recombinant human cathepsin L (rhCathepsin L) enzyme to concentrations of 2 ng/μL and 0.4 ng/μL, respectively; equal volume of two working solutions of enzyme was taken, mixed well and incubated at 25° C. for 60 minutes;

the compounds to be tested were 5-fold diluted with a multi-channel pipette to the 8th concentration, i.e., diluted from 1 mM to 12.8 nM. Then 1× experimental buffer was used to dilute each compound to be tested by gradient into a 4% DMSO working solution. The working solution was added to corresponding wells for 5 μL/well, and duplicate experiment was set. The mixture was centrifuged at 1000 rpm for 1 minute;

5 μL/well of the enzyme mixture after incubation was taken and added to the white microwell plate. At this time, the amount of DPP1 enzyme in each well was 5 ng; 1× experimental buffer in 5 μL/well was added to the blank control well;

Gly-Arg-AMC (hydrochloride) was diluted to 25 μM with 1× assay buffer. The diluted mixture in 10 μL/well was added to a white microwell plate. The substrate concentration was 12.5 μM at this time, and the microplate was centrifuged in a centrifuge at 1000 rpm for 1 minute. The concentration of the compound decreased from 10 μM to 0.128 nM. After centrifugation, the microplate was covered with membrane and incubated at 25° C. for 60 minutes;

after incubation, fluorescence detection was performed using a multi-label analyzer with an excitation wavelength of 360 nm and an emission wavelength of 460 nm.

Data Analysis:

Using the equation (Sample−Min)/(Max−Min)×100% to convert the raw data into enzyme activity, the $IC_{50}$ value might be obtained by curve fitting with four parameters (obtained by "log (inhibitor) vs. response—Variable slope" mode in GraphPad Prism).

Max: Contains recombinant human cathepsin C/DPP1, recombinant human cathepsin L (rhCathepsin L), and Gly-Arg-AMC (hydrochloride)

Min: No recombinant human cathepsin C/DPP1 and recombinant human cathepsin L (rhCathepsin L)

Table 1 provides the inhibitory activity of the compounds of the present disclosure on DPP1 enzyme.

TABLE 1

Test results of inhibitory activity of compounds of the present disclosure on DPP1 enzyme

| Compound | $IC_{50}$ (nM) |
|---|---|
| Compound 2 | 26.78 |
| Compound 4 | 10.83 |
| Compound 5 | 28.27 |
| Compound 6 | 0.84 |
| Compound 7 | 2.52 |
| Compound 8 | 3.57 |
| Compound 9 | 14.03 |
| Compound 10 | 4.39 |
| Compound 12 | 2.38 |
| Compound 13 | 20.36 |
| Compound 14 | 28.09 |
| Compound 15 | 3.65 |
| Compound 16 | 9.18 |
| Compound 17 | 22.52 |
| Compound 18 | 1.23 |
| Compound 19 | 4.55 |
| Compound 20 | 11.46 |
| Compound 21 | 17.34 |
| Compound 22 | 0.76 |
| Compound 24 | 1.00 |

Conclusion: The compounds of the present disclosure exhibit significant inhibitory activity against DPP1 enzyme.

Experimental Example 2: Activity Test of Inhibiting DPP1 in U937 Cells

Experimental Materials:

1) Experimental Reagents and Consumables

| Name | Brand No. |
|---|---|
| U937 | Procell-CL-0239 |
| RPMI1640 medium | BI-01-100-1ACS |
| Fetal bovine serum | Gibco-10099-141 |
| Double antibody (penicillin, streptomycin) | Procell-PB180120 |
| Cell plate | COSTAR-3603 |

2) Experimental Instruments

| Name | Brand No. |
|---|---|
| Cell counting plate | Solelybio |
| Victor Nivo | PerkinElmer |

Experimental Methods:

1) Cell Inoculation (1) Cell culture medium: 89% RPMI1640, 10% fetal bovine serum, and 1% penicillin-streptomycin;

(2) the culture medium was preheated in a 37° C. water bath;

(3) the cell suspension in the cell culture flask was taken out and put into a 15 mL centrifuge tube; the tube was put into a centrifuge at 1000 rpm/min and centrifuged for 5 minutes;

(4) after centrifugation, the supernatant was discarded, and 2 mL of culture medium was added to resuspend the cells; an appropriate amount of cell suspension was taken out and mix well with trypan blue, then about 0.01 mL of cell suspension was taken out and counted;

(5) the cell suspension was diluted with culture medium to the required cell density of 6.67×10^5 cells per milliliter;

(6) 30 µL of cell suspension was added to each well of the cell plate, and the cell plate was put in a 37° C. incubator containing 5% $CO_2$ for further use;

(7) the required amount of cell and culture medium were transferred to a new T75 culture flask to continue the culturing.

2) Drug Addition (1) The compound to be tested was prepared into a 10 mM solution with DMSO;

(2) 5-fold dilution was performed on the compound to 8 gradient concentration, that is, duplicate experiment was set with the concentration from 2 mM to 0.0256 µM; 78 µL of culture medium was added to the middle plate, and then the compound after gradient dilution in 2 µL per well was transferred to the middle plate according to the corresponding position; after mixing well, the compound in 10 µL per well was transferred to the cell plate, and the final concentration of the compound transferred to the cell plate was from 10 µM to 0.128 nM. The cell plate was placed in a carbon dioxide incubator for 1 day;

(3) after incubation for 1 hour, 100 µM Gly-Phe-AFC probe solution was added thereto, that is, 60 mM Gly-Phe-AFC probe stock solution was diluted with culture medium to 500 µM working solution; the working solution in 10 µL per well was transferred into the cell plate, and the cell plate was incubated in a carbon dioxide incubator for 1 hour;

3) the Plate was Read, and the Data were Analyzed:

(1) plate reading: after the cell incubation was completed, the cell plate was taken out, and the plate was read on Victor Nivo.

Data Analysis:

Using the equation (Sample−Min)/(Max−Min)×100% to convert the raw data into inhibition rate, the $IC_{50}$ value might be obtained by curve fitting with four parameters (obtained by "log (inhibitor) vs. response—Variable slope" mode in GraphPad Prism). Table 2 provides the inhibitory activity of the compounds of the present disclosure on DPP1 of U937 cells.

TABLE 2

Test results of inhibitory activity of compounds of the present disclosure on DPP1 of U937 cells

| Compound | $IC_{50}$ (nM) |
|---|---|
| Compound 2 | 8.95 |
| Compound 4 | 1.32 |
| Compound 5 | 9.32 |
| Compound 6 | 0.64 |
| Compound 7 | 2.49 |
| Compound 8 | 2.40 |

TABLE 2-continued

| Test results of inhibitory activity of compounds of the present disclosure on DPP1 of U937 cells | |
|---|---|
| Compound | $IC_{50}$ (nM) |
| Compound 10 | 8.53 |
| Compound 12 | 1.81 |
| Compound 13 | 6.33 |
| Compound 14 | 2.79 |
| Compound 18 | 5.43 |
| Compound 19 | 8.70 |
| Compound 20 | 9.58 |
| Compound 21 | 9.27 |
| Compound 24 | 3.12 |

Conclusion: The compounds of the present disclosure exhibit good inhibitory activity against DPP1 of U937 cells.

Experimental Example 3: Pharmacokinetic Evaluation of the Compound of the Present Disclosure in Rats Experimental purpose: To test the pharmacokinetics of the compound in CD-1 mice in vivo Experimental materials: CD-1 mice (male, 20 to 40 g, 4 to 6 weeks old, Beijing Vital River)

Experimental Operation:

The pharmacokinetic characteristics of the compound in rodents after intravenous injection and oral administration were tested according to the standard protocol. In the experiment, the candidate compound was formulated into clear solutions, and a single intravenous injection and oral administration were respectively given to two mice. The vehicle of intravenous injection and oral administration was 1:1:8 DMSO/Solutol/water. The whole blood samples within 24 hours were collected in commercial EDTA2K anticoagulant tubes. The tubes were centrifuged at 6000 g for 3 minutes. The supernatant was separated to obtain plasma samples. 20 times the volume of acetonitrile solution containing internal standard was added to precipitate protein. The mixture was centrifuged. The supernatant was take out. An equal volume of water was added. Then the mixture was centrifuged to take the supernatant as the sample for sampling. Plasma concentration was quantitatively analyzed by LC-MS/MS analysis method, and pharmacokinetic parameters were calculated, such as apparent volume of distribution, clearance rate, half-life, area under the drug-time curve. The experimental results are shown in Table 3.

Conclusion: The compound of the present disclosure shows better bioavailability, higher area under the drug-time curve, lower clearance rate, and volume of distribution at steady state in the pharmacokinetics of CD-1 mice.

Experimental Example 4: Pharmacokinetic Evaluation of the Compound of the Present Disclosure in Rats Experimental purpose: To test the pharmacokinetics of the compound in SD rats in vivo Experimental materials: SD rats (male, 200 to 300 g, 6 to 10 weeks old, Beijing Vital River)

Experimental Operation:

The pharmacokinetic characteristics of the compound in rodents after intravenous injection and oral administration were tested according to the standard protocol. In the experiment, the candidate compound was formulated into clear solutions, and a single intravenous injection and oral administration were respectively given to two rats. The vehicle of intravenous injection and oral administration is 5:95 DMSO and 10% hydroxypropyl β-cyclodextrin aqueous solution. The whole blood samples within 24 hours were collected in commercial EDTA2K anticoagulant tubes. The tubes were centrifuged at 6000 g for 3 minutes. The supernatant was separated to obtain plasma samples. 20 times the volume of acetonitrile solution containing internal standard was added to precipitate protein. The mixture was centrifuged. The supernatant was take out. An equal volume of water was added. Then the mixture was centrifuged to take the supernatant as the sample for sampling. Plasma concentration was quantitatively analyzed by LC-MS/MS analysis method, and pharmacokinetic parameters were calculated, such as apparent volume of distribution, clearance rate, half-life, area under the drug-time curve.

The experimental results are shown in Table 4.

TABLE 3

Pharmacokinetic test results of the compound of the present disclosure in mice

| Test sample | Dose | Peak concentration Cmax (nmol/L) | Clearance rate CL (mL/min/kg) | Volume of distribution at steady state Vdss (L/kg) | Half life $T_{1/2}$ (PO, h) | Area under drug-time curve $AUC_{0-\infty}$ PO (hr · nM) | Bioavailability F (%) |
|---|---|---|---|---|---|---|---|
| Compound 8 | Intravenous injection (2.0 mg/kg) Oral administration (10.0 mg/kg) | 2307 | 18.7 | 8.3 | 4.6 | 17008 | 79.6 |

TABLE 4

Pharmacokinetic test results of the compound of the present disclosure in rats

| Test sample | Dose | Peak concentration Cmax (nmol/L) | Clearance rate CL (mL/min/kg) | Volume of distribution at steady state Vdss (L/kg) | Half life $T_{1/2}$ (PO, h) | Area under drug-time curve $AUC_{0-\infty}$ PO (hr · nM) | Bioavailability F (%) |
|---|---|---|---|---|---|---|---|
| Compound 8 | Intravenous injection (2.0 mg/kg) Oral administration (10.0 mg/kg) | 2237 | 13.1 | 1.9 | 3.2 | 11864 | 39.1 |

Conclusion: The compound of the present disclosure shows better bioavailability, higher area under the drug-time curve, lower clearance rate, and volume of distribution at steady state in the pharmacokinetics of SD rats.

Experimental Example 5: Evaluation of Mouse Tissue (Bone Marrow) Distribution of the Compound of the Present Disclosure Experimental purpose: To test the distribution of the compound of the present disclosure in the bone marrow and plasma of CD-1 mice Experimental materials: CD-1 mice (male, 20 to 40 g, 4 to 6 weeks old, Beijing Vital River)

Experimental Operation:

The content of the compound in the bone marrow and plasma of mice after oral administration was tested according to the standard protocol. In the experiment, the candidate compound was formulated into a clear solution. The vehicle was 5:95 DMSO and 10% hydroxypropyl β-cyclodextrin aqueous solution. A dose of 5 mg/kg was given to mice as a single oral administration. The whole blood samples and bone marrow samples were collected at 0.25, 0.5, 1, 2, 4, 6, and 24 hours, respectively. The whole blood samples were collected in commercial EDTA2K anticoagulant tubes. The tubes were centrifuged at 6000 g for 3 minutes. The supernatant was separated to obtain plasma samples. The acetonitrile solution containing internal standard was added to precipitate protein. The mixture was centrifuged. The supernatant was take out. An equal volume of water was added. After mixing well, plasma concentration was quantitatively analyzed by LC-MS/MS analysis method, and the area under the drug-time curve was calculated. The femur and tibia on both sides of the mice were taken, and the muscle was removed. One end was cut off, placed in a centrifuge tube with the open end downwards. The tubes were centrifuged at 8000 rpm for 1 minute. The precipitate was bone marrow. The bone marrow was mixed with 50% methanol-water, grinded into a homogenate. The homogenate was added with an acetonitrile solution containing an internal standard to precipitate protein. The mixture was centrifuged to take the supernatant, added with an equal volume of water. After mixing well, the drug concentration in bone marrow was quantitatively analyzed by LC-MS/MS analysis method, and the area under the drug-time curve was calculated.

The calculation formula of bone marrow/plasma distribution coefficient is: Bone marrow/Plasma Ratio=bone marrow $AUC_{0\text{-}last}$/plasma $AUC_{0\text{-}last}$. The experimental results are shown in Table 5.

TABLE 5

Mouse bone marrow/plasma distribution test results of the compound in the present disclosure

| Test sample | Bone marrow: Peak concentration Cmax (nmol/kg) | Bone marrow: Area under drug-time curve $AUC_{0\text{-}last}$ PO (hr · nmol/kg) | Plasma: Peak concentration Cmax (nmol/L) | Plasma: Area under drug-time curve $AUC_{0\text{-}last}$ PO (hr · nmol/L) | Bone marrow/plasma distribution coefficient |
|---|---|---|---|---|---|
| Compound 8 | 6113 | 82362 | 2302 | 18362 | 4.5 |

Conclusion: The compound of the present disclosure has higher distribution in the bone marrow of CD-1 mice.

Experimental Example 6: Evaluation of Rat Tissue (Bone Marrow) Distribution of the Compound of the Present Disclosure Experimental purpose: To test the distribution of the compound in the bone marrow and plasma of SD rats Experimental materials: SD rats (male, 200 to 300 g, 6 to 10 weeks old, Beijing Vital River)

Experimental Operation:

The content of the compound in the bone marrow and plasma of rats after oral administration was tested according to the standard protocol. In the experiment, the candidate compound was formulated into a clear solution. The vehicle was 5:95 DMSO and 10% hydroxypropyl β-cyclodextrin aqueous solution. A dose of 5 mg/kg was given to rats as a single oral administration. The whole blood samples and bone marrow samples were collected at 0.25, 0.5, 1, 2, 4, 6, and 24 hours, respectively. The whole blood samples were collected in commercial EDTA2K anticoagulant tubes. The tubes were centrifuged at 6000 g for 3 minutes. The supernatant was separated to obtain plasma samples. The acetonitrile solution containing internal standard was added to precipitate protein. The mixture was centrifuged. The supernatant was take out. An equal volume of water was added. After mixing well, plasma concentration was quantitatively analyzed by LC-MS/MS analysis method, and the area under the drug-time curve was calculated. The left femur of the rat was taken, and the muscle was removed. One end was cut off, placed in a centrifuge tube with the open end downwards. The tubes were centrifuged at 8000 rpm for 1 minute. The precipitate was bone marrow. The bone marrow was mixed with 50% methanol-water, grinded into a homogenate. The homogenate was added with an acetonitrile solution containing an internal standard to precipitate protein. The mixture was centrifuged to take the supernatant, added with an equal volume of water. After mixing well, the drug concentration in bone marrow was quantitatively analyzed by LC-MS/MS analysis method, and the area under the drug-time curve was calculated.

The calculation formula of bone marrow/plasma distribution coefficient is: Bone marrow/Plasma Ratio=bone marrow $AUC_{0\text{-}last}$/plasma $AUC_{0\text{-}last}$. The experimental results are shown in Table 6.

TABLE 6

Rat bone marrow/plasma distribution test results of the compound in the present disclosure

| Test sample | Bone marrow: Peak concentration Cmax (nmol/kg) | Bone marrow: Area under drug-time curve $AUC_{0\text{-}last}$ PO (hr · nmol/kg) | Plasma: Peak concentration Cmax (nmol/L) | Plasma: Area under drug-time curve $AUC_{0\text{-}last}$ PO (hr · nmol/L) | Bone marrow/plasma distribution coefficient |
|---|---|---|---|---|---|
| Compound 8 | 5014 | 68856 | 1019 | 9902 | 7.0 |

Conclusion: The compound of the present disclosure has higher distribution in the bone marrow of SD rats.

Experimental Example 7: In Vivo Efficacy Evaluation of the Compound of the Present Disclosure on the Activity of Neutrophil Elastase in Rat Bone Marrow Experimental purpose: To evaluate the efficacy of the compound of the present disclosure on the activity of bone marrow neutrophil elastase in SD rats.

Experimental materials: SD rats (male, 200 to 300 g, 6 to 10 weeks old, Beijing Vital River)

Experimental Operation:

Experimental animals were administrated in groups according to Table 7. Two hours after the last administration, the bone marrow of the animals was collected. Red blood cells were firstly lysed with erythrocyte lysate. Lymphocytes were retained, and then the lymphocytes were lysed with lymphocyte lysate. The supernatant was taken for protein quantification and assay of neutrophil elastase enzyme activity. The neutrophil elastase activity was further calculated in the samples. The administration regimen is shown in Table 7,

TABLE 7

Grouping and administration scheme of experimental animals

| Group | Number of rats | Compound | Dose (mg/kg) | Route of administration | Frequency and days of administration |
|---|---|---|---|---|---|
| 1 | 6 | Vehicle group (5:95 DMSO and 10% hydroxypropyl β-cyclodextrin aqueous solution) | — | Gavage | Twice a day, 7 days |
| 2 | 6 | Compound 8 | 2 | Gavage | Twice a day, 7 days |

Experimental Indexes:

The elastase activity of neutrophils in bone marrow samples was calculated. The experimental results are shown in FIG. 1.

Conclusion: The compound of the present disclosure can significantly inhibit the activity of neutrophil elastase in rats in vivo.

What is claimed is:

1. A compound of formula (II) or a pharmaceutically acceptable salt thereof, (II)

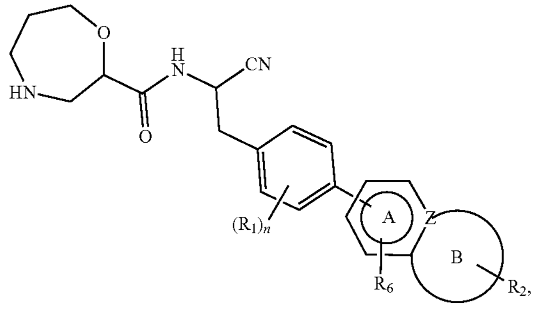

wherein

Z is selected from N and C;

the structural moiety

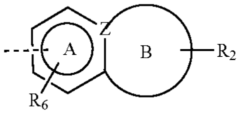

is selected from

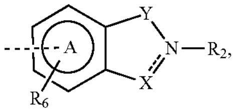

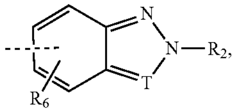

and

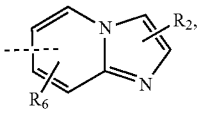

wherein the structure moiety

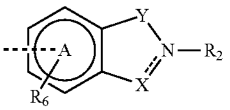

is selected from

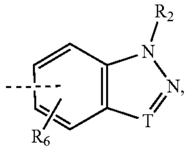

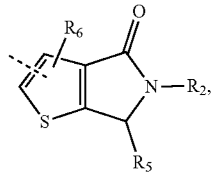

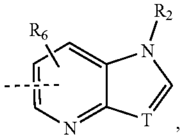

, and

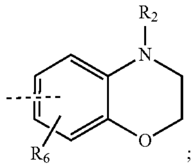

;

each ⫽ is independently selected from a single bond and a double bond, wherein when ⫽ is selected from the double bond, $R_2$ is absent;

each T is independently selected from N and $CR_3$;

each $R_1$ is independently selected from H, F, Cl, Br, I, —OH, —$NH_2$, —CN, and $C_{1-3}$ alkyl, wherein the $C_{1-3}$ alkyl is optionally substituted by 1, 2, or 3 $R_a$;

$R_2$ is selected from H, F, Cl, Br, I, =O, —OH, —$NH_2$, —CN, $C_{1-3}$ alkyl, and 5- to 6-membered heterocycloalkyl, wherein the $C_{1-3}$ alkyl and 5- to 6-membered heterocycloalkyl are each independently and optionally substituted by 1, 2, or 3 $R_b$;

$R_3$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_c$;

$R_5$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_e$;

$R_6$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_f$, each $R_a$ is independently selected from F, Cl, Br, I, —O, —OH, —$NH_2$, and —CN;

each $R_b$ is independently selected from F, Cl, Br, I, =O, —OH, —$NH_2$, —CN, and $C_{1-3}$ alkyl;

each $R_c$ is independently selected from F, Cl, Br, I, =O, —OH, —$NH_2$, and —CN;

each $R_d$ is independently selected from F, Cl, Br, I, =O, —OH, —$NH_2$, and —CN;

each $R_e$ is independently selected from F, Cl, Br, I, =O, —OH, —$NH_2$, and —CN;

each $R_f$ is independently selected from F, Cl, Br, I, =O, —OH, —$NH_2$, and —CN;

n is selected from 1, 2, 3, and 4;

the 5- to 6-membered heterocycloalkyl contains 1, 2, 3, or 4 heteroatoms or heteroatom groups independently selected from —O—, —NH—, —S—, and —N—.

2. The compound or the pharmaceutically acceptable salt thereof according to claim 1, wherein the compound has a structure of formula (II'):

(II)

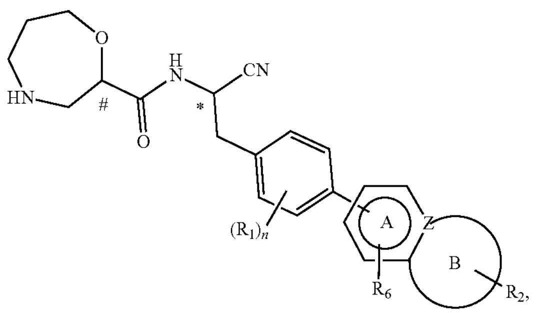

the carbon atoms with "*" and "#" are chiral carbon atoms, which exist in an (R) or(S) single enantiomer form or an (R) or(S) single enantiomer-rich form.

3. The compound or the pharmaceutically acceptable salt thereof according to claim 1, wherein $R_b$ is selected from F, Cl, Br, and $CH_3$, or $R_1$ is selected from H, F, Cl, and $—CH_3$.

4. The compound or the pharmaceutically acceptable salt thereof according to claim 1, wherein $R_2$ is selected from H, $—CH_3$,

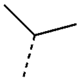, 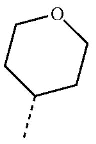, and 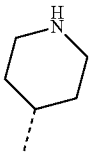, wherein the $—CH_3$,

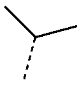, 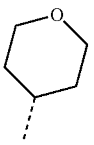, and 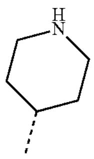

are each independently and optionally substituted by 1, 2, or 3 $R_b$.

5. The compound or the pharmaceutically acceptable salt thereof according to claim 4, wherein $R_2$ is selected from H, $—CH_3$,

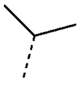, 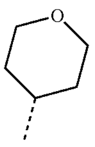, 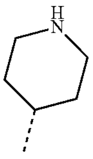, and 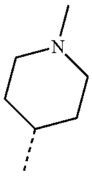.

6. The compound or the pharmaceutically acceptable salt thereof according to claim 1, wherein $R_3$ is selected from H, F, CI, and Br.

7. The compound or the pharmaceutically acceptable salt thereof according to claim 1, wherein $R_5$ is selected from H and $—CH_3$.

8. The compound or the pharmaceutically acceptable salt thereof according to claim 1, wherein $R_6$ is selected from H, F, CI, and Br.

9. The compound or the pharmaceutically acceptable salt thereof according to claim 1, wherein the structural moiety

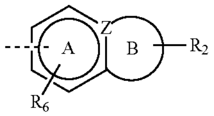

is selected from

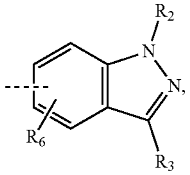 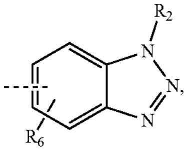

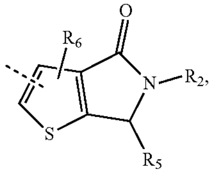

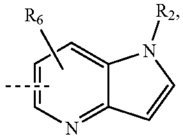 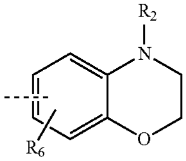 ,

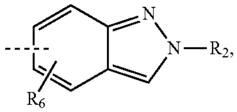 and 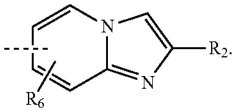

10. The compound or the pharmaceutically acceptable salt thereof according to claim 9, wherein the structural moiety

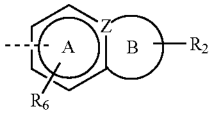

is selected from

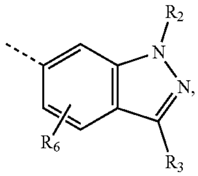 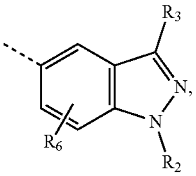

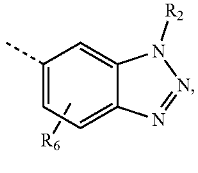 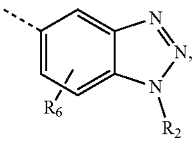

-continued

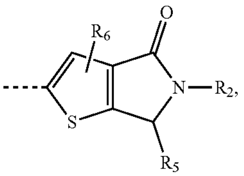 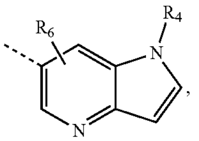

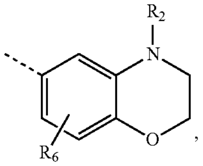 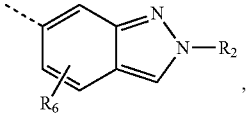

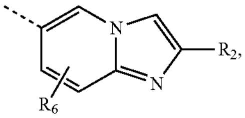 and 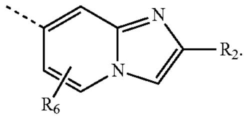

11. The compound or the pharmaceutically acceptable salt thereof according to claim 10, wherein the structural moiety

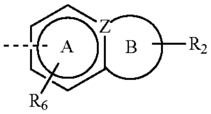

is selected from

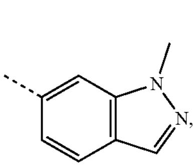 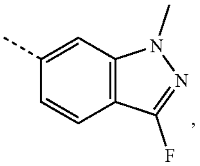

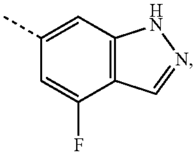 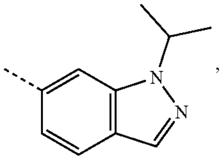

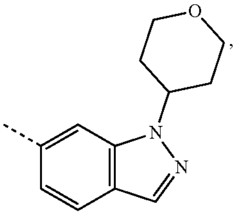 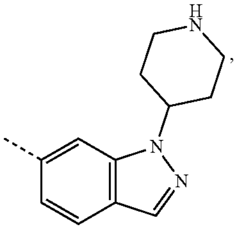

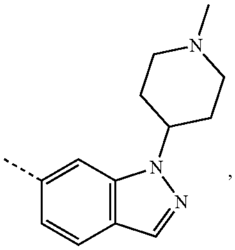 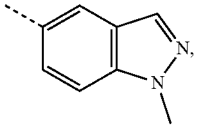

-continued

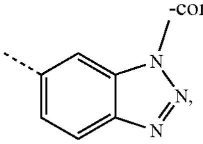 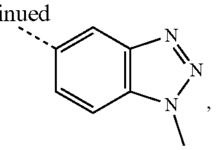

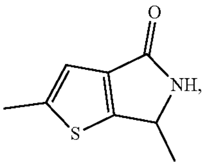 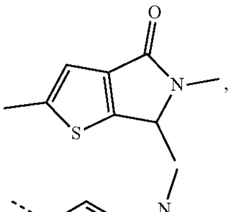

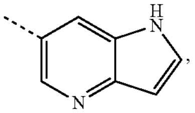 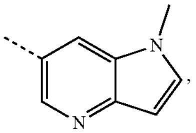

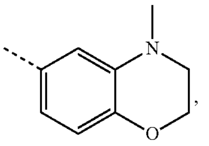 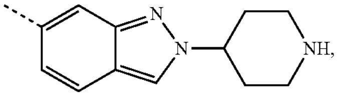

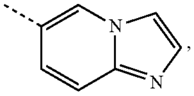 and 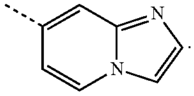

12. The compound or the pharmaceutically acceptable salt thereof according to claim 1, wherein the compound has a structure of formula (II-1):

(II-1)

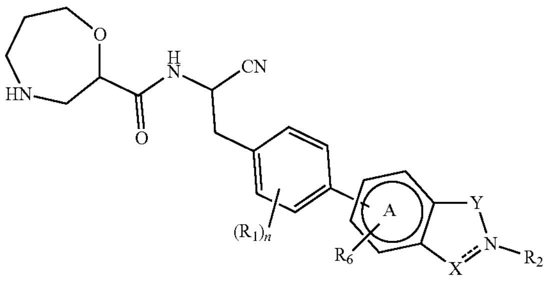

13. The compound or the pharmaceutically acceptable salt thereof according to claim 12, wherein the compound has a structure of formula (II'-1):

(II'-1)

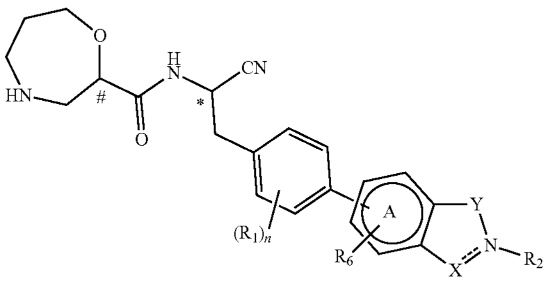

the carbon atoms with "*" and "#" are chiral carbon atoms, which exist in an (R) or(S) single enantiomer form or an (R) or(S) single enantiomer-rich form.

14. The compound or the pharmaceutically acceptable salt thereof according to claim 12, wherein the compound is a compound of formula (I):

wherein (I)

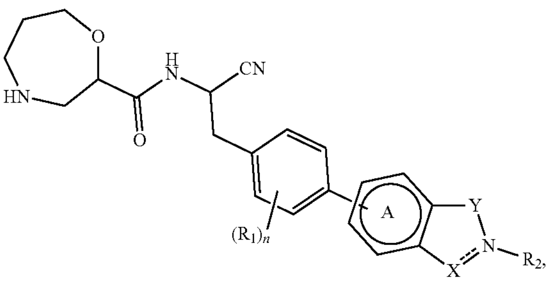

the structural moiety

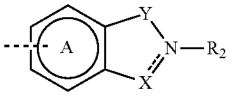

is selected from

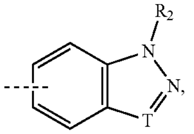

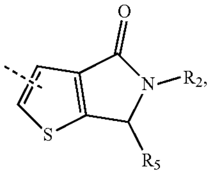

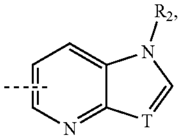 and 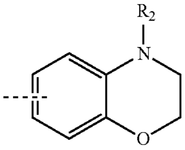 ;

each ⸗ is independently selected from a single bond and a double bond, wherein when ⸗ is selected from the double bond, $R_2$ is absent;

each T is independently selected from N and $CR_3$;

$R_3$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_c$;

$R_5$ is selected from H, F, Cl, Br, I, —OH, —$NH_2$, —CN, and $C_{1-3}$ alkyl, wherein the $C_{1-3}$ alkyl is optionally substituted by 1, 2, or 3 $R_e$;

each $R_c$ is independently selected from F, Cl, Br, I, —O, —OH, —$NH_2$, and —CN;

each $R_d$ is independently selected from F, Cl, Br, I, —O, —OH, —$NH_2$, and —CN;

each Re is independently selected from F, Cl, Br, I, —O, —OH, —$NH_2$, and —CN.

15. The compound or the pharmaceutically acceptable salt thereof according to claim 14, wherein the compound has a structure of formula (I-1) or (1-3):

(I-1)

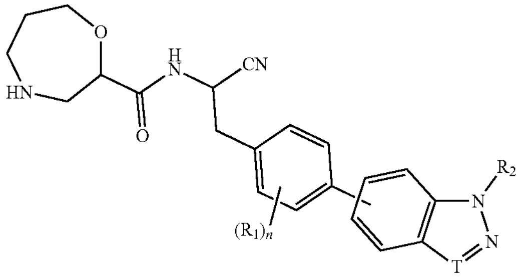

or (I-3)

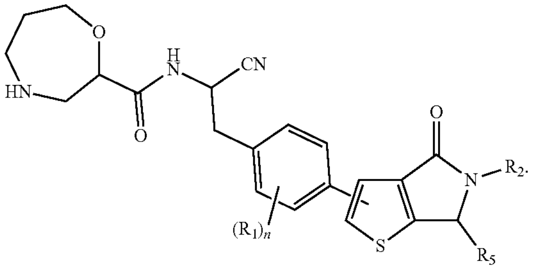

16. The compound or the pharmaceutically acceptable salt thereof according to claim 15, wherein the compound has a structure of formula (I-1A), (I-1B), or (I-3A):

(I-1A)

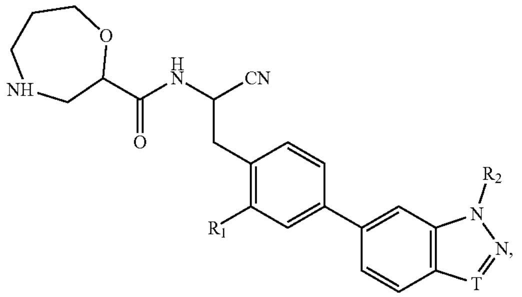

(I-1B)

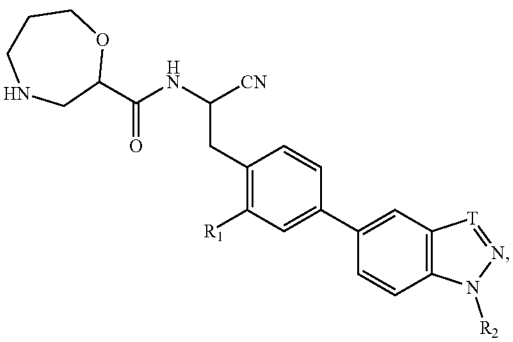

or

-continued (I-3A)

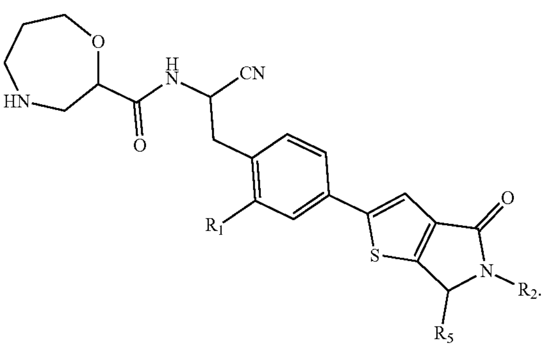

17. The compound or the pharmaceutically acceptable salt thereof according to claim 16, wherein the compound has a structure of formula (I'-1A), (I'-1B), or (I'-3A):

(I'-1A)

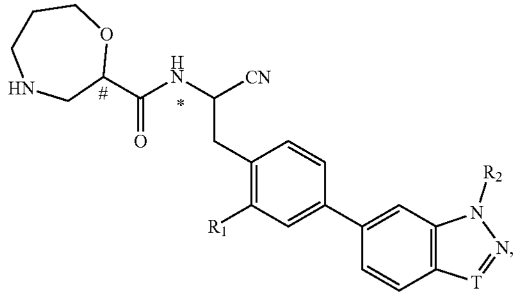

(I'-1B)

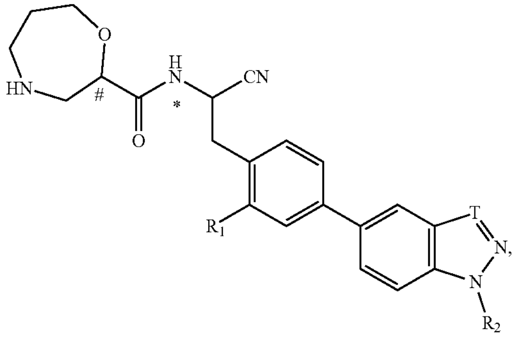

or (I'-3A)

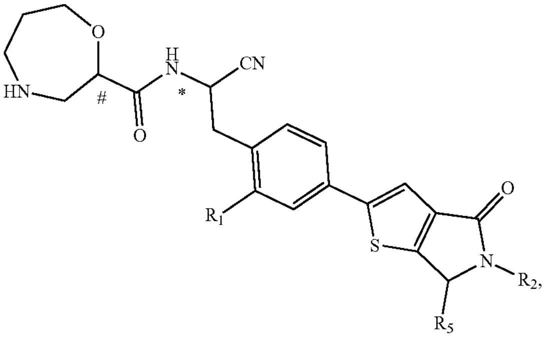

wherein the carbon atoms with "*" and "#" are chiral carbon atoms, which exist in an (R) or(S) single enantiomer form or an (R) or(S) single enantiomer-rich form.

18. A compound of the following formula, or a pharmaceutically acceptable salt thereof, selected from:

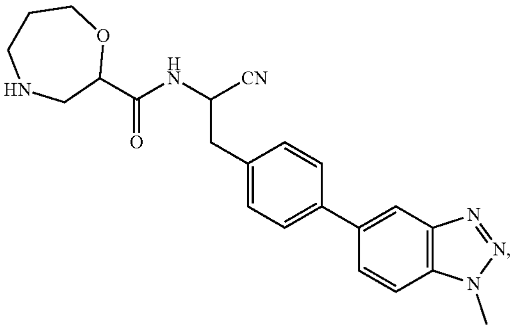

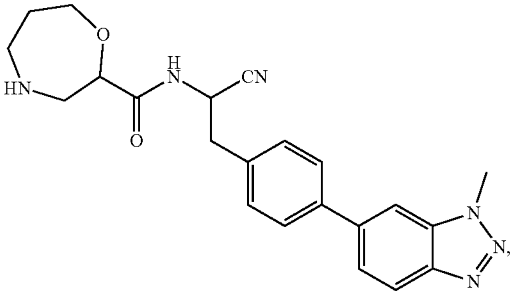

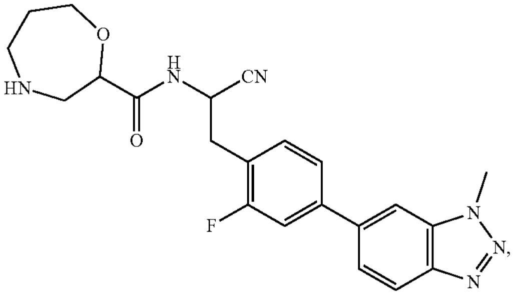

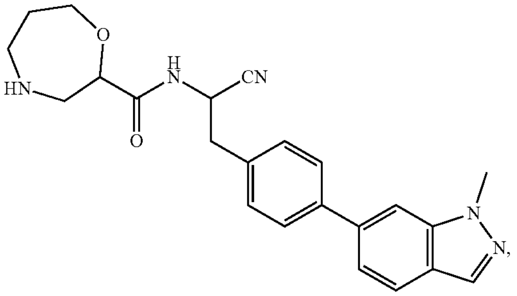

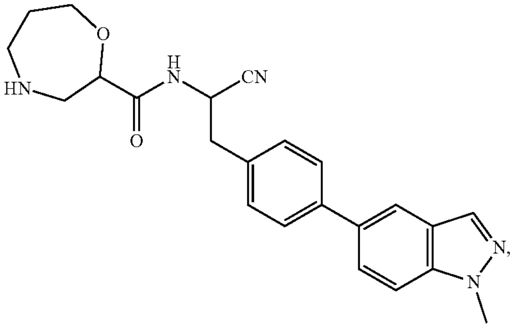

-continued
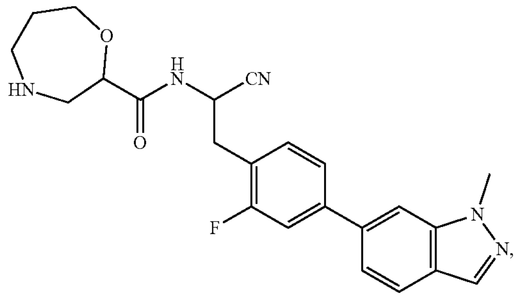
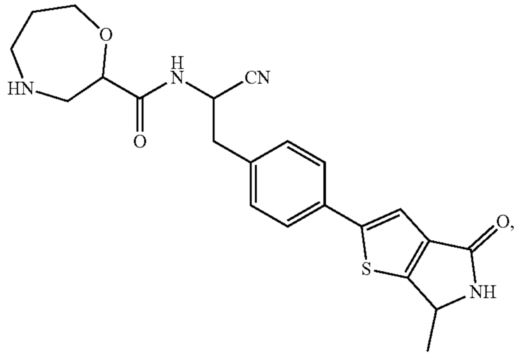
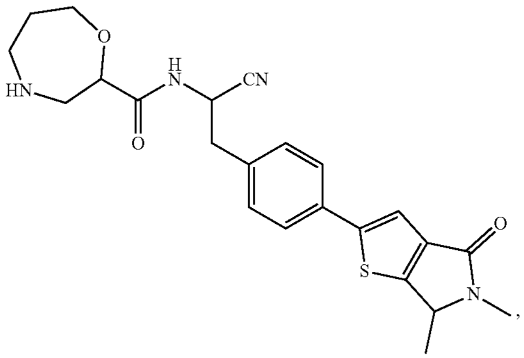
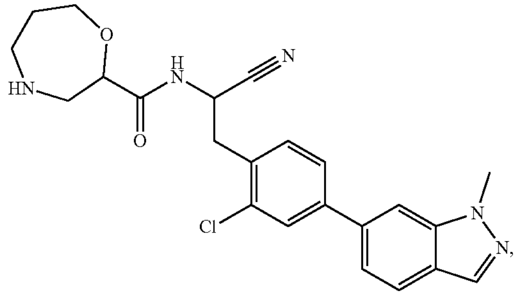
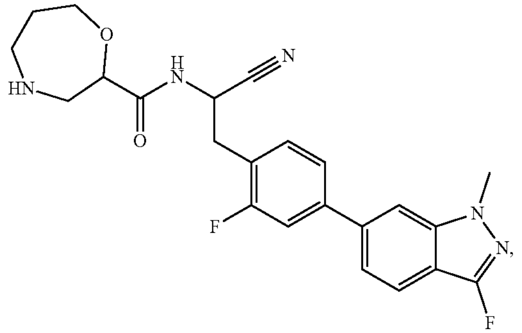
-continued
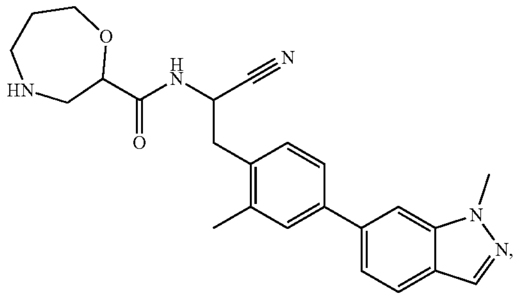
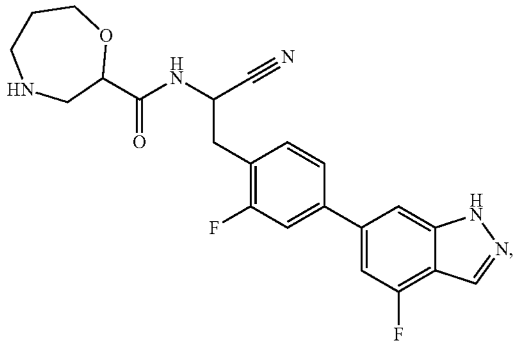
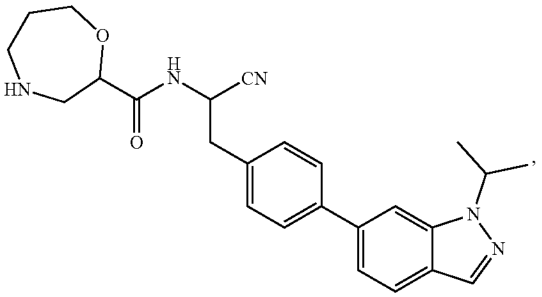
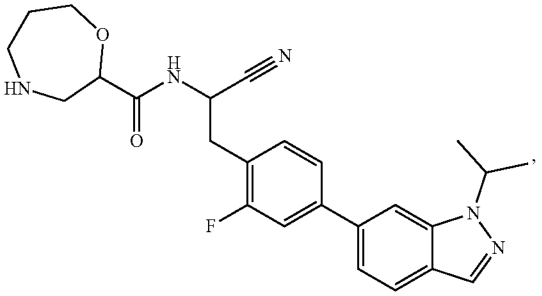
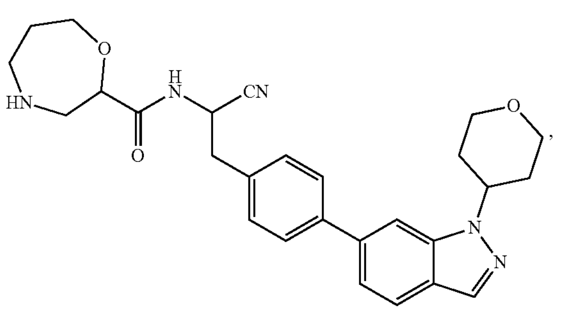

-continued
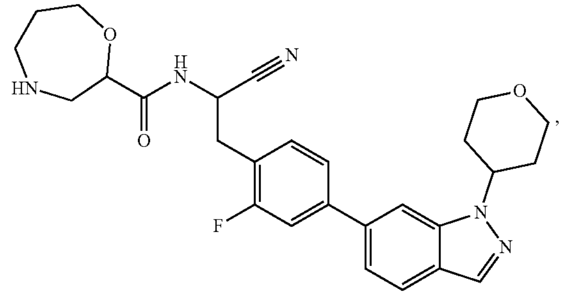
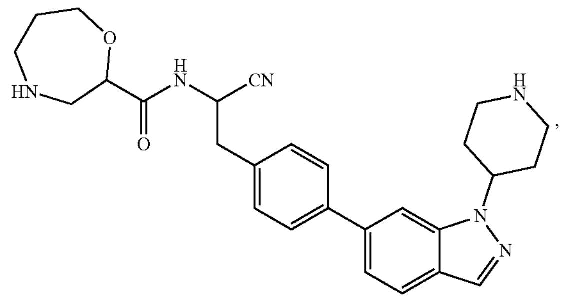
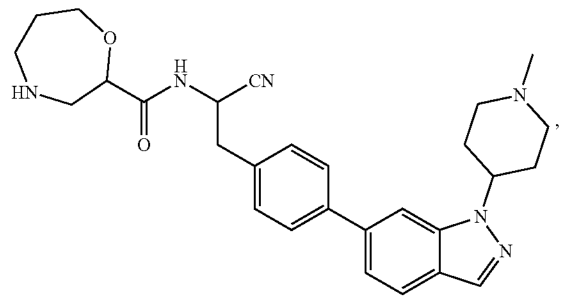
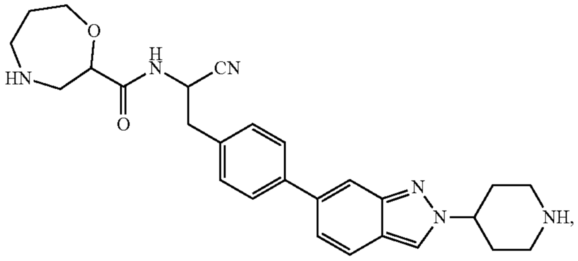
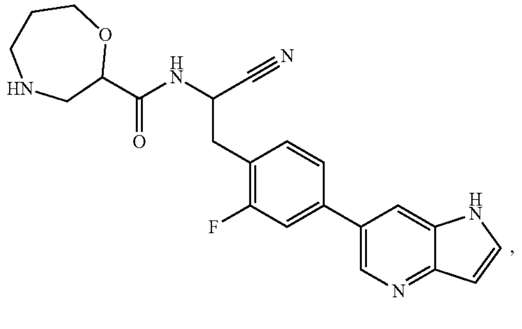
-continued
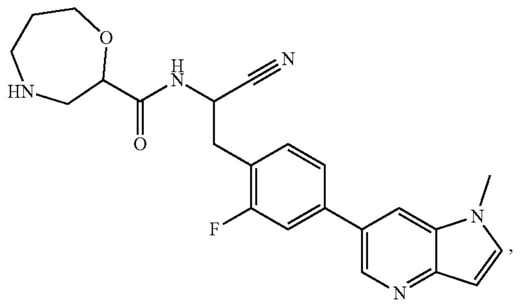
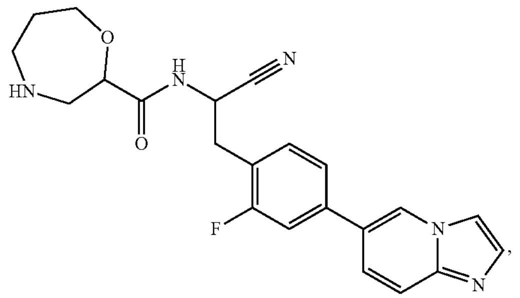
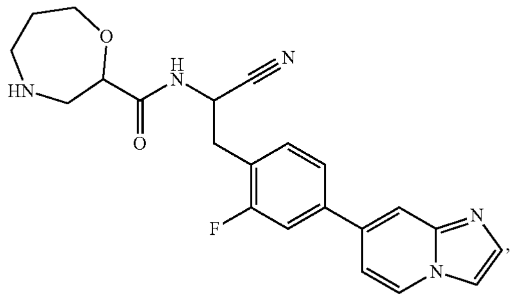
and
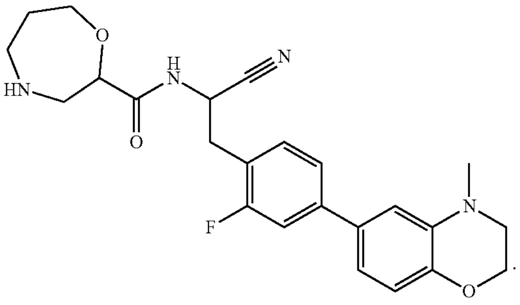
19. The compound or the pharmaceutically acceptable salt thereof according to claim 18, wherein the compound is:
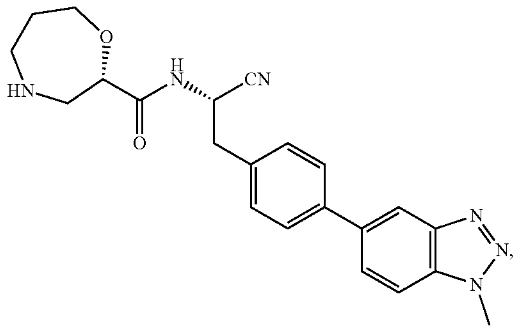

-continued
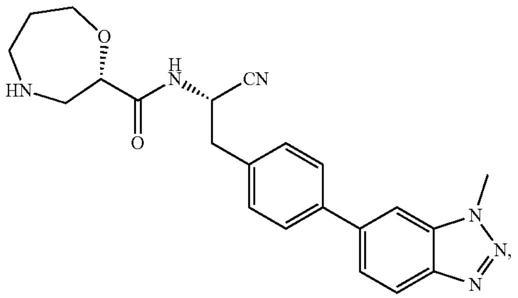
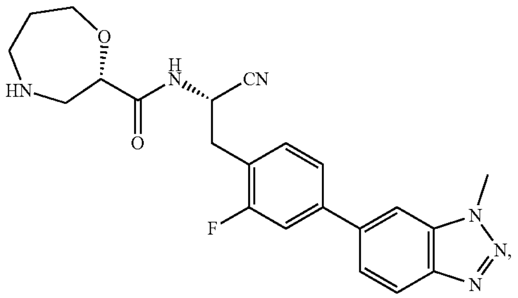
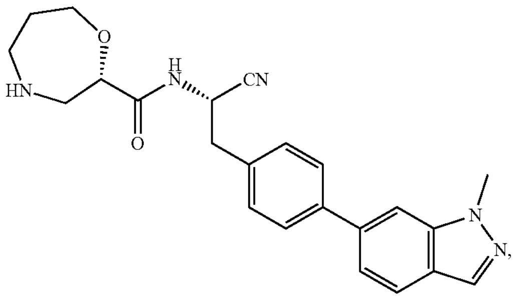
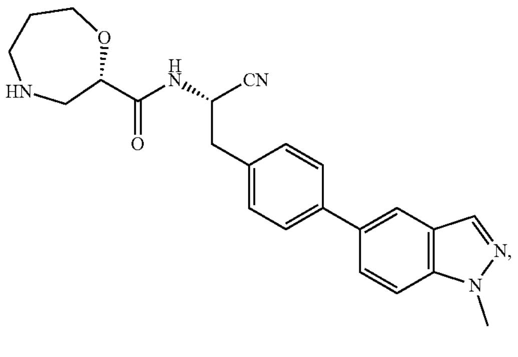
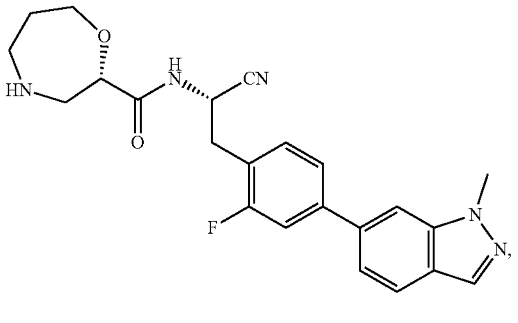
-continued
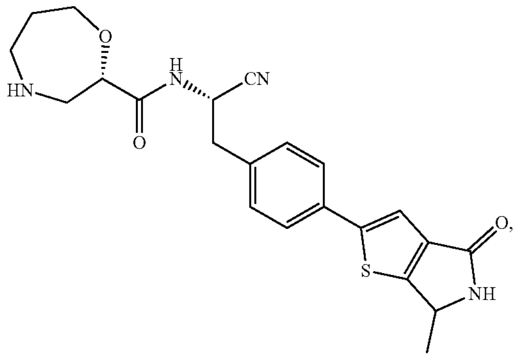
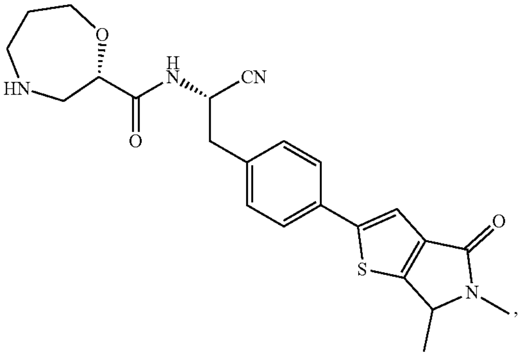
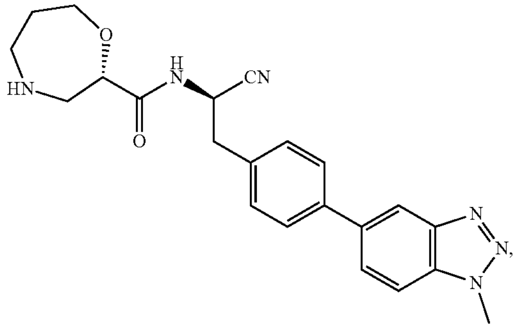
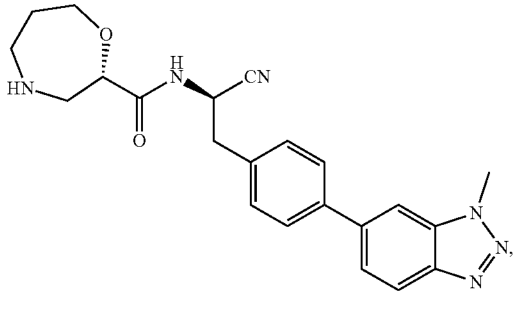
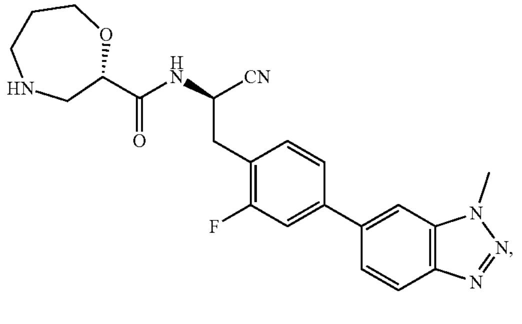

-continued
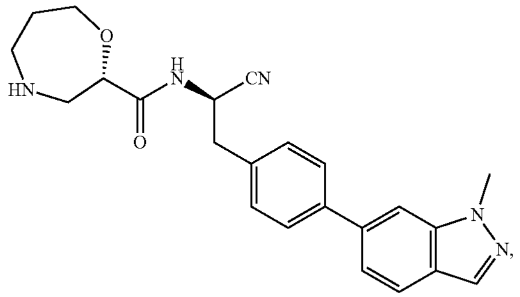
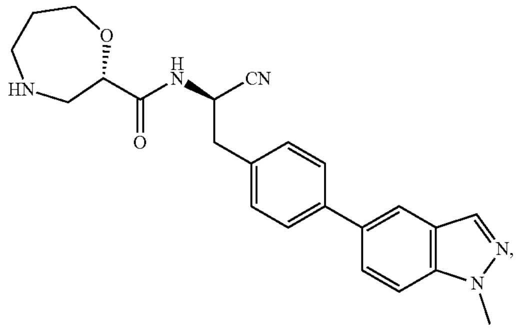
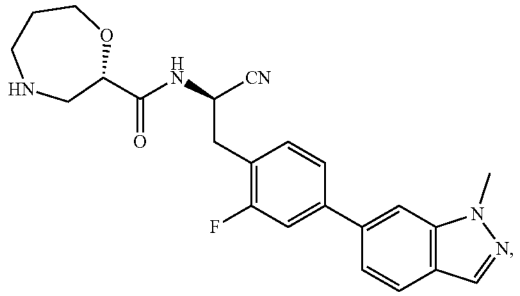
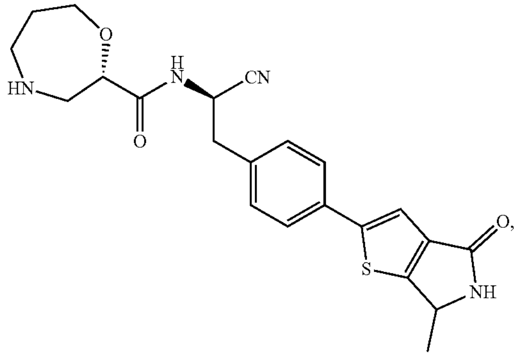
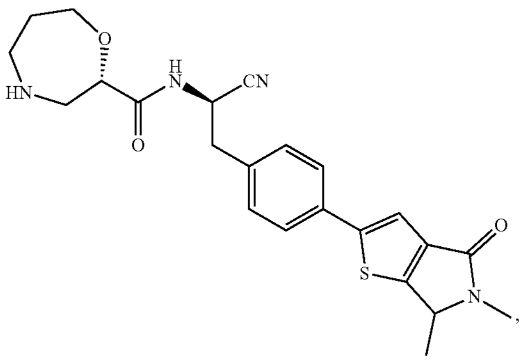
-continued
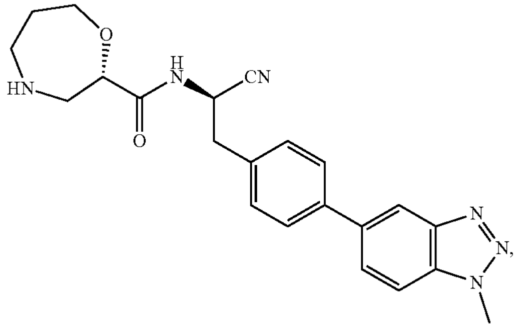
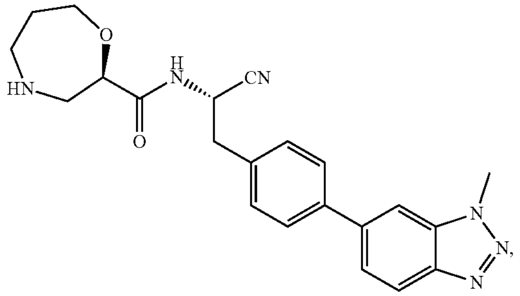
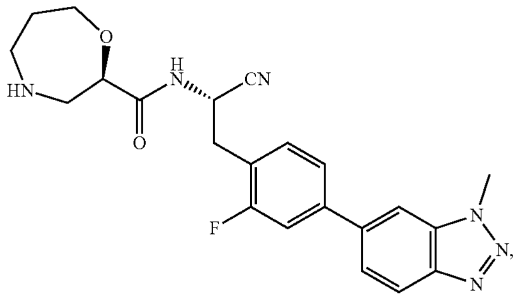
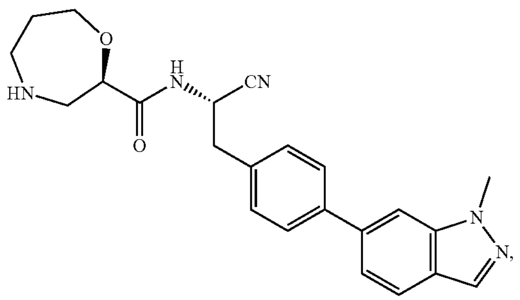
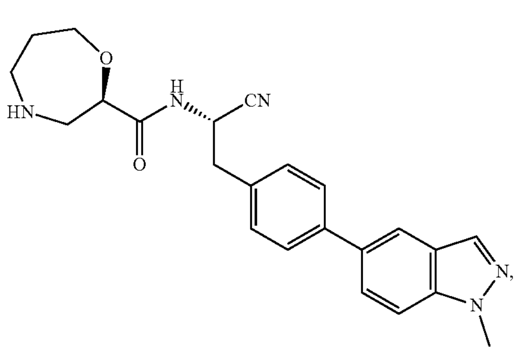

-continued
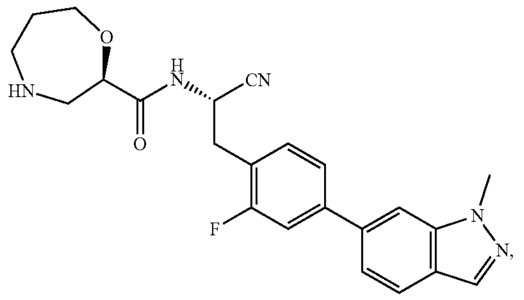
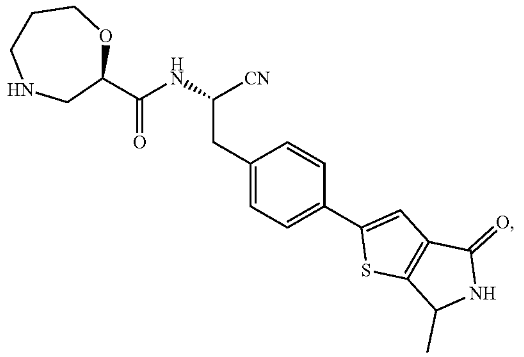
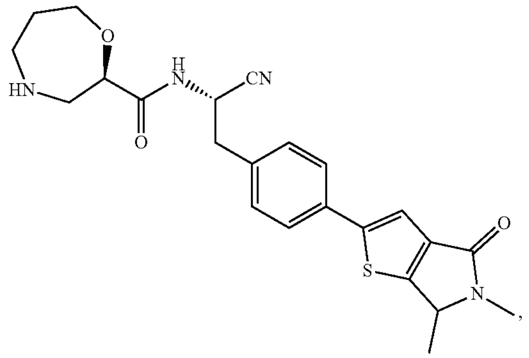
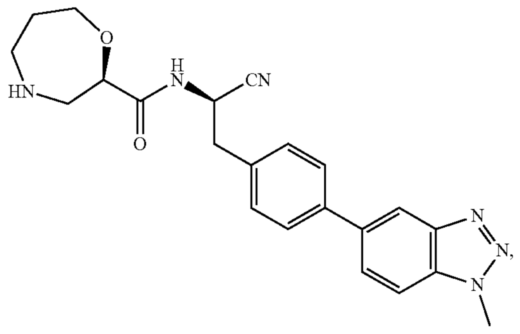
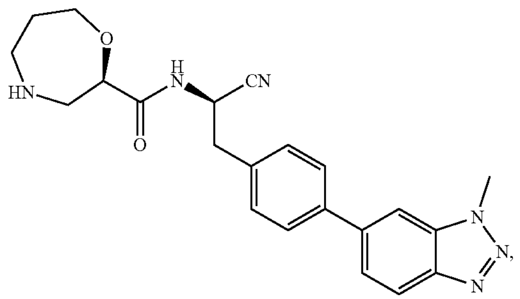
-continued
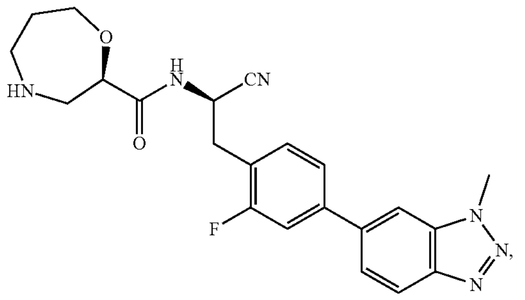
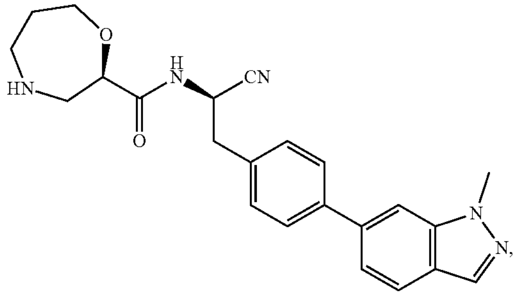
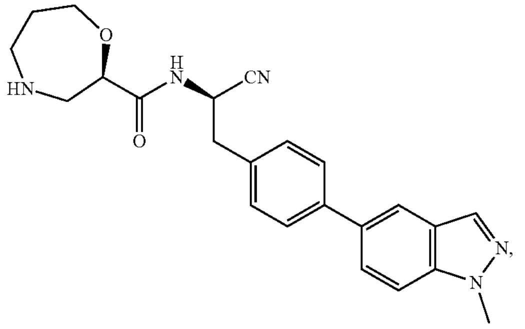
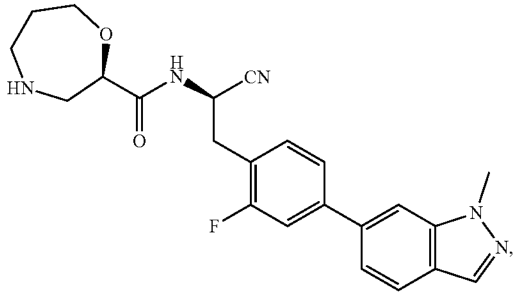
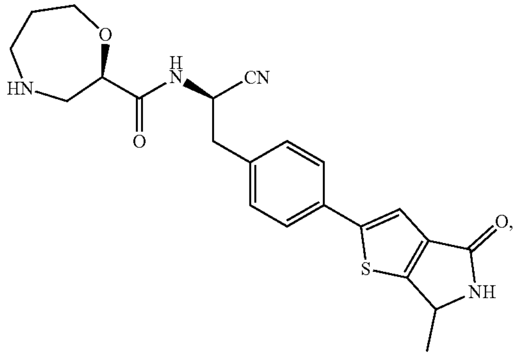

-continued
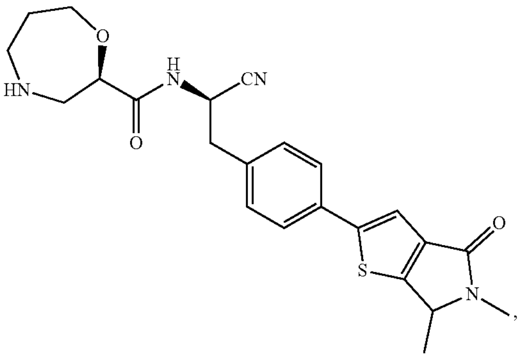
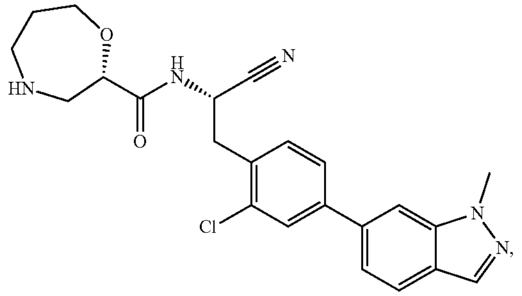
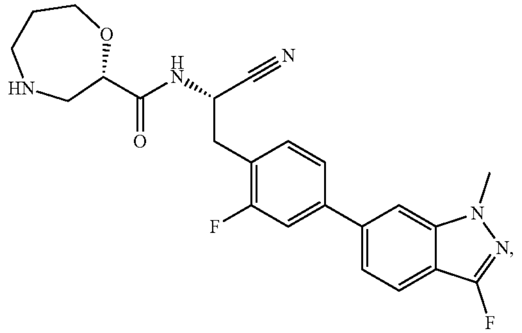
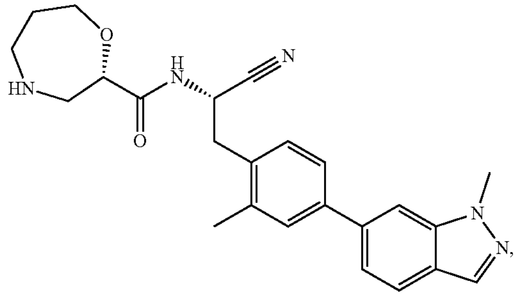
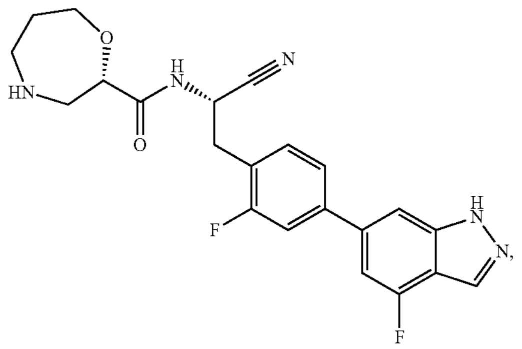
-continued
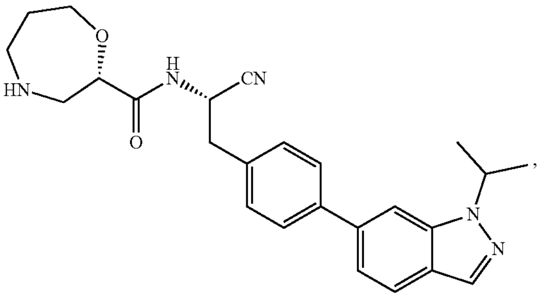
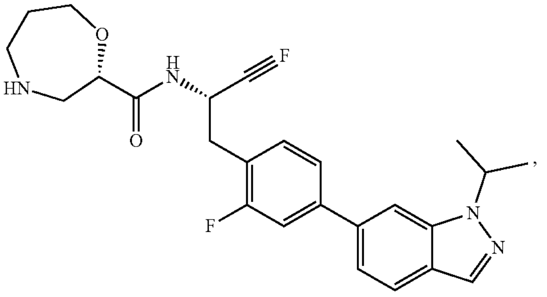
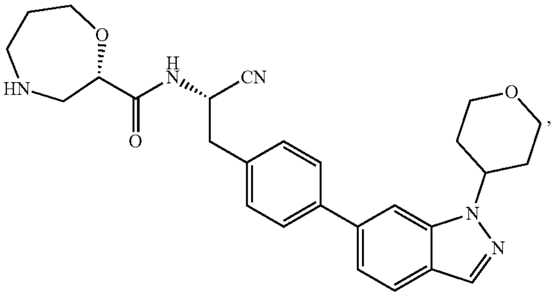
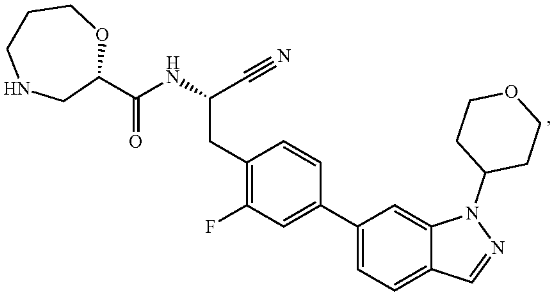
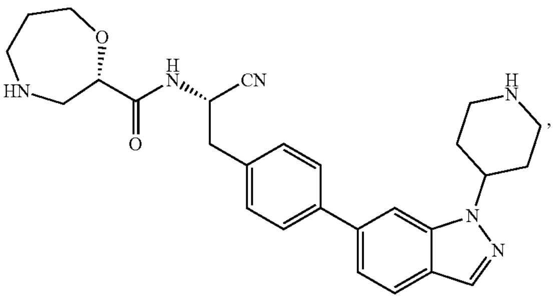

-continued
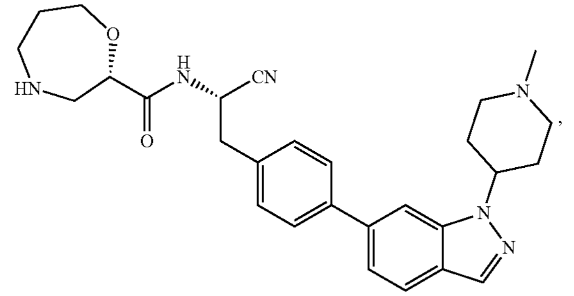
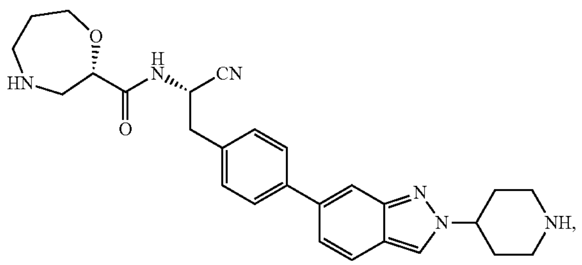
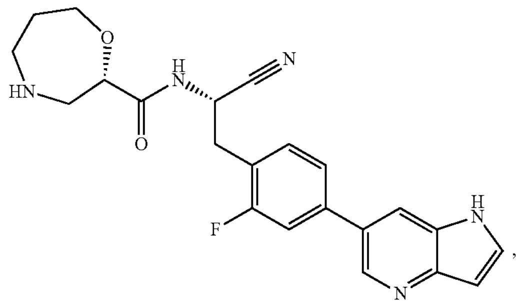
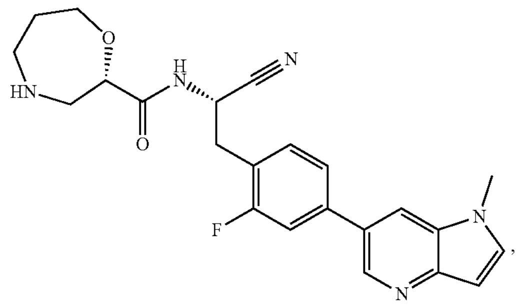
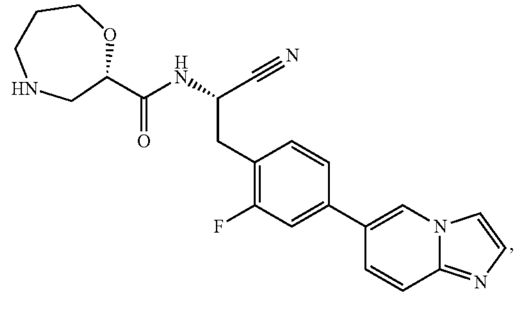
-continued
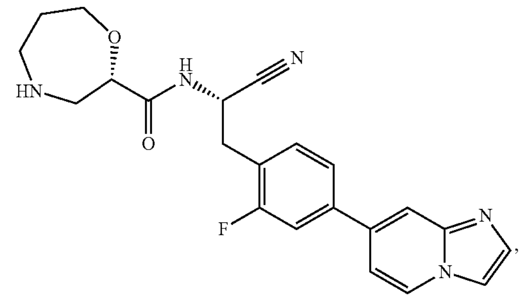
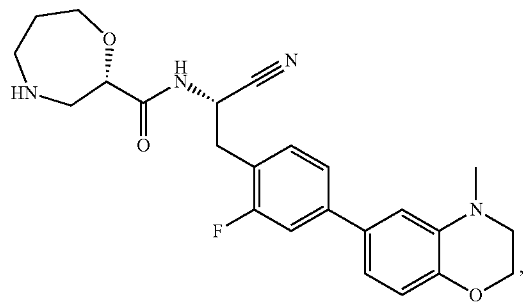
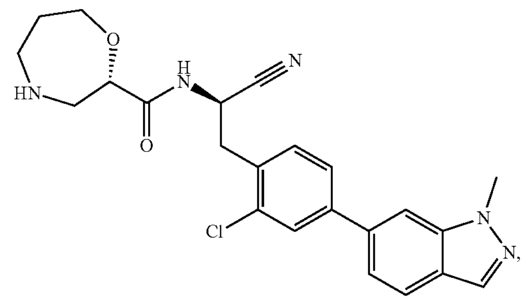
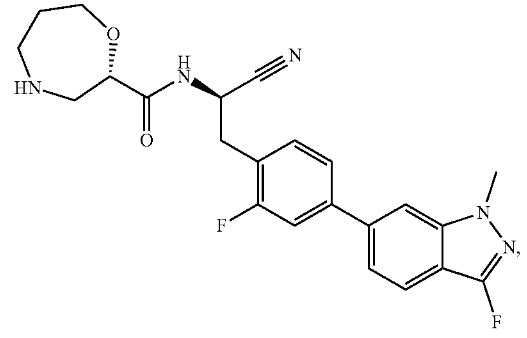
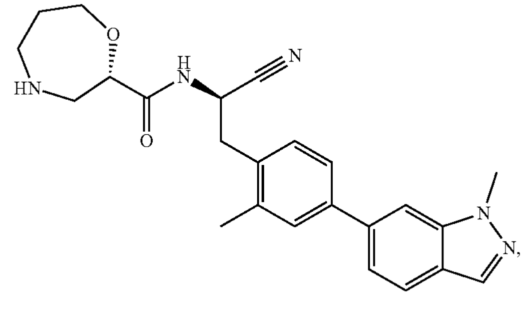

-continued
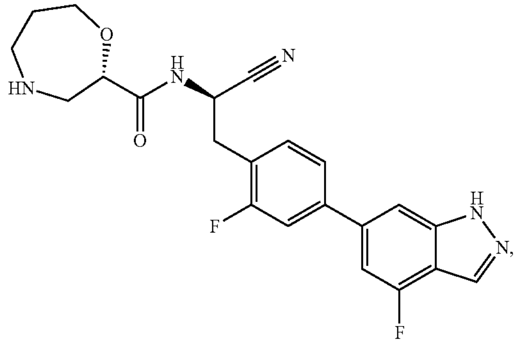
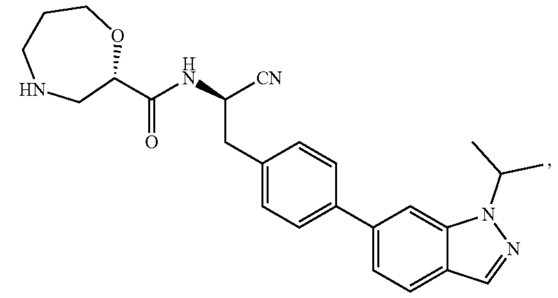
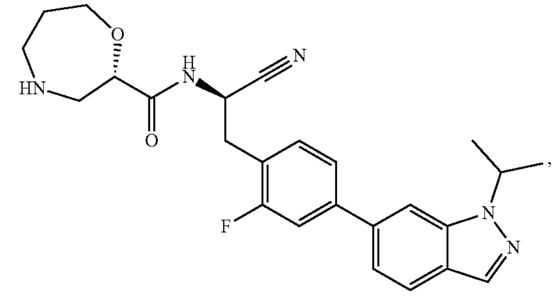
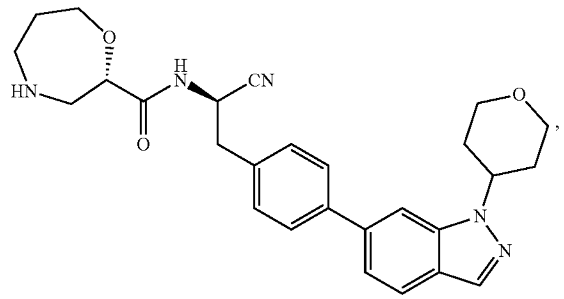
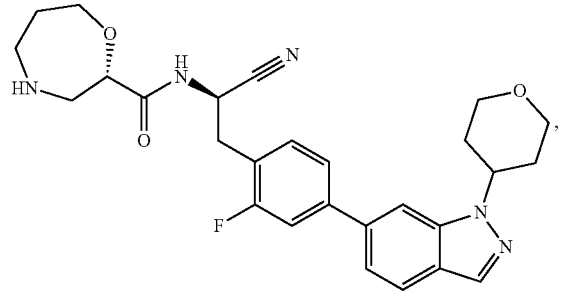
-continued
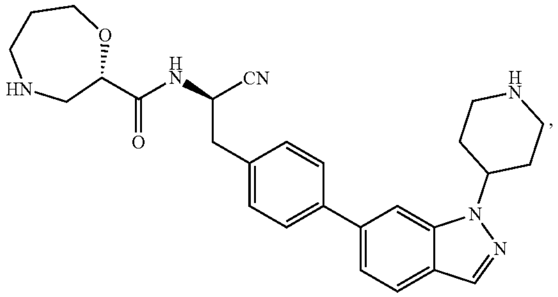
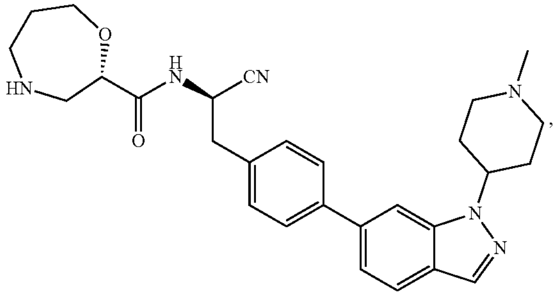
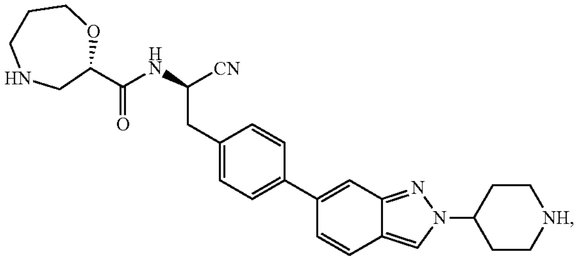
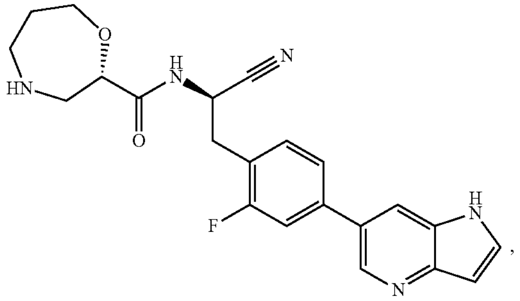
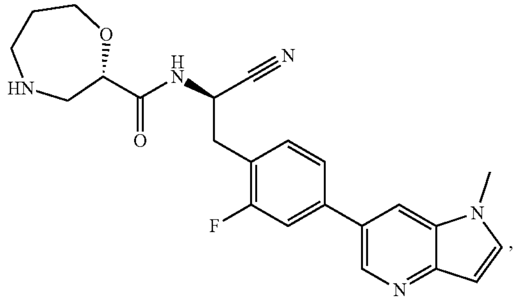

-continued

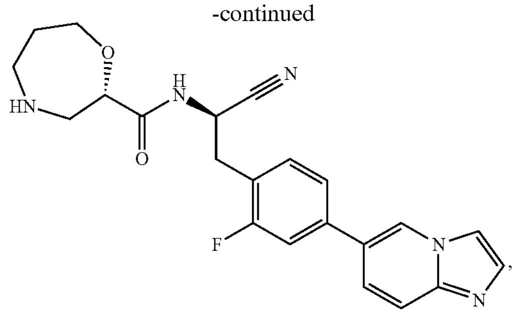

,

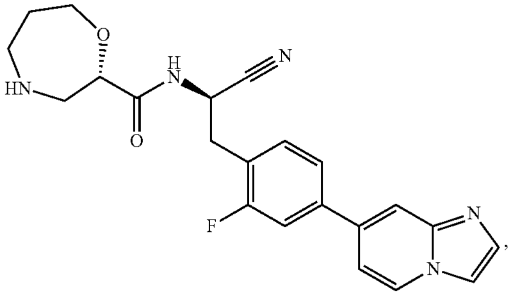

, or

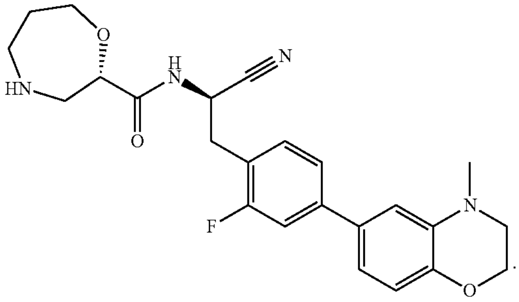

.

20. A method for inhibiting DPP1 in a subject comprising administering the compound of claim 1, or a pharmaceutically acceptable salt thereof, to the subject in need thereof.

21. A method for inhibiting DPP1 in a subject comprising administering to the subject in need thereof the compound of claim 18, or a pharmaceutically acceptable salt thereof.

22. A compound of formula (II):

(II)

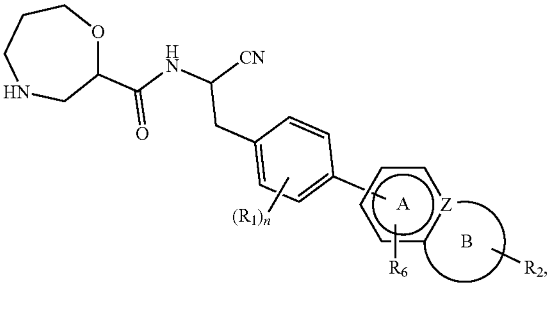

or a pharmaceutically acceptable salt thereof, wherein: the structural moiety

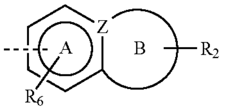

is

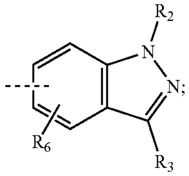

$R_1$ is selected from H, F, Cl, and —$CH_3$;

$R_2$ is selected from H, —$CH_3$,

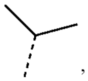

,

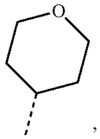

,

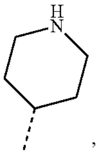

, and

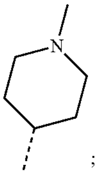

;

$R_3$ is selected from H, F, Cl, and Br;

$R_6$ is selected from H, F, Cl, and Br; and n is 1.

23. The compound of claim 22, or a pharmaceutically acceptable salt thereof, wherein:

$R_1$ is selected from H and F;

$R_2$ is selected from H and —$CH_3$;

$R_3$ is H; and $R_6$ is H.

24. The compound of claim 22, wherein the compound is selected from:

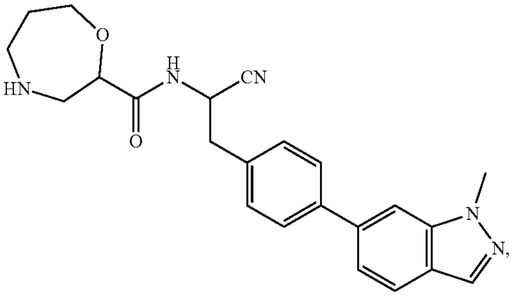

,

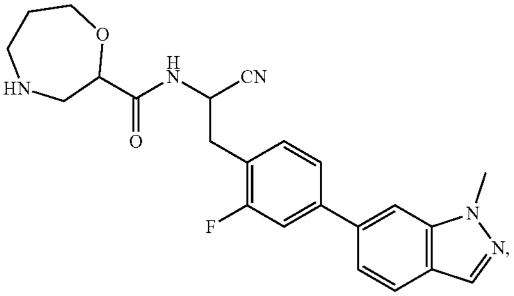 [SMILES: Cn1ncc2ccc(-c3ccc(CC(C#N)NC(=O)C4CNCCCO4)c(F)c3)cc21]

,

-continued
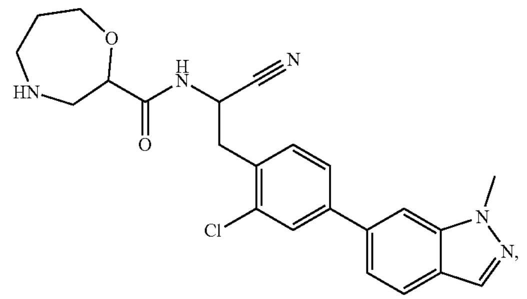
,
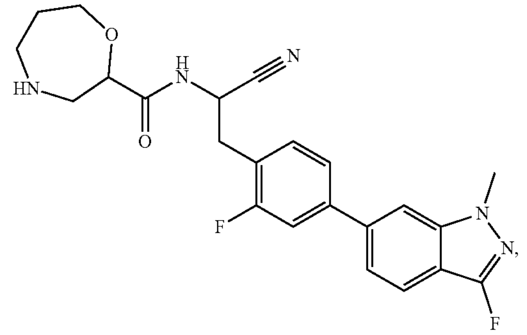
,
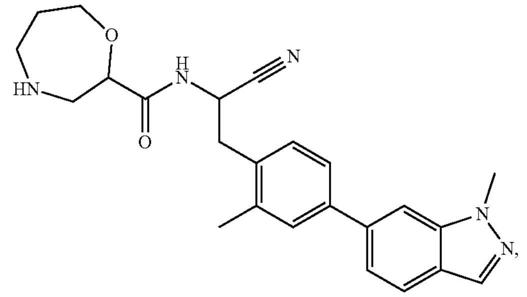
,
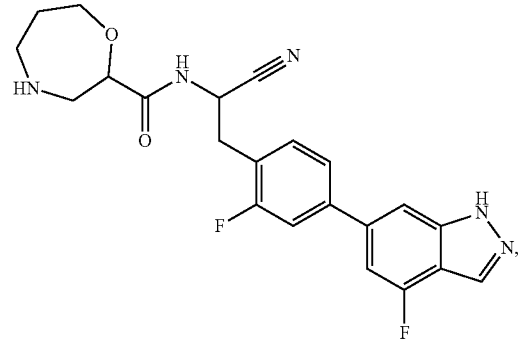
,
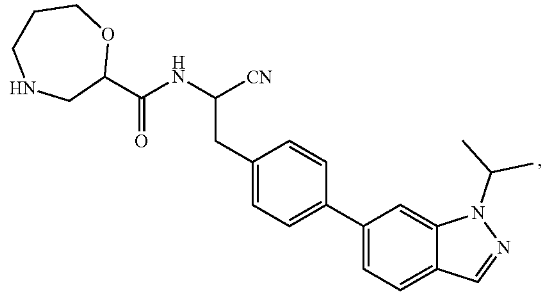
,
-continued
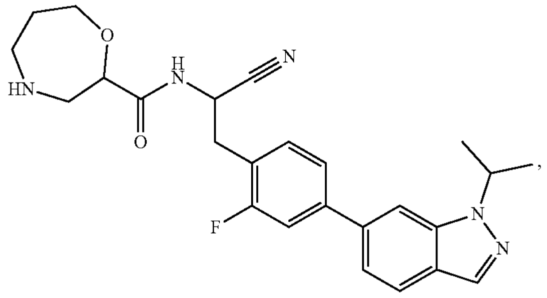
,
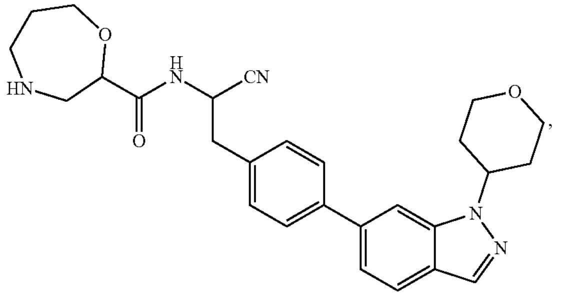
,
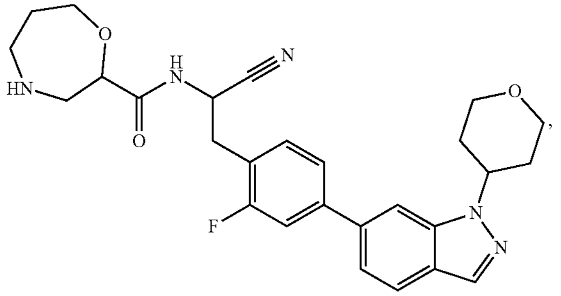
,
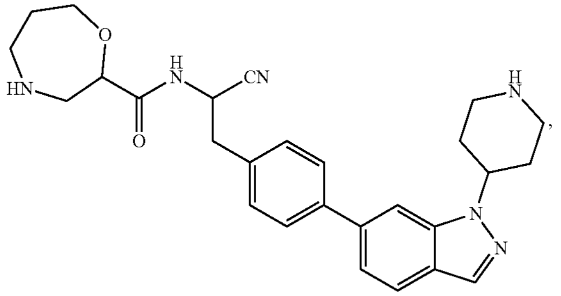
,
and
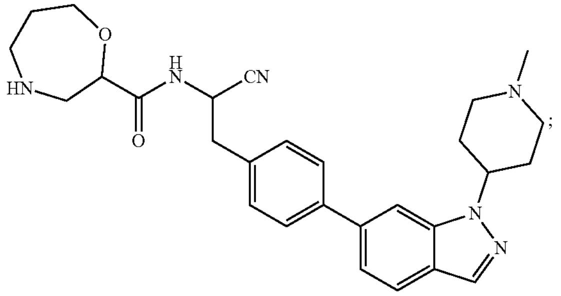
;
or a pharmaceutically acceptable salt thereof.
25. The compound of claim 22, wherein the compound is selected from:

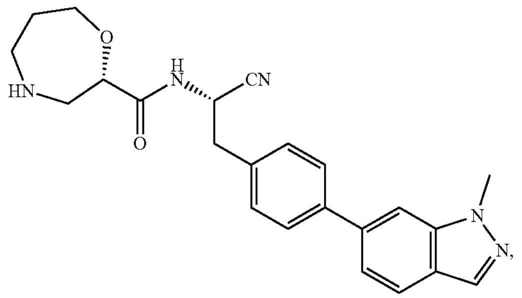
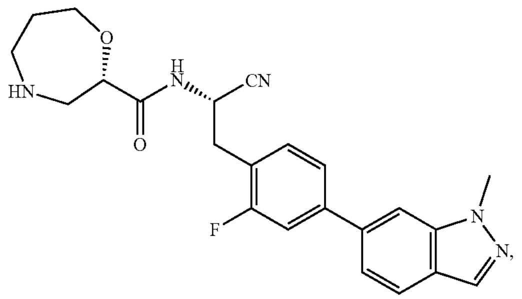 [SMILES: Cn1ncc2ccc(-c3ccc(C[C@@H](C#N)NC(=O)[C@@H]4CNCCCO4)c(F)c3)cc21]
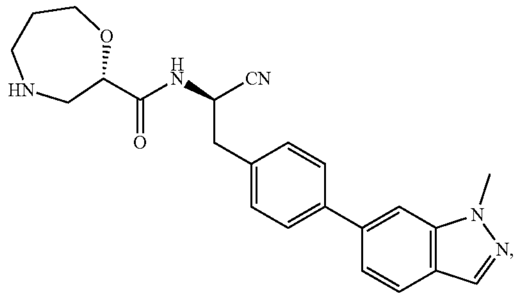
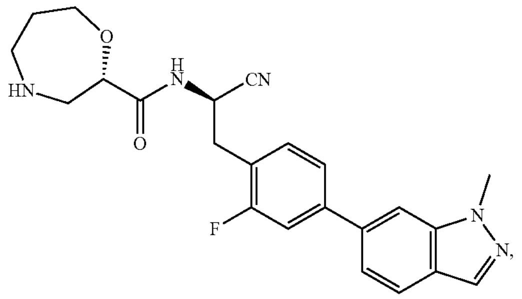 [SMILES: Cn1ncc2ccc(-c3ccc(C[C@H](C#N)NC(=O)[C@@H]4CNCCCO4)c(F)c3)cc21]
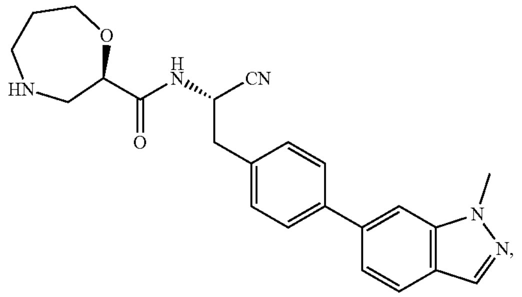
-continued
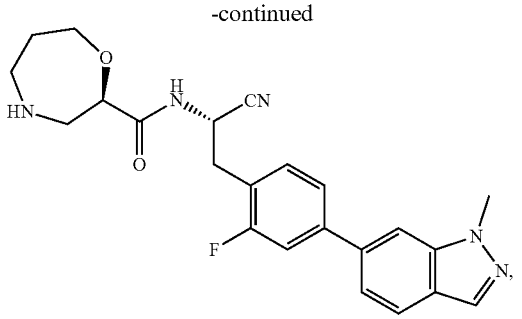
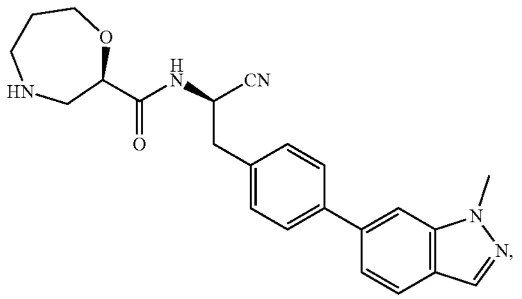
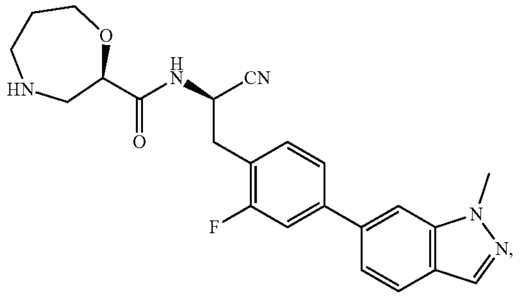
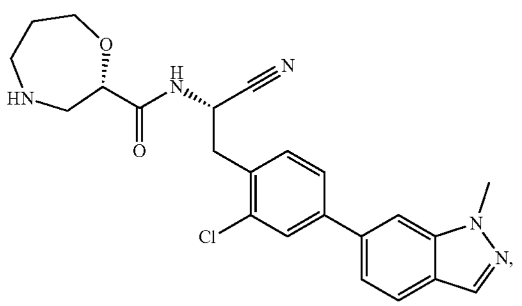
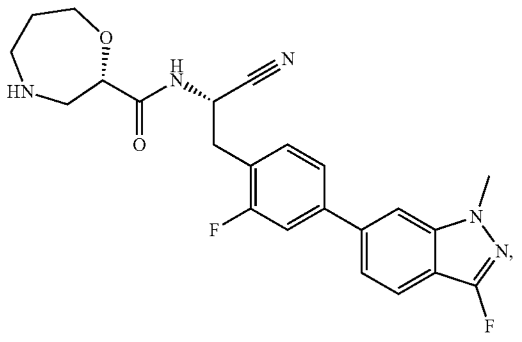

-continued
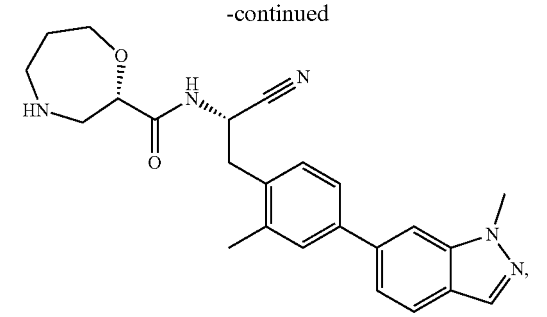
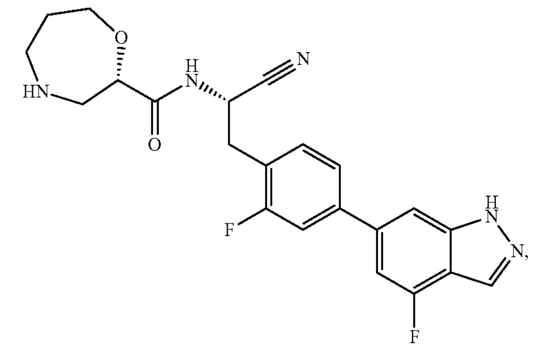
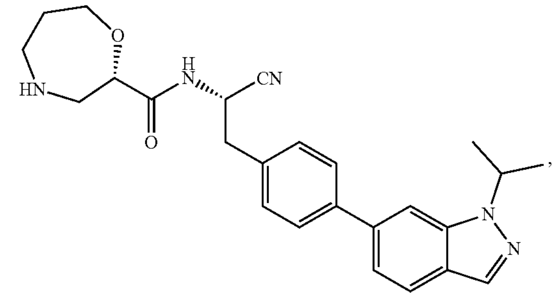
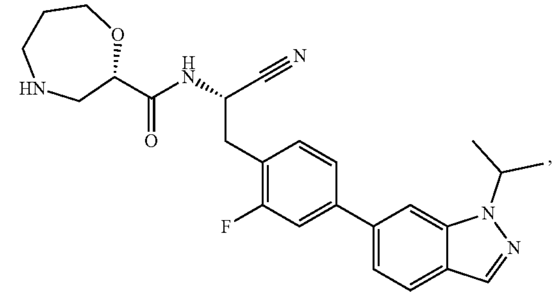
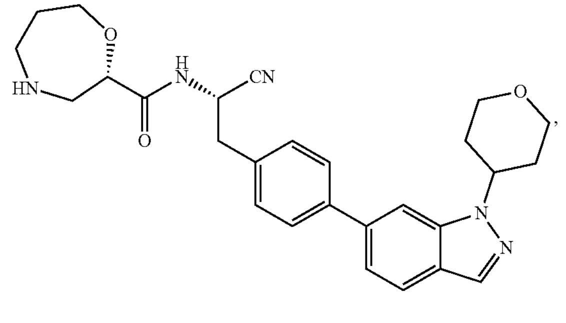
-continued
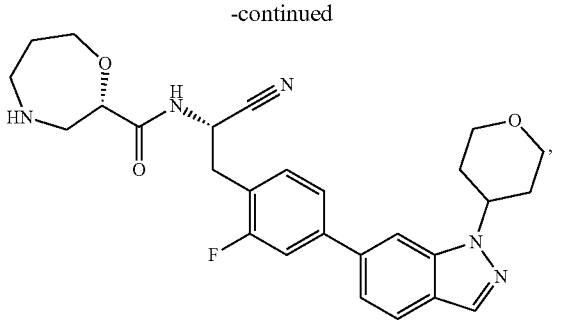
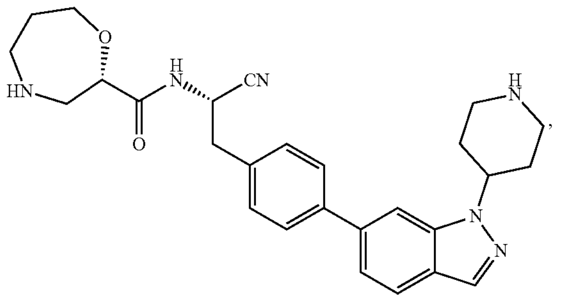
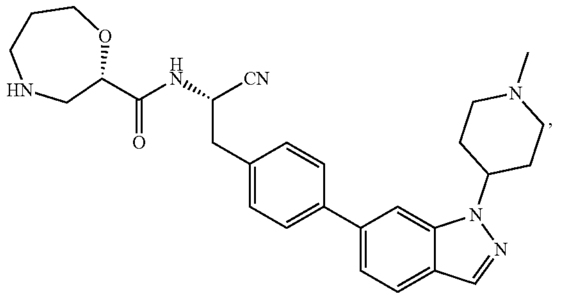
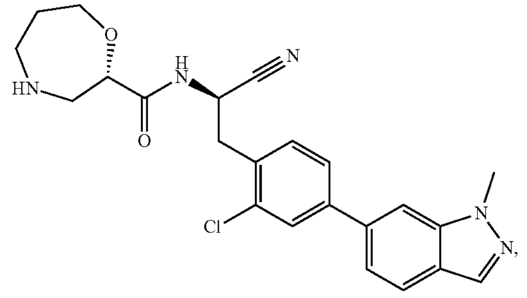
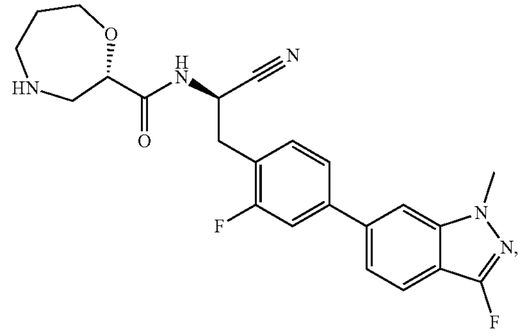

-continued
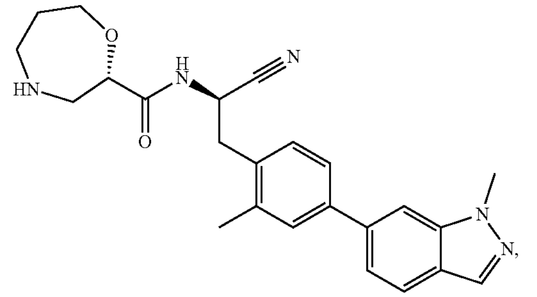
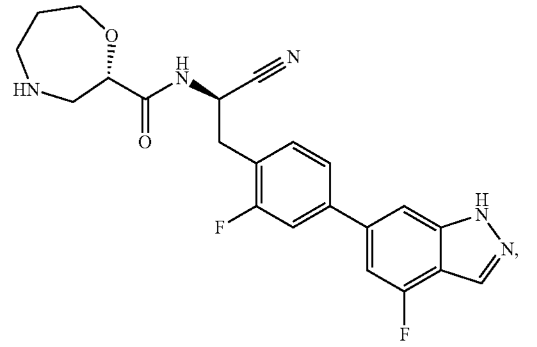
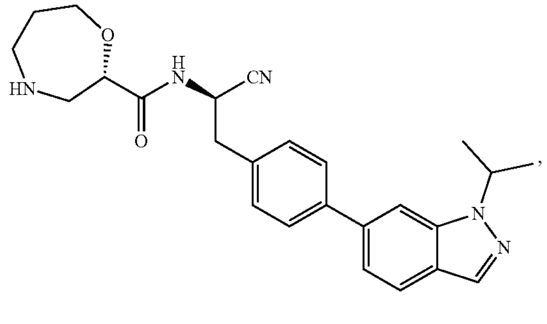
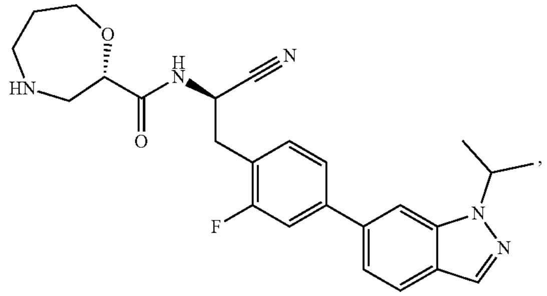
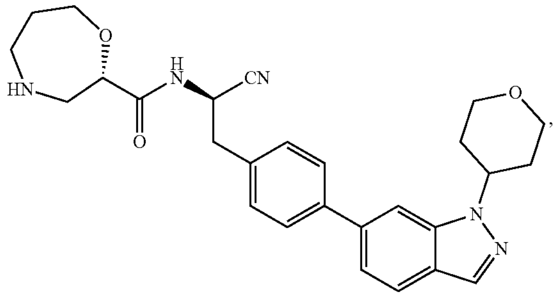
-continued
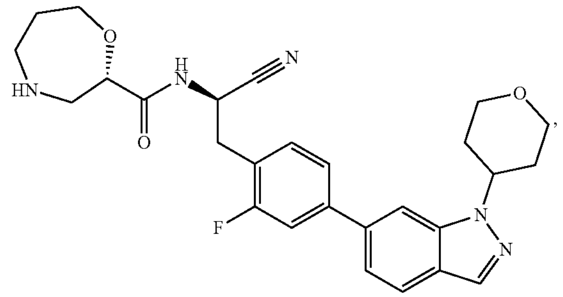
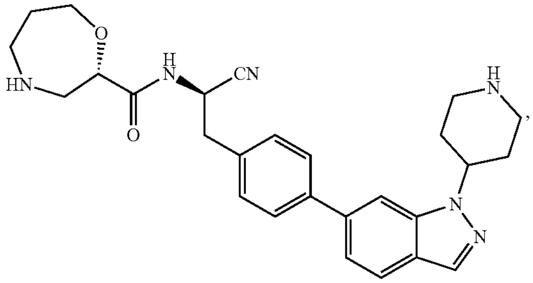
and
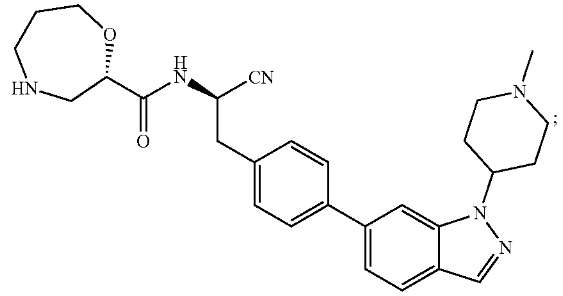
or a pharmaceutically acceptable salt thereof.
26. A compound having the following structure:
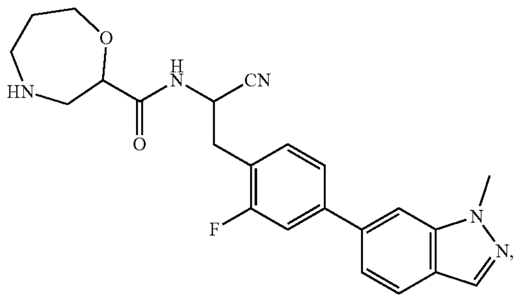
or a pharmaceutically acceptable salt thereof.

27. A compound having the following structure:

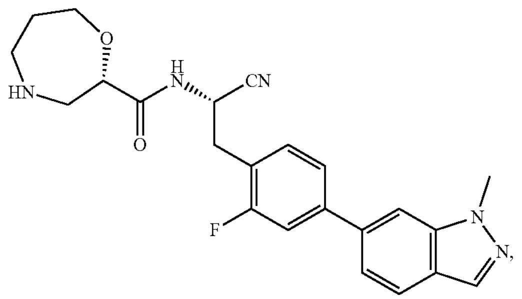

or a pharmaceutically acceptable salt thereof.

28. A compound having the following structure:

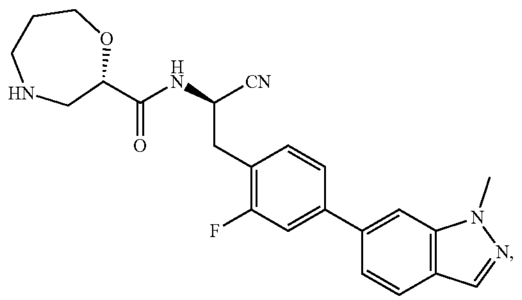

or a pharmaceutically acceptable salt thereof.

29. A method for treating chronic obstructive pulmonary disease (COPD) or bronchiectasis in a human comprising administering to the human in need thereof the compound of claim 22, or a pharmaceutically acceptable salt thereof.

30. A method for treating chronic obstructive pulmonary disease (COPD) or bronchiectasis in a human comprising administering to the human in need thereof the compound of claim 24, or a pharmaceutically acceptable salt thereof.

31. A method for treating chronic obstructive pulmonary disease (COPD) or bronchiectasis in a human comprising administering to the human in need thereof the compound of claim 25, or a pharmaceutically acceptable salt thereof.

32. A method for treating chronic obstructive pulmonary disease (COPD) or bronchiectasis in a human comprising administering to the human in need thereof the compound of claim 26, or a pharmaceutically acceptable salt thereof.

33. A method for treating chronic obstructive pulmonary disease (COPD) or bronchiectasis in a human comprising administering to the human in need thereof the compound of claim 27, or a pharmaceutically acceptable salt thereof.

34. A method for treating chronic obstructive pulmonary disease (COPD) or bronchiectasis in a human comprising administering to the human in need thereof the compound of claim 28, or a pharmaceutically acceptable salt thereof.

* * * * *